United States Patent
Rudd et al.

(10) Patent No.: US 10,961,215 B2
(45) Date of Patent: Mar. 30, 2021

(54) N-ARYL AND N-HETEROARYL PIPERIDINE DERIVATIVES AS LIVER X RECEPTOR BETA AGONISTS, COMPOSITIONS, AND THEIR USE

(71) Applicant: Merck Sharp & Dohme Corp., Rahway, NJ (US)

(72) Inventors: Michael T. Rudd, Collegeville, PA (US); Zhaoyang Meng, Ambler, PA (US); Jenny Wai, Harleysville, PA (US); David Jonathan Bennett, Winchester, MA (US); Edward J. Brnardic, Lansdale, PA (US); Nigel J. Liverton, Harleysville, PA (US); Shawn J. Stachel, Perkasie, PA (US); Yongxin Han, Needham, MA (US); Paul Tempest, Taipei (TW); Jiuxiang Zhu, Shanghai (CN); Xuewang Xu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 32 days.

(21) Appl. No.: 16/341,602

(22) PCT Filed: Oct. 9, 2017

(86) PCT No.: PCT/US2017/055685
§ 371 (c)(1),
(2) Date: Apr. 12, 2019

(87) PCT Pub. No.: WO2018/071313
PCT Pub. Date: Apr. 19, 2018

(65) Prior Publication Data
US 2020/0039951 A1    Feb. 6, 2020

(30) Foreign Application Priority Data
Oct. 14, 2016 (WO) ................ PCT/CN2016/102098

(51) Int. Cl.
*C07D 401/04* (2006.01)
*C07D 211/26* (2006.01)
*C07D 405/14* (2006.01)

(52) U.S. Cl.
CPC .......... *C07D 401/04* (2013.01); *C07D 211/26* (2013.01); *C07D 405/14* (2013.01)

(58) Field of Classification Search
CPC .................................................. C07D 401/04
USPC ........................................................ 546/194
See application file for complete search history.

(56) References Cited

U.S. PATENT DOCUMENTS

| 8,952,004 B2 | 2/2015 | Ginn et al. |
| 2009/0203710 A1 | 8/2009 | Ohtake et al. |
| 2010/0075987 A1* | 3/2010 | Wood ........................ A61P 5/50 |
| | | 514/255.05 |

FOREIGN PATENT DOCUMENTS

| WO | 2011051282 A1 | 5/2011 |
| WO | 2016022521 A1 | 2/2016 |
| WO | 2017083216 A1 | 5/2017 |
| WO | 2017083219 A1 | 5/2017 |
| WO | 2017095758 A1 | 6/2017 |
| WO | 2018071315 A2 | 4/2018 |
| WO | 2018071317 A1 | 4/2018 |

OTHER PUBLICATIONS

Stachel, SJ, Identification and in Vivo Evaluation of Liver X Receptor β-Selective Agonists for the Potential Treatment of Alzheimer's Disease, Journal of Medicinal Chemistry, 2016, 3489-3498, vol. 59, No. 7.
International Search Report for PCT/CN2016/102098 dated Jun. 28, 2017, 17 pages.
International Search Report for PCT/US2017/055690 dated Dec. 1, 2017, 10 pages.

* cited by examiner

*Primary Examiner* — Nizal S Chandrakumar
(74) *Attorney, Agent, or Firm* — Sylvia A. Ayler; Catherine D. Fitch

(57) ABSTRACT

In its many embodiments, the present invention provides certain substituted N-aryl and N-heteroaryl piperidine compounds of the Formula (I):

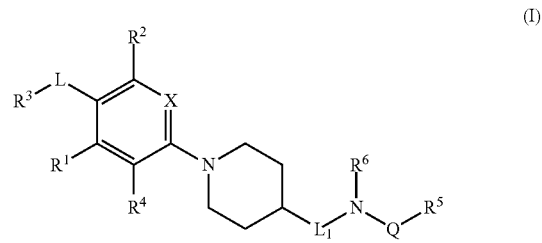

and pharmaceutically acceptable salts thereof, wherein $R^1$, $R^2$, $R^3$, L, $R^4$, $L_1$, Q, $R^5$ and $R^6$ are as defined herein. The novel compounds of the invention, and pharmaceutically acceptable compositions comprising a compound thereof, may be useful as Liver X-β receptor (LXRβ) agonists, and may be useful for treating or preventing pathologies related thereto. Such pathologies include, but are not limited to, inflammatory diseases and diseases characterized by defects in cholesterol and lipid metabolism, such as Alzheimer's disease.

19 Claims, No Drawings

N-ARYL AND N-HETEROARYL PIPERIDINE DERIVATIVES AS LIVER X RECEPTOR BETA AGONISTS, COMPOSITIONS, AND THEIR USE

FIELD OF THE INVENTION

The present invention provides certain N-aryl and N-heteroaryl piperidine compounds of formula (I), and compositions comprising these compounds, as liver X receptor β (LXRβ) agonists, which may be useful for treating or preventing pathologies related thereto. Such pathologies include, but are not limited to, inflammatory diseases and diseases characterized by defects in cholesterol and lipid metabolism, such as Alzheimer's disease.

BACKGROUND OF THE INVENTION

Alzheimer's disease is a common neurodegenerative disease affecting the elderly, resulting in progressive memory impairment, loss of language and visuospatial skills, and behavior deficits. Clinical, genetic, epidemiological and biochemical evidence suggest that dysfunctional cholesterol metabolism is implicated in the pathogenesis of Alzheimer's Disease. Hypercholesterolemia and low levels of high density lipoprotein are well-established risk factors for Alzheimer's Disease. It has been suggested that vascular, genetic and amyloid factors, in combination with diet and lifestyle, contribute to the cause and progression of Alzheimer's Disease. Hooijmans et al, *Eur J Pharmacol* 585 (2008), 176-196.

The liver X receptor (LXR) is a member of the nuclear receptor family of transcription factors, and is a part of the cholesterol regulation pathway. There are two identified isoforms of LXRs. LXRα is found in liver, intestine and in macrophages, while LXRβ is widely expressed in many tissues and is considered a ubiquitous receptor. Typically, the activity of nuclear receptors is controlled by small lipophilic moieties, such as hormones, fatty acids, bile acids, cholesterol precursors and oxysterols. Lala, *Curr Opinions Invest Drugs* 2005, 6:934-943. Cholesterol precursors such as desmosterol and oxysterols are known to bind and activate LXRs.

LXRs have demonstrated a role in the physiological metabolism of lipid and cholesterol, and thus are believed to have an important role in metabolic disorders such as hyperlipidemia and atherosclerosis. Activation of LXRs reduces cholesterol absorption, thereby reducing the ability of the body to take up cholesterol. Consistently, deletion of LXRs in mice leads to impaired cholesterol and bile acid metabolism. See Peet et al, *Cell* 1998, 93(5): 693-704. Activation of LXRs also increase peripheral cholesterol efflux systems, and impact the elimination of cholesterol by regulating cholesterol excretion into bile. See Cao et al, *Drug News Perspect* 20004, 17(1), 35-41.

LXRs also regulate lipid homeostasis in the brain. The connection between metabolic disorders and Alzheimer's Disease suggests that LXRs may have a role in the Alzheimer's disease pathway. Activation of LXRs also inhibit inflammation and pro-inflammatory expression in the body. Zelcer et al, *J Clin Invest* 2006, 116:3 (607-614). Thus, LXRs may serve as targets for the treatment of inflammatory diseases. However, activation of hepatic LXRα is believed to be the underlying cause of liver steatosis and hyperlipidemia associated with dual LXRα/β small agonist molecules developed to date.

LXRs have also been proposed as possible therapeutics to treat a number of cancers e.g. prostate, breast, ovarian, melanoma, pancreas, lung, colon and hematological malignancy (Lin, C-Y and Gustafsson, J-A, (2015) Nature Reviews Cancer 15, 216-224).

LXRβ is the predominant brain isoform. See Song et al, *Ann NY Acad Sci* 195, 761:38-49. LXRβ knockout male mice demonstrated adult-onset motor neuron degeneration. (Andersson et al, *Proc Nat'l Acad Sci USA* 2005, 8; 1902 (1)):3857-3862), and the LXRα and LXRβ double knockout mice develop neurodegenerative changes in brain tissue. (Wang et al, Proc Natl Acad Sci USA. 2002, 99(21):13878-83). Therefore development of selective LXRβ agonists could be a therapeutic approach to neurodegenerative diseases such as AD and avoid the peripheral adverse lipid effects that have been linked to LXRα.

Applicants have now discovered a series of LXRβ selective agonists. Thus, the compounds of the invention, which are selective LXRβ agonists, may be useful in the treatment of Alzheimer's disease, inflammatory diseases, and diseases characterized by defects in cholesterol and lipid metabolism.

SUMMARY OF THE INVENTION

The present invention provides certain N-aryl and N-heteroaryl piperidine compounds, which are collectively or individually referred to herein as "compound(s) of the invention", as described herein. The compounds of the invention are selective agonists of LXRβ, and may be useful for treating or preventing diseases or pathologies related thereto.

In one embodiment, the compounds of the invention have the structural Formula (I):

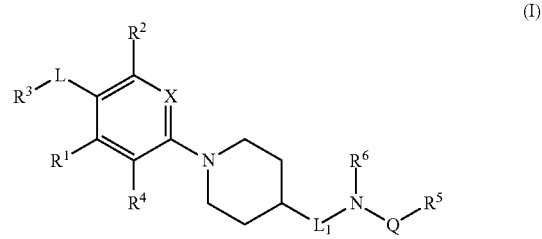

or a pharmaceutically acceptable salt thereof, wherein:

X is selected from —N— and —CH—;

$R^1$ is selected from H, methyl, and halogen;

$R^2$ is selected from H, halogen, cyano, cyclopropyl, —$CH_3$, and —$OCH_3$;

$R^4$ is selected from H, halogen, and methyl;

-L- is a divalent moiety selected from —C(O)— and —S(O)$_2$—;

$R^3$ is —N($R^{N1}$)($R^{N2}$), wherein:

$R^{N1}$ is selected from H and —($C_1$-$C_6$)alkyl; and $R^{N2}$ is selected from H, —($C_1$-$C_6$)alkyl, cyclopropyl, —O—($C_1$-$C_6$)alkyl, —OH, halogen, —CN, and —($C_1$-$C_6$)alkyl which is substituted with 1 or 2 groups independently selected from:

—OH, halogen, —CN, optionally substituted phenyl, (wherein said optional substitutents on said phenyl are 1 to 3 groups independently selected from OH, CN, —($C_1$-$C_4$)alkyl, —($C_1$-$C_4$)alkoxyl), optionally substituted heteroaryl, (wherein said optional substituents on said heteroaryl are 1 to 3 groups independently selected from —($C_1$-$C_6$)alkyl, —($C_1$-$C_4$)alkoxyl, and cyclopropyl), optionally substituted cyclopropyl (wherein said optional substituents on said cyclopropyl are 1 to 3 groups independently selected from —($C_1$-$C_6$)alkyl), and optionally substituted heterocycloalkyl (wherein said optional substitutents on said heterocycloalkyl are 1 to 3 groups independently selected from halogen, —OH, oxo, CN, and —($C_1$-$C_6$)alkyl, or, alternatively, $R^{N1}$ and $R^{N2}$ are taken together with the nitrogen atom to which they are shown attached to form a 4-, 5-, or 6-membered fully saturated heterocyclic ring comprising (including the nitrogen atom) 1, 2, or 3 ring heteroatoms selected from N, N-oxide, O, S, and S-oxide, wherein said heterocyclic ring is unsubstituted or substituted with 1, 2, or 3 substituents independently selected from halogen, —OH, oxo, CN, —($C_1$-$C_6$) alkyl, amino-substituted —($C_1$-$C_6$)alkyl (wherein said amino is 1, 2, or 3 groups independently selected from —$NH_2$, —N($C_1$-$C_4$alkyl)$_2$, and —NH ($C_1$-$C_4$alkyl)), —O—($C_1$-$C_6$)alkyl, —($C_1$-$C_6$)alkyl-OH, —($C_1$-$C_6$)haloalkyl, —C(O)O—($C_1$-$C_6$)alkyl, cyclopropyl, spirocyclopropyl, —$CH_2$—NHC(O) O—($C_1$-$C_6$)alkyl, —$CH_2$—N($CH_3$)C(O)O—($C_1$-$C_6$)alkyl, phenyl, benzyl, —NHC(O)-phenyl, heteroaryl, —($C_1$-$C_4$)alkylheteroaryl, and heterocycloalkyl;

-$L_1$- is a divalent moiety selected from:

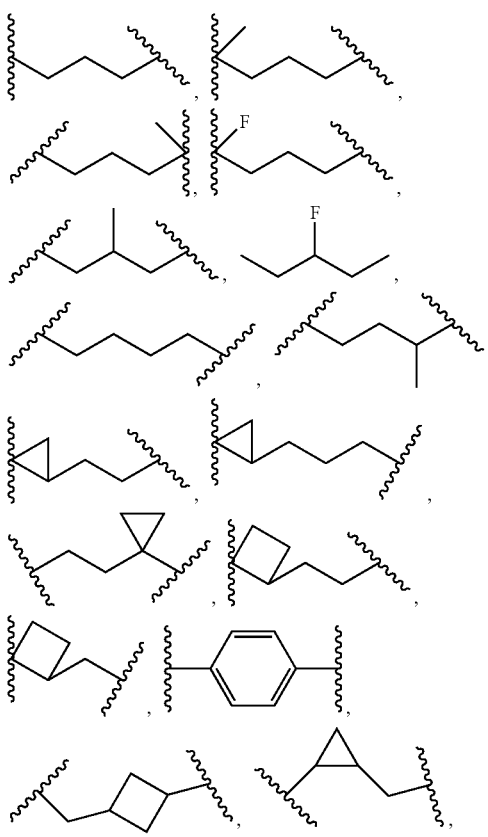

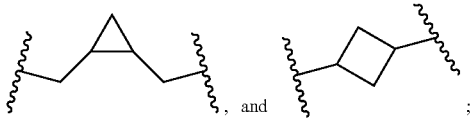

Q is a bond or a divalent moiety selected from —C(O)—, —S(O)$_2$—, and —C(O)O—; and $R^5$ is selected from:
—C($R^{5A}$)($R^{5B}$)($R^{5C}$), wherein:
each of $R^{5A}$, $R^{5B}$ and $R^{5C}$ is independently selected from: H, halogen, OH, $NH_2$, $NHCH_3$, —($C_1$-$C_6$)alkyl, —($C_1$-$C_6$)haloalkyl, —($C_1$-$C_6$)alkenyl, —($C_1$-$C_6$)alkynyl, —($C_3$-$C_6$)cycloalkyl, —($C_3$-$C_6$)cycloalkyl substituted with —($C_1$-$C_6$)alkyl, —($C_1$-$C_6$)alkenyl, —($C_1$-$C_6$) alkynyl, phenyl, phenyl substituted with from 1 to 3 groups independently selected from halogen, OH, —$NH_2$, —($C_1$-$C_6$)alkyl, —O—($C_1$-$C_6$)alkyl, cyclopropyl, —O—($C_1$-$C_6$)haloalkyl, —O-cyclopropyl, and —C(O)O—($C_1$-$C_6$)alkyl,

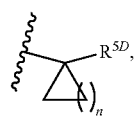

wherein n is an integer from 1 to 4;

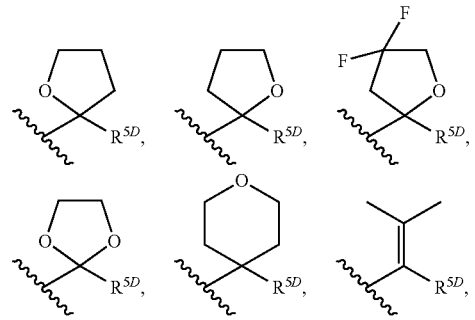

wherein $R^{5D}$ is selected from H, —($C_1$-$C_6$)alkyl, —($C_1$-$C_6$)haloalkyl, phenyl, and phenyl substituted with from 1 to 3 groups independently selected from OH, halogen, —($C_1$-$C_6$)alkyl, and —O—($C_1$-$C_6$)alkyl, and phenyl, wherein:
said phenyl is unsubstituted or substituted with 1, 2, or 3 groups independently selected from halogen, CN, —($C_1$-$C_6$)alkyl, and —($C_1$-$C_6$)haloalkyl; and $R^6$ is H or $CH_3$.

In other embodiments, the invention provides compositions, including pharmaceutical compositions, comprising one or more compounds of the invention (e.g., one compound of the invention) or a pharmaceutically acceptable salt thereof, optionally together with one or more additional therapeutic agents, optionally in an acceptable (e.g., pharmaceutically acceptable) carrier or diluent.

In another embodiment, the invention is directed to methods of treating an inflammatory disease or a disease characterized by defects in cholesterol or lipid metabolism, in a patient in need thereof by administering to the patient a compound of the invention or a pharmaceutically acceptable salt thereof. Non-limiting examples of such inflammatory diseases and diseases characterized by defects in cholesterol or lipid metabolism are described below.

In another embodiment, the invention provides for the use of a compound of the invention in the manufacture of a medicament for treating an inflammatory disease or a disease characterized by defects in cholesterol or lipid metabolism in a patient in need thereof. Non-limiting examples of such inflammatory diseases and diseases characterized by defects in cholesterol or lipid metabolism are described below.

In another embodiment, the invention is directed to a method of treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of a compound of the invention in the manufacture of a medicament for treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of any of the compounds of the invention for use as a medicament, or in medicine, or in therapy.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I) as described above, and pharmaceutically acceptable salts thereof.

In another embodiment, in Formula (I), X is N.

In another embodiment, in Formula (I), X is CH.

The following alternative embodiments of $R^1$ apply to Formula (I) and also to each of the embodiments described hereinabove.

In another embodiment, in Formula (I), $R^1$ is selected from H, methyl, F, and Cl.

In another embodiment, in Formula (I), $R^1$ is H.

The following alternative embodiments of $R^2$ apply to Formula (I) and also to each of the embodiments and alternative embodiments, and all combinations of embodiments, described hereinabove.

In another embodiment, in Formula (I), $R^2$ is selected from H, Cl, cyano, cyclopropyl, —$CH_3$, and —$OCH_3$.

In another embodiment, in Formula (I), $R^2$ is Cl.

In another embodiment, in Formula (I), $R^2$ is cyano.

In another embodiment, in Formula (I), $R^2$ is cyclopropyl.

In another embodiment, in Formula (I), $R^2$ is $CH_3$.

In another embodiment, in Formula (I), $R^2$ is $OCH_3$.

The following alternative embodiments of $R^4$ apply to Formula (I) and also to each of the embodiments and alternative embodiments, and all combinations of embodiments, described hereinabove.

In another embodiment, in Formula (I), $R^4$ is H, —$CH_3$, or chloro.

The following alternative embodiments of L apply to Formula (I) and also to each of the embodiments and alternative embodiments, and all combinations of embodiments, described hereinabove.

In another embodiment, in Formula (I): L is —C(O)—.

The following alternative embodiments of $R^3$ apply to Formula (I) and also to each of the embodiments and alternative embodiments, and all combinations of embodiments, described hereinabove.

In another embodiment, in Formula (I), $R^3$ is —N($R^{N1}$)($R^{N2}$), wherein:

$R^{N1}$ is selected from H and —($C_1$-$C_6$)alkyl; and $R^{N2}$ is selected from H, —($C_1$-$C_6$)alkyl, cyclopropyl, —O—($C_1$-$C_6$)alkyl, —OH, halogen, —CN, and —($C_1$-$C_6$)alkyl which is substituted with 1 or 2 groups independently selected from:

—OH, halogen, —CN, optionally substituted phenyl, (wherein said optional substitutents on said phenyl are 1 to 3 groups independently selected from OH, CN, —($C_1$-$C_4$)alkyl, —($C_1$-$C_4$)alkoxyl), optionally substituted heteroaryl, (wherein said optional substituents on said heteroaryl are 1 to 3 groups independently selected from —($C_1$-$C_6$)alkyl, —($C_1$-$C_4$) alkoxyl, and cyclopropyl), optionally substituted cyclopropyl (wherein said optional substituents on said cyclopropyl are 1 to 3 groups independently selected from —($C_1$-$C_6$)alkyl), and optionally substituted heterocycloalkyl (wherein said optional substitutents on said heterocycloalkyl are 1 to 3 groups independently selected from halogen, —OH, oxo, CN, and —($C_1$-$C_6$)alkyl.

In another embodiment, in Formula (I):

$R^3$ is —N($R^{N1}$)($R^{N2}$), wherein:

$R^{N1}$ is selected from H, methyl, and ethyl; and $R^{N2}$ is H, methyl, ethyl, —O-methyl, —O-ethyl, OH, fluoro, chloro, —CN, substituted methyl, or substituted ethyl, wherein each said substituent is 1 or 2 groups independently selected from:

OH, fluoro, chloro, —CN, optionally substituted phenyl, (wherein said optional substitutents on said phenyl are 1 to 3 groups independently selected from OH, CN, methyl, ethyl, —O-methyl, and —O-ethyl), optionally substituted heteroaryl, (wherein said optional substituents on said heteroaryl are 1 to 3 groups independently selected from methyl, ethyl, —O— methyl, —O-ethyl, and cyclopropyl), optionally substituted cyclopropyl (wherein said optional substituents on said cyclopropyl are 1 to 3 groups independently selected from methyl and ethyl, optionally substituted heterocycloalkyl (wherein said optional substitutents on said heterocycloalkyl are 1 to 3 groups independently selected from halogen, —OH, oxo, CN, methyl, and ethyl, —O-methyl, —O-ethyl, —OH, F, Cl, and —CN.

In each of these embodiments, non-limiting examples of said optionally substituted heteroaryl include: pyridyl, pyrazinyl, furanyl, thienyl, pyrimidinyl, isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, oxindolyl, indolyl, azaindolyl, imidazolyl, thienopyridyl, imidazopyridyl, isoquinolinyl, benzoazaindolyl, and triazinyl. In one embodiment, said optionally substituted heteroaryl is isoxazolyl, oxadiazolyl, or thiazolyl.

In each of these embodiments, non-limiting examples of said optionally substituted heterocycloalkyl include: tetrahydrofuranyl and morpholinyl.

In each of these embodiments, non-limiting examples of said optionally substituted cycloalkyl include cyclopropyl, cyclobutyl, cyclopentyl and cyclohexyl.

In another embodiment, in Formula (I), $R^3$ is —N($R^{N1}$)($R^{N2}$), wherein $R^{N1}$ and $R^{N2}$ are each independently selected from H, methyl, ethyl, n-propyl, i-propyl, —CH$_2$CH$_2$—OH, cyclopropyl, —CH$_2$-oxadiazolyl, —CH$_2$-triazolyl (wherein said oxadiazolyl and said triazolyl are each optionally substituted with methyl or cyclopropyl). In another such embodiment, L is —C(O)—.

In another embodiment, in Formula (I), and in each of the embodiments and alternative embodiments described hereinabove, L is —C(O)—; and $R^3$ is —N(CH$_3$)$_2$ or —NH(CH$_3$).

In another embodiment, in Formula (I), $R^3$ is —N($R^{N1}$)($R^{N2}$), wherein:
$R^{N1}$ and $R^{N2}$ are taken together with the nitrogen atom to which they are shown attached to form a 4-, 5-, or 6-membered fully saturated heterocyclic ring comprising (including the nitrogen atom) 1, 2, or 3 ring heteroatoms selected from N, N-oxide, O, S, and S-oxide,
wherein said heterocyclic ring is unsubstituted or substituted with 1, 2, or 3 substituents independently selected from halogen, —OH, oxo, CN, —(C$_1$-C$_6$)alkyl, amino-substituted —(C$_1$-C$_6$)alkyl (wherein said amino is 1, 2, or 3 groups independently selected from —NH$_2$, —N(C$_1$-C$_4$alkyl)$_2$, and —NH(C$_1$-C$_4$alkyl)), —O—(C$_1$-C$_6$)alkyl, —(C$_1$-C$_6$)alkyl-OH, —(C$_1$-C$_6$)haloalkyl, —C(O)O—(C$_1$-C$_6$)alkyl, cyclopropyl, spirocyclopropyl, —CH$_2$—NHC(O)O—(C$_1$-C$_6$)alkyl, —CH$_2$—N(CH$_3$)C(O)O—(C$_1$-C$_6$)alkyl, phenyl, benzyl, —NHC(O)-phenyl, heteroaryl, —(C$_1$-C$_4$)alkylheteroaryl, and heterocycloalkyl;

In the immediately preceding embodiment, non-limiting examples of said unsubstituted or substituted heterocyclic ring include azetidinyl, pyrrolidinyl, piperidinyl, and morpholinyl.

In an alternative of each of the preceding embodiments of $R^3$, L is —C(O)—.

The following alternative embodiments of $R^5$ apply to Formula (I) and also to each of the embodiments and alternative embodiments, and all combinations of embodiments, described hereinabove.

In one embodiment, in Formula (I):
$R^5$ is —C($R^{5A}$)($R^{5B}$)($R^{5C}$),
wherein each of $R^{5A}$, $R^{5B}$ and $R^{5C}$ is independently selected from H, F, Cl, OH, NH$_2$, NHCH$_3$, —(C$_1$-C$_6$)alkyl, —(C$_1$-C$_6$)haloalkyl, —(C$_1$-C$_6$)alkenyl, —(C$_1$-C$_6$)alkynyl, —(C$_3$-C$_6$)cycloalkyl, —(C$_3$-C$_6$)cycloalkyl substituted with —(C$_1$-C$_6$)alkyl, —(C$_1$-C$_6$)alkenyl, —(C$_1$-C$_6$)alkynyl, phenyl, phenyl substituted with from 1 to 3 groups independently selected from F, Cl, —(C$_1$-C$_6$)alkyl, —O—(C$_1$-C$_6$)alkyl, and —C(O)O—(C$_1$-C$_6$)alkyl.

In an alternative of the immediately preceding embodiment,
$R^{5A}$ is OH;
$R^{5B}$ is —(C$_1$-C$_3$)fluoroalkyl; and
$R^{5C}$ is selected from NH$_2$, NHCH$_3$, —(C$_1$-C$_6$)alkyl, —(C$_1$-C$_4$)fluoroalkyl, phenyl, (wherein said phenyl substituted with from 1-3 groups independently selected from halogen —(C$_1$-C$_6$)alkyl, and —(C$_1$-C$_6$)alkoxy), cyclopropyl (wherein said cyclopropyl is optionally substituted with —(C$_1$-C$_6$)alkyl), cyclobutyl (wherein said cyclobutyl is optionally substituted with —(C$_1$-C$_6$)alkyl), ethenyl, and ethynyl.

In another embodiment, in Formula (I), $R^5$ is

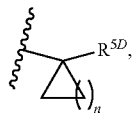

wherein n is an integer from 1 to 4; and $R^{5D}$ is as defined in Formula (I).

In another embodiment, in Formula (I), $R^5$ is

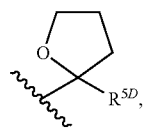

where $R^{5D}$ is as defined in Formula (I). In an alternative of this embodiment, $R^{5D}$ is selected from H, —(C$_1$-C$_6$)alkyl, —(C$_1$-C$_6$)haloalkyl, phenyl, and phenyl substituted with from 1 to 3 groups independently selected from OH, F, Cl, methyl, ethyl, n-propyl, i-propyl, —O-methyl, and —O-ethyl.

In another embodiment, in Formula (I), $R^5$ is

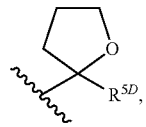

where R is as defined in Formula (I). In an alternative of this embodiment, $R^{5D}$ is selected from H, —(C$_1$-C$_6$)alkyl, —(C$_1$-C$_6$)haloalkyl, phenyl, and phenyl substituted with from 1 to 3 groups independently selected from OH, F, Cl, methyl, ethyl, n-propyl, i-propyl, —O-methyl, and —O-ethyl.

In another embodiment, in Formula (I), $R^5$ is

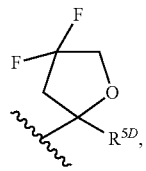

where $R^{5D}$ is as defined in Formula (I). In an alternative of this embodiment, $R^{5D}$ is selected from H, —(C$_1$-C$_6$)alkyl, —(C$_1$-C$_6$)haloalkyl, phenyl, and phenyl substituted with from 1 to 3 groups independently selected from OH, F, Cl, methyl, ethyl, n-propyl, i-propyl, —O-methyl, and —O-ethyl.

In another embodiment, in Formula (I), $R^5$ is

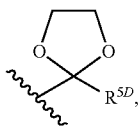

where $R^{5D}$ is as defined in Formula (I). In an alternative of this embodiment, $R^{5D}$ is selected from H, —$(C_1$-$C_6)$alkyl, —$(C_1$-$C_6)$haloalkyl, phenyl, and phenyl substituted with from 1 to 3 groups independently selected from OH, F, Cl, methyl, ethyl, n-propyl, i-propyl, —O-methyl, and —O-ethyl.

In another embodiment, in Formula (I), $R^5$ is

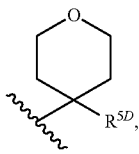

where $R^{5D}$ is as defined in Formula (I). In an alternative of this embodiment, $R^{5D}$ is selected from H, —$(C_1$-$C_6)$alkyl, —$(C_1$-$C_6)$haloalkyl, phenyl, and phenyl substituted with from 1 to 3 groups independently selected from OH, F, Cl, methyl, ethyl, n-propyl, i-propyl, —O-methyl, and —O-ethyl.

In another embodiment, in Formula (I), $R^5$ is

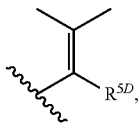

where $R^{5D}$ is as defined in Formula (I). In an alternative of this embodiment, $R^{5D}$ is selected from H, —$(C_1$-$C_6)$alkyl, —$(C_1$-$C_6)$haloalkyl, phenyl, and phenyl substituted with from 1 to 3 groups independently selected from OH, F, Cl, methyl, ethyl, n-propyl, i-propyl, —O-methyl, and —O-ethyl.

In another embodiment, in Formula (I), $R^5$ is phenyl, wherein said phenyl is unsubstituted or substituted with 1, 2, or 3 groups independently selected from halogen, CN, —$(C_1$-$C_6)$alkyl, and —$(C_1$-$C_6)$haloalkyl.

The following alternative embodiments of Q apply to Formula (I) and also to each of the embodiments and alternative embodiments, and all combinations of embodiments, described hereinabove.

In another embodiment, Q is a bond. In another embodiment, Q is —C(O)—. In another embodiment, Q is —S(O)$_2$—. In another embodiment, Q is —C(O)O—.

Specific non-limiting embodiments of compounds of the invention are shown in the examples below. All valences not shown explicitly filled in the pictured example compounds of the invention are assumed to be filled by hydrogen such that all valences are satisfied unless otherwise indicated.

In another embodiment, 1 to 3 carbon atoms of the compounds of the invention may be replaced with 1 to 3 silicon atoms so long as all valence requirements are satisfied.

In another embodiment, there is provided a composition comprising a compound of the invention and a pharmaceutically acceptable carrier or diluent.

In one embodiment, the invention is directed to methods of treating a patient (preferably a human) for inflammatory diseases and diseases characterized by defects in cholesterol or lipid metabolism, by administering to the patient a compound of the invention or a pharmaceutically acceptable salt thereof.

The invention is also directed to the use of a compound of the invention for treating inflammatory diseases and diseases characterized by defects in cholesterol or lipid metabolism, by administering to a patient (preferably a human) a compound of the invention or a pharmaceutically acceptable salt thereof.

The invention is also directed to medicaments or pharmaceutical compositions for treating inflammatory diseases and diseases characterized by defects in cholesterol or lipid metabolism, by administering to a patient (preferably a human) a compound of the invention, or a pharmaceutically acceptable salt thereof, and a pharmaceutically acceptable carrier.

The invention is further directed to a the manufacture of a medicament or a composition for inflammatory diseases and diseases characterized by defects in cholesterol or lipid metabolism, by administering to a patient (preferably a human) a compound of the invention or a pharmaceutically acceptable salt thereof, with one or more pharmaceutically acceptable carriers.

Exemplary inflammatory diseases and diseases characterized by defects in cholesterol or lipid metabolism for which the compounds of the invention may be useful include neurodegenerative and neurological diseases, such as Alzheimer's Disease, Neimann-Pick disease type C1, Parkinson's Disease, amyotrophic lateral sclerosis, stroke, age-related macular degeneration, psychiatric disorders such as schizophrenia and depression, and metabolic disorders such as cardiovascular disease, obesity and diabetes.

The present invention is directed to the use of the compounds of the invention as LXRβ agonists in a patient or subject such as a mammal in need of such activity, comprising the administration of an effective amount of the compound. In addition to humans, a variety of other mammals can be treated according to the method of the present invention.

The compounds of the invention may have utility in treating or ameliorating Alzheimer's disease. The compounds may also be useful in treating or ameliorating other inflammatory diseases and diseases characterized by defects in cholesterol and lipid metabolism, such as Neimann-Pick disease type C1, Parkinson's Disease, amyotrophic lateral sclerosis, stroke, age-related macular degeneration, psychiatric disorders such as schizophrenia and depression, and metabolic disorders such as cardiovascular disease, obesity and diabetes.

For example, the compounds of the invention may be useful for the prevention of dementia of the Alzheimer's type, as well as for the treatment of early stage, intermediate stage or late stage dementia of the Alzheimer's type.

Potential cardiovascular conditions or disorders for which the compounds of the invention may be useful include atherosclerosis, hypertension, hyperlipidemia, coronary heart disease, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, vascular complications of diabetes, obesity (including abdominal obesity) and endotoxemia.

The compounds of the invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease.

The compounds of the invention may also be useful for the treatment of Type 2 diabetes, and conditions and disorders related to Type 2 diabetes, such as (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

The compounds of the invention may also have utility in treating certain kinds of cancers which are affected by the LXR mechanism. Such cancers include, but are not limited to, prostate, breast, ovarian, melanoma, pancreas, lung, colon and hematological malignancy. (Lin, C—Y and Gustafsson, J-A, (2015) Nature Reviews Cancer 15, 216-224).

The compounds of the invention may be used in combination with one or more other drugs in the treatment of diseases or conditions for which the compounds of the invention have utility, where the combination of the drugs together are safer or more effective than either drug alone. Additionally, the compounds of the invention may be used in combination with one or more other drugs that treat, prevent, control, ameliorate, or reduce the risk of side effects or toxicity of the compounds of the invention. Such other drugs may be administered, by a route and in an amount commonly used contemporaneously or sequentially with the compounds of the invention. Accordingly, the pharmaceutical compositions of the present invention include those that contain one or more other active ingredients, in addition to the compounds of the invention. The combinations may be administered as part of a unit dosage form combination product, or as a kit or treatment protocol wherein one or more additional drugs are administered in separate dosage forms as part of a treatment regimen.

Examples of combinations of the compounds of the invention include combinations with anti-Alzheimer's Disease agents, for example: other LXRβ agonists; beta-secretase inhibitors including verubecestat (N-[3-[(5R)-3-amino-2,5-dimethyl-1,1-dioxo-6H-1,2,4-thiadiazin-5-yl]-4-fluorophenyl]-5-fluoropyridine-2-carboxamide); alpha 7 nicotinic agonists; ADAM 10 ligands or activators; gamma-secretase inhibitors, such as LY450139 and TAK 070; gamma secretase modulators; tau phosphorylation inhibitors; glycine transport inhibitors; ApoE4 conformational modulators; NR2B antagonists; androgen receptor modulators; blockers of Aβ 15 cortico formation; 5-HT4 agonists, such as PRX-03140; 5-HT6 antagonists, such as xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab; anti-inflammatory compounds such as I-flurbiprofen, nitroflurbiprofen; PPAR gamma agonists, such as pioglitazone and rosiglitazone; CB-1 receptor antagonists or CB-1 receptor inverse agonists; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine and ladostigil; growth hormone secretagogues such as ibutamoren, ibutamoren mesylate, and capromorelin; histamine H3 receptor antagonists; AMPA agonists or AMPA modulators; PDE IV inhibitors; GABAA inverse agonists; GSK30 inhibitors; neuronal nicotinic agonists; selective M1 agonists; HDAC inhibitors; and microtubule affinity regulating kinase (MARK) ligands; dimebon; or other drugs that affect receptors or enzymes that either increase the efficacy, safety, convenience, or reduce unwanted side effects or toxicity of the compounds of the invention.

Other examples of combinations of the compounds of the invention include combinations with anti-obesity agents such as apolipoprotein-B secretion/microsomal triglyceride transfer protein (apo-B/MTP) inhibitors, 1β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $β_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y antagonists (e.g., NPY Y5 receptor antagonists) thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™, available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like.

Other examples of combinations of the compounds of the invention include combinations with antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aricept™) and other acetylcholinesterase inhibitors); neuroprotective agents (e.g., memantine); antipsychotic medications (e.g., ziprasidone (Geodon™), risperidone and olanzapine); insulin and insulin analogs (e.g., LysPro insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide™, glimepiride, repaglinide, meglitinide; biguanides:

metformin, phenformin, buformin; alpha2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, Avandia™; fatty acid oxidation inhibitors: clomoxir, etomoxir; alpha-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex: fenfluramine; vanadate and vanadium complexes (e.g., Naglivan™) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. Non-limiting examples of HMG-CoA reductase inhibitors include statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof, fluvastatin, particularly the sodium salt thereof, atorvastatin, particularly the calcium salt thereof, cerivastatin, particularly the sodium salt thereof, and nisvastatin.

The compounds of the invention may also be administered in combination with a naturally occurring compound that acts to lower plasma cholesterol levels. Such naturally occurring compounds are commonly called nutraceuticals and include, for example, garlic extract, Hoodia plant extracts, and niacin.

Other examples of combinations of the compounds of the invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, corticotrophi, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be used in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compounds of the invention may be used in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Other examples of combinations of the compounds of the invention include combinations with agents for the treatment of stroke or stroke recovery. Examples of such second agents for treatment of stroke include, but are not limited to, aspirin, intercellular adhesion molecule (ICAM)-I and LFA-I antagonists including antibodies such as enlimomab (an anti-ICAM-1 monoclonal antibody), and anti-CD18 and anti-CD 1Ia antibodies, human anti-leukocytic antibodies such as Hu23F2G, glycoprotein lib Ilia antagonists such as eptifibatide (INTEGRELIN™), direct thrombin inhibitors, external or local ultrasound, mechanical clot retrieval or inaceration, fibrinolytic agents, neuronal wound healing agents such as basic fibroblast growth factor (e.g., FIBLAST™), neuroprotective agents such as citicoline, magnesium, nalmefene, dizocilpine, nimodipine, lamotrigine, sipatrigine, lubeluzole, mexiletine, clomethiazole, calcium and sodium channel blocking agents, beta-amino-3-hydroxy-5-methylisoxazole-4-proprionic acid antagonist, a serotonin agonist, a transmembrane potassium channel modulator, agents that inhibit astrocyte activation (e.g., ONO 2506), antioxidants (e.g., MCI-186), anti-adhesion monoclonal antibodies and antagonists and antibodies inhibiting platelet aggregation such as argatroban and abciximab (REOPRO™), phenytoin, nitrogen oxides, CNS-protective therapies, free-radical scavengers such as tirilazad, reactive oxygen metabolites, and antioxidants, and other thrombolytic agents than tenecteplase, as defined below, such as, for example, acylated plasminogen-streptokinase activator complex (APSAC), single-chain urokinase-plasminogen activator (scu-PA), thrombin-like enzymes from snake venoms such as ancrod, streptokinase (e.g., SAKSTAR™), urokinase, anistreplase, alteplase, saruplase, reteplase, lanoteplase (SUN-9216; Genetics Institute Inc.), plasmin, a truncated form of plasmin (microplasmin; ThromboGenics Ltd), a direct-acting thrombolytic with non-thrombolytic—related neuroprotective activities, recombinant *Desmodus rotundus* salivary plasminogen activator (rDSPA) alpha-1 (Schering/Teijin Pharmaceuticals), a mutant fibrin-activated human plasminogen (BB 101 53; British Biotech Inc.), staphylokinase, fibrolase, prourokinase (intra-arterial administration directly into M1 or M2 arterial thrombus), monteplase (modified rtPA), pamiteplase, tisokinase, and vampire bat plasminogen activator, a spin-trap agent such as NXY-059 (cerovive), clopidogrel, n-methyl-dextro-aspartic acid receptor blocking agent, an anticonvulsive agent, a caspase 3 inhibitor, ((tert butylimino)methyl) 1,3 (benzenedisulfonate disodium n oxide), ebselen, glutathione peroxidase, norphenazone, rovelizumab, lactacystin beta-lactone, tsukubaenolide, 4 phosphonomethylpipecolic acid, eliprodil, antibodies to ganglioside GM1; and thrombolytic agents, including streptokinase, acylated plasminogen-streptokinase activator complex (APSAC), urokinase, single-chain urokinase-plasminogen activator (scu-PA), thrombin-like enzymes from snake venoms such as ancrod (Bell, W. "Defibrinogenating enzymes" In Colman et al (eds), *Hemostasis and Thrombosis* Lippincott, Philadelphia (1987) p. 886), tPA, and biologically active variants of each of the above.

Other examples of combinations of the compounds of the invention include combinations with agents for the treatment of depression or anxiety, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), alpha-adrenoreceptor antagonists, atypical anti-depressants, benzodiazepines, 5-HT$_{1A}$ agonists or antagonists, especially 5-HT$_{1A}$ partial agonists, 19orticotrophin releasing factor (CRF) antagonists, and pharmaceutically acceptable salts thereof.

Other examples of combinations of the compounds of the invention include combinations with agents for the treatment of diabetes or diabetes conditions, including dipeptidyl peptidase IV (DPP-IV) inhibitors (including isoleucine thiazolidide vildagliptin, stigaliptin, and saxagliptin); SGLT inhibitors (e.g., gliflozins such as dapagliflozin, empagliflozin, canagliflozin, ipragliflozin, tofogliflozin, sergliflozin etabonate, remogliflozin etabonate, ertugliflozin, and luseogliflozin/TS-071), insulin sensitizers, including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, tesaglitazar, TAK-559, PPARa agonists, such as fenofibric acid derivatives (gemfibrozil, clofibrate, fenofibrate and bezafibrate), and selective PPAR gamma modulators (SPPARγM's); (ii) biguanides such as metformin and phenformin, and (iii) protein tyrosine phosphatase-1B (PTP-1B) inhibitors; insulin or insulin mimetics; sulfonylureas and other insulin secretagogues, such as tolbutamide, glyburide, glipizide, glimepiride, and meglitinides, such as nateglinide and repaglinide; α-glucosidase inhibitors (such as acarbose and miglitol); glucagon receptor antagonists; GLP-1, GLP-1 analogues or mimetics, and GLP-1 receptor agonists, such as exendin-4 (exenatide), liraglutide; GIP and GIP mimetics and GIP receptor agonists; PACAP, PACAP mimetics, and PACAP receptor agonists; cholesterol lowering agents; PPAR delta agonists; antiobesity agents; ileal bile acid transporter inhibitors; agents intended for use in inflammatory conditions such as aspirin, non-steroidal anti-inflammatory drugs (NSAIDs), glucocorticoids, azulfidine, and selective cyclooxygenase-2 (COX-2) inhibitors; antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers; glucokinase activators (GKAs); inhibitors of 11-β-hydroxysteroid dehydrogenase type 1; inhibitors of cholesteryl ester transfer protein (CETP), such as torcetrapib; and inhibitors of fructose 1,6-bisphosphatase.

The subject or patient to whom the compounds of the invention is administered is generally a human being, male or female, in whom LXRβ agonism is desired, but may also encompass other mammals, such as dogs, cats, mice, rats, cattle, horses, sheep, rabbits, monkeys, chimpanzees or other apes or primates, for which treatment of the above noted disorders is desired.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, and they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to 10 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain or to the same methyl group. Non-limiting examples of suitable alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halo group defined above.

"Alkenyl" means an aliphatic hydrocarbon group containing at least one carbon-carbon double bond and which may be straight or branched and comprising 2 to 10 carbon atoms in the straight or branched chain. Branched means that one or more lower alkyl groups such as methyl, ethyl propyl, ethenyl or propenyl are attached to a linear or branched_alkenyl chain. "Lower alkenyl" means 2 to 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising 2 to 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means 2 to 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). (Such =O groups may be referred to herein as "oxo", further described below.) As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

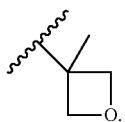

"Oxo" is defined as a oxygen atom that is double bonded to a ring carbon in a cycloalkyl, cycloalkenyl, heterocyclyl, heterocyclenyl, or other ring described herein, e.g.,

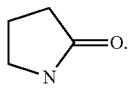

It should be noted that in hetero-atom containing ring systems of this invention, there are no hydroxyl groups on carbon atoms adjacent to a N, O or S as well as there are no N or S groups on carbon adjacent to another heteroatom.

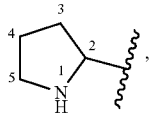

there is no —OH attached directly to carbons marked 2 and 5.

"Alkoxy" means an —O-alkyl group in which the alkyl group is as previously described. Non-limiting examples of alkoxy groups include methoxy, ethoxy, n-propoxy, iso-propoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in —N($R^6$)$_2$, or a variable appears more than once in a structure presented herein, the variables can be the same or different.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the formula or by the name.

The line —— , as a bond generally indicates a mixture of, or either of, the possible isomers, e.g., containing (R)- and (S)-stereochemistry. For example:

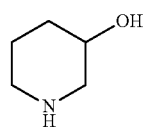

means

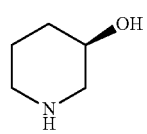

and/or

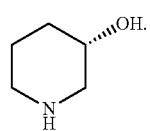

The wavy line 〜〜〜, as used herein, indicates a point of attachment to the rest of the compound. Lines drawn into the ring systems, such as, for example:

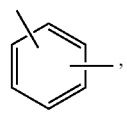

indicate that the indicated line (bond) may be attached to any of the substitutable ring carbon atoms.

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

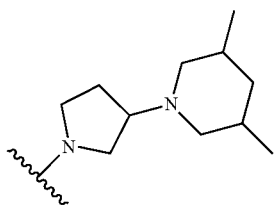 [SMILES: *N1CCC(N2CC(C)CC(C)C2)C1]

represents

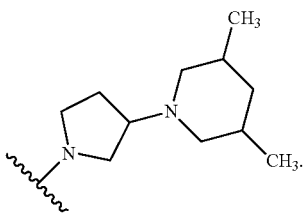 [SMILES: *N1CCC(N2CC(C)CC(C)C2)C1]

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of*

*Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from 0.001 to 500 mg/kg of body weight/day of the compound of the invention. In one embodiment, the dosage is from 0.01 to 25 mg/kg of body weight/day of a compound of the invention, or a pharmaceutically acceptable salt or solvate of said compound. In another embodiment, the quantity of active compound in a unit dose of preparation may be varied or adjusted from 1 mg to 100 mg, preferably from 1 mg to 50 mg, more preferably from 1 mg to 25 mg, according to the particular application. In another embodiment, a typical recommended daily dosage regimen for oral administration can range from 1 mg/day to 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comprising one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

The compounds of the invention can be made according to procedures that will be apparent to those of ordinary skill in the art. Several methods for preparing the compounds of this invention are illustrated in the Schemes and examples herein. Starting materials are available commercially or are made according to procedures known in the art or as illustrated herein. The following examples are provided so that the invention might be more fully understood. These examples are illustrative only and should not be construed as limiting the scope of the invention.

General Scheme A outlines a method for preparing compounds of the type A-7. A suitably protected amino alcohol (A-1) can be deprotected to A-2 and then selectively coupled to chloro-triflate or fluorobenzene A-3 to yield A-4. Oxidation to aldehyde A-5 and reductive amination with an amine can give A-6 which is lastly coupled to desired carboxylic acid to yield A-7.

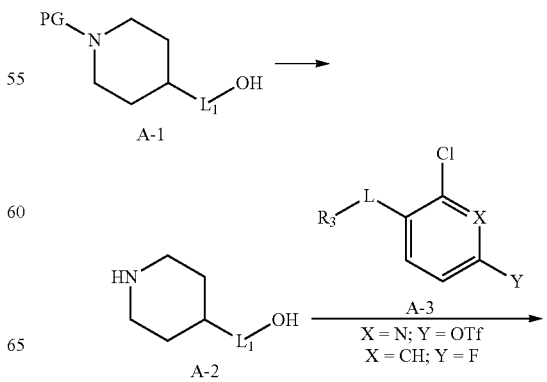

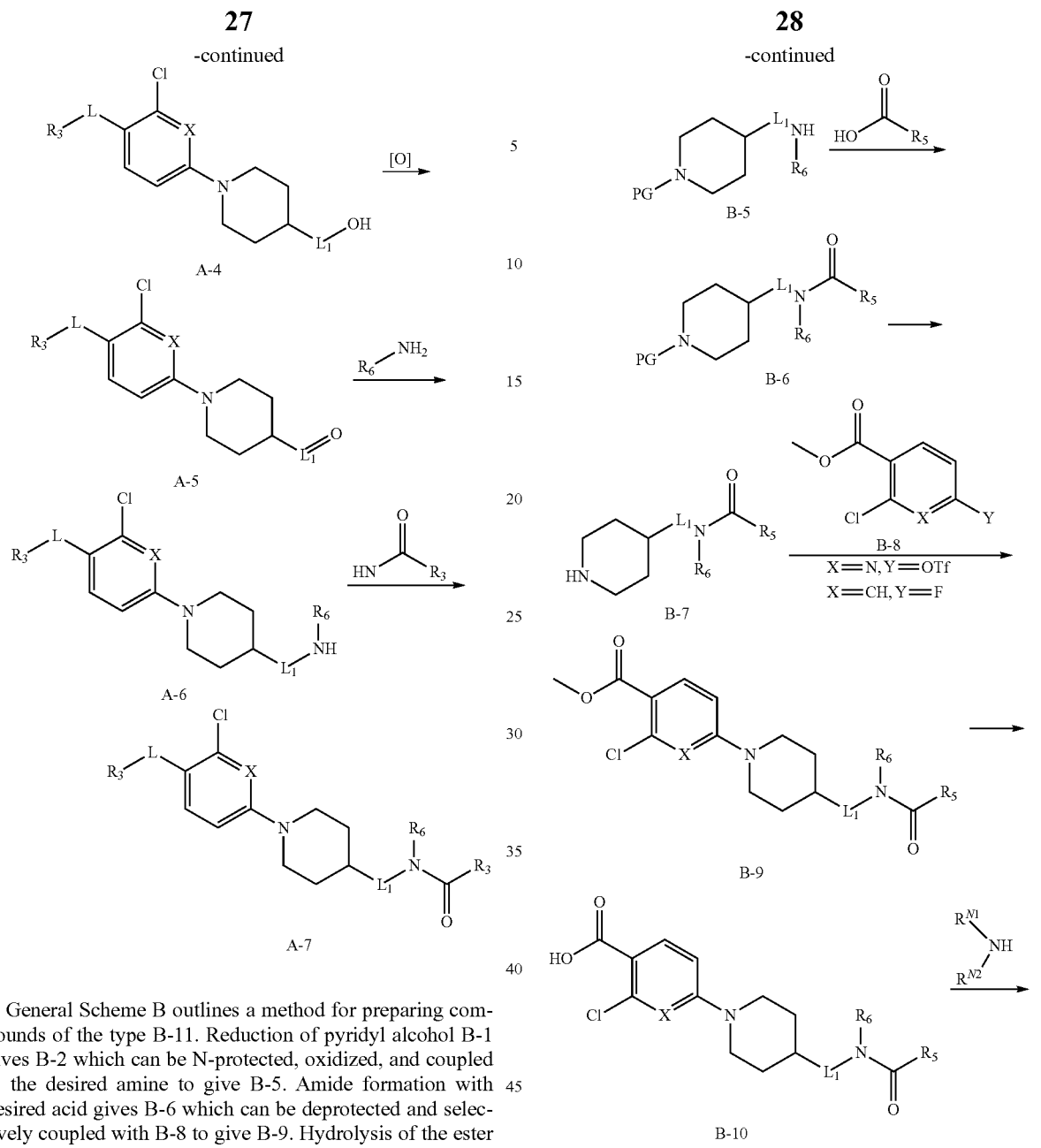

General Scheme B outlines a method for preparing compounds of the type B-11. Reduction of pyridyl alcohol B-1 gives B-2 which can be N-protected, oxidized, and coupled to the desired amine to give B-5. Amide formation with desired acid gives B-6 which can be deprotected and selectively coupled with B-8 to give B-9. Hydrolysis of the ester and coupling to the desired amines gives B-11.

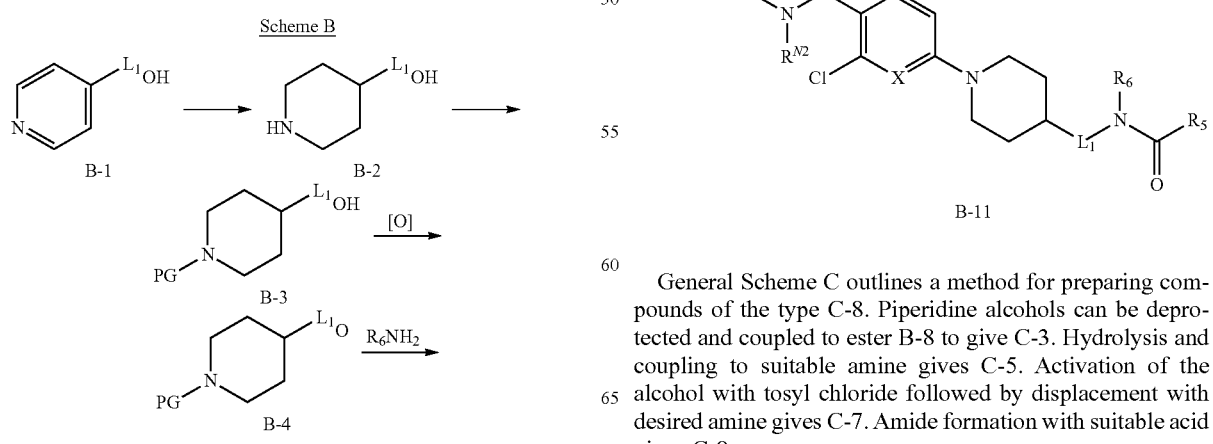

General Scheme C outlines a method for preparing compounds of the type C-8. Piperidine alcohols can be deprotected and coupled to ester B-8 to give C-3. Hydrolysis and coupling to suitable amine gives C-5. Activation of the alcohol with tosyl chloride followed by displacement with desired amine gives C-7. Amide formation with suitable acid gives C-8.

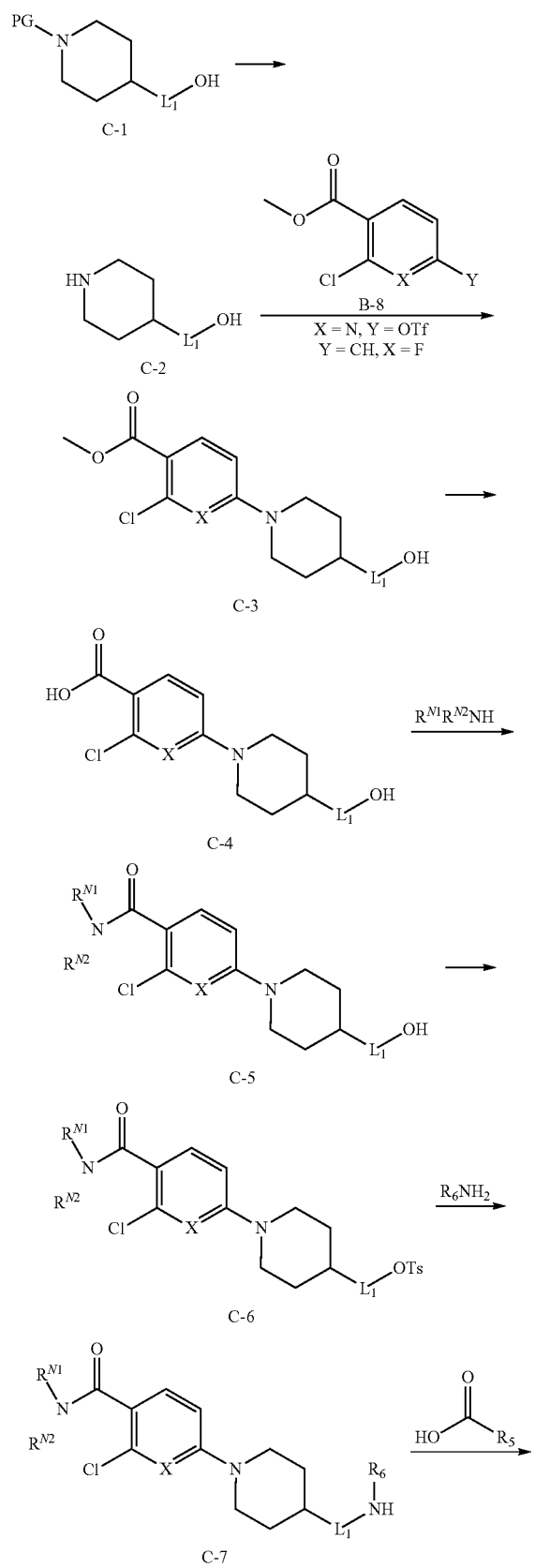
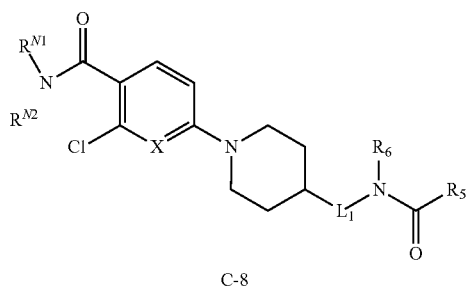

General Scheme D outlines a method for preparing compounds of the type D-10. Protected aminoalcohol D-1 is reacted with phthalimide under Mitsunobu conditions to give D-2 which is subsequently deprotected and reprotected with an orthogonal protecting group to yield D-4. Selective mono-deprotection and coupling with B-8 gives D-6. Hydrolysis of the ester and coupling with desired amine gives D-8. Deprotection of the remaining amine and coupling to suitable acids gives D-10.

Scheme D

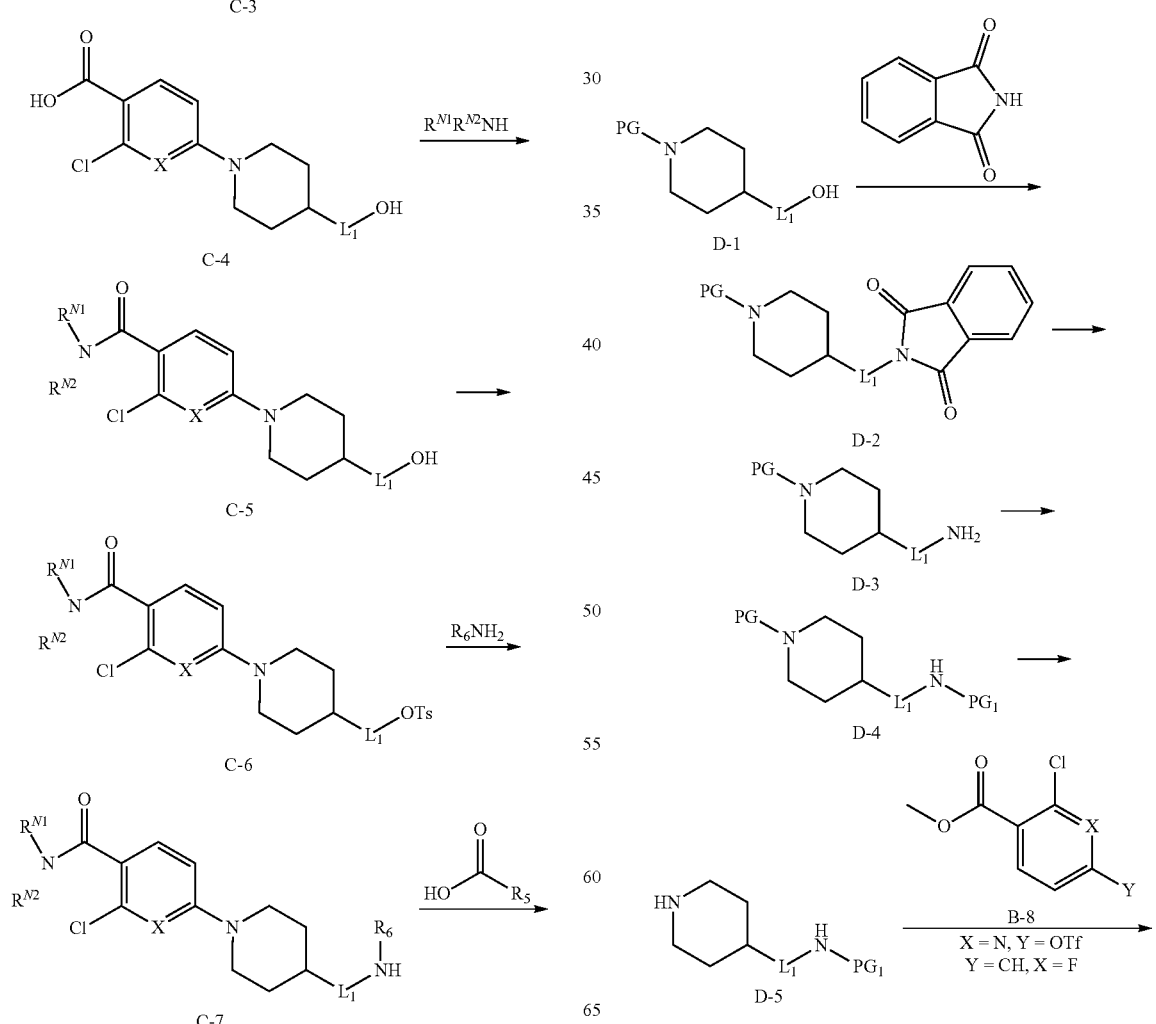

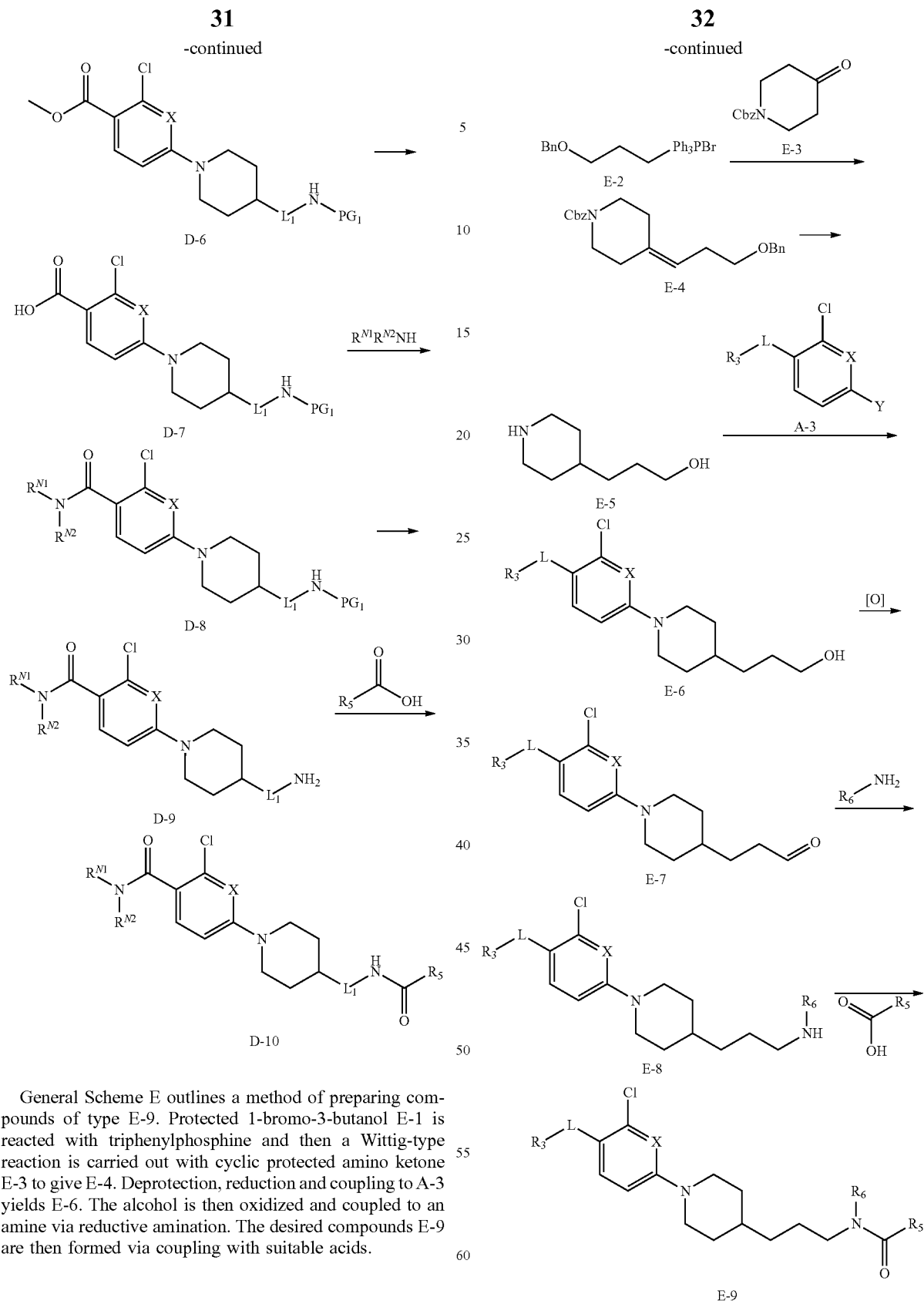

General Scheme E outlines a method of preparing compounds of type E-9. Protected 1-bromo-3-butanol E-1 is reacted with triphenylphosphine and then a Wittig-type reaction is carried out with cyclic protected amino ketone E-3 to give E-4. Deprotection, reduction and coupling to A-3 yields E-6. The alcohol is then oxidized and coupled to an amine via reductive amination. The desired compounds E-9 are then formed via coupling with suitable acids.

Scheme E

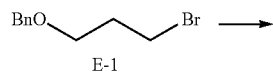

E-1

General Scheme F outlines a method of preparing compounds of type F-6. Protected diamine F-1 is acylated, deprotected, and then reacted with an ester containing appropriately activated pyridyl group to give F-4. Hydrolysis and coupling to a suitable amine gives F-6.

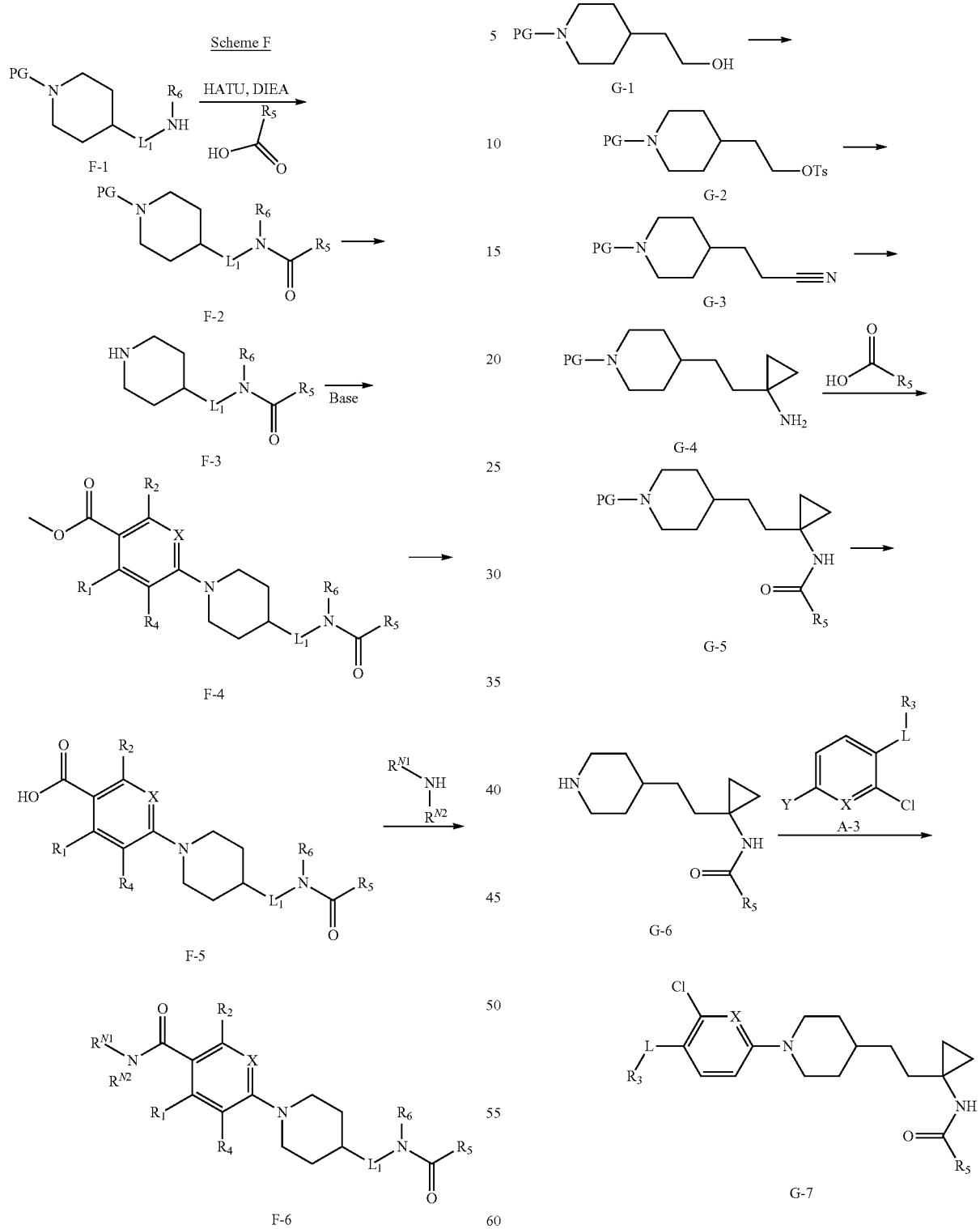

General Scheme G outlines a method of preparing compounds of type G-7. Protected amino alcohol G-1 is activated with tosyl chloride and then cyanide displacement followed by cyclopropanation gives G-4. Coupling to a suitable acid, deprotection, and addition to A-3 gives G-7.

General Scheme H outlines a method of preparing compounds of type H-7. Protected aminocyclohexanone H1 is converted to triflate H-2 with is coupled to nitro-containing aromatic boronic acid equivalent. Reduction, amide formation, and deprotected gives H-6 which can be coupled with a suitable aromatic electrophile to produce H-7.

Scheme H

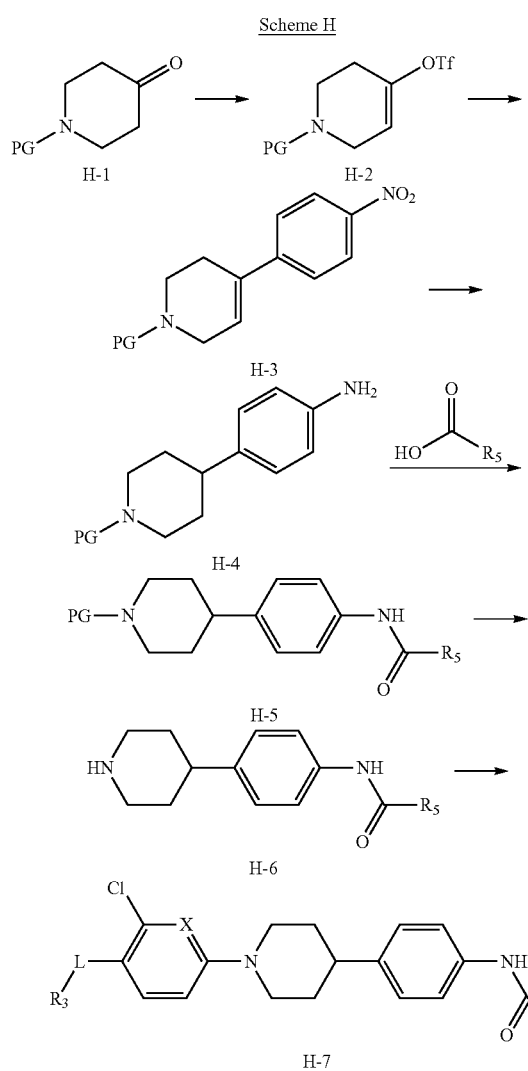

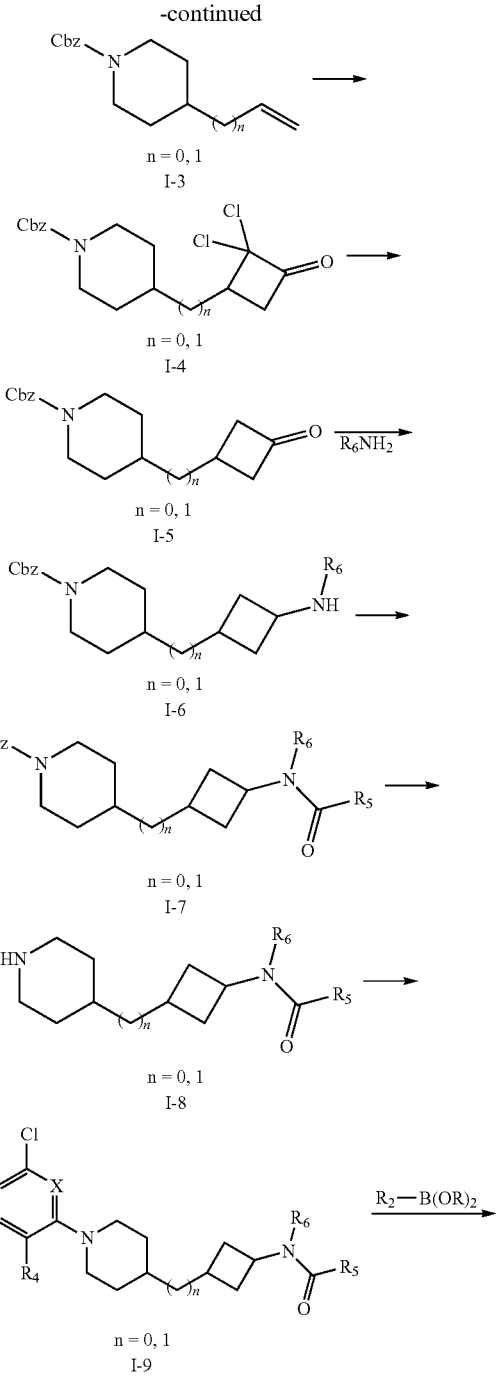

General Scheme I outlines a method of preparing compounds of type I-9 and I-10. Protected aminoalcohol I-1 is oxidized, olefinated, and then reacted with dichloroketene to give cyclobutane 1-4. Dechlorination, reductive amination, and amide formation gives 1-7. Deprotection and coupling with suitable aromatic electrophile gives I-9 which can be optionally converted to a 2-alkylpyridyl compound I-10 via a Suzuki reaction.

Scheme I

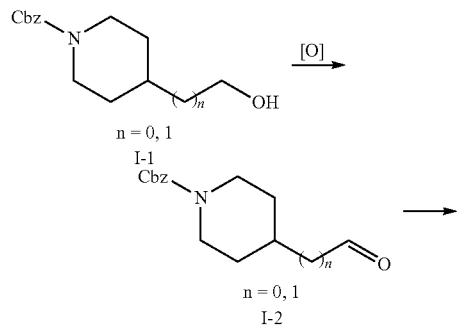

List of Abbreviations

BOP (benzotriazol-1-yloxy)tris(dimethylamino)phosphonium hexafluorophosphate
Br₂BH—SMe₂ dibromoborane-methylsulfide complex
CDI N,N'-carbonyldiimidazole
Cs₂CO₃ cesium carbonate
DCC N,N'-dicyclohexylcarbodiimide
DCE dichloroethane
DCM dichloromethane
DIAD diisopropyl azodicarboxylate
DIBAL-H diisobutylaluminum hydride
DIEA diisopropylethylamine
DMF dimethylformamide
DMSO dimethyl sulfoxide
Dppf diphenylphosphinoferrocene
EDC N-(3-dimethylaminopropyl)-N'-ethylcarbodiimide
Et₂O diethyl ether
Et₃N triethylamine
EtOAc ethyl acetate
EtOH ethanol
HATU O-(7-azabenzotriazol-1-yl)-N,N,N',N'-tetramethyluronium hexafluorophosphate
HCl hydrochloric acid
(HF)₃-Et₃N triethylamine trihydrofluoride
IPA isopropanol
K₂CO₃ potassium carbonate
KHSO₄ potassium bisulfate
LiOH lithium hydroxide
MeCN acetonitrile
MeOH methanol
MgSO₄ magnesium Sulfate
Na₂SO₄ sodium sulfate
NaHCO₃ sodium bicarbonate
NaOH sodium hydroxide
n-BuLi n-butyl lithium
NIS N-iodosuccinimide
Pd(Ph₃P)₄ tetrakis(triphenylphosphine) palladium (0)
Pd/C palladium on carbon
PdCl₂(dppf)-CH₂Cl₂ adduct dichloro[1,1'-bis(diphenylphosphino)ferrocene]palladium (II) dichloromethane adduct
PE Petroleum ether
POCl₃ phosphorous oxychloride
PPh₃ triphenylphosphine
RT, r.t., rt room temperature
TBTU O-benzotriazol-1-yl-N,N,N',N'-tetramethyluronium tetrafluoroborate
Tf₂O triflic anhydride
TFA trifluoroacetatic acid
TfOH trifluoromethanesulfonic acid
THF tetrahydofuran

Example 1-1

(R)-2-chloro-N,N-dimethyl-6-(4-(3-(3,3,3-trifluoro-2-hydroxy-N-methyl-2-phenylpropanamido)propyl)piperidin-1-yl)nicotinamide

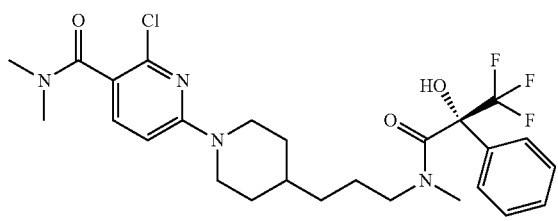

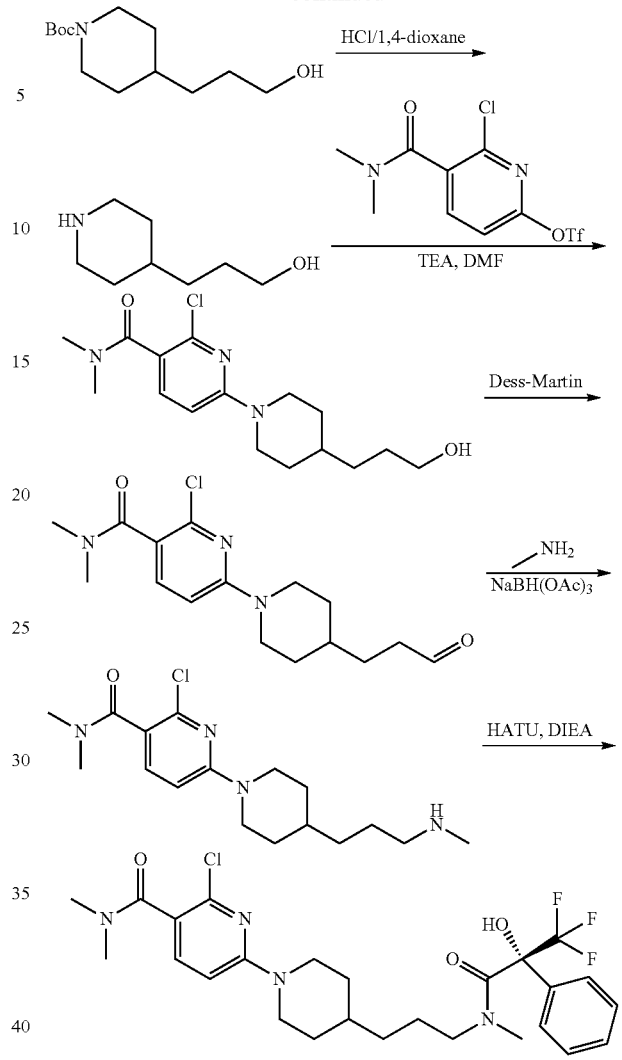

The solution of tert-butyl 4-(3-hydroxypropyl)piperidine-1-carboxylate (5 g, 20.6 mmol) in 2M HCl/1,4-dioxane (20 mL) was stirred for 2 h at rt. Then the mixture was concentrated in vacuo to give crude 3-(piperidin-4-yl)propan-1-ol. LRMS m/z (M+H) 144.0 found, 144.1 required.

2-chloro-6-(4-(3-hydroxypropyl)piperidin-1-yl)-N,N-dimethylnicotinamid

A 35 mL vial was charged with 3-(piperidin-4-yl)propan-1-ol (1.0 g, 5.6 mmol, 1.0 eq), 6-chloro-5-(dimethylcarbamoyl)pyridin-2-yl trifluoromethanesulfonate (1.8 g, 5.6 mmol, 1.0 eq), Et₃N (1.7 g, 16.8 mmol, 3.0 eq) and DMF (8 mL). The sealed vial was irradiated under microwave on a CEM Synthesizer at 60° C. for 45 min. After cooling to room temperature, the mixture was purified by reverse-phase HPLC directly (Mobile Phase: MeOH/H₂O (10 mM NH₄HCO₃)) to give 2-chloro-6-(4-(3-hydroxypropyl)piperidin-1-yl)-N,N-dimethylnicotinamide. LRMS m/z (M+H) 326.2 found, 326.2 required.

2-chloro-N,N-dimethyl-6-(4-(3-oxopropyl)piperidin-1-yl)nicotinamide

To a solution of 2-chloro-6-(4-(3-hydroxypropyl)piperidin-1-yl)-N,N-dimethylnicotinamide (1.0 g, 3.1 mmol, 1.0 eq) in DCM (10 mL) was added Dess-Martin Periodinane (2.0 g, 4.6 mmol, 1.5 eq) at rt. After stirring at rt for 2 h, the solid was filtered off and the filtrate was diluted with EtOAc (80 mL). The organic phase was washed with 1N NaOH (20 mL), water (10 mL×3), brine (10 mL×3) and dried over anhydrous $Na_2SO_4$. The organic phase was concentrated and the residue was purified by silica gel column chromatography (PE:EtOAc=5:1 to 1:1) to get 2-chloro-N,N-dimethyl-6-(4-(3-oxopropyl)piperidin-1-yl)nicotinamide. LRMS m/z (M+H) 324.1 found, 324.1 required.

2-chloro-N,N-dimethyl-6-(4-(3-(methylamino)propyl)piperidin-1-yl)nicotinamide

To the solution of 2-chloro-N,N-dimethyl-6-(4-(3-oxopropyl)piperidin-1-yl)nicotinamide (324 mg, 1.0 mmol, 1 eq) and methylamine (5 mL, 5 mmol, 1M in THF, 5 eq) in DCE (10 mL) was added dropwise titanium isopropoxide (568 mg, 2.0 mmol, 2 eq) at 0° C. under $N_2$ atmosphere. After stirring overnight at rt, $NaBH_4$ (114 mg, 3.0 mmol, 3 eq) was added. The resulting mixture was stirred at rt for another 1 h. The reaction mixture was poured into 20 mL HCl (6N) at 0° C. carefully and stirred for 1 h. The aqueous phase was basified with aqueous NaOH and extracted with DCM/MeOH (10/1, 50 mL*3). The combined organic layers were dried over anhydrous $MgSO_4$ and concentrated. The crude product was purified by reverse-phase HPLC (Mobile Phase: MeOH/$H_2O$ (10 mM $NH_4HCO_3$)) to afford 2-chloro-N,N-dimethyl-6-(4-(3-(methylamino)propyl)piperidin-1-yl) nicotinamide. LRMS m/z (M+H) 339.3 found, 339.2 required.

(R)-2-chloro-N,N-dimethyl-6-(4-(3-(3,3,3-trifluoro-2-hydroxy-N-methyl-2-phenylpropanamido)propyl) piperidin-1-yl)nicotinamide A mixture of 2-chloro-N,N-dimethyl-6-(4-(3-(methylamino)propyl)piperidin-1-yl)nicotinamide (34 mg, 0.1 mmol, 1.0 eq), (R)-3,3,3-trifluoro-2-hydroxy-2-phenylpropanoic acid (26 mg, 0.12 mmol, 1.2 eq), HATU (46 mg, 0.12 mmol, 1.2 eq), and DIEA (39 mg, 0.3 mmol, 3.0 eq) in THF (2 mL) was stirred at rt overnight. The mixture was directly purified by reverse-phase HPLC (Mobile phase: methanol/water (10 mM $NH_4HCO_3$)) to afford (R)-2-chloro-N,N-dimethyl-6-(4-(3-(3,3,3-trifluoro-2-hydroxy-N-methyl-2-phenylpropanamido)propyl)piperidin-1-yl)nicotinamide. LRMS m/z (M+H) 541.2 found, 541.2 required.

Using the procedure described in Example 1-1, but replacing (S)-3,3,3-trifluoro-2-hydroxy-2-phenylpropanoic acid with the appropriate acid in last step, the examples in Table 1 were prepared.

TABLE 1

| Example | Structure | IUPAC Name | LRMS, found [M + H]+ |
|---|---|---|---|
| 1-1 | 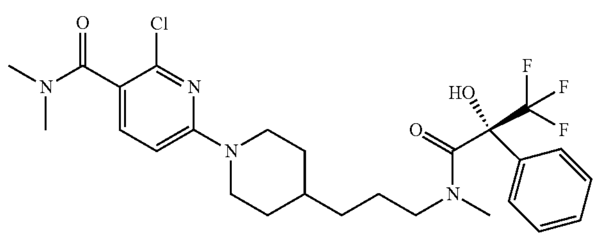 [SMILES: CN(C)C(=O)c1ccc(N2CCC(CCCN(C)C(=O)[C@](O)(c3ccccc3)C(F)(F)F)CC2)nc1Cl] | (R)-2-chloro-N,N-dimethyl-6-(4-(3-(3,3,3-trifluoro-2-hydroxy-N-methyl-2-phenylpropanamido)propyl)piperidin-1-yl)nicotinamide | 541.2 |
| 1-2 | 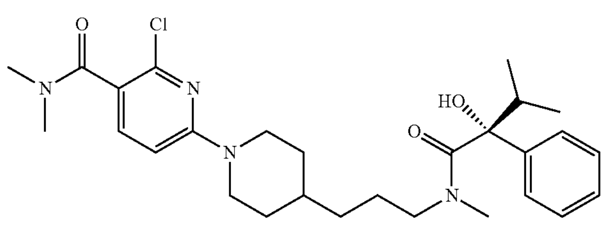 [SMILES: CC(C)[C@](O)(C(=O)N(C)CCCC1CCN(c2ccc(C(=O)N(C)C)c(Cl)n2)CC1)c1ccccc1] | (R)-2-chloro-6-(4-(3-(2-hydroxy-N,3-dimethyl-2-phenylbutanamido)propyl)piperidin-1-yl)-N,N-dimethylnicotinamide | 515.3 |
| 1-3 | 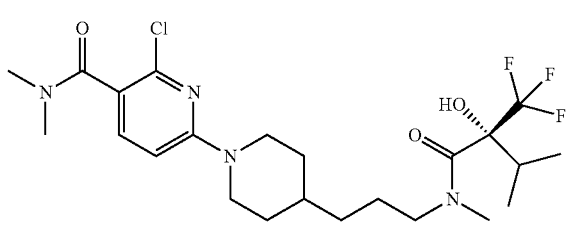 [SMILES: CC(C)[C@@](O)(C(=O)N(C)CCCC1CCN(c2ccc(C(=O)N(C)C)c(Cl)n2)CC1)C(F)(F)F] | (R)-2-chloro-6-(4-(3-(2-hydroxy-N,3-dimethyl-2-(trifluoromethyl)butanamido)propyl)piperidin-1-yl)-N,N-dimethylnicotinamide | 507.2 |

TABLE 1-continued

| Example | Structure | IUPAC Name | LRMS, found [M + H]+ |
|---|---|---|---|
| 1-4 | 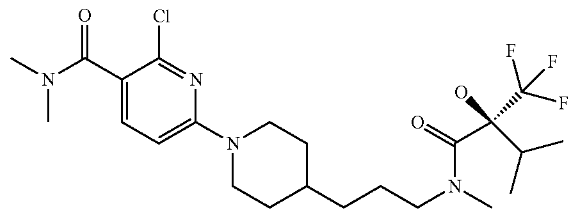 [SMILES: CC(C)[C@](O)(C(=O)N(C)CCCC1CCN(c2ccc(C(=O)N(C)C)c(Cl)n2)CC1)C(F)(F)F] | (S)-2-chloro-6-(4-(3-(2-hydroxy-N,3-dimethyl-2-(trifluoromethyl)butanamido)propyl)piperidin-1-yl)-N,N-dimethylnicotinamide | 507.2 |
| 1-5 | 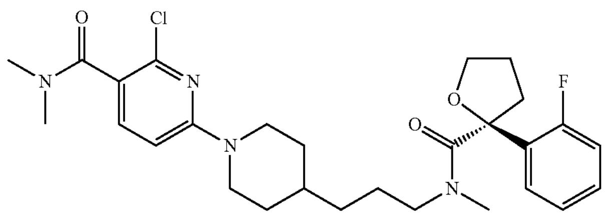 [SMILES: CN(C)C(=O)c1ccc(N2CCC(CCCN(C)C(=O)[C@@]3(c4ccccc4F)CCCO3)CC2)nc1Cl] | (S)-2-chloro-6-(4-(3-(2-(2-fluorophenyl)-N-methyl-tetrahydrofuran-2-carboxamido)propyl)piperidin-1-yl)-N,N-dimethylnicotinamide | 531.1 |
| 1-6 | 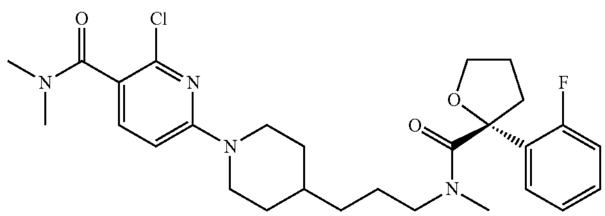 [SMILES: CN(C)C(=O)c1ccc(N2CCC(CCCN(C)C(=O)[C@]3(c4ccccc4F)CCCO3)CC2)nc1Cl] | (R)-2-chloro-6-(4-(3-(2-(2-fluorophenyl)-N-methyl-tetrahydrofuran-2-carboxamido)propyl)piperidin-1-yl)-N,N-dimethylnicotinamide | 531.1 |
| 1-7 | 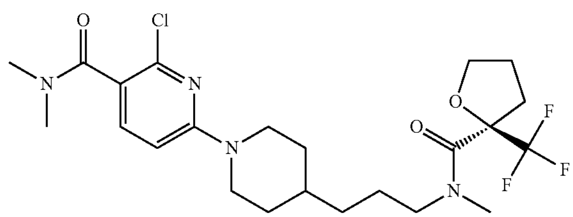 [SMILES: CN(C)C(=O)c1ccc(N2CCC(CCCN(C)C(=O)[C@@]3(C(F)(F)F)CCCO3)CC2)nc1Cl] | (R)-2-chloro-N,N-dimethyl-6-(4-(3-(N-methyl-2-(trifluoromethyl)-tetrahydrofuran-2-carboxamido)propyl)piperidin-1-yl)nicotinamide | 505.2 |
| 1-8 | 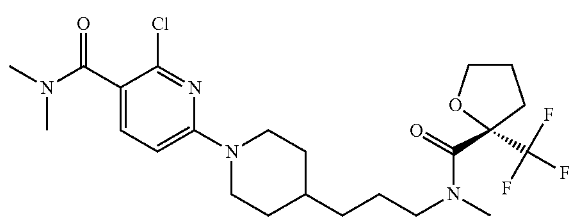 [SMILES: CN(C)C(=O)c1ccc(N2CCC(CCCN(C)C(=O)[C@]3(C(F)(F)F)CCCO3)CC2)nc1Cl] | (S)-2-chloro-N,N-dimethyl-6-(4-(3-(N-methyl-2-(trifluoromethyl)-tetrahydrofuran-2-carboxamido)propyl)piperidin-1-yl)nicotinamide | 505.2 |
| 1-9 | 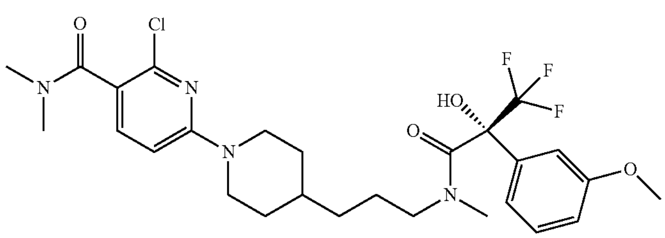 | (R)-2-chloro-N,N-dimethyl-6-(4-(3-(3,3,3-trifluoro-2-hydroxy-2-(3-methoxyphenyl)-N-methylpropanamido)propyl)piperidin-1-yl)nicotinamide | 571.2 |

TABLE 1-continued

| Example | Structure | IUPAC Name | LRMS, found [M + H]+ |
|---|---|---|---|
| 1-10 | 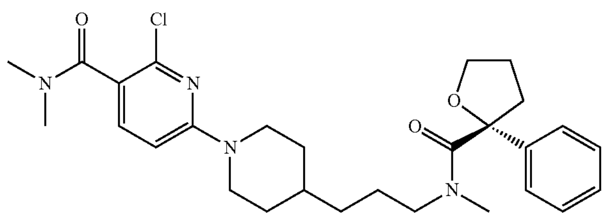 [SMILES: CN(C)C(=O)c1ccc(N2CCC(CCCN(C)C(=O)[C@]3(c4ccccc4)CCCO3)CC2)nc1Cl] | (R)-2-chloro-N,N-dimethyl-6-(4-(3-(N-methyl-2-phenyl-tetrahydrofuran-2-carboxamido)propyl)piperidin-1-yl)nicotinamide | 513.2 |
| 1-11 | 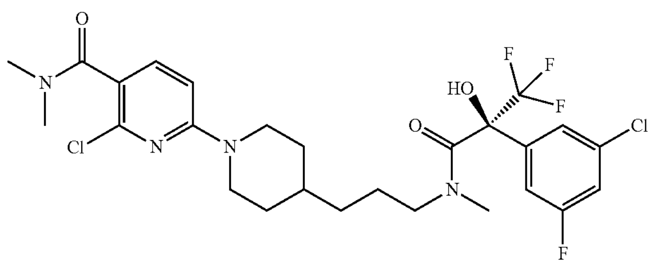 [SMILES: CN(C)C(=O)c1ccc(N2CCC(CCCN(C)C(=O)[C@@](O)(c3cc(F)cc(Cl)c3)C(F)(F)F)CC2)nc1Cl] | (S)-2-chloro-6-(4-(3-(2-(3-chloro-5-fluorophenyl)-3,3,3-trifluoro-2-hydroxy-N-methylpropanamido)propyl)piperidin-1-yl)-N,N-dimethylnicotinamide | 593.2 |
| 1-12 | 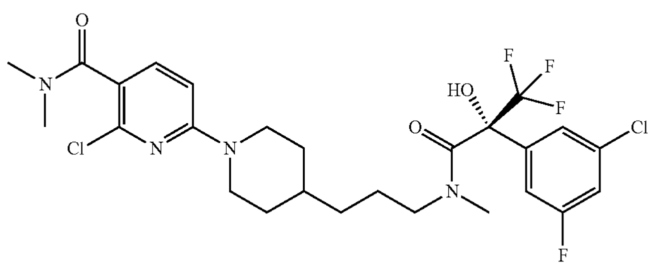 [SMILES: CN(C)C(=O)c1ccc(N2CCC(CCCN(C)C(=O)[C@](O)(c3cc(F)cc(Cl)c3)C(F)(F)F)CC2)nc1Cl] | (R)-2-chloro-6-(4-(3-(2-(3-chloro-5-fluorophenyl)-3,3,3-trifluoro-2-hydroxy-N-methylpropanamido)propyl)piperidin-1-yl)-N,N-dimethylnicotinamide | 593.2 |
| 1-13 | 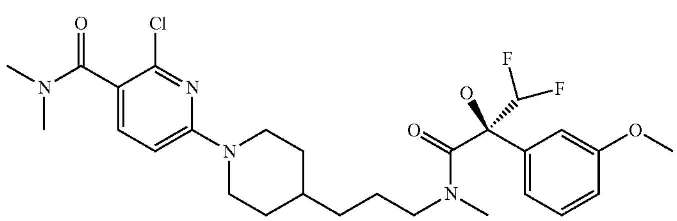 | (S)-2-chloro-6-(4-(3-(3,3-difluoro-2-hydroxy-2-(3-methoxyphenyl)-N-methylpropanamido)propyl)piperidin-1-yl)-N,N-dimethylnicotinamide | 553.2 |
| 1-14 | 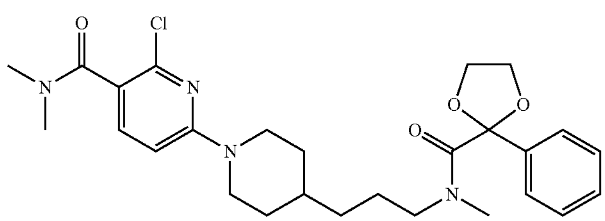 [SMILES: CN(C)C(=O)c1ccc(N2CCC(CCCN(C)C(=O)C3(c4ccccc4)OCCO3)CC2)nc1Cl] | 2-chloro-N,N-dimethyl-6-(4-(3-(N-methyl-2-phenyl-1,3-dioxolane-2-carboxamido)propyl)piperidin-1-yl)nicotinamide | 515.2 |
| 1-15 | 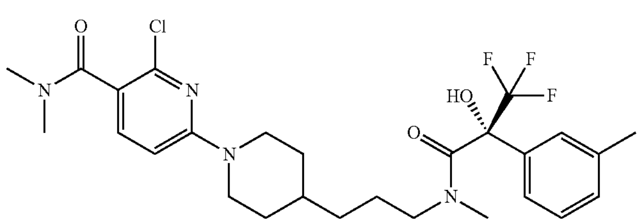 | (R)-2-chloro-N,N-dimethyl-6-(4-(3-(3,3,3-trifluoro-2-hydroxy-N-methyl-2-m-tolylpropanamido)propyl)piperidin-1-yl)nicotinamide | 555.2 |

TABLE 1-continued

| Example | Structure | IUPAC Name | LRMS, found [M + H]+ |
|---|---|---|---|
| 1-16 | 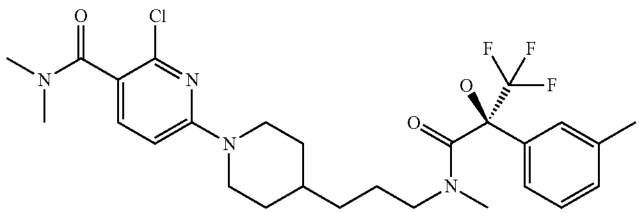 | (S)-2-chloro-N,N-dimethyl-6-(4-(3-(3,3,3-trifluoro-2-hydroxy-N-methyl-2-m-tolylpropanamido)propyl)piperidin-1-yl)nicotinamide | 555.2 |
| 1-17 | 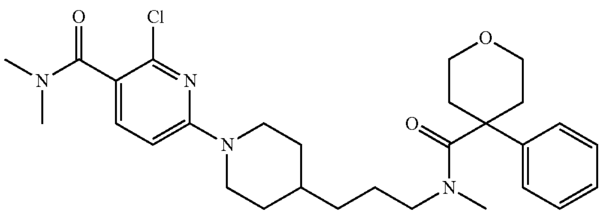 [SMILES: CN(C)C(=O)c1ccc(N2CCC(CCCN(C)C(=O)C3(c4ccccc4)CCOCC3)CC2)nc1Cl] | 2-chloro-N,N-dimethyl-6-(4-(3-(N-methyl-4-phenyl-tetrahydro-2H-pyran-4-carboxamido)propyl)piperidin-1-yl)nicotinamide | 527.2 |
| 1-18 | 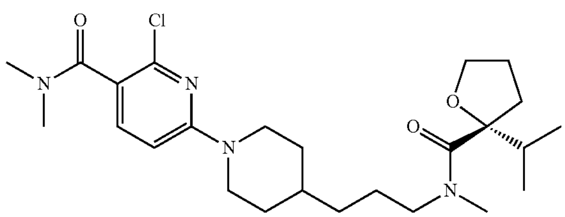 [SMILES: CC(C)[C@@]1(C(=O)N(C)CCCC2CCN(c3ccc(C(=O)N(C)C)c(Cl)n3)CC2)CCCO1] | (R)-2-chloro-6-(4-(3-(2-isopropyl-N-methyl-tetrahydrofuran-2-ycarboxamido)propyl)piperidin-1-yl)-N,N-dimethylnicotinamide | 479.3 |
| 1-19 | 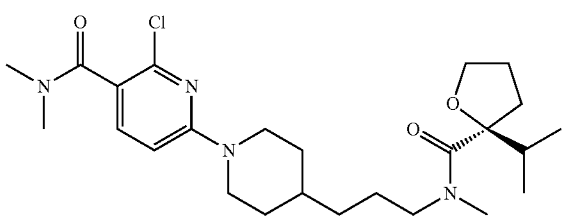 [SMILES: CC(C)[C@]1(C(=O)N(C)CCCC2CCN(c3ccc(C(=O)N(C)C)c(Cl)n3)CC2)CCCO1] | (S)-2-chloro-6-(4-(3-(2-isopropyl-N-methyl-tetrahydrofuran-2-carboxamido)propyl)piperidin-1-yl)-N,N-dimethylnicotinamide | 479.3 |
| 1-20 | 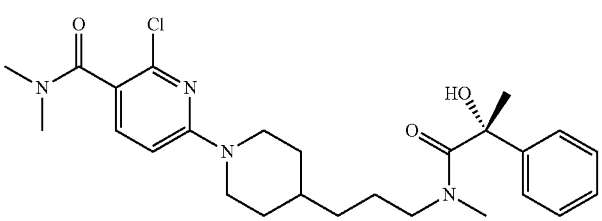 [SMILES: CN(C)C(=O)c1ccc(N2CCC(CCCN(C)C(=O)[C@](C)(O)c3ccccc3)CC2)nc1Cl] | (R)-2-chloro-6-(4-(3-(2-hydroxy-N-methyl-2-phenylpropanamido)propyl)piperidin-1-yl)-N,N-dimethylnicotinamide | 487.0 |
| 1-21 | 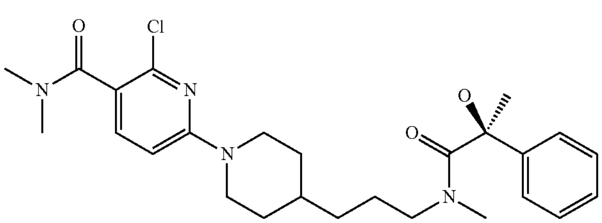 [SMILES: CN(C)C(=O)c1ccc(N2CCC(CCCN(C)C(=O)[C@@](C)(O)c3ccccc3)CC2)nc1Cl] | (S)-2-chloro-6-(4-(3-(2-hydroxy-N-methyl-2-phenylpropanamido)propyl)piperidin-1-yl)-N,N-dimethylnicotinamide | 487.2 |

TABLE 1-continued

| Example | Structure | IUPAC Name | LRMS, found [M + H]+ |
|---|---|---|---|
| 1-22 | 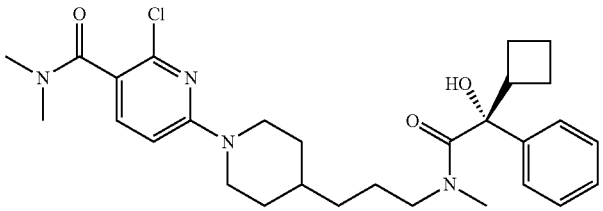 [SMILES: CN(C)C(=O)c1ccc(N2CCC(CCCN(C)C(=O)[C@](O)(c3ccccc3)C3CCC3)CC2)nc1Cl] | (R)-2-chloro-6-(4-(3-(2-cyclobutyl-2-hydroxy-N-methyl-2-phenylaceetamido)propyl)piperidin-1-yl)-N,N-dimethylnicotinamide | 527.3 |
| 1-23 | 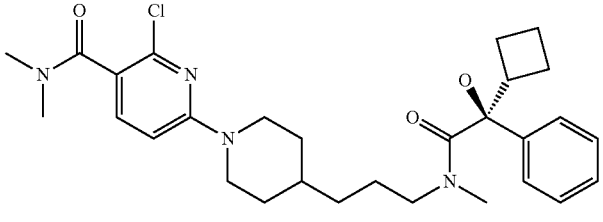 [SMILES: CN(C)C(=O)c1ccc(N2CCC(CCCN(C)C(=O)[C@@](O)(c3ccccc3)C3CCC3)CC2)nc1Cl] | (S)-2-chloro-6-(4-(3-(2-cyclobutyl-2-hydroxy-N-methyl-2-phenylacetamido)propyl)piperidin-1-yl)-N,N-dimethylnicotinamide | 527.3 |
| 1-24 | 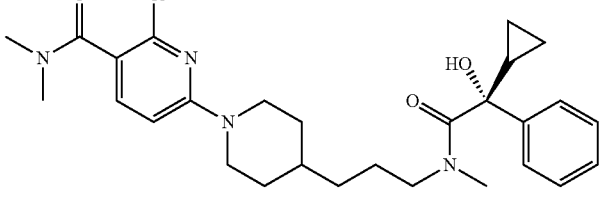 | (R)-2-chloro-6-(4-(3-(2-cyclopropyl-2-hydroxy-N-methyl-2-phenylacetamido)propyl)piperidin-1-yl)-N,N-dimethylnicotinamide | 513.2 |
| 1-25 | 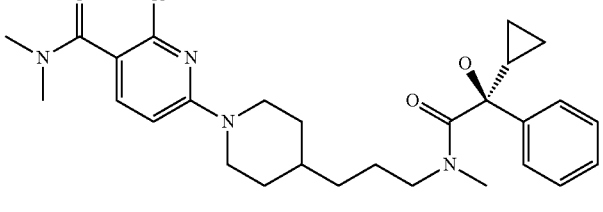 | (S)-2-chloro-6-(4-(3-(2-cyclopropyl-2-hydroxy-N-methyl-2-phenylacetamido)propyl)piperidin-1-yl)-N,N-dimethylnicotinamide | 513.2 |
| 1-26 | 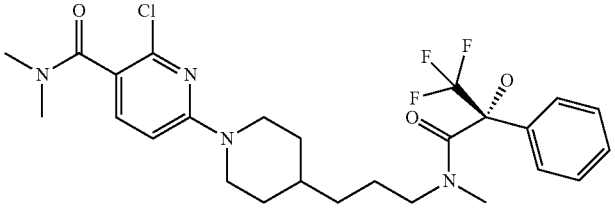 [SMILES: CN(C)C(=O)c1ccc(N2CCC(CCCN(C)C(=O)[C@](O)(c3ccccc3)C(F)(F)F)CC2)nc1Cl] | (R)-2-chloro-N,N-dimethyl-6-(4-(3-(3,3,3-trifluoro-2-hydroxy-N-methyl-2-phenylpropanamido)propyl)piperidin-1-yl)nicotinamide | 541.2 |
| 1-27 | 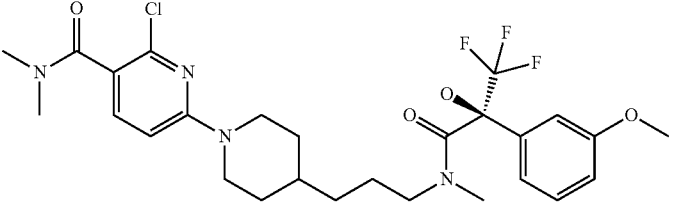 | (S)-2-chloro-N,N-dimethyl-6-(4-(3-(3,3,3-trifluoro-2-hydroxy-2-(3-methoxyphenyl)-N-methylpropanamido)propyl)piperidin-1-yl)nicotinamide | 571.2 |

TABLE 1-continued

| Example | Structure | IUPAC Name | LRMS, found [M + H]+ |
|---|---|---|---|
| 1-28 | 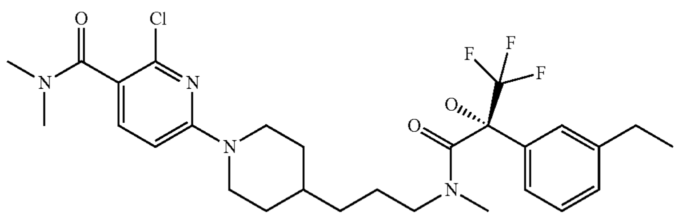 [SMILES: CCc1cccc([C@@](O)(C(=O)N(C)CCCC2CCN(c3ccc(C(=O)N(C)C)c(Cl)n3)CC2)C(F)(F)F)c1] | (R)-2-chloro-6-(4-(3-(2-(3-ethylphenyl)-3,3,3-trifluoro-2-hydroxy-N-methylpropanamido)propyl)piperidin-1-yl)-N,N-dimethylnicotinamide | 569.1 |
| 1-29 | 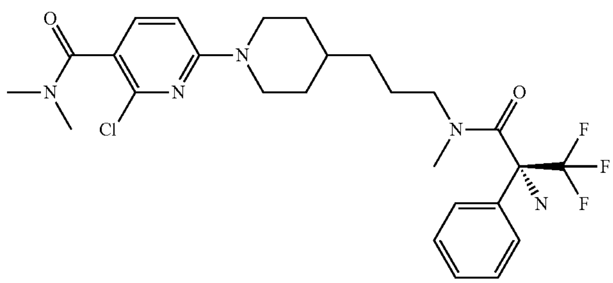 [SMILES: CN(C)C(=O)c1ccc(N2CCC(CCCN(C)C(=O)[C@](N)(c3ccccc3)C(F)(F)F)CC2)nc1Cl] | (R)-6-(4-(3-(2-amino-3,3,3-trifluoro-N-methyl-2-phenylpropanamido)propyl)piperidin-1-yl)-2-chloro-N,N-dimethylnicotinamide | 540.2 |
| 1-30 | 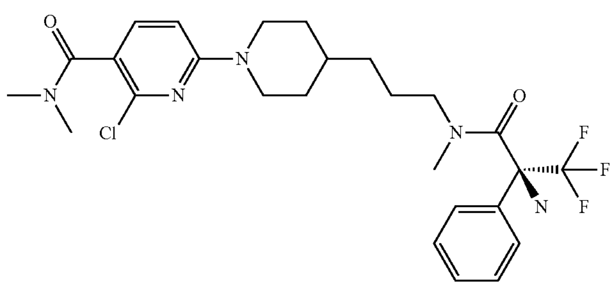 [SMILES: CN(C)C(=O)c1ccc(N2CCC(CCCN(C)C(=O)[C@@](N)(c3ccccc3)C(F)(F)F)CC2)nc1Cl] | (S)-6-(4-(3-(2-amino-3,3,3-trifluoro-N-methyl-2-phenylpropanamido)propyl)piperidin-1-yl)-2-chloro-N,N-dimethylnicotinamide | 540.2 |
| 1-31 | 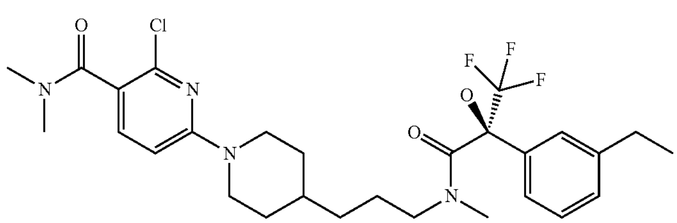 [SMILES: CCc1cccc([C@](O)(C(=O)N(C)CCCC2CCN(c3ccc(C(=O)N(C)C)c(Cl)n3)CC2)C(F)(F)F)c1] | (S)-2-chloro-6-(4-(3-(2-(3-ethylphenyl)-3,3,3-trifluoro-2-hydroxy-N-methylpropanamido)propyl)piperidin-1-yl)-N,N-dimethylnicotinamide | 569.1 |
| 1-32 | 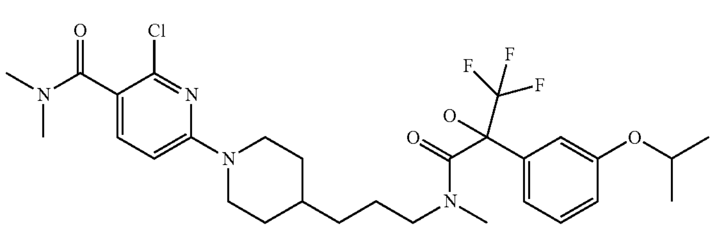 [SMILES: CC(C)Oc1cccc(C(O)(C(=O)N(C)CCCC2CCN(c3ccc(C(=O)N(C)C)c(Cl)n3)CC2)C(F)(F)F)c1] | 2-chloro-N,N-dimethyl-6-(4-(3-(3,3,3-trifluoro-2-hydroxy-2-(3-isopropoxyphenyl)-N-methylpropanamido)propyl)piperidin-1-yl)nicotinamide | 599.1 |

TABLE 1-continued

| Example | Structure | IUPAC Name | LRMS, found [M + H]+ |
|---|---|---|---|
| 1-33 | 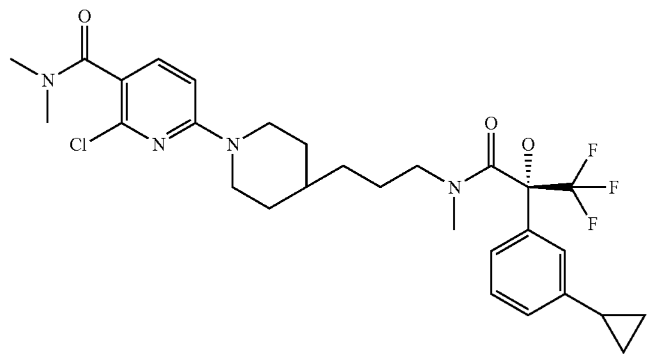 [SMILES: CN(C)C(=O)c1ccc(N2CCC(CCCN(C)C(=O)[C@](O)(c3cccc(C4CC4)c3)C(F)(F)F)CC2)nc1Cl] | (R)-2-chloro-6-(4-(3-(2-(3-cyclopropylphenyl)-3,3,3-trifluoro-2-hydroxy-N-methylpropanamido)propyl)piperidin-1-yl)-N,N-dimethylnicotinamide | 581.2 |
| 1-34 | 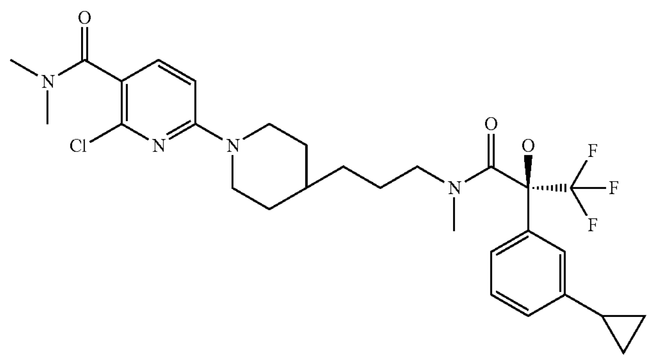 [SMILES: CN(C)C(=O)c1ccc(N2CCC(CCCN(C)C(=O)[C@@](O)(c3cccc(C4CC4)c3)C(F)(F)F)CC2)nc1Cl] | (S)-2-chloro-6-(4-(3-(2-(3-cyclopropylphenyl)-3,3,3-trifluoro-2-hdyroxy-N-methylpropanamido)propyl)piperidin-1-yl)-N,N-dimethylnicotinamide | 581.2 |
| 1-35 | 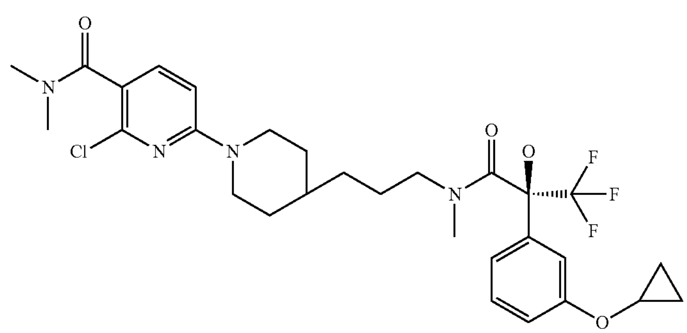 [SMILES: CN(C)C(=O)c1ccc(N2CCC(CCCN(C)C(=O)[C@@](O)(c3cccc(OC4CC4)c3)C(F)(F)F)CC2)nc1Cl] | (S)-2-chloro-6-(4-(3-(2-(3-cyclopropoxyphenyl)-3,3,3-trifluoro-2-hydroxy-N-methylpropanamido)propyl)piperidin-1-yl)-N,N-dimethylnicotinamide | 597.2 |
| 1-36 | 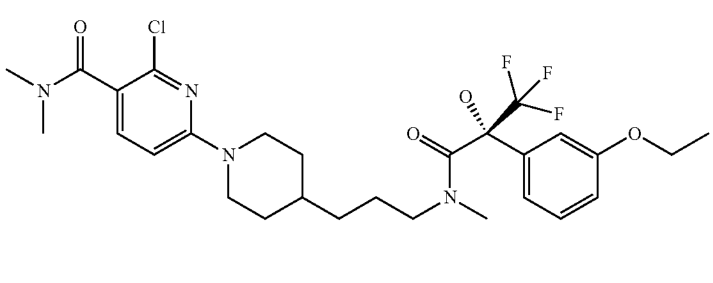 [SMILES: CCOc1cccc([C@@](O)(C(=O)N(C)CCCC2CCN(c3ccc(C(=O)N(C)C)c(Cl)n3)CC2)C(F)(F)F)c1] | (R)-2-chloro-6-(4-(3-(2-(3-ethoxyphenyl)-3,3,3-trifluoro-2-hydroxy-N-methylpropanamido)propyl)piperidin-1-yl)-N,N-dimethylnicotinamide | 585.1 |

TABLE 1-continued

| Example | Structure | IUPAC Name | LRMS, found [M + H]+ |
|---|---|---|---|
| 1-37 | 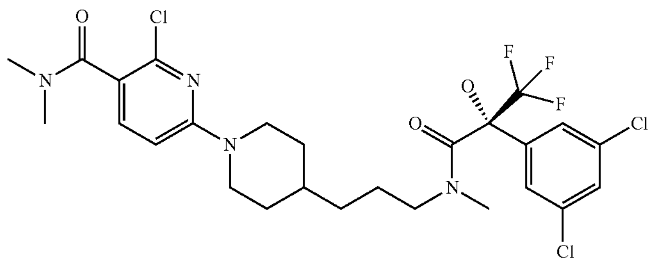 [SMILES: CN(C)C(=O)c1ccc(N2CCC(CCCN(C)C(=O)[C@](O)(c3cc(Cl)cc(Cl)c3)C(F)(F)F)CC2)nc1Cl] | (R)-2-chloro-6-(4-(3-(2-(3,5-dichlorophenyl)-3,3,3-trifluoro-2-hydroxy-N-methylpropanamido)propyl)piperidin-1-yl)-N,N-dimethylnicotinamide | 609.1 |
| 1-38 | 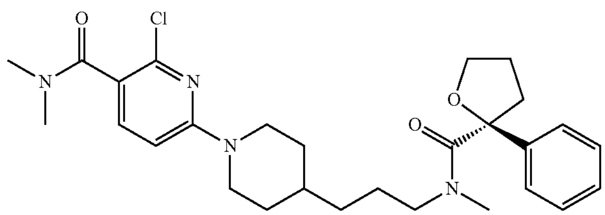 [SMILES: CN(C)C(=O)c1ccc(N2CCC(CCCN(C)C(=O)[C@@]3(c4ccccc4)CCCO3)CC2)nc1Cl] | (S)-2-chloro-N,N-dimethyl-6-(4-(3-(N-methyl-2-phenyltetrahydrofuran-2-carboxamido)propyl)piperidin-1-yl)nicotinamide | 513.3 |
| 1-39 | 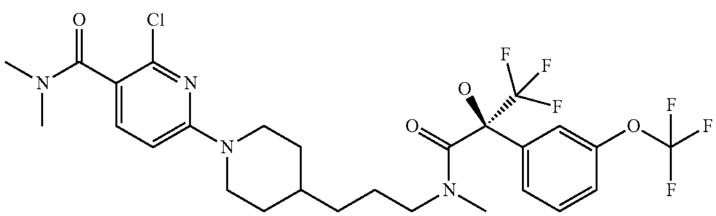 [SMILES: CN(C)C(=O)c1ccc(N2CCC(CCCN(C)C(=O)[C@@](O)(c3cccc(OC(F)(F)F)c3)C(F)(F)F)CC2)nc1Cl] | (S)-2-chloro-N,N-dimethyl-6-(4-(3-(3,3,3-trifluoro-2-hydroxy-N-methyl-2-(3-(trifluoromethoxy)phenyl)propanamido)propyl)piperidin-1-yl)nicotinamide | 625.2 |
| 1-40 | 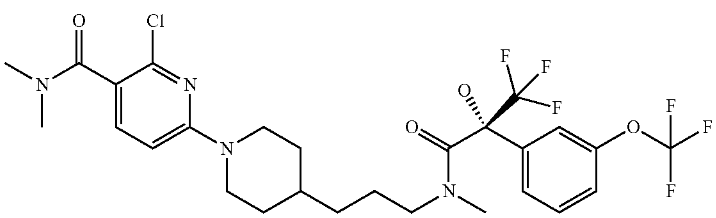 [SMILES: CN(C)C(=O)c1ccc(N2CCC(CCCN(C)C(=O)[C@](O)(c3cccc(OC(F)(F)F)c3)C(F)(F)F)CC2)nc1Cl] | (R)-2-chloro-N,N-dimethyl-6-(4-(3-(3,3,3-trifluoro-2-hydroxy-N-methyl-2-(3-(trifluoromethoxy)phenyl)propanamido)propyl)piperidin-1-yl)nicotinamide | 625.2 |
| 1-41 | 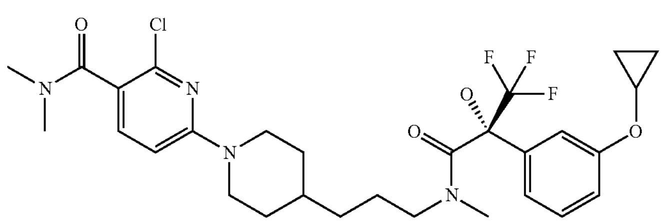 [SMILES: CN(C)C(=O)c1ccc(N2CCC(CCCN(C)C(=O)[C@](O)(c3cccc(OC4CC4)c3)C(F)(F)F)CC2)nc1Cl] | (R)-2-chloro-6-(4-(3-(2-(3-cyclopropoxyphenyl)-3,3,3-trifluoro-2-hydroxy-N-methylpropanamido)propyl)piperidin-1-yl)-N,N-dimethylnicotinamide | 597.2 |
| 1-42 | 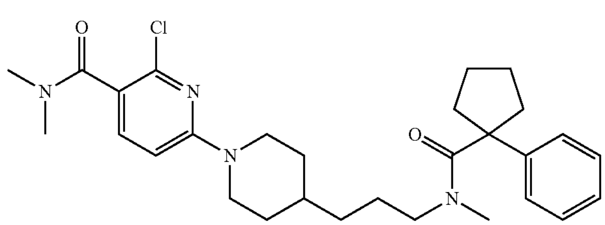 [SMILES: CN(C)C(=O)c1ccc(N2CCC(CCCN(C)C(=O)C3(c4ccccc4)CCCC3)CC2)nc1Cl] | 2-chloro-N,N-dimethyl-6-(4-(3-(N-methyl-1-phenylcyclopentanecarboxamido)propyl)piperidin-1-yl)nicotinamide | 511.3 |

TABLE 1-continued

| Example | Structure | IUPAC Name | LRMS, found [M + H]+ |
|---|---|---|---|
| 1-43 | 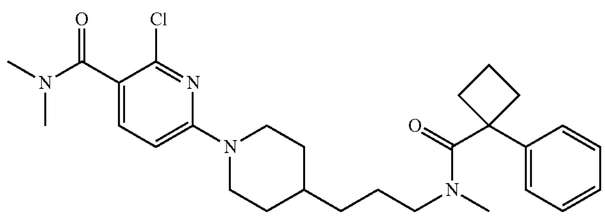 [SMILES: CN(C)C(=O)c1ccc(N2CCC(CCCN(C)C(=O)C3(c4ccccc4)CCC3)CC2)nc1Cl] | 2-chloro-N,N-dimethyl-6-(4-(3-(N-methyl-1-phenyl-cyclobutanecarboxamido)propyl)piperidin-1-yl)nicotinamide | 497.2 |
| 1-44 | 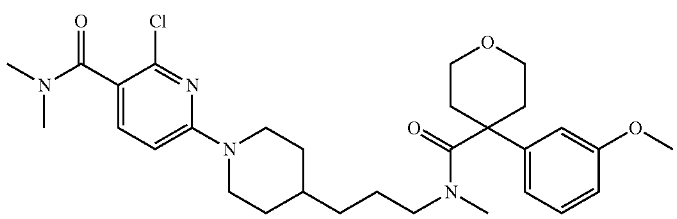 | 2-chloro-6-(4-(3-(4-(3-methoxyphenyl)-N-methyltetrahydro-2H-pyran-4-carboxamido)propyl)piperidin-1-yl)-N,N-dimethylnicotinamide | 557.3 |
| 1-45 | 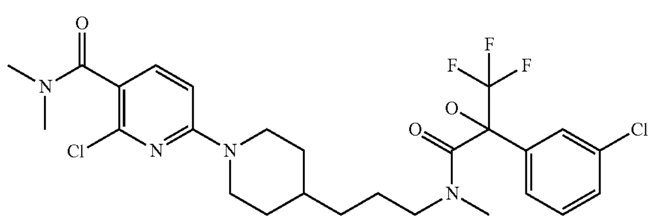 [SMILES: CN(C)C(=O)c1ccc(N2CCC(CCCN(C)C(=O)C(O)(c3cccc(Cl)c3)C(F)(F)F)CC2)nc1Cl] | 2-chloro-N,N-dimethyl-6-(4-(3-(3,3,3-trifluoro-2-hydroxy-2-(3-hydroxyphenyl)-N-methylpropanamido)propyl)piperidin-1-yl)nicotinamide | 557.3 |
| 1-46 | 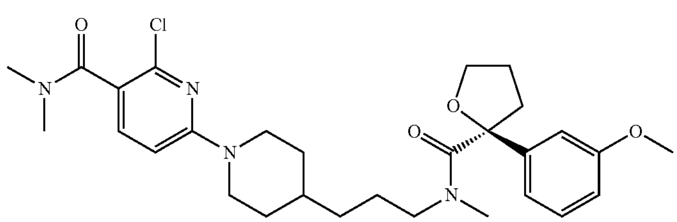 | (S)-2-chloro-6-(4-(3-(2-(3-methoxyphenyl)-N-methyltetrahydrofuran-2-carboxamido)propyl)piperidin-1-yl)-N,N-dimethylnicotinamide | 543.3 |
| 1-47 | 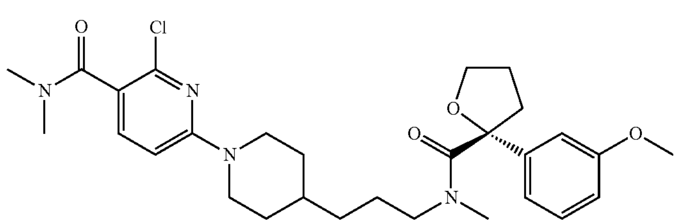 | (R)-2-chloro-6-(4-(3-(2-(3-methoxyphenyl)-N-methyltetrahydrofuran-2-carboxamido)propyl)piperidin-1-yl)-N,N-dimethylnicotinamide | 543.3 |
| 1-48 | 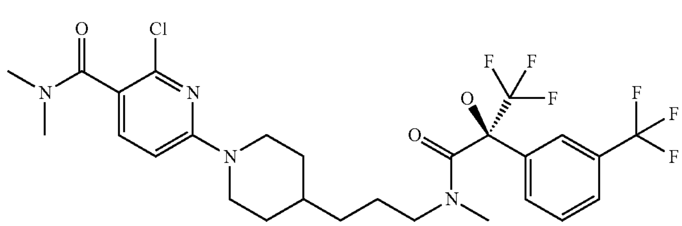 [SMILES: CN(C)C(=O)c1ccc(N2CCC(CCCN(C)C(=O)[C@@](O)(c3cccc(C(F)(F)F)c3)C(F)(F)F)CC2)nc1Cl] | (S)-2-chloro-N,N-dimethyl-6-(4-(3-(3,3,3-trifluoro-2-hydroxy-N-methyl-2-(3-(trifluoromethyl)phenyl)propanamido)propyl)piperidin-1-yl)nicotinamide | 609.2 |

TABLE 1-continued

| Example | Structure | IUPAC Name | LRMS, found [M + H]+ |
|---|---|---|---|
| 1-49 | 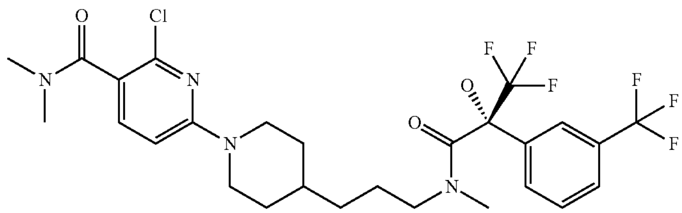 [SMILES: CN(C)C(=O)c1ccc(N2CCC(CCCN(C)C(=O)[C@](O)(c3cccc(C(F)(F)F)c3)C(F)(F)F)CC2)nc1Cl] | (R)-2-chloro-N,N-dimethyl-6-(4-(3-(3,3,3-trifluoro-2-hydroxy-N-methyl-2-(3-(trifluoromethyl)phenyl)propanamido)propyl)piperidin-1-yl)nicotinamide | 609.2 |
| 1-50 | 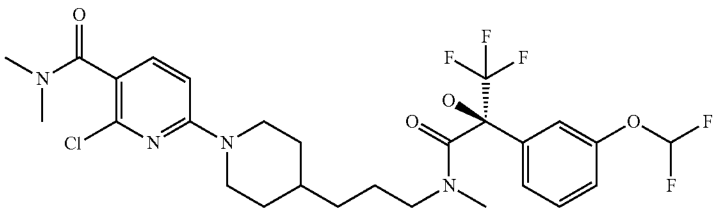 [SMILES: CN(C)C(=O)c1ccc(N2CCC(CCCN(C)C(=O)[C@@](O)(c3cccc(OC(F)F)c3)C(F)(F)F)CC2)nc1Cl] | (S)-2-chloro-6-(4-(3-(2-(3-(difluoromethoxy)phenyl)-3,3,3-trifluoro-2-hydroxy-N-methylpropanamido)propyl)piperidin-1-yl)-N,N-dimethylnicotinamide | 607.2 |
| 1-51 | 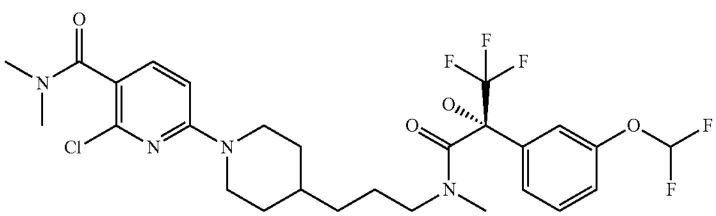 [SMILES: CN(C)C(=O)c1ccc(N2CCC(CCCN(C)C(=O)[C@](O)(c3cccc(OC(F)F)c3)C(F)(F)F)CC2)nc1Cl] | (R)-2-chloro-6-(4-(3-(2-(3-(difluoromethoxy)phenyl)-3,3,3-trifluoro-2-hydroxy-N-methylpropanamido)propyl)piperidin-1-yl)-N,N-dimethylnicotinamide | 607.2 |
| 1-52 | 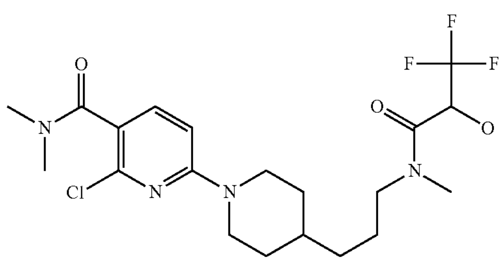 [SMILES: CN(C)C(=O)c1ccc(N2CCC(CCCN(C)C(=O)C(O)C(F)(F)F)CC2)nc1Cl] | 2-chloro-N,N-dimethyl-6-(4-(3-(3,3,3-trifluoro-2-hydroxy-N-methylpropanamido)propyl)piperidin-1-yl)nicotinamide | 465.2 |
| 1-53 | 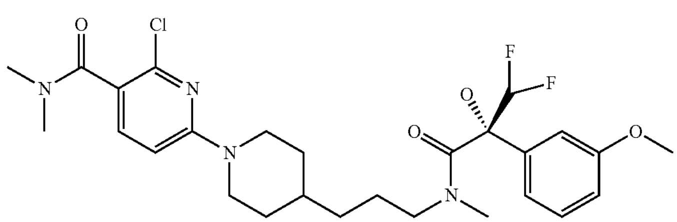 | (R)-2-chloro-6-(4-(3-(3,3-difluoro-2-hydroxy-2-(3-methoxyphenyl)-N-methylpropanamido)propyl)piperidin-1-yl)-N,N-dimethylnicotinamide | 553.2 |
| 1-54 | 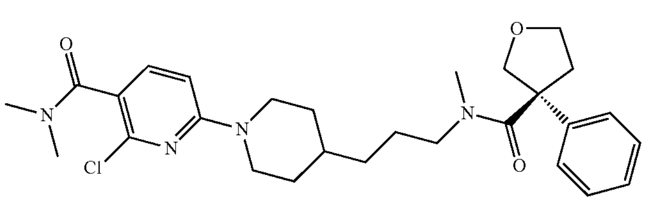 [SMILES: CN(C)C(=O)c1ccc(N2CCC(CCCN(C)C(=O)[C@]3(c4ccccc4)CCOC3)CC2)nc1Cl] | (S)-2-chloro-N,N-dimethyl-6-(4-(3-(N-methyl-3-phenyltetrahydrofuran-3-carboxamido)propyl)piperidin-1-yl)nicotinamide | 513.3 |

TABLE 1-continued

| Example | Structure | IUPAC Name | LRMS, found [M + H]+ |
|---|---|---|---|
| 1-55 | 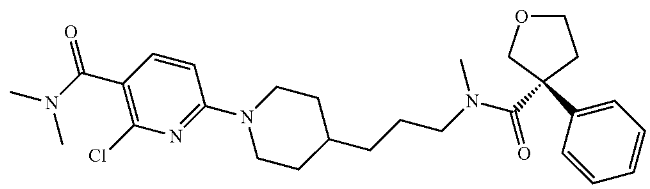 [SMILES: CN(C)C(=O)c1ccc(N2CCC(CCCN(C)C(=O)[C@@]3(c4ccccc4)CCOC3)CC2)nc1Cl] | (R)-2-chloro-N,N-dimethyl-6-(4-(3-(N-methyl-3-phenyltetrahydrofuran-3-carboxamido)propyl)piperidin-1-yl)nicotinamide | 513.3 |
| 1-56 | 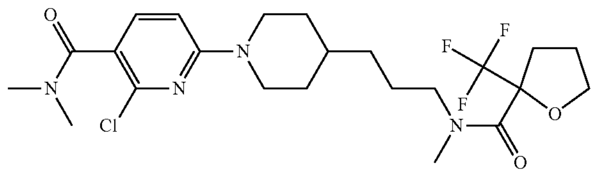 [SMILES: CN(C)C(=O)c1ccc(N2CCC(CCCN(C)C(=O)C3(C(F)(F)F)CCCO3)CC2)nc1Cl] | 2-chloro-N,N-dimethyl-6-(4-(3-(N-methyl-2-(trifluoromethyl)tetrahydrofuran-2-carboxamido)propyl)piperidin-1-yl)nicotinamide | 505.2 |
| 1-57 | 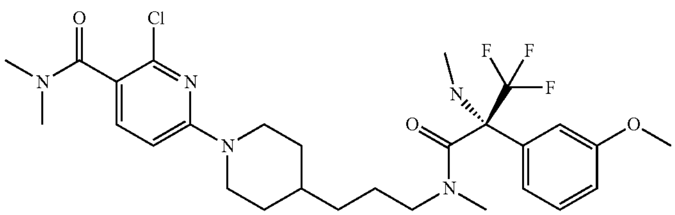 | (R)-2-chloro-N,N-dimethyl-6-(4-(3-(3,3,3-trifluoro-2-(3-methoxyphenyl)-N-methyl-2-(methylamino)propanamido)propyl)piperidin-1-yl)nicotinamide | 584.2 |
| 1-58 | 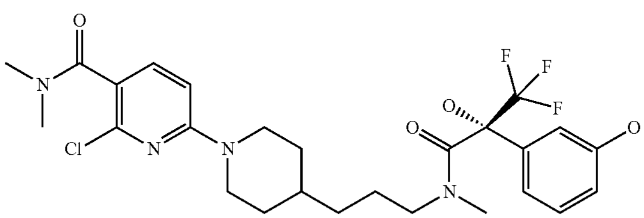 [SMILES: CN(C)C(=O)c1ccc(N2CCC(CCCN(C)C(=O)[C@](O)(c3cccc(O)c3)C(F)(F)F)CC2)nc1Cl] | (R)-2-chloro-N,N-dimethyl-6-(4-(3-(3,3,3-trifluoro-2-hdyroxy-2-(3-hydroxyphenyl)-N-methylpropanamido)propyl)piperidin-1-yl)nicotinamide | 557.2 |
| 1-59 | 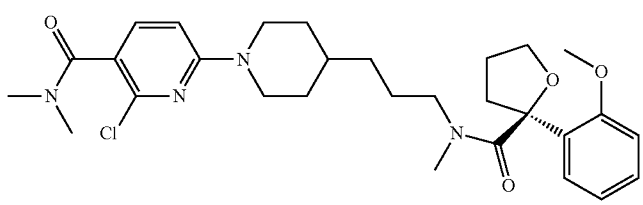 [SMILES: COc1ccccc1[C@]1(C(=O)N(C)CCCC2CCN(c3ccc(C(=O)N(C)C)c(Cl)n3)CC2)CCCO1] | (S)-2-chloro-6-(4-(3-(2-(2-methoxyphenyl)-N-methyltetrahydrofuran-2-carboxamido)propyl)piperidin-1-yl)-N,N-dimethylnicotinamide | 543.2 |
| 1-60 | 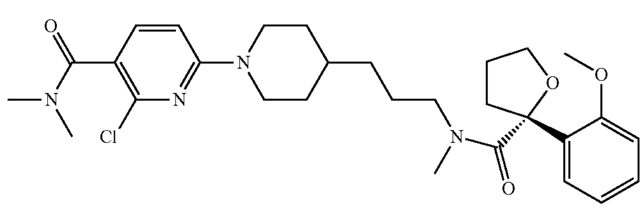 [SMILES: COc1ccccc1[C@@]1(C(=O)N(C)CCCC2CCN(c3ccc(C(=O)N(C)C)c(Cl)n3)CC2)CCCO1] | (R)-2-chloro-6-(4-(3-(2-(2-methoxyphenyl)-N-methyltetrahydrofuran-2-carboxamido)propyl)piperidin-1-yl)-N,N-dimethylnicotinamide | 543.2 |
| 1-61 | 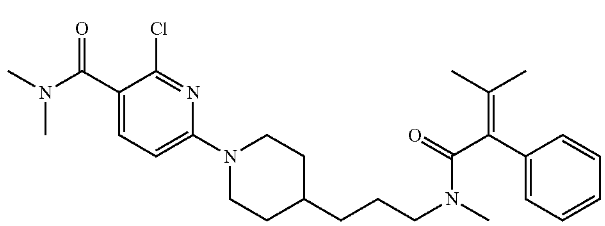 [SMILES: CC(C)=C(C(=O)N(C)CCCC1CCN(c2ccc(C(=O)N(C)C)c(Cl)n2)CC1)c1ccccc1] | 2-chloro-6-(4-(3-(N,3-dimethyl-2-phenylbut-2-enamido)propyl)piperidin-1-yl)-N,N-dimethylnicotinamide | 497.2 |

TABLE 1-continued

| Example | Structure | IUPAC Name | LRMS, found [M + H]+ |
|---|---|---|---|
| 1-62 | 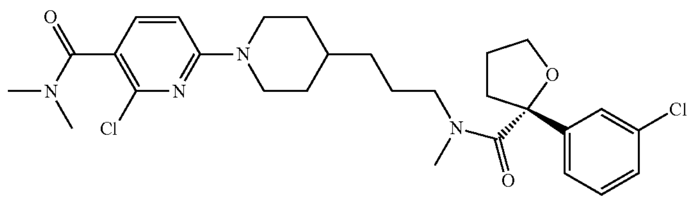 [SMILES: CN(C)C(=O)c1ccc(N2CCC(CCCN(C)C(=O)[C@]3(c4cccc(Cl)c4)CCCO3)CC2)nc1Cl] | (R)-2-chloro-6-(4-(3-(2-(3-chlorophenyl)-N-methyltetrahydrofuran-2-carboxamido)propyl)piperidin-1-yl)-N,N-dimethylnicotinamide | 547.2 |
| 1-63 | 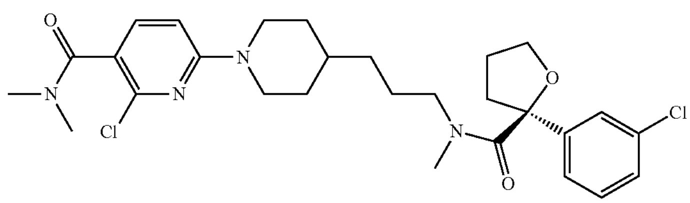 [SMILES: CN(C)C(=O)c1ccc(N2CCC(CCCN(C)C(=O)[C@@]3(c4cccc(Cl)c4)CCCO3)CC2)nc1Cl] | (S)-2-chloro-6-(4-(3-(2-(3-chlorophenyl)-N-methyltetrahydrofuran-2-carboxamido)propyl)piperidin-1-y)-N,N-dimethylnicotinamide | 547.2 |
| 1-64 | 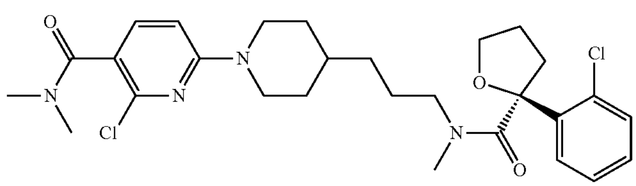 [SMILES: CN(C)C(=O)c1ccc(N2CCC(CCCN(C)C(=O)[C@@]3(c4ccccc4Cl)CCCO3)CC2)nc1Cl] | (S)-2-chloro-6-(4-(3-(2-(2-chlorophenyl)-N-methyltetrahydrofuran-2-carboxamido)propyl)piperidin-1-yl)-N,N-dimethylnicotinamide | 547.2 |
| 1-65 | 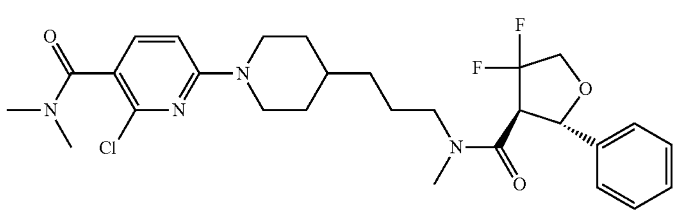 [SMILES: CN(C)C(=O)c1ccc(N2CCC(CCCN(C)C(=O)[C@@H]3[C@@H](c4ccccc4)OCC3(F)F)CC2)nc1Cl] | (S)-2-chloro-6-(4-(3-(4,4-difluoro-N-methyl-2-phenyltetrahydrofuran-2-carboxamido)propyl)piperidin-1-yl)-N,N-dimethylnicotinamide | 549.3 |
| 1-66 | 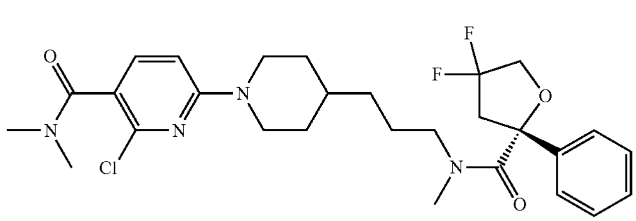 [SMILES: CN(C)C(=O)c1ccc(N2CCC(CCCN(C)C(=O)[C@]3(c4ccccc4)CC(F)(F)CO3)CC2)nc1Cl] | (R)-2-chloro-6-(4-(3-(4,4-difluoro-N-methyl-2-phenyltetrahydrofuran-2-carboxamido)propyl)piperidin-1-yl)-N,N-dimethylnicotinamide | 549.3 |

Example 2-1
(R)-2-chloro-N-isopropyl-6-(4-(3-(3,3,3-trifluoro-2-hydroxy-2-(3-methoxyphenyl)-N-methylpropanamido)propyl)piperidin-1-yl)nicotinamide
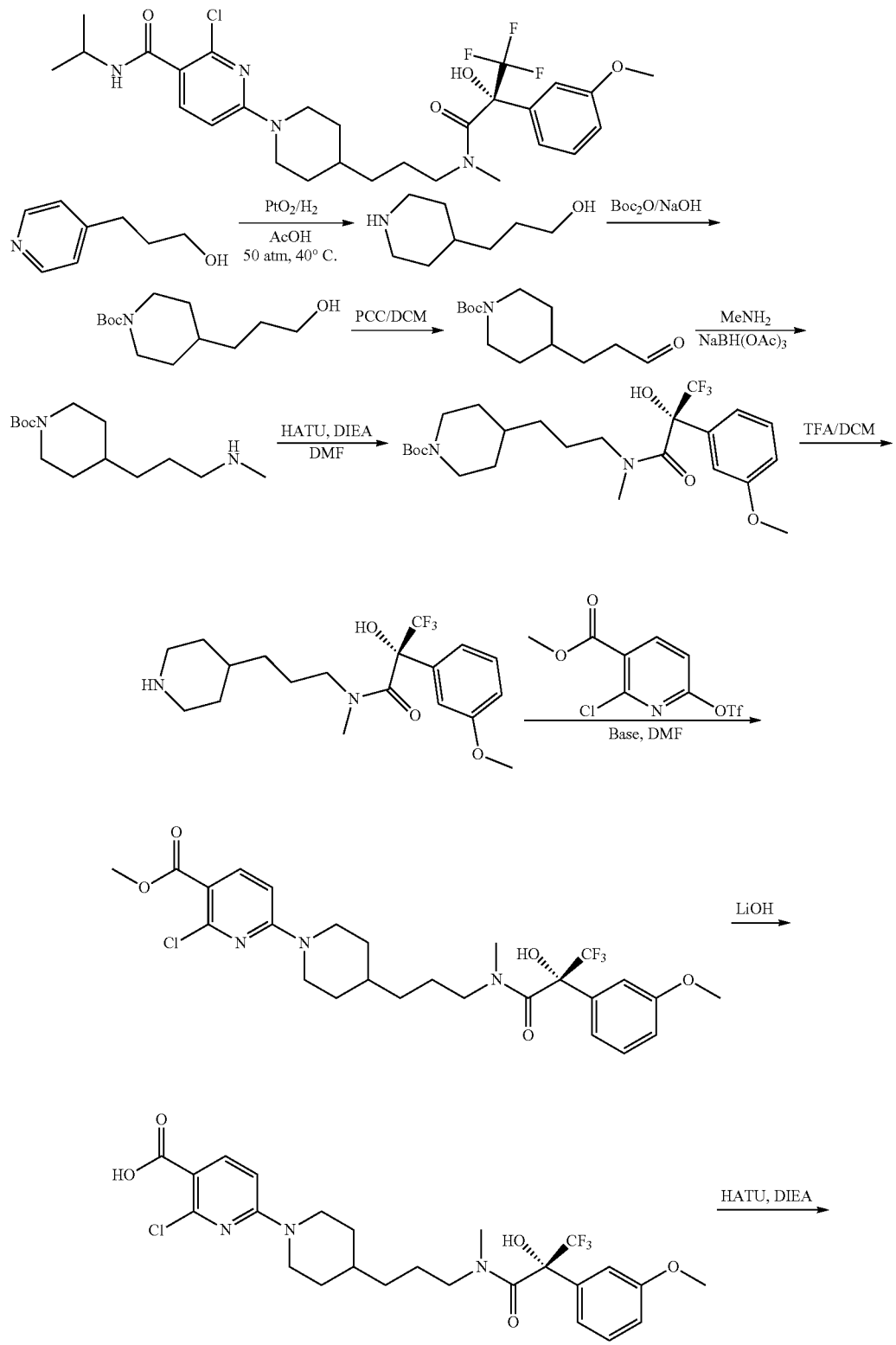

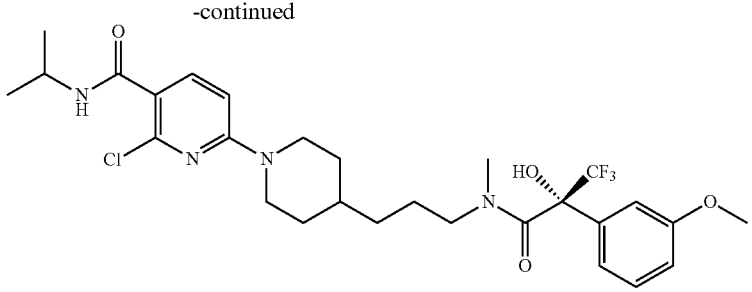

3-(piperidin-4-yl)propan-1-ol

To a solution of 3-(pyridin-4-yl)propan-1-ol (20.0 g, 0.15 mol) in AcOH (300 mL) was added PtO$_2$ (2.5 g, 11.0 mmol). The mixture was sealed and stirred at 40° C. under 735 psi hydrogen for 24 h. After cooling to rt, the catalyst was filtered off and the filtrate was concentrated under reduced pressure. The crude was dissolved with DCM (1 L) and organic phase was washed with sat. Na$_2$CO$_3$ (100 mL×3), dried over anhydrous Na$_2$SO$_4$, filtered and concentrated to afford 3-(piperidin-4-yl)propan-1-ol which was used in next step without purification. LRMS m/z (M+H) 144.1 found, 144.1 required.

tert-butyl 4-(3-hydroxypropyl)piperidine-1-carboxylate

To a solution of 3-(piperidin-4-yl)propan-1-ol (8.1 g, 56.7 mmol) and 3M NaOH (100 mL) in dioxane (300 mL) was added a solution of Boc$_2$O (15.0 g, 68.0 mmol) in dioxane (30 mL) dropwise at 0° C. After stirring at rt for 12 h, the solvent was removed under reduced pressure and the residue was dissolved in EtOAc (600 mL). The organic phase was washed with sat. NH$_4$Cl (30 mL), NaHCO$_3$ (30 mL) and brine (30 mL), dried over anhydrous Na$_2$SO$_4$, filtered and concentrated to afford tert-butyl 4-(3-hydroxypropyl)piperidine-1-carboxylate as which was used in next step without purification. LRMS m/z (M-55) 188.1 found, 188.2 required.

tert-butyl 4-(3-oxopropyl)piperidine-1-carboxylate

To a solution of tert-butyl 4-(3-hydroxypropyl)piperidine-1-carboxylate (5.0 g, 20.5 mmol) in DCM (80 mL) was added PCC (8.8 g, 41 mmol) at rt. The mixture was then stirred at rt for 12 h. LC-MS showed most SM consumed and target product formed. The mixture was directly purified by silica gel chromatography (EtOAc/PE=5/95) to get tert-butyl 4-(3-oxopropyl)piperidine-1-carboxylate. LRMS m/z (M+Na) 264.1 found, 264.2 required.

tert-butyl 4-(3-(methylamino)propyl)piperidine-1-carboxylate

To a solution of tert-butyl 4-(3-oxopropyl)piperidine-1-carboxylate (2.0 g, 8.3 mmol), methylamine (30 mL, 30 mmol, 1M in THF) and acetic acid (2 drops) was added NaBH(OAc)$_3$ (8.3 g, 41.5 mmol) at rt. The mixture was stirred at rt overnight and quenched with sat. NaHCO$_3$ (50 mL). The mixture was extracted with MeOH/DCM (5/95, 50 mL×3). The combined organic phase was dried over anhydrous Na$_2$SO$_4$, filtered and concentrated. The residue was purified by Prep-TLC (MeOH/DCM=3/97) to get tert-butyl 4-(3-(methylamino)propyl)piperidine-1-carboxylate. LRMS m/z (M+H) 257.3 found, 257.2 required.

(R)-tert-butyl 4-(3-(3,3,3-trifluoro-2-hydroxy-2-(3-methoxyphenyl)-N-methylpropanamido)propyl)piperidine-1-carboxylate A mixture of tert-butyl 4-(3-(methylamino)propyl)piperidine-1-carboxylate (300 mg, 1.2 mmol), (R)-3,3,3-trifluoro-2-hydroxy-2-(3-methoxyphenyl)propanoic acid (325 mg, 1.3 mmol), DIEA (470 mg, 3.6 mmol) and HATU (912 mg, 2.4 mmol) in DMF (5.0 mL) was stirred at rt overnight. The product was directly purified by reverse-phase HPLC (Mobile phase: methanol/water (10 mM NH$_4$HCO$_3$)) to afford (R)-tert-butyl 4-(3-(3,3,3-trifluoro-2-hydroxy-2-(3-methoxyphenyl)-N-methylpropanamido)propyl)piperidine-1-carboxylate. LRMS m/z (M+H) 489.3 found, 489.2 required.

(R)-3,3,3-trifluoro-2-hydroxy-2-(3-methoxyphenyl)-N-methyl-N-(3-(piperidin-4-yl)propyl)propanamide A mixture of (R)-tert-butyl 4-(3-(3,3,3-trifluoro-2-hydroxy-2-(3-methoxyphenyl)-N-methylpropanamido)propyl)piperidine-1-carboxylate (150 mg, 0.3 mmol) and TFA (2.5 mL) in DCM (2.5 mL) was stirred at rt overnight. The solvent was removed under reduced pressure and the residue was suspended in sat. NaHCO$_3$ (30 mL) and extracted with DCM (15 mL×3). The combined organic phase was washed with brine (15 mL), dried over anhydrous Na$_2$SO$_4$, filtered and concentrated in vacuo to afford (R)-3,3,3-trifluoro-2-hydroxy-2-(3-methoxyphenyl)-N-methyl-N-(3-(piperidin-4-yl)propyl)propanamide which was used in next step without purification. LRMS m/z (M+H) 389.2 found, 389.2 required.

(R)-methyl 2-chloro-6-(4-(3-(3,3,3-trifluoro-2-hydroxy-2-(3-methoxyphenyl)-N-methylpropanamido)propyl)piperidin-1-yl)nicotinate To a solution of (R)-3,3,3-trifluoro-2-hydroxy-2-(3-methoxyphenyl)-N-methyl-N-(3-(piperidin-4-yl)propyl)propanamide (7) (280 mg, 0.72 mmol) in DMF (2.5 mL) was added methyl 2-chloro-6-(trifluoromethylsulfonyloxy)nicotinate (252 mg, 0.79 mmol). After stirring at 80° C. for 2 h, the mixture was directly purified by reverse-phase HPLC (mobile phase: methanol/water (10 mM NH$_4$HCO$_3$)) to afford (R)-methyl 2-chloro-6-(4-(3-(3,3,3-trifluoro-2-hydroxy-2-(3-methoxyphenyl)-N-methylpropanamido)propyl)piperidin-1-yl)nicotinate. LRMS m/z (M+H) 558.2 found, 558.2 required.

(R)-2-chloro-6-(4-(3-(3,3,3-trifluoro-2-hydroxy-2-(3-methoxyphenyl)-N-methylpropanamido)propyl)piperidin-1-yl)nicotinic acid To a solution of (R)-methyl 2-chloro-6-(4-(3-(3,3,3-trifluoro-2-hydroxy-2-(3-methoxyphenyl)-N-methylpropanamido)propyl)piperidin-1-yl)nicotinate (280 mg, 0.5 mmol) in MeOH (9 mL) was added LiOH.H$_2$O (42 mg, 1 mmol) and water (3 mL) at rt. The resulting mixture was stirred at rt for 3 h, then acidified to pH=5.0 with 1N HCl, and then extracted with EtOAc (50 mL). The organic phase was washed with water (10 mL), brine (10 mL), dried over anhydrous Na$_2$SO$_4$, filtered and concentrated in vacuo to afford (R)-2-chloro-6-(4-(3-(3,3,3-trifluoro-2-hydroxy-2-(3-methoxyphenyl)-N-methylpropanamido)propyl)piperidin-1-yl)nicotinic acid. LRMS m/z (M+H) 544.2 found, 544.2 required.

(R)-2-chloro-N-isopropyl-6-(4-(3-(3,3,3-trifluoro-2-hydroxy-2-(3-methoxyphenyl)-N-methylpropanamido)propyl)piperidin-1-yl)nicotinamide A solution of (R)-2-chloro-6-(4-(3-(3,3,3-trifluoro-2-hydroxy-2-(3-methoxyphenyl)-N-methylpropanamido)propyl)piperidin-1-yl)nicotinic acid (16 mg, 0.03 mmol), isopropylamine (7 mg, 0.12 mmol), HATU (18 mg, 0.047 mmol), DIEA (12 mg, 0.093 mL) in THF (2 mL) was stirred at rt overnight. The mixture was directly purified by reverse-phase HPLC (mobile phase: methanol/water (10 mM NH$_4$HCO$_3$)) to afford (R)-2-chloro-N-isopropyl-6-(4-(3-(3,3,3-trifluoro-2-hydroxy-2-(3-methoxyphenyl)-N-methylpropanamido)propyl)piperidin-1-yl)nicotinamide. LRMS m/z (M+H) 585.2 found, 585.2 required. $^1$H NMR (400 MHz, CDCl$_3$): δ 8.1 (d, J=8.8 Hz, 1H), 7.32 (t, J=8.8 Hz, 1H), 7.02-6.90 (m, 3H), 6.65 (d, J=7.6 Hz, 1H), 6.54 (d, J=8.8 Hz, 1H), 4.4-4.2 (m, 2H), 3.9 (s, 3H), 3.5-2.8 (m, 8H), 1.78-1.60 (m, 3H), 1.22 (d, J=6.4 Hz, 6H), 1.1-0.61 (m, 6H).

Using the procedure described in Example 2-1, but replacing isopropylamine with suitable amines in the last step and/or replacing methyl 2-chloro-6-(trifluoromethylsulfonyloxy) nicotinate with suitable aromatic electrophiles in the seventh step, the following compounds in Table 2 were prepared.

TABLE 2

| Example | Structure | IUPAC Name | LRMS, found [M + H]+ |
| --- | --- | --- | --- |
| 2-1 | 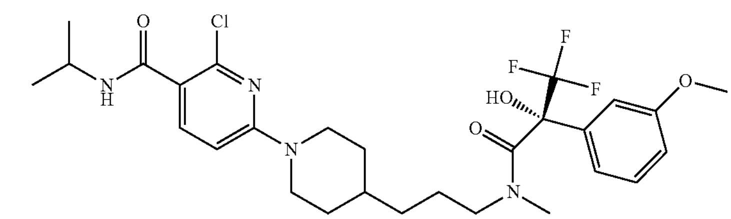 [SMILES: COc1cccc([C@@](O)(C(=O)N(C)CCCC2CCN(c3ccc(C(=O)NC(C)C)c(Cl)n3)CC2)C(F)(F)F)c1] | (R)-2-chloro-N-isopropyl-6-(4-(3-(3,3,3-trifluoro-2-hydroxy-2-(3-methoxyphenyl)-N-methylpropanamido)propyl)piperidin-1-yl)nicotinamide | 585.2 |
| 2-2 | 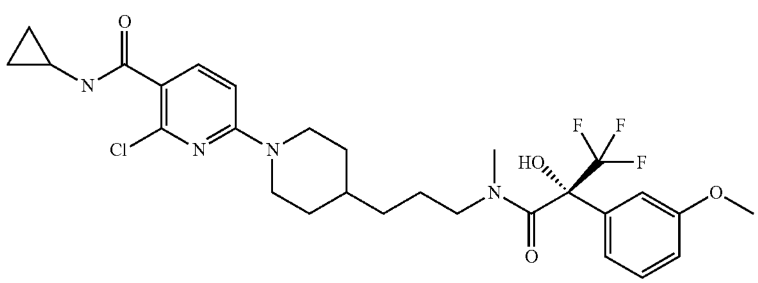 [SMILES: COc1cccc([C@@](O)(C(=O)N(C)CCCC2CCN(c3ccc(C(=O)NC4CC4)c(Cl)n3)CC2)C(F)(F)F)c1] | (R)-2-chloro-N-cyclopropyl-6-(4-(3-(3,3,3-trifluoro-2-hydroxy-2-(3-methoxyphenyl)-N-methylpropanamido)propyl)piperidin-1-yl)nicotinamide | 583.2 |
| 2-3 | 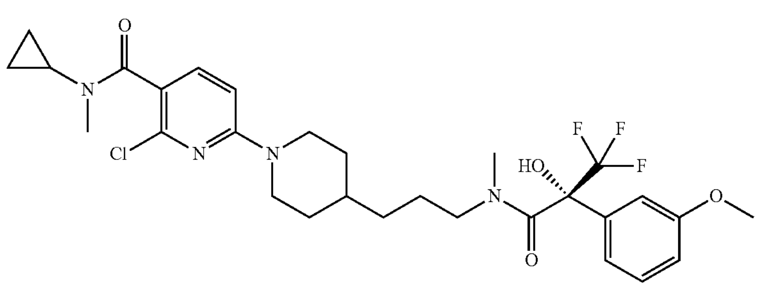 [SMILES: COc1cccc([C@@](O)(C(=O)N(C)CCCC2CCN(c3ccc(C(=O)N(C)C4CC4)c(Cl)n3)CC2)C(F)(F)F)c1] | (R)-2-chloro-N-cyclopropyl-N-methyl-6-(4-(3-(3,3,3-trifluoro-2-hydroxy-2-(3-methoxyphenyl)-N-methylpropanamido)propyl)piperidin-1-yl)nicotinamide | 597.2 |
| 2-4 | 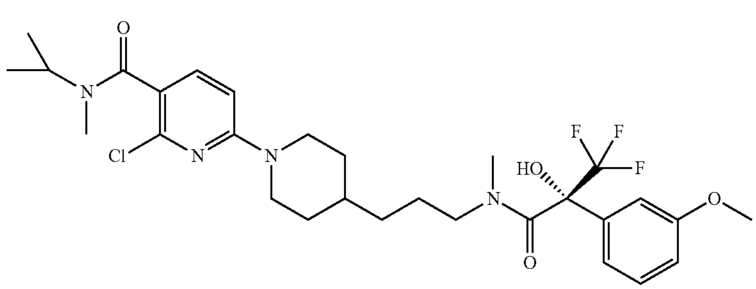 [SMILES: COc1cccc([C@@](O)(C(=O)N(C)CCCC2CCN(c3ccc(C(=O)N(C)C(C)C)c(Cl)n3)CC2)C(F)(F)F)c1] | (R)-2-chloro-N-isopropyl-N-methyl-6-(4-(3-(3,3,3-trifluoro-2-hydroxy-2-(3-methoxyphenyl)-N-methylpropanamido)propyl)piperidin-1-yl)nicotinamide | 599.2 |

TABLE 2-continued

| Example | Structure | IUPAC Name | LRMS, found [M + H]+ |
|---|---|---|---|
| 2-5 | 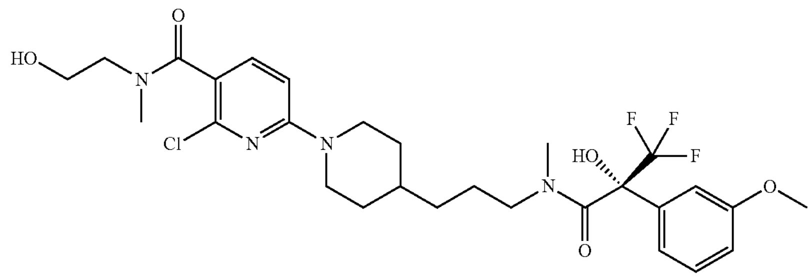 [SMILES: COc1cccc([C@@](O)(C(=O)N(C)CCCC2CCN(c3ccc(C(=O)N(C)CCO)c(Cl)n3)CC2)C(F)(F)F)c1] | (R)-2-chloro-N-(2-hydroxyethyl)-N-methyl-6-(4-(3-(3,3,3-trifluoro-2-hydroxy-2-(3-methoxyphenyl)-N-methylpropanamido)propyl)piperidin-1-yl)nicotinamide | 601.2 |
| 2-6 | 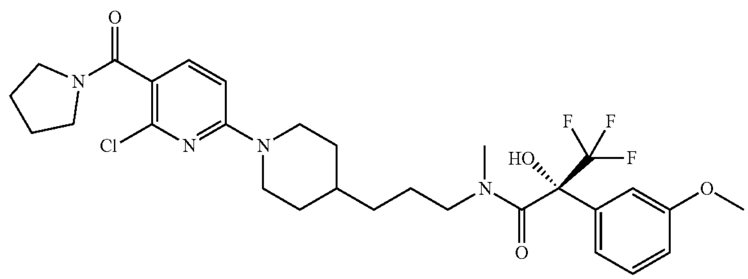 [SMILES: COc1cccc([C@@](O)(C(=O)N(C)CCCC2CCN(c3ccc(C(=O)N4CCCC4)c(Cl)n3)CC2)C(F)(F)F)c1] | (R)-N-(3-(1-(6-chloro-5-(pyrrolidine-1-carbonyl)pyridin-2-yl)piperidin-4-yl)propyl)-3,3,3-trifluoro-2-hydroxy-2-(3-methoxyphenyl)-N-methylpropanamide | 597.2 |
| 2-7 | 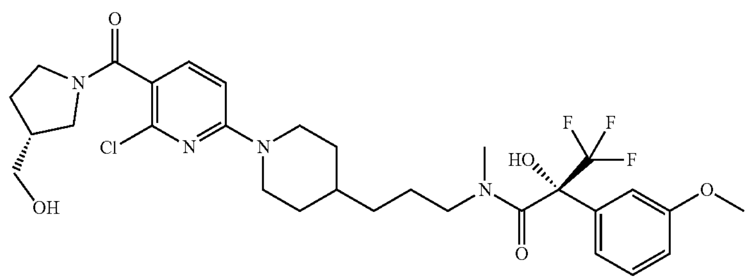 [SMILES: COc1cccc([C@@](O)(C(=O)N(C)CCCC2CCN(c3ccc(C(=O)N4CC[C@@H](CO)C4)c(Cl)n3)CC2)C(F)(F)F)c1] | (R)-N-(3-(1-(6-chloro-5-((R)-3-(hydroxymethyl)pyrrolidine-1-carbonyl)pyridin-2-yl)piperidin-4-yl)propyl)-3,3,3-trifluoro-2-hydroxy-2-(3-methoxyphenyl)-N-methylpropanamide | 627.3 |
| 2-8 | 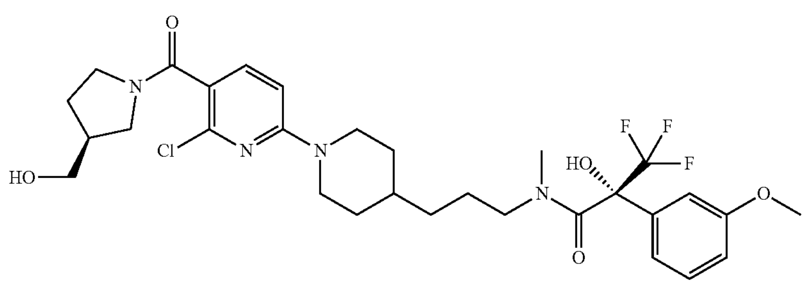 [SMILES: COc1cccc([C@@](O)(C(=O)N(C)CCCC2CCN(c3ccc(C(=O)N4CC[C@H](CO)C4)c(Cl)n3)CC2)C(F)(F)F)c1] | (R)-N-(3-(1-(6-chloro-5-((S)-3-(hydroxymethyl)pyrrolidine-1-carbonyl)pyridin-2-yl)piperidin-4-yl)propyl)-3,3,3-trifluoro-2-hydroxy-2-(3-methoxyphenyl)-N-methylpropanamide | 627.3 |
| 2-9 | 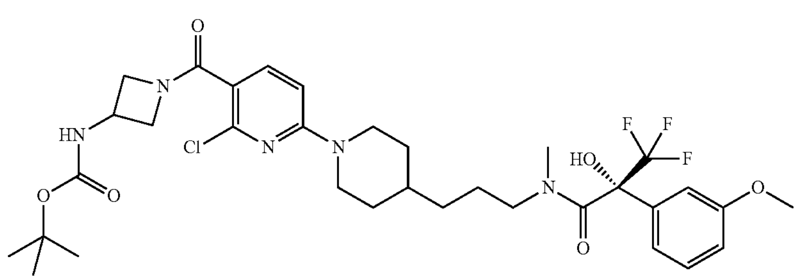 [SMILES: COc1cccc([C@@](O)(C(=O)N(C)CCCC2CCN(c3ccc(C(=O)N4CC(NC(=O)OC(C)(C)C)C4)c(Cl)n3)CC2)C(F)(F)F)c1] | (R)-tert-butyl 1-(2-chloro-6-(4-(3-(3,3,3-trifluoro-2-hydroxy-2-(3-methoxyphenyl)-N-methylpropanamido)propyl)piperidin-1-yl)nicotinoyl)azetidin-3-ylcarbamate | 698.3 |

TABLE 2-continued

| Example | Structure | IUPAC Name | LRMS, found [M + H]+ |
|---|---|---|---|
| 2-10 | 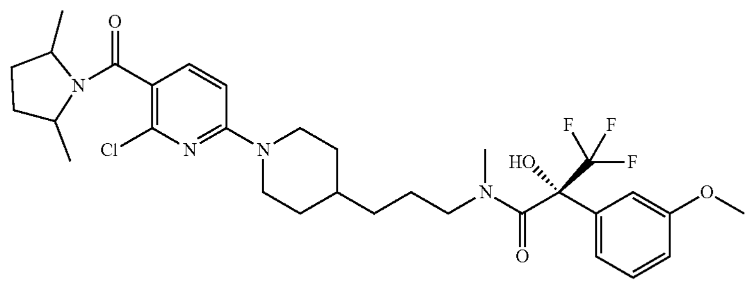 [SMILES: COc1cccc([C@@](O)(C(=O)N(C)CCCC2CCN(c3ccc(C(=O)N4C(C)CCC4C)c(Cl)n3)CC2)C(F)(F)F)c1] | (2R)-N-(3-(1-(6-chloro-5-(2,5-dimethylpyrrolidine-1-carbonyl)pyridin-2-yl)piperidin-4-yl)propyl)-3,3,3-trifluoro-2-hydroxy-2-(3-methoxyphenyl)-N-methylpropanamide | 625.2 |
| 2-11 | 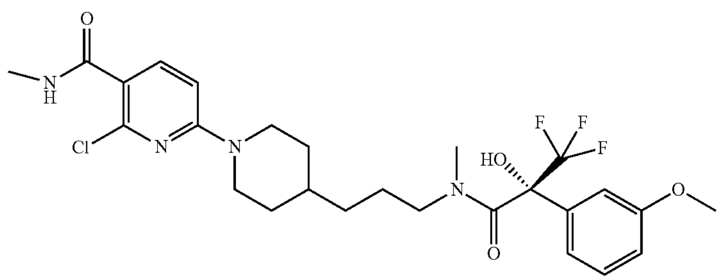 | (R)-2-chloro-N-methyl-6-(4-(3-(3,3,3-trifluoro-2-hydroxy-2-(3-methoxyphenyl)-N-methylpropanamido)propyl)piperidin-1-yl)nicotinamide | 557.2 |
| 2-12 | 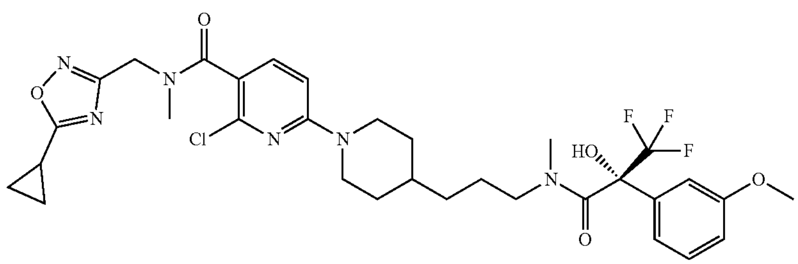 [SMILES: COc1cccc([C@@](O)(C(=O)N(C)CCCC2CCN(c3ccc(C(=O)N(C)Cc4noc(C5CC5)n4)c(Cl)n3)CC2)C(F)(F)F)c1] | (R)-2-chloro-N-((5-cyclopropyl-1,2,4-oxadiazol-3-yl)methyl)-N-methyl-6-(4-(3-(3,3,3-trifluoro-2-hydroxy-2-(3-methoxyphenyl)-N-methylpropanamido)propyl)piperidin-1-yl)nicotinamide | 579.2 |
| 2-13 | 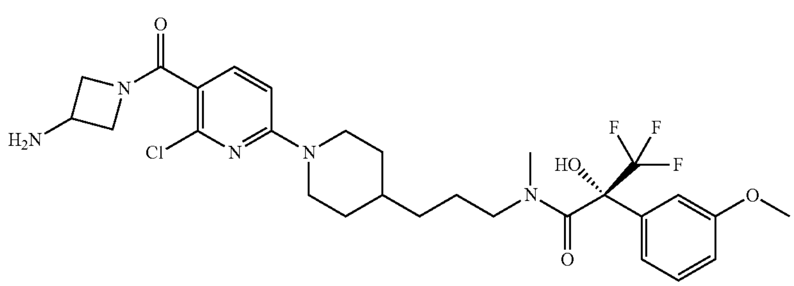 [SMILES: COc1cccc([C@@](O)(C(=O)N(C)CCCC2CCN(c3ccc(C(=O)N4CC(N)C4)c(Cl)n3)CC2)C(F)(F)F)c1] | (R)-N-(3-(1-(5-(3-aminoazetidine-1-carbonyl)-6-chloropyridin-2-yl)piperidin-4-yl)propyl)-3,3,3-trifluoro-2-hydroxy-2-(3-methoxyphenyl)-N-methylpropanamide | 598.2 |
| 2-14 | 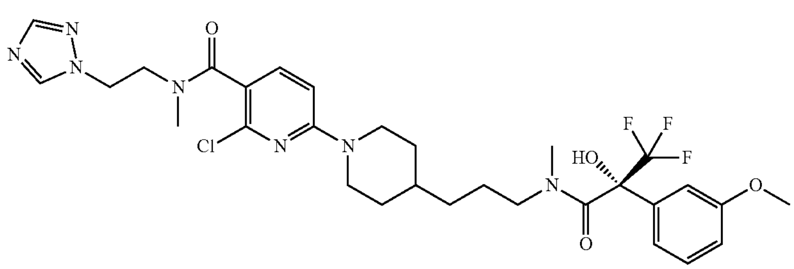 [SMILES: COc1cccc([C@@](O)(C(=O)N(C)CCCC2CCN(c3ccc(C(=O)N(C)CCn4cncn4)c(Cl)n3)CC2)C(F)(F)F)c1] | (R)-N-(2-(1H-1,2,4-triazol-1-yl)ethyl)-2-chloro-N-methyl-6-(3-(3-(3,3,3-trifluoro-2-hydroxy-2-(3-methoxyphenyl)-N-methylpropanamido)propyl)piperidin-1-yl)nicotinamide | 652.2 |

TABLE 2-continued

| Example | Structure | IUPAC Name | LRMS, found [M + H]+ |
|---|---|---|---|
| 2-15 | 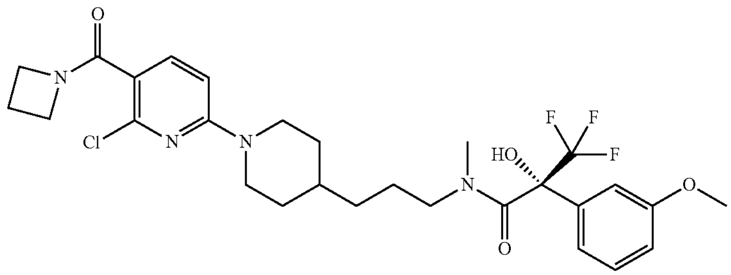 [SMILES: COc1cccc([C@@](O)(C(=O)N(C)CCCC2CCN(c3ccc(C(=O)N4CCC4)c(Cl)n3)CC2)C(F)(F)F)c1] | (R)-N-(3-(1-(5-(azetidine-1-carbonyl)-6-chloropyridin-2-yl)piperidin-4-yl)propyl)-3,3,3-trifluoro-2-hydroxy-2-(3-methoxyphenyl)-N-methylpropanamide | 583.2 |
| 2-16 | 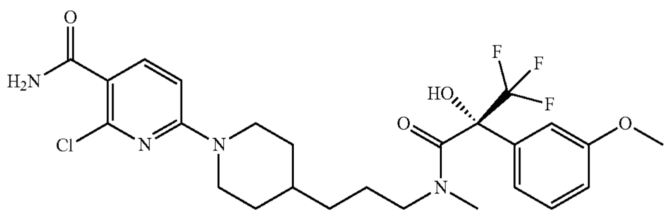 [SMILES: COc1cccc([C@@](O)(C(=O)N(C)CCCC2CCN(c3ccc(C(N)=O)c(Cl)n3)CC2)C(F)(F)F)c1] | (R)-2-chloro-6-(4-(3-(3,3,3-trifluoro-2-hydroxy-2-(3-methoxyphenyl)-N-methylpropanamido)propyl)piperidin-1-yl)nicotinamide | 543.2 |
| 2-17 | 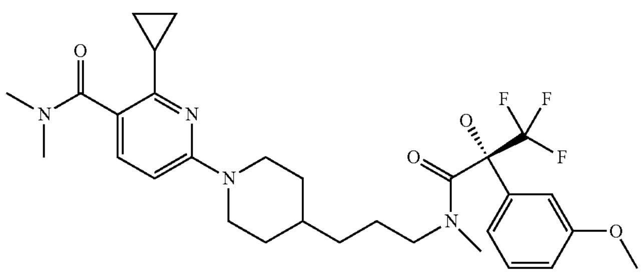 | (R)-2-cyclopropyl-N,N-dimethyl-6-(4-(3-(3,3,3-trifluoro-2-hydroxy-2-(3-methoxyphenyl)-N-methylpropanamido)propyl)piperidin-1-yl)nicotinamide | 577.3 |
| 2-18 | 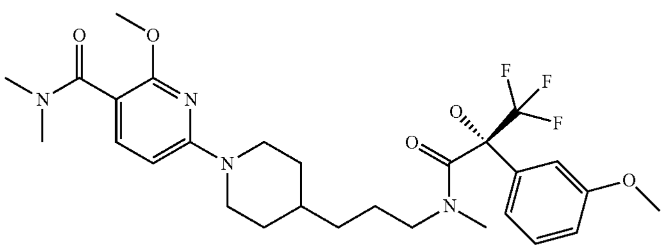 | (R)-2-methoxy-N,N-dimethyl-6-(4-(3-(3,3,3-trifluoro-2-hydroxy-2-(3-methoxyphenyl)-N-methylpropanamido)propyl)piperidin-1-yl)nicotinamide | 567.3 |
| 2-19 | 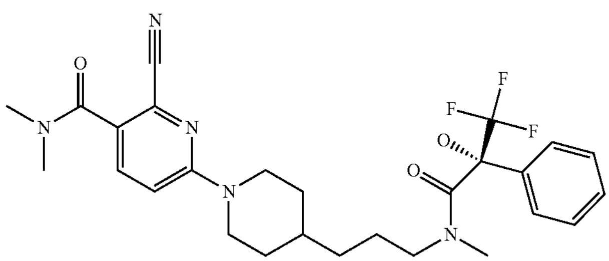 [SMILES: CN(C)C(=O)c1ccc(N2CCC(CCCN(C)C(=O)[C@](O)(c3ccccc3)C(F)(F)F)CC2)nc1C#N] | (R)-2-cyano-N,N-dimethyl-6-(4-(3-(3,3,3-trifluoro-2-hydroxy-N-methyl-2-phenylpropanamido)propyl)piperidin-1-yl)nicotinamide | 532.2 |
| 2-20 | 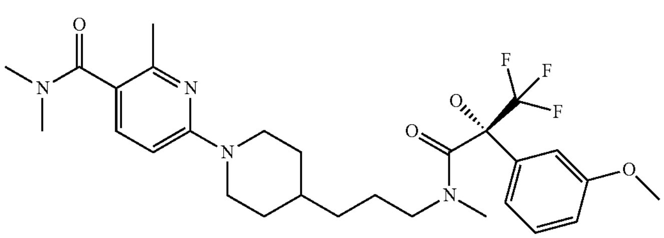 | (R)-N,N,2-trimethyl-6-(4-(3-(3,3,3-trifluoro-2-hydroxy-2-(3-methoxyphenyl)-N-methylpropanamido)propyl)piperidin-1-yl)nicotinamide | 551.2 |

TABLE 2-continued

| Example | Structure | IUPAC Name | LRMS, found [M + H]+ |
|---|---|---|---|
| 2-21 | 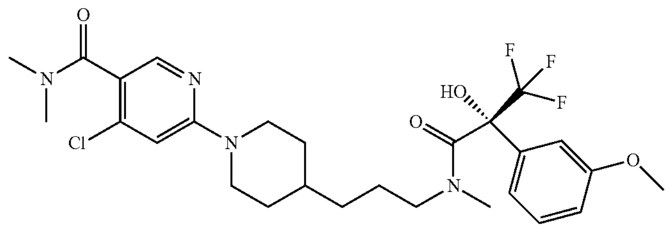 | (R)-4-chloro-N,N-dimethyl-6-(4-(3-(3,3,3-trifluoro-2-hydroxy-2-(3-methoxyphenyl)-N-methylpropanamido)propyl)piperidin-1-yl)nicotinamide | 571.1 |
| 2-22 | 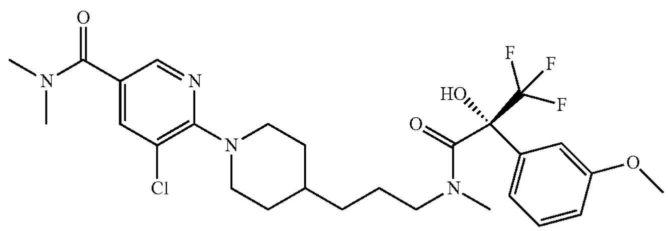 | (R)-5-chloro-N,N-dimethyl-6-(4-(3-(3,3,3-trifluoro-2-hydroxy-2-(3-methoxyphenyl)-N-methylpropanamido)propyl)piperidin-1-yl)nicotinamide | 571.2 |

Example 3-1 and 3-2

2-chloro-N,N-dimethyl-6-(4-((S)-2-methyl-3-((R)-3,3,3-trifluoro-2-hydroxy-2-(3-methoxyphenyl)-N-methylpropanamido)propyl)piperidin-1-yl)nicotinamide and 2-chloro-N,N-dimethyl-6-(4-((R)-2-methyl-3-((R)-3,3,3-trifluoro-2-hydroxy-2-(3-methoxyphenyl)-N-methylpropanamido)propyl)piperidin-1-yl)nicotinamide, respectively

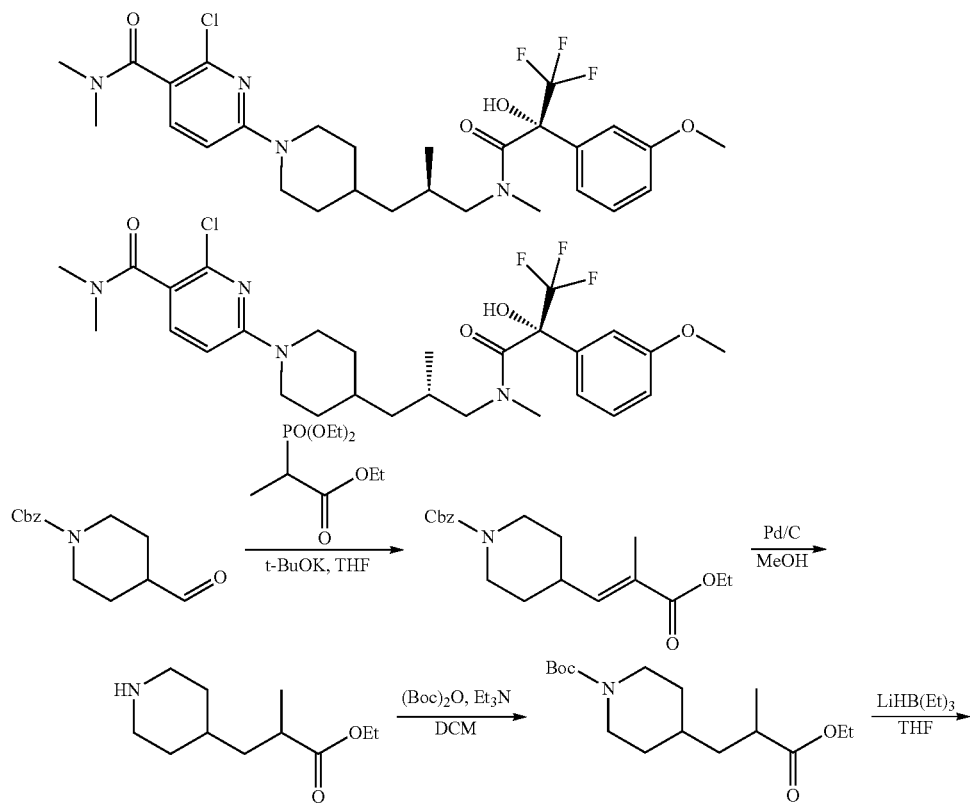

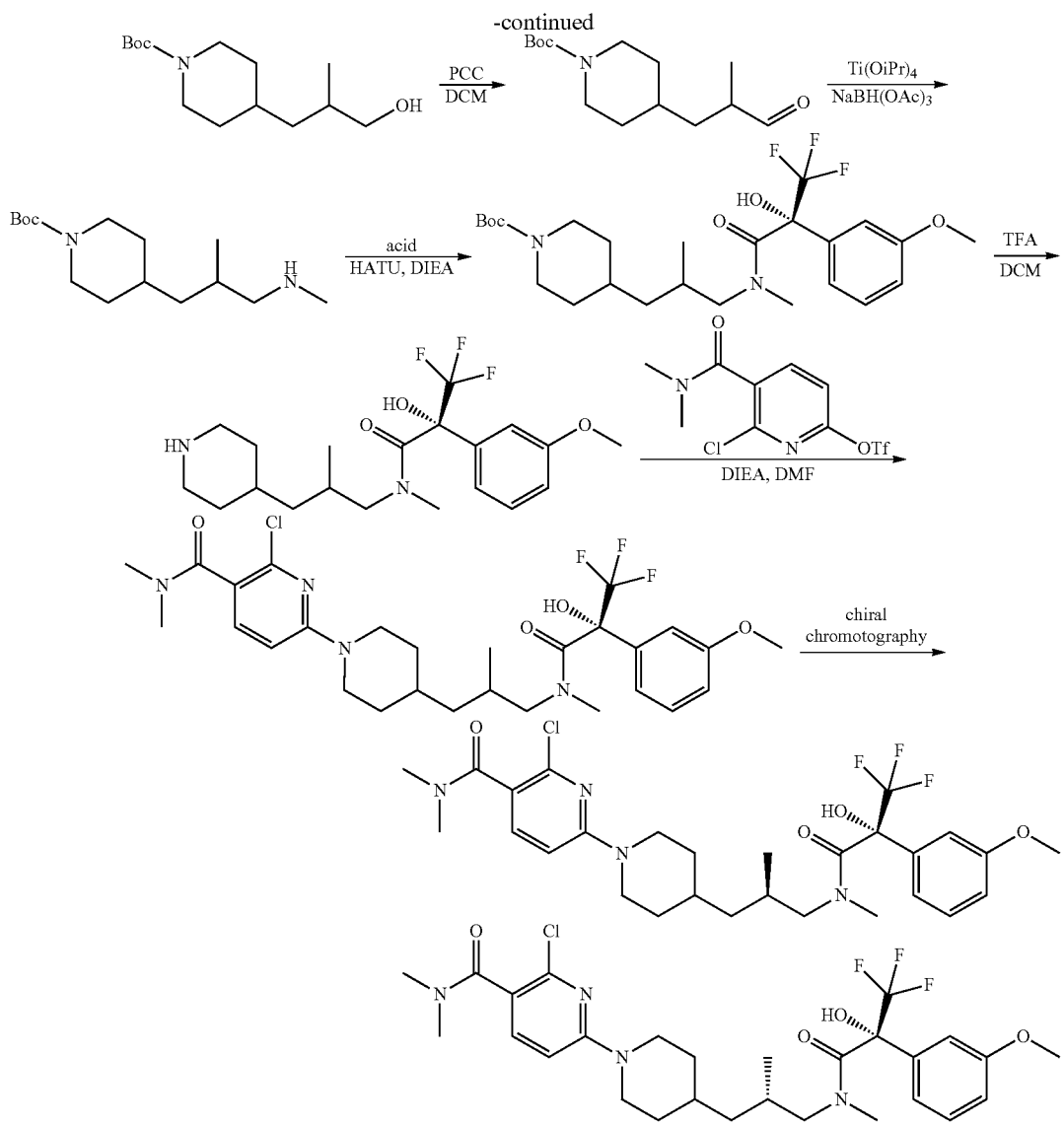

(E)-benzyl 4-(3-ethoxy-2-methyl-3-oxoprop-1-enyl)piperidine-1-carboxylate

To a solution of t-BuOK (1.36 g, 12 mmol) in THF (100 mL) was added ethyl 2-(diethoxyphosphoryl)propanoate (2.89 g, 12 mmol) at 0° C. After stirring at 0° C. for 0.5 h, benzyl 4-formylpiperidine-1-carboxylate (2 g, 8.7.5 mmol) in THF (20 mL) was added to the mixture. The resulting mixture was stirred at rt overnight. The solvent was removed and the residue was diluted with EtOAc (200 mL). The organic phase was washed with water (50 mL×3), brine (10 mL×3) and dried over anhydrous Na$_2$SO$_4$. The organic layer was concentrated in vacuo and purified by column chromatography (silica gel: 300-400 mesh, PE/EtOAc=3/1 to 1/1) to get pure (E)-benzyl 4-(3-ethoxy-2-methyl-3-oxoprop-1-enyl)piperidine-1-carboxylate. LRMS m/z (M+H) 332.1 found, 332.2 required.

Ethyl 2-methyl-3-(piperidin-4-yl)propanoate

A mixture of (E)-benzyl 4-(3-ethoxy-2-methyl-3-oxoprop-1-enyl)piperidine-1-carboxylate (2.5 g, 7.5 mmol) and 10% dry Pd/C (250 mg) in MeOH (30 mL) was degassed and backfilled with H$_2$ (three times). The mixture was stirred at rt under H$_2$ balloon overnight, and the catalyst was filtered off and the filtrate was concentrated in vacuo to get ethyl 2-methyl-3-(piperidin-4-yl)propanoate which was used in next step directly. LRMS m/z (M+H) 200.1 found, 200.1 required.

tert-butyl 4-(3-ethoxy-2-methyl-3-oxopropyl)piperidine-1-carboxylate

A mixture of ethyl 2-methyl-3-(piperidin-4-yl)propanoate (1.5 g, 7.5 mmol), (Boc)$_2$O (1.6 g, 7.5 mmol) and TEA (909 mg, 9 mmol) in DCM (50 mL) was stirred at rt for 2 h. The organic phase was washed with water (20 mL), brine (10 mL) and dried over anhydrous Na$_2$SO$_4$. The organic phase was concentrated and the residue was purified by column chromatography (silica gel: 300-400 mesh, PE/EtOAc=8/1 to 3/1) to get tert-butyl 4-(3-ethoxy-2-methyl-3-oxopropyl)piperidine-1-carboxylate. LRMS m/z (M-100) 200.2 found, 200.2 required.

tert-butyl 4-(3-hydroxy-2-methylpropyl)piperidine-1-carboxylate

To a solution of tert-butyl 4-(3-ethoxy-2-methyl-3-oxopropyl)piperidine-1-carboxylate (2.2 g, 7.3 mmol) in THF (20 mL) was added SUPER-H (22 mmol, 22 mL, 1 M in THF) at 0° C. After stirring at overnight, the mixture was quenched with methanol (30 mL) and the solvent was removed under reduced pressure. The residue was dissolved with EtOAc (200 mL). The organic phase was washed with water (20 mL×3), brine (10 mL×3) and dried over anhydrous Na$_2$SO$_4$. The organic phase was concentrated and the residue was purified by column chromatography (silica gel: 300-400 mesh, PE/EtOAc=8/1 to 3/1) to afford tert-butyl 4-(3-hydroxy-2-methylpropyl)piperidine-1-carboxylate. LRMS m/z (M-55) 202.2 found, 202.2 required.

tert-butyl 4-(2-methyl-3-oxopropyl)piperidine-1-carboxylate

To a solution of tert-butyl 4-(3-hydroxy-2-methylpropyl)piperidine-1-carboxylate (0.9 g, 3.5 mmol) in DCM (20 mL) was added PCC (1.13 g, 5.25 mmol) at rt. The mixture was stirred at 30° C. for 2 h and diluted with Et$_2$O (150 mL). The organic phase was washed with water (50 mL×3), brine (10 mL×3) and dried over anhydrous Na$_2$SO$_4$. The organic phase was concentrated and the residue was purified by column chromatography (silica gel: 300-400 mesh, PE/EtOAc=8/1) to afford tert-butyl 4-(2-methyl-3-oxopropyl)piperidine-1-carboxylate. LRMS m/z (M-55) 200.2 found, 200.2 required.

tert-butyl 4-(2-methyl-3-(methylamino)propyl)piperidine-1-carboxylate

To a solution of tert-butyl 4-(2-methyl-3-oxopropyl)piperidine-1-carboxylate (230 mg, 0.90 mmol) in DCE (5 mL) was added MeNH$_2$ (1.0 mL, 1 mmol, 1M in THF), titanium isopropoxide (384 mg, 1.35 mmol). The mixture was stirred at rt for 3 h and then NaHB(OAc)$_3$ (570 mg, 2.7 mmol) was added to the mixture. The resulting mixture was stirred at rt overnight and quenched with aq NH$_4$Cl (30 mL). The aqueous was extracted with EtOAc (30 mL×3) and the combined organic phase was washed with brine (10 mL), dried over anhydrous Na$_2$SO$_4$, filtered and concentrated. The residue was purified by column chromatography (silica gel: 300-400 mesh, PE/EtOAc=5/1) to afford tert-butyl 4-(2-methyl-3-(methylamino)propyl)piperidine-1-carboxylate. LRMS m/z (M+H) 271.2 found, 271.2 required.

tert-butyl-4-(2-methyl-3-((R)-3,3,3-trifluoro-2-hydroxy-2-(3-methoxyphenyl)-N-methylpropanamido)propyl)piperidine-1-carboxylate A mixture of tert-butyl 4-(2-methyl-3-(methylamino)propyl)piperidine-1-carboxylate (194 mg, 0.72 mmol), (R)-3,3,3-trifluoro-2-hydroxy-2-(3-methoxyphenyl)propanoic acid (216 mg, 0.86 mmol), HATU (357 mg, 0.94 mmol) and DIEA (0.2 mL, 1.2 mmol) in THF (5 mL) was stirred at rt overnight. The mixture was directly purified by reverse-phase HPLC (mobile phase: methanol/water (10 mM NH$_4$HCO$_3$)) to afford tert-butyl-4-(2-methyl-3-((R)-3,3,3-trifluoro-2-hydroxy-2-(3-methoxyphenyl)-N-methylpropanamido)propyl)piperidine-1-carboxylate. LRMS m/z (M+H) 503.3 found, 503.2 required.

(2R)-3,3,3-trifluoro-2-hydroxy-2-(3-methoxyphenyl)-N-methyl-N-(2-methyl-3-(piperidin-4-yl)propyl)propanamide To a solution of tert-butyl-4-(2-methyl-3-((R)-3,3,3-trifluoro-2-hydroxy-2-(3-methoxyphenyl)-N-methylpropanamido)propyl)piperidine-1-carboxylate (140 mg, 0.28 mmol) in DCM (2.5 mL) was added TFA (0.25 mL). The mixture was stirred at rt for 1 h and concentrated in vacuo to give the crude (2R)-3,3,3-trifluoro-2-hydroxy-2-(3-methoxyphenyl)-N-methyl-N-(2-methyl-3-(piperidin-4-yl)propyl)propanamide which was used in next step without purification. LRMS m/z (M+H) 403.2 found, 403.2 required.

2-chloro-N,N-dimethyl-6-(4-(2-methyl-3-((R)-3,3,3-trifluoro-2-hydroxy-2-(3-methoxyphenyl)-N-methylpropanamido)propyl)piperidin-1-yl)nicotinamide To a solution of (2R)-3,3,3-trifluoro-2-hydroxy-2-(3-methoxyphenyl)-N-methyl-N-(2-methyl-3-(piperidin-4-yl)propyl)propanamide (96 mg, 0.186 mmol) and DIEA (48 mg, 0.37 mmol) in DMF (2.5 mL) was added 6-chloro-5-(dimethylcarbamoyl)pyridin-2-yl trifluoromethanesulfonate (68 mg, 0.2 mmol). The mixture was heated to 80° C. for 2 h. The mixture was directly purified by reverse-phase HPLC (mobile phase: methanol/water (10 mM NH$_4$HCO$_3$)) to afford 2-chloro-N,N-dimethyl-6-(4-(2-methyl-3-((R)-3,3,3-trifluoro-2-hydroxy-2-(3-methoxyphenyl)-N-methylpropanamido)propyl)piperidin-1-yl)nicotinamide. LRMS m/z (M+H) 585.2 found, 585.2 required. The product was resolved by Chiral HPLC (column: AY-H (250*4.6 mm 5 um); mobile phase: n-hexane (0.1% DEA):EtOH 0.1% DEA)=70:30; flow: 1.0 mL/min; temperature: 40° C.) to afford two isomers: 2-chloro-N,N-dimethyl-6-(4-((S)-2-methyl-3-((R)-3,3,3-trifluoro-2-hydroxy-2-(3-methoxyphenyl)-N-methylpropanamido)propyl)piperidin-1-yl)nicotinamide (RT=7.29 min). $^1$H NMR (400 MHz, CDCl$_3$): δ 7.39 (d, J=8.4 Hz, 1H), 7.30 (t, J=8 Hz, 1H), 6.98-6.90 (m, 3H), 6.52 (d, J=8.8 Hz, 1H), 5.76 (br, 1), 4.32-4.26 (m, 2H), 3.79 (s, 3H), 3.56-3.51 (m, 1H), 3.10-2.60 (m, 12H), 1.76-1.73 (m, 4H), 1.29-0.89 (m, 7H) and 2-chloro-N,N-dimethyl-6-(4-((R)-2-methyl-3-((R)-3,3,3-trifluoro-2-hydroxy-2-(3-methoxyphenyl)-N-methylpropanamido)propyl)piperidin-1-yl)nicotinamide (RT=10.24 min). $^1$H NMR (400 MHz, CDCl$_3$): δ 7.39 (d, J=8.4 Hz, 1H), 7.30 (t, J=8 Hz, 1H), 7.03-6.90 (m, 3H), 6.52 (d, J=8.8 Hz, 1H), 5.85 (br, 1), 4.30-4.28 (m, 2H), 3.78 (s, 3H), 3.44-3.39 (m, 1H), 3.21-3.18 (m, 1H), 3.10 (s, 3H), 2.95 (s, 3H), 2.90-2.80 (m, 2H), 2.63 (s, 3H), 1.76-1.73 (m, 4H), 1.29-0.89 (m, 7H). Absolute stereochemistry of each isomer not definitively established.

Using the procedures described in Example 3-1, but replacing ethyl 2-(diethoxyphosphoryl)propanoate with appropriate acetates and/or methylamine with suitable amines, the compounds in Table 3 were prepared.

TABLE 3

| Example | Structure | IUPAC Name | LRMS, found [M + H]+ |
|---|---|---|---|
| 3-1 | 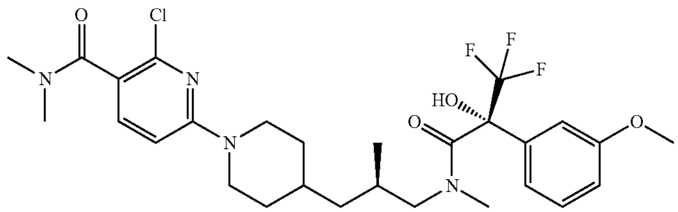 | 2-chloro-N,N-dimethyl-6-(4-((S)-2-methyl-3-((R)-3,3,3-trifluoro-2-hydroxy-2-(3-methoxyphenyl)-N-methylpropanamido)propyl)piperidin-1-yl)nicotinamide | 585.2 |
| 3-2 | 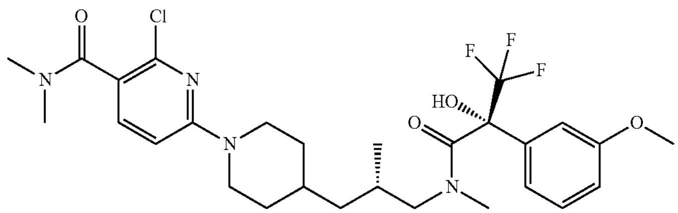 | 2-chloro-N,N-dimethyl-6-(4-((R)-2-methyl-3-((R)-3,3,3-trifluoro-2-hydroxy-2-(3-methoxyphenyl)-N-methylpropanamido)propyl)piperidin-1-yl)nicotinamide | 585.2 |
| 3-3 | 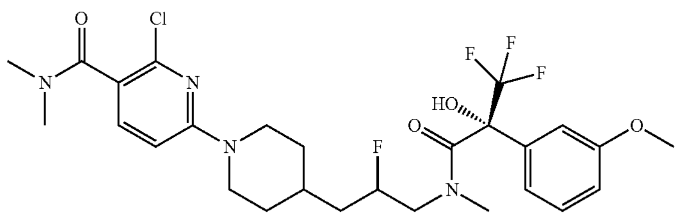 | 2-chloro-6-(4-(2-fluoro-3-((R)-3,3,3-trifluoro-2-hydroxy-2-(3-methoxyphenyl)-N-methylpropanamido)propyl)piperidin-1-yl)-N,N-dimethylnicotinamide | 589.2 |
| 3-4 | 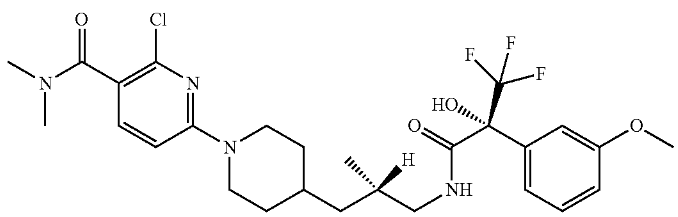 | 2-chloro-N,N-dimethyl-6-(4-((S)-2-methyl-3-((R)-3,3,3-trifluoro-2-hydroxy-2-(3-methoxyphenyl)propanamido)propyl)piperidin-1-yl)nicotinamide | 571.2 |
| 3-5 | 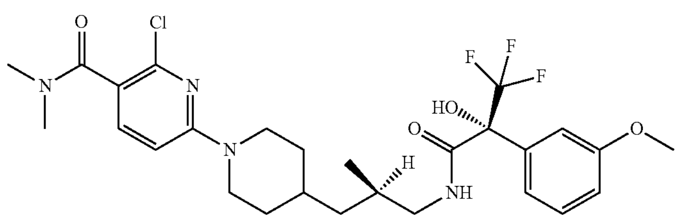 | 2-chloro-N,N-dimethyl-6-(4-((R)-2-methyl-3-((R)-3,3,3-trifluoro-2-hydroxy-2-(3-methoxylpropanamido)propyl)piperidin-1-yl)nicotinamide | 571.2 |
| 3-6 | 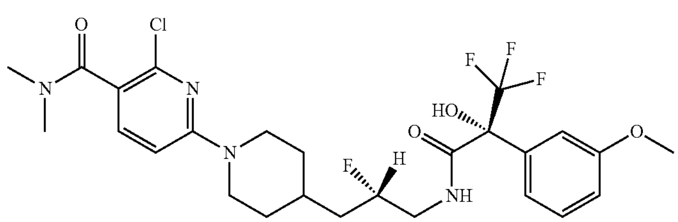 | 2-chloro-6-(4-((S)-2-fluoro-3-((R)-3,3,3-trifluoro-2-hydroxy-2-(3-methoxypropanamido)propyl)piperidin-1-yl)-N,N-dimethylnicotinamide | 575.2 |
| 3-7 | 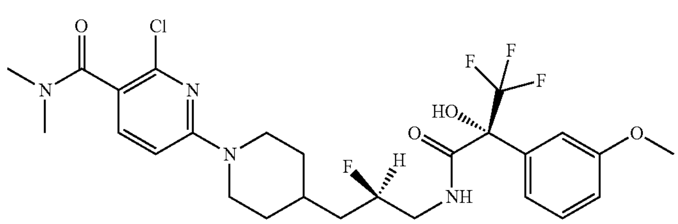 | 2-chloro-6-(4-((R)-2-fluoro-3-((R)-3,3,3-trifluoro-2-hydroxy-2-(3-methoxyphenyl)propanamido)propyl)piperidin-1-yl)-N,N-dimethylnicotinamide | 575.2 |

Example 4-1

(R)-2-chloro-N,N-dimethyl-4-(4-(3-(3,3,3-trifluoro-2-hydroxy-2-(3-methoxyphenyl)-N-methylpropanamido)propyl)piperidin-1-yl)benzamide

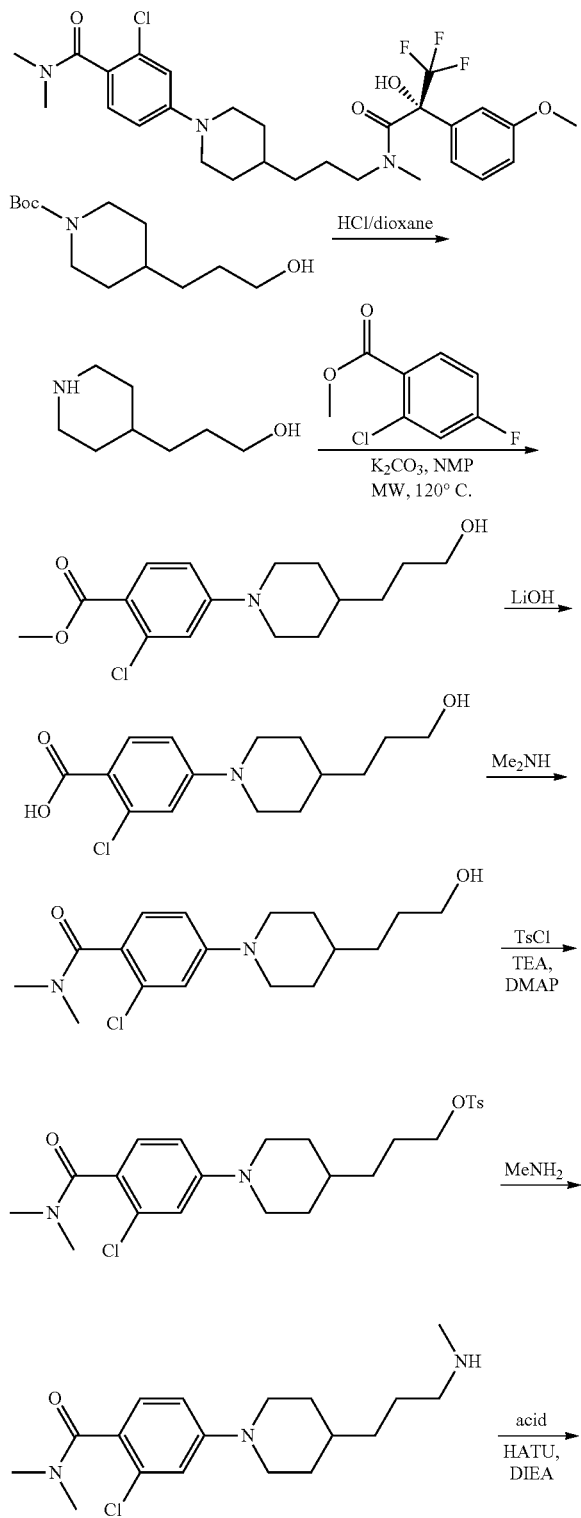

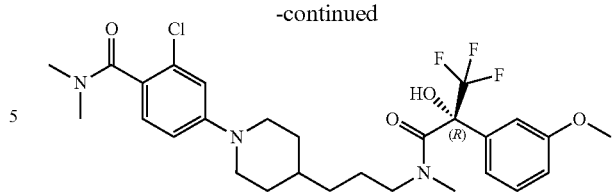

3-(piperidin-4-yl)propan-1-ol

A mixture of tert-butyl 4-(3-hydroxypropyl)piperidine-1-carboxylate (500 mg, 2 mmol) and 4M HCl/dioxane (5 mL, 20 mmol) was stirred at rt for 2 h. The solvent was removed under reduced pressure to give 3-(piperidin-4-yl)propan-1-ol. LRMS m/z (M+H) 144.1 found, 144.1 required.

methyl 2-chloro-4-(4-(3-hydroxypropyl)piperidin-1-yl)benzoate

A mixture of 3-(piperidin-4-yl)propan-1-ol hydrochloride (338 mg, 1.9 mmol), methyl 2-chloro-4-fluorobenzoate (532 mg, 2.8 mmol) and $K_2CO_3$ (780 mg, 5.6 mmol) in NMP (4 mL) was heated to 120° C. in a CEM Microwave Reactor for 1 h. The mixture was diluted with EtOAc (100 mL) and the organic layer was washed with water (10 mL), brine (10 mL), dried over anhydrous $Na_2SO_4$, filtered and concentrated. The crude was purified by reverse-phase HPLC (mobile phase: methanol/water (0.5% TFA)) to give methyl 2-chloro-4-(4-(3-hydroxypropyl)piperidin-1-yl)benzoate. LRMS m/z (M+H) 312.1 found, 312.1 required.

2-chloro-4-(4-(3-hydroxypropyl)piperidin-1-yl)benzoic acid

A mixture of methyl 2-chloro-4-(4-(3-hydroxypropyl)piperidin-1-yl)benzoate (102 mg, 0.33 mmol), 1M aq LiOH (3.3 mL, 3.3 mmol) in THF (3 mL) was stirred at 50° C. overnight. The mixture was adjusted to pH=3.0 with 1N HCl and extracted with DCM/MeOH (10/1, 50 mL×3). The organic layer was washed with brine (20 mL), dried over anhydrous $Na_2SO_4$, filtered and concentrated to give 2-chloro-4-(4-(3-hydroxypropyl)piperidin-1-yl)benzoic acid, which was used in next step without purification. LRMS m/z (M+H) 298.1 found, 298.1 required.

2-chloro-4-(4-(3-hydroxypropyl)piperidin-1-yl)-N,N-dimethylbenzamide

A mixture of 2-chloro-4-(4-(3-hydroxypropyl)piperidin-1-yl)benzoic acid (88 mg, 0.3 mmol). dimethylamine hydrochloride (49 mg, 0.6 mmol), HATU (169 mg, 0.45 mmol) and DIEA (58 mg, 0.45 mmol) in DMF (3 mL) was stirred at rt overnight. The crude mixture was directly purified by reverse-phase HPLC (mobile phase: methanol/water (10 mM $NH_4HCO_3$)) to give 2-chloro-4-(4-(3-hydroxypropyl)piperidin-1-yl)-N,N-dimethylbenzamide. LRMS m/z (M+H) 325.1 found, 325.2 required.

3-(1-(3-chloro-4-(dimethylcarbamoyl)phenyl)piperidin-4-yl)propyl 4-methylbenzenesulfonate To a solution of 2-chloro-4-(4-(3-hydroxypropyl)piperidin-1-yl)-N,N-dimethylbenzamide (58 mg, 0.18 mmol), triethylamine (56 mg, 0.55 mmol) and DMAP (22 mg, 0.18 mmol) in DCM (2 mL) at room temperature was added 4-methylbenzene-1-sulfonyl chloride (53 mg, 0.28 mmol). The resulting mixture was stirred overnight and DCM was removed. The residue was dissolved with EtOAc (100 mL) and the organic layer was washed with 10% citric acid (10 mL), saturated NaHCO$_3$ (10 mL), brine (10 mL), dried over anhydrous Na$_2$SO$_4$, filtered and concentrated to give 3-(1-(3-chloro-4-(dimethylcarbamoyl)phenyl)piperidin-4-yl)propyl 4-methylbenzenesulfonate. LRMS m/z (M+H) 479.1 found, 479.2 required.

2-chloro-N,N-dimethyl-4-(4-(3-(methylamino)propyl)piperidin-1-yl)benzamide

A mixture of 3-(1-(3-chloro-4-(dimethylcarbamoyl)phenyl)piperidin-4-yl)propyl 4-methylbenzenesulfonate (67 mg, 0.14 mmol) and methylamine (2 mL, 4 mmol, 2M in THF) was sealed and heated to 60° C. overnight. The mixture was diluted with EtOAc (50 mL) and the organic layer was washed with saturated NaHCO$_3$ (10 mL), brine (10 mL), dried over anhydrous Na$_2$SO$_4$, filtered and concentrated to give 2-chloro-N,N-dimethyl-4-(4-(3-(methylamino)propyl)piperidin-1-yl)benzamide which was used in next step directly. LRMS m/z (M+H) 338.3 found, 338.2 required.

(R)-2-chloro-N,N-dimethyl-4-(4-(3-(3,3,3-trifluoro-2-hydroxy-2-(3-methoxyphenyl)-N-methylpropanamido)propyl)piperidin-1-yl)benzamide A mixture of 2-chloro-N,N-dimethyl-4-(4-(3-(methylamino)propyl)piperidin-1-yl)benzamide (10 mg, 0.030 mmol), (R)-3,3,3-trifluoro-2-hydroxy-2-(3-methoxyphenyl)propanoic acid (11 mg, 0.044 mmol), HATU (17 mg, 0.044 mmol) and DIEA (6 mg, 0.46 mmol) in DMF (1 mL) was stirred at rt for 2 h. The crude product was directly purified by reverse-phase HPLC (mobile phase: methanol/water (10 mM NH$_4$HCO$_3$)) to give (R)-2-chloro-N,N-dimethyl-4-(4-(3-(3,3,3-trifluoro-2-hydroxy-2-(3-methoxyphenyl)-N-methylpropanamido)propyl)piperidin-1-yl)benzamide. LRMS m/z (M+H) 570.2 found, 570.2 required.

Using the procedure described in example 4-1, but replacing (R)-3,3,3-trifluoro-2-hydroxy-2-(3-methoxyphenyl)propanoic acid with the appropriate acid at last step, and/or replacing dimethylamine hydrochloride with an appropriate amine in the fourth step and/or replacing tert-butyl 4-(3-hydroxypropyl)piperidine-1-carboxylate with the appropriate carboxylate in the first step the examples in Table 4 were prepared.

TABLE 4

| Example | Structure | IUPAC Name | LRMS, found [M + H]+ |
| --- | --- | --- | --- |
| 4-1 | 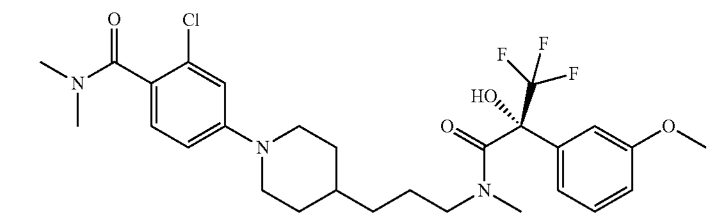 | (R)-2-chloro-N,N-dimethyl-4-(4-(3-(3,3,3-trifluoro-2-hydroxy-2-(3-methoxyphenyl)-N-methylpropanamido)propyl)piperidin-1-yl)benzamide | 570.2 |
| 4-2 | 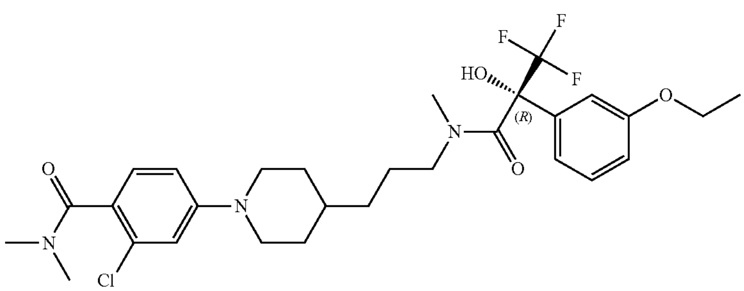 | (R)-2-chloro-4-(4-(3-(2-(3-ethoxyphenyl)-3,3,3-trifluoro-2-hydroxy-N-methylpropanamido)propyl)piperidin-1-yl)-N,N-dimethylbenzamide | 584.2 |
| 4-3 | 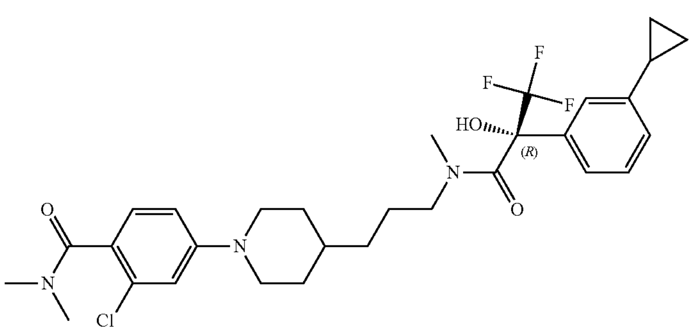 | (R)-2-chloro-4-(4-(3-(2-(3-cyclopropylphenyl)-3,3,3-trifluoro-2-hydroxy-N-methylpropanamido)propyl)piperidin-1-yl)-N,N-dimethylbenzamide | 580.2 |

TABLE 4-continued

| Example | Structure | IUPAC Name | LRMS, found [M + H]+ |
|---|---|---|---|
| 4-4 | 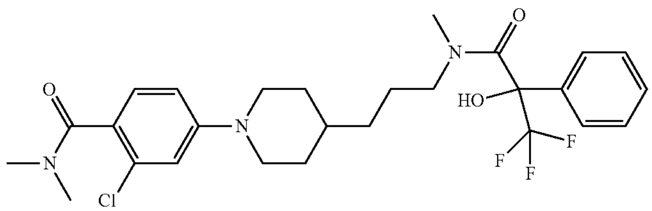 [SMILES: CN(C)C(=O)c1ccc(N2CCC(CCCN(C)C(=O)C(O)(c3ccccc3)C(F)(F)F)CC2)cc1Cl] | 2-chloro-N,N-dimethyl-4-(4-(3-(3,3,3-trifluoro-2-hydroxy-N-methyl-2-phenylpropanamido)propyl)piperidin-1-yl)benzamide | 540.2 |
| 4-5 | 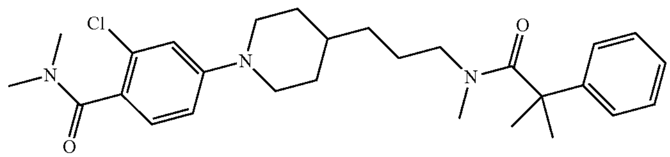 [SMILES: CN(C)C(=O)c1ccc(N2CCC(CCCN(C)C(=O)C(C)(C)c3ccccc3)CC2)cc1Cl] | 2-chloro-4-(4-(3-(N,2-dimethyl-2-phenylpropanamido)propyl)piperidin-1-yl)-N,N-dimethylbenzamide | 484.3 |
| 4-6 | 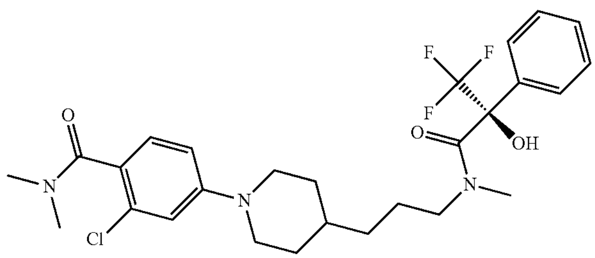 | 2-chloro-N,N-dimethyl-4-(4-(3-(3,3,3-trifluoro-2-hydroxy-N-methyl-2-phenylpropanamido)propyl)piperidin-1-yl)benzamide | 540.2 |
| 4-7 | 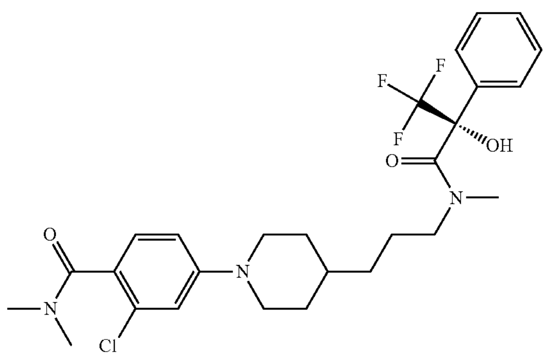 | 2-chloro-N,N-dimethyl-4-(4-(3-(3,3,3-trifluoro-2-hydroxy-N-methyl-2-phenylpropanamido)propyl)piperidin-1-yl)benzamide | 540.2 |
| 4-8 | 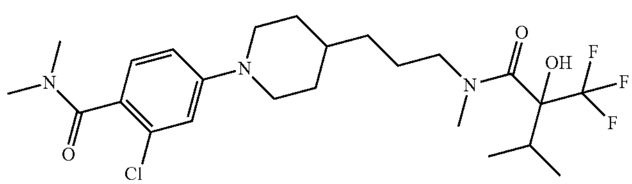 [SMILES: CC(C)C(O)(C(=O)N(C)CCCC1CCN(c2ccc(C(=O)N(C)C)c(Cl)c2)CC1)C(F)(F)F] | 2-chloro-4-(4-(3-(2-hydroxy-N,3-dimethyl-2-(trifluoromethyl)butanamido)propyl)piperidin-1-yl)-N,N-dimethylbenzamide | 506.2 |
| 4-9 | 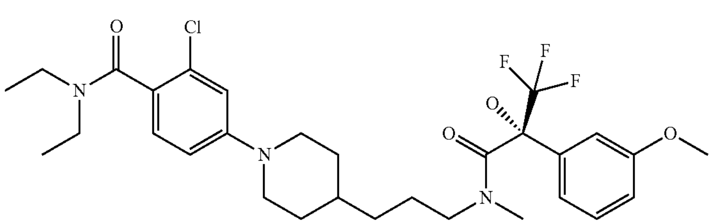 [SMILES: CCN(CC)C(=O)c1ccc(N2CCC(CCCN(C)C(=O)[C@](O)(c3cccc(OC)c3)C(F)(F)F)CC2)cc1Cl] | (R)-2-chloro-N,N-diethyl-4-(4-(3-(3,3,3-trifluoro-2-hydroxy-2-(3-methoxyphenyl)-N-methylpropanamido)propyl)piperidin-1-yl)benzamide | 598.3 |

TABLE 4-continued

| Example | Structure | IUPAC Name | LRMS, found [M + H]+ |
|---|---|---|---|
| 4-10 | 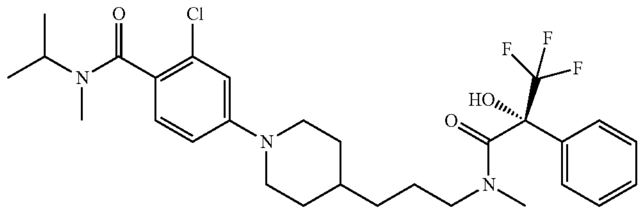 [SMILES: CC(C)N(C)C(=O)c1ccc(N2CCC(CCCN(C)C(=O)[C@](O)(c3ccccc3)C(F)(F)F)CC2)cc1Cl] | (R)-2-chloro-N-isopropyl-N-methyl-4-(4-(3-(3,3,3-trifluoro-2-hydroxy-N-methyl-2-phenylpropanamido)propyl)piperidin-1-yl)benzamide | 568.2 |
| 4-11 | 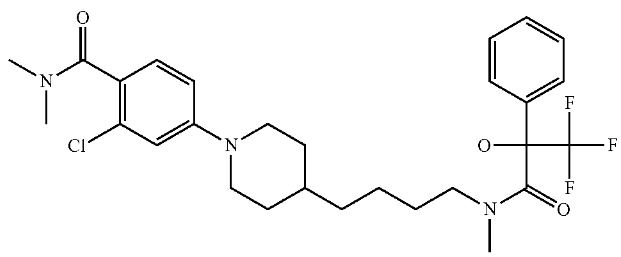 [SMILES: CN(C)C(=O)c1ccc(N2CCC(CCCCN(C)C(=O)C(O)(c3ccccc3)C(F)(F)F)CC2)cc1Cl] | 2-chloro-N,N-dimethyl-4-(4-(4-(3,3,3-trifluoro-2-hydroxy-N-methyl-2-phenylpropanamido)butyl)piperidin-1-yl)benzamide | 554.2 |

Example 5-1

2-chloro-N,N-dimethyl-4-(4-(3-(3,3,3-trifluoro-2-hydroxy-2-phenylpropanamido)propyl)piperidin-1-yl)benzamide

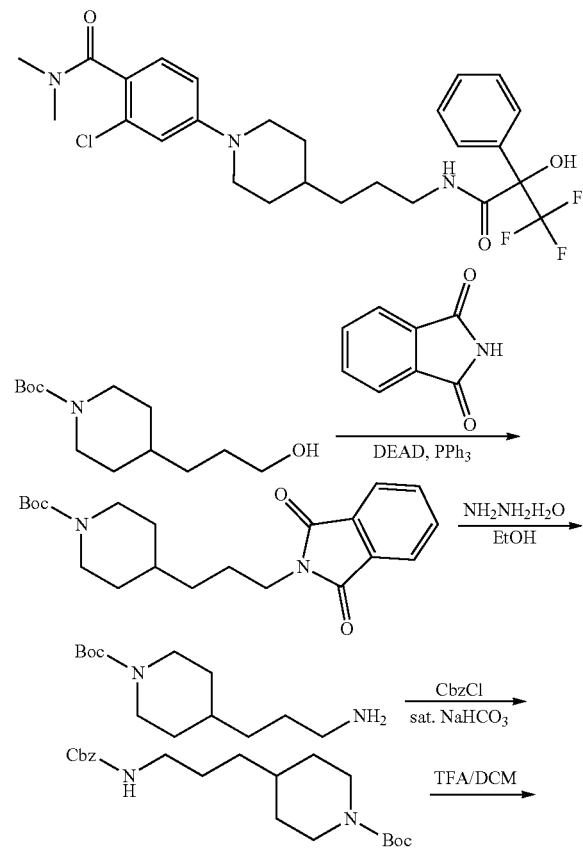

-continued

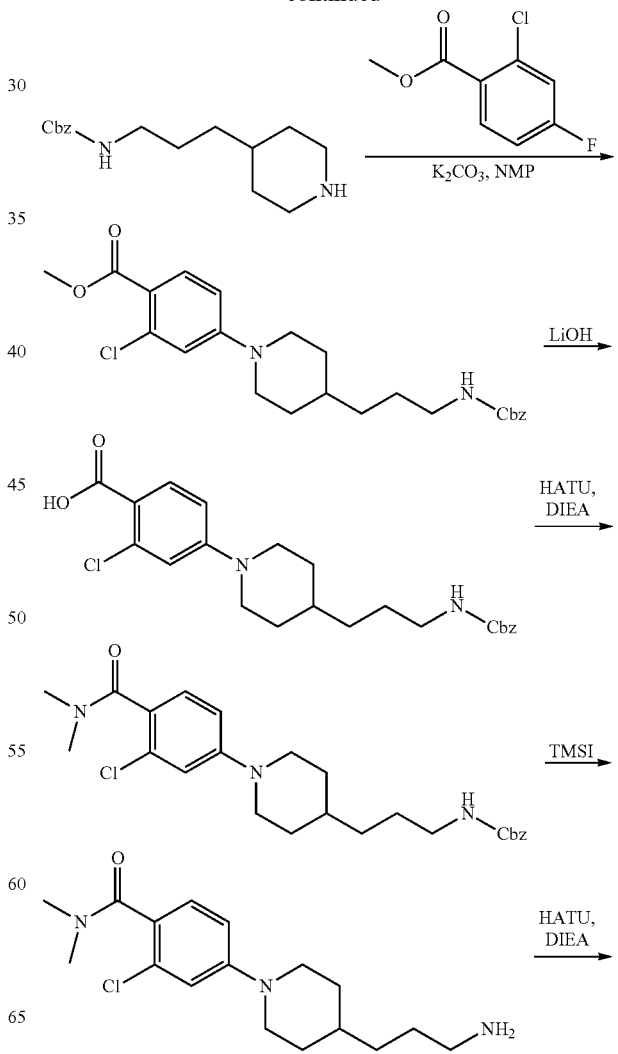

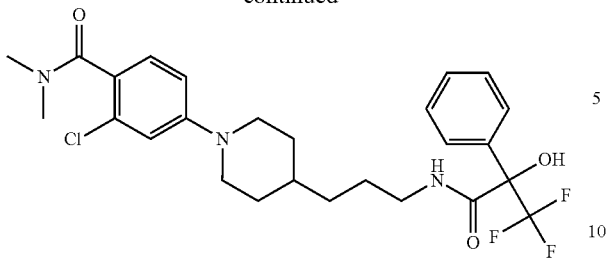

tert-butyl 4-(3-(1,3-dioxoisoindolin-2-yl)propyl)piperidine-1-carboxylate

To a solution of tert-butyl 4-(3-hydroxypropyl)piperidine-1-carboxylate (1.2 g, 4.9 mmol) and isoindoline-1,3-dione (880 mg, 6 mmol) in THF (20 mL) was added PPh$_3$ (1.9 g, 7.3 mmol), DEAD (1.27 g, 7.3 mmol) at rt. The resulting mixture was stirred at rt overnight and diluted with EtOAc (50 mL). The organic layer was washed with brine (5 mL×2) and dried over anhydrous Na$_2$SO$_4$. The organic phase was concentrated and the residue was purified by silica gel chromatography (PE/EtOAc=3/1) to afford tert-butyl 4-(3-(1,3-dioxoisoindolin-2-yl)propyl)piperidine-1l-carboxylate (1.3 g, 70%). LRMS m/z (M+H) 373.3 found, 373.2 required.

tert-butyl 4-(3-aminopropyl)piperidine-1-carboxylate

To a solution of tert-butyl 4-(3-(1,3-dioxoisoindolin-2-yl)propyl)piperidine-1-carboxylate (1.3 g, 3.5 mmol) in EtOH (20 mL) was added 85% hydrazine hydrate (3 mL). The mixture was stirred at 90° C. for 3 h and then the solid was filtered off. The filtrate was concentrated under reduced pressure and the residue was suspended in DCM (50 mL) and filtered. The filtrate was concentrated to give the crude tert-butyl 4-(3-aminopropyl)piperidine-1-carboxylate (800 mg, 95%) which was used in next step directly. LRMS m/z (M+H) 243.2 found, 243.2 required.

tert-butyl 4-(3-(benzyloxycarbonylamino)propyl)piperidine-1-carboxylate

A mixture of tert-butyl 4-(3-aminopropyl)piperidine-1-carboxylate (600 mg, 2.5 mmol), benzyl carbonochloridate (850 mg, 5 mmol) and sat. NaHCO$_3$ (5 mL) in THF (10 mL) was stirred at rt overnight. The solvent was removed and the residue was dissolved with EtOAc (150 mL). The organic phase was washed with brine (10 mL×2), dried over anhydrous Na$_2$SO$_4$, concentrated in vacuo to give tert-butyl 4-(3-(benzyloxycarbonylamino)propyl)piperidine-1-carboxylate (760 mg, 80%) which was used in next step directly. LRMS m/z (M+H) 377.2 found, 377.2 required.

benzyl 3-(piperidin-4-yl)propylcarbamate

A mixture of tert-butyl 4-(3-(benzyloxycarbonylamino)propyl)piperidine-1-carboxylate (760 mg, 2 mmol), TFA (1 mL) and DCM (10 mL) was stirred at rt overnight. The solvent was removed in vacuo to give benzyl 3-(piperidin-4-yl)propylcarbamate (450 mg, 82%) which was used in next step directly. LRMS m/z (M+H) 277.1 found, 277.2 required.

methyl 2-chloro-4-(4-(3-hydroxypropyl)piperidin-1-yl)benzoate

A mixture of benzyl 3-(piperidin-4-yl)propylcarbamate (450 mg, 1.6 mmol), methyl 2-chloro-4-fluorobenzoate (451 mg, 2.4 mmol), and K$_2$CO$_3$ (440 mg, 3.2 mmol) in NMP (4 mL) was heated to 120° C. in a CEM Microwave Reactor for 1 h. The mixture was directly purified by reverse-phase HPLC (mobile phase: methanol/water (10 mM TFA)) to give methyl 2-chloro-4-(4-(3-hydroxypropyl)piperidin-1-yl)benzoate (400 mg, 55%). LRMS m/z (M+H) 445.2 found, 445.2 required.

4-(4-(3-(benzyloxycarbonylamino)propyl)piperidin-1-yl)-2-chlorobenzoic acid

A mixture of methyl 2-chloro-4-(4-(3-hydroxypropyl)piperidin-1-yl)benzoate (400 mg, 0.9 mmol), 1M aq LiOH (4 mL, 4 mmol) in THF (4 mL) was stirred at 50° C. overnight. The mixture was adjusted to pH=3.0 with 1M HCl and extracted with DCM/MeOH (10/1, 50 mL×3). The organic layer was washed with brine (20 mL), dried over anhydrous Na$_2$SO$_4$, filtered and concentrated to give 4-(4-(3-(benzyloxycarbonylamino)propyl)piperidin-1-yl)-2-chlorobenzoic acid (320 mg, 82%) which was used in next step without purification. LRMS m/z (M+H) 431.2 found, 431.2 required.

benzyl 3-(1-(3-chloro-4-(dimethylcarbamoyl)phenyl)piperidin-4-yl)propylcarbamate A mixture of 4-(4-(3-(benzyloxycarbonylamino)propyl)piperidin-1-yl)-2-chlorobenzoic acid (300 mg, 0.7 mmol), dimethylamine hydrochloride (113 mg, 1.4 mmol), HATU (399 mg, 1.05 mmol) and DIEA (180 mg, 1.4 mmol) in DMF (3 mL) was stirred at rt overnight. The crude mixture was directly purified by reverse-phase HPLC (mobile phase: methanol/water (10 mM NH$_4$HCO$_3$)) to give benzyl 3-(1-(3-chloro-4-(dimethylcarbamoyl)phenyl)piperidin-4-yl)propylcarbamate (240 mg, 75%). LRMS m/z (M+H) 458.2 found, 458.2 required.

benzyl 3-(1-(3-chloro-4-(dimethylcarbamoyl)phenyl)piperidin-4-yl)propylcarbamate A mixture of benzyl 3-(1-(3-chloro-4-(dimethylcarbamoyl)phenyl)piperidin-4-yl)propylcarbamate (240 mg, 0.52 mmol). TMSI (208 mg, 1.04 mmol) and DCM (3 mL) was stirred at rt for 2 h. The mixture was quenched with methanol (1 mL) and the solvent was removed under reduced pressure. The residue was purified by reverse-phase HPLC (mobile phase: methanol/water (10 mM NH$_4$HCO$_3$)) to give benzyl 3-(1-(3-chloro-4-(dimethylcarbamoyl)phenyl)piperidin-4-yl)propylcarbamate (100 mg, 59%). LRMS m/z (M+H) 324.3 found, 324.2 required.

2-chloro-N,N-dimethyl-4-(4-(3-(3,3,3-trifluoro-2-hydroxy-2-phenylpropanamido)propyl)piperidin-1-yl)benzamide A mixture of benzyl 3-(1-(3-chloro-4-(dimethylcarbamoyl)phenyl)piperidin-4-yl)propylcarbamate (10 mg, 0.030 mmol). 3,3,3-trifluoro-2-hydroxy-2-phenylpropanoic acid (10 mg, 0.045 mmol), HATU (17 mg, 0.045 mmol) and DIEA (6 mg, 0.46 mmol) in DMF (1 mL) was stirred at rt for 2 h. The crude product was directly purified by reverse-phase HPLC (mobile phase: methanol/water (10 mM NH$_4$HCO$_3$)) to give (2-chloro-N,N-dimethyl-4-(4-(3-(3,3,3-trifluoro-2-hydroxy-2-phenylpropanamido)propyl)piperidin-1-yl)benzamide (5.6 mg, 34%). LRMS m/z (M+H) 526.2 found, 526.2 required.

Using the procedure described in example 5-1, but replacing 3,3,3-trifluoro-2-hydroxy-2-phenylpropanoic acid with the appropriate acylating group at last step or replacing methyl 2-chloro-4-fluorobenzoate with methyl 2-chloro-6-(trifluoromethylsulfonyloxy)nicotinate at the fifth step, the examples in Table 5 were prepared.

TABLE 5

| Example | Structure | IUPAC Name | LRMS, found [M + H]+ |
|---|---|---|---|
| 5-1 | 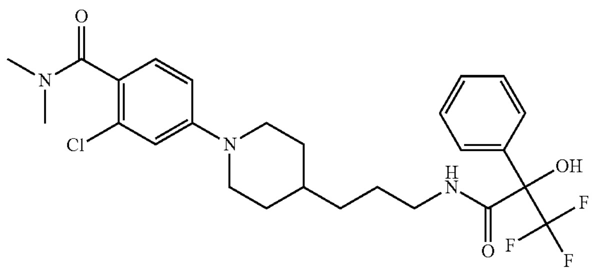 [SMILES: CN(C)C(=O)c1ccc(N2CCC(CCCNC(=O)C(O)(c3ccccc3)C(F)(F)F)CC2)cc1Cl] | 2-chloro-N,N-dimethyl-4-(4-(3-(3,3,3-trifluoro-2-hydroxy-2-phenylpropanamido)propyl)piperidin-1-yl)benzamide | 526.2 |
| 5-2 | 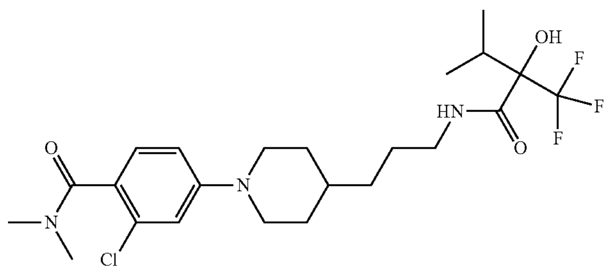 [SMILES: CC(C)C(O)(C(=O)NCCCC1CCN(c2ccc(C(=O)N(C)C)c(Cl)c2)CC1)C(F)(F)F] | 2-chloro-4-(4-(3-(2-hydroxy-3-methyl-2-(trifluoromethyl)butanamido)propyl)piperidin-1-yl)-N,N-dimethylbenzamide | 492.1 |
| 5-3 | 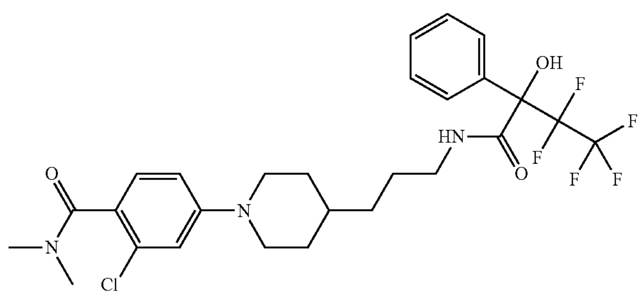 [SMILES: CN(C)C(=O)c1ccc(N2CCC(CCCNC(=O)C(O)(c3ccccc3)C(F)(F)C(F)(F)F)CC2)cc1Cl] | 2-chloro-N,N-dimethyl-4-(4-(3-(3,3,4,4,4-pentafluoro-2-hydroxy-2-phenylbutanamido)propyl)piperidin-1-yl)benzamide | 576.2 |
| 5-4 | 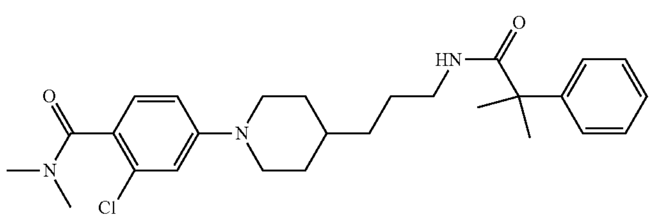 [SMILES: CN(C)C(=O)c1ccc(N2CCC(CCCNC(=O)C(C)(C)c3ccccc3)CC2)cc1Cl] | 2-chloro-N,N-dimethyl-4-(4-(3-(2-methyl-2-phenylpropanamido)propyl)piperidin-1-yl)benzamide | 470.3 |
| 5-5 | 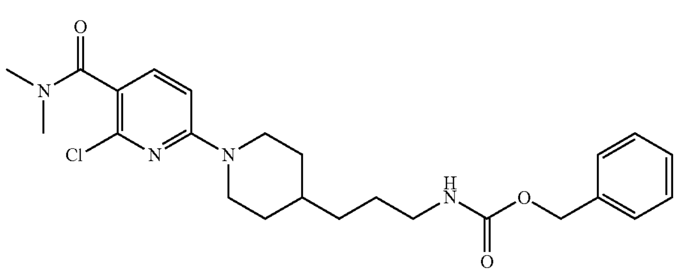 [SMILES: CN(C)C(=O)c1ccc(N2CCC(CCCNC(=O)OCc3ccccc3)CC2)nc1Cl] | benzyl 3-(1-(6-chloro-5-(dimethylcarbamoyl)pyridin-2-yl)piperidin-4-yl)propylcarbamate | 459.2 |

TABLE 5-continued

| Example | Structure | IUPAC Name | LRMS, found [M + H]+ |
|---|---|---|---|
| 5-6 | 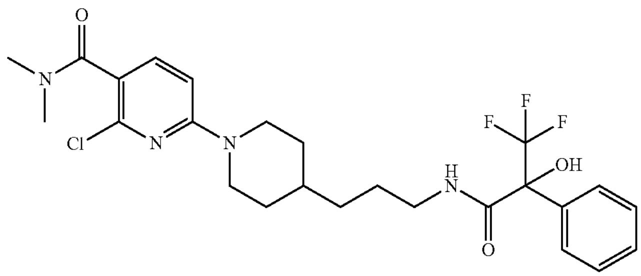 [SMILES: CN(C)C(=O)c1ccc(N2CCC(CCCNC(=O)C(O)(c3ccccc3)C(F)(F)F)CC2)nc1Cl] | 2-chloro-N,N-dimethyl-6-(4-(3-(3,3,3-trifluoro-2-hydroxy-2-phenylpropanamido)propyl)piperidin-1-yl)nicotinamide | 527.2 |
| 5-7 | 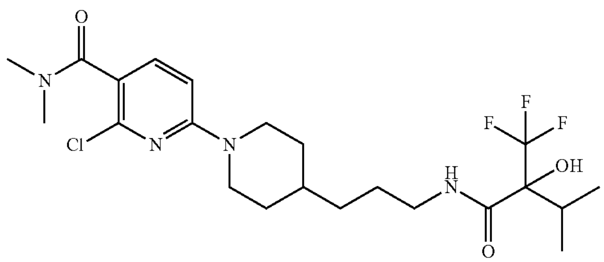 [SMILES: CC(C)C(O)(C(=O)NCCCC1CCN(c2ccc(C(=O)N(C)C)c(Cl)n2)CC1)C(F)(F)F] | 2-chloro-6-(4-(3-(2-hydroxy-3-methyl-2-(trifluoromethyl)butanamido)propyl)piperidin-1-yl)-N,N-dimethylnicotinamide | 493.1 |
| 5-8 | 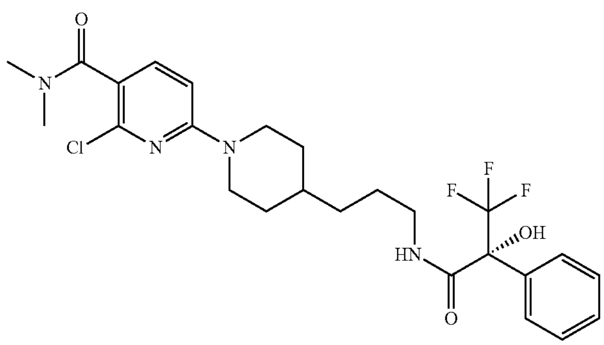 [SMILES: CN(C)C(=O)c1ccc(N2CCC(CCCNC(=O)[C@](O)(c3ccccc3)C(F)(F)F)CC2)nc1Cl] | (R)-2-chloro-N,N-dimethyl-6-(4-(3-(3,3,3-trifluoro-2-hydroxy-2-phenylpropanamido)propyl)piperidin-1-yl)nicotinamide | 527.2 |
| 5-9 | 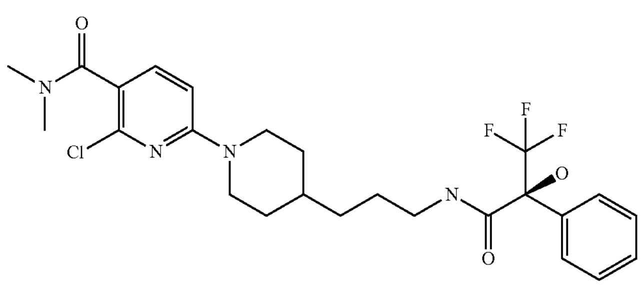 [SMILES: CN(C)C(=O)c1ccc(N2CCC(CCCNC(=O)[C@@](O)(c3ccccc3)C(F)(F)F)CC2)nc1Cl] | (S)-2-chloro-N,N-dimethyl-6-(4-(3-(3,3,3-trifluoro-2-hydroxy-2-phenylpropanamido)propyl)piperidin-1-yl)nicotinamide | 527.2 |
| 5-10 | 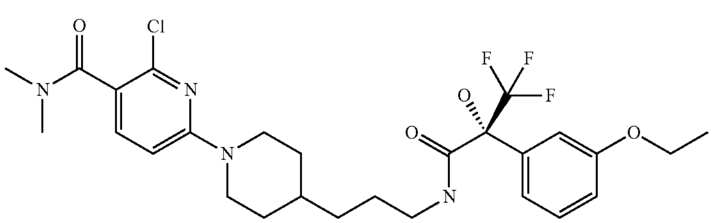 [SMILES: CCOc1cccc([C@@](O)(C(=O)NCCCC2CCN(c3ccc(C(=O)N(C)C)c(Cl)n3)CC2)C(F)(F)F)c1] | (R)-2-chloro-6-(4-(3-(2-(3-ethoxyphenyl)-3,3,3-trifluoro-2-hydroxypropanamido)propyl)piperidin-1-yl)-N,N-dimethylnicotinamide | 571.2 |

TABLE 5-continued

| Example | Structure | IUPAC Name | LRMS, found [M + H]+ |
|---|---|---|---|
| 5-11 | 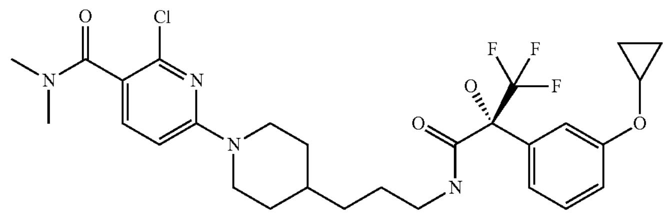 [SMILES: CN(C)C(=O)c1ccc(N2CCC(CCCNC(=O)[C@](O)(c3cccc(OC4CC4)c3)C(F)(F)F)CC2)nc1Cl] | (R)-2-chloro-6-(4-(3-(2-(3-cyclopropoxyphenyl)-3,3,3-trifluoro-2-hydroxypropanamido)propyl)piperidin-1-yl)-N,N-dimethylnicotinamide | 583.2 |
| 5-12 | 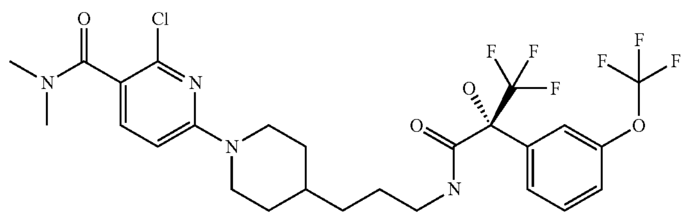 [SMILES: CN(C)C(=O)c1ccc(N2CCC(CCCNC(=O)[C@](O)(c3cccc(OC(F)(F)F)c3)C(F)(F)F)CC2)nc1Cl] | (R)-2-chloro-N,N-dimethyl-6-(4-(3-(3,3,3-trifluoro-2-hydroxy-2-(3-(trifluoromethoxy)phenyl)propanamido)propyl)piperidin-1-yl)nicotinamide | 611.2 |
| 5-13 | 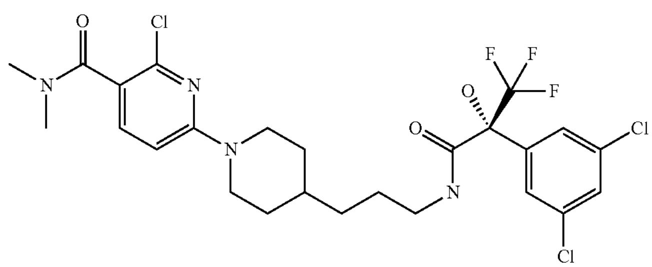 [SMILES: CN(C)C(=O)c1ccc(N2CCC(CCCNC(=O)[C@](O)(c3cc(Cl)cc(Cl)c3)C(F)(F)F)CC2)nc1Cl] | (R)-2-chloro-6-(4-(3-(2-(3,5-dichlorophenyl)-3,3,3-trifluoro-2-hydroxypropanamido)propyl)piperidin-1-yl)-N,N-dimethylnicotinamide | 595.1 |
| 5-14 | 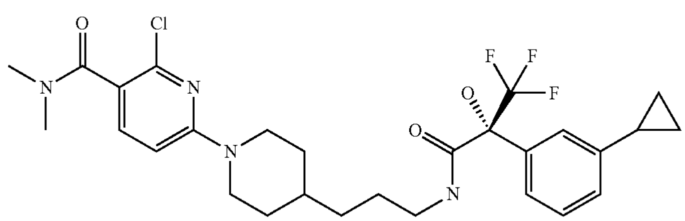 [SMILES: CN(C)C(=O)c1ccc(N2CCC(CCCNC(=O)[C@](O)(c3cccc(C4CC4)c3)C(F)(F)F)CC2)nc1Cl] | (R)-2-chloro-6-(4-(3-(2-(3-cyclopropylphenyl)-3,3,3-trifluoro-2-hydroxy-propanamido)propyl)piperidin-1-yl)-N,N-dimethylnicotinamide | 567.2 |
| 5-15 | 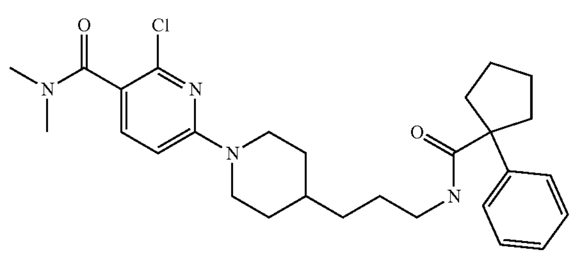 [SMILES: CN(C)C(=O)c1ccc(N2CCC(CCCNC(=O)C3(c4ccccc4)CCCC3)CC2)nc1Cl] | 2-chloro-N,N-dimethyl-6-(4-(3-(1-phenylcyclopentanecarboxamido)propyl)piperidin-1-yl)nicotinamide | 497.3 |
| 5-16 | 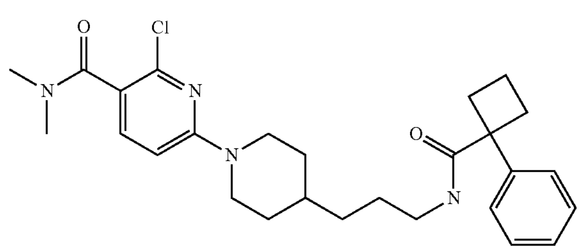 [SMILES: CN(C)C(=O)c1ccc(N2CCC(CCCNC(=O)C3(c4ccccc4)CCC3)CC2)nc1Cl] | 2-chloro-N,N-dimethyl-6-(4-(3-(1-phenylcyclobutanecarboxamido)propyl)piperidin-1-yl)nicotinamide | 483.2 |

TABLE 5-continued

| Example | Structure | IUPAC Name | LRMS, found [M + H]+ |
|---|---|---|---|
| 5-17 | 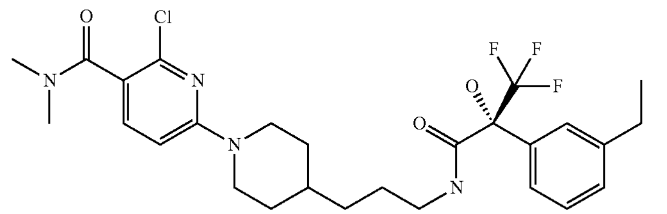 [SMILES: CCc1cccc([C@@](O)(C(=O)NCCCC2CCN(c3ccc(C(=O)N(C)C)c(Cl)n3)CC2)C(F)(F)F)c1] | (R)-2-chloro-6-(4-(3-(2-(3-ethylphenyl)-3,3,3-trifluoro-2-hydroxypropanamido)propyl)piperidin-1-yl)-N,N-dimethylnicotinamide | 555.2 |
| 5-18 | 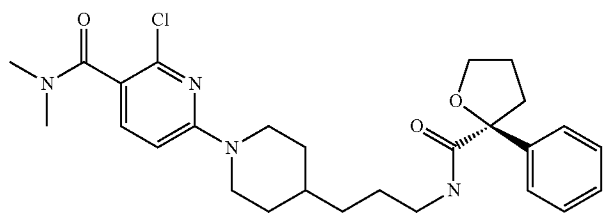 [SMILES: CN(C)C(=O)c1ccc(N2CCC(CCCNC(=O)[C@@]3(c4ccccc4)CCCO3)CC2)nc1Cl] | (S)-2-chloro-N,N-dimethyl-6-(4-(3-(2-phenyltetrahydrofuran-2-carboxamido)propyl)piperidin-1-yl)nicotinamide | 499.1 |
| 5-19 | 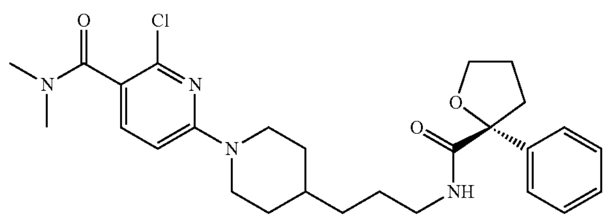 [SMILES: CN(C)C(=O)c1ccc(N2CCC(CCCNC(=O)[C@]3(c4ccccc4)CCCO3)CC2)nc1Cl] | (R)-2-chloro-N,N-dimethyl-6-(4-(3-(2-phenyltetrahydrofuran-2-carboxamido)propyl)piperidin-1-yl)nicotinamide | 499.1 |
| 5-20 | 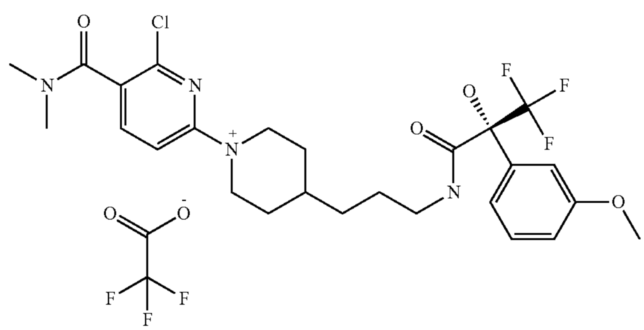 | (R)-2-chloro-N,N-dimethyl-6-(4-(3-(3,3,3-trifluoro-2-hydroxy-2-(3-methoxyphenyl)propanamido)propyl)piperidin-1-yl)nicotinamide | 557.2 |
| 5-21 | 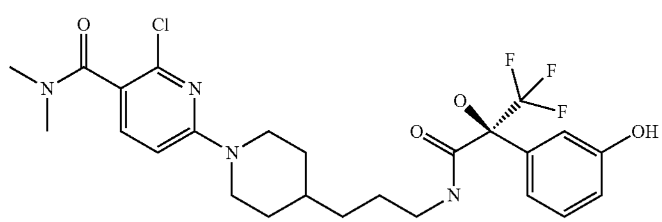 [SMILES: CN(C)C(=O)c1ccc(N2CCC(CCCNC(=O)[C@@](O)(c3cccc(O)c3)C(F)(F)F)CC2)nc1Cl] | (S)-2-chloro-N,N-dimethyl-6-(4-(3-(3,3,3-trifluoro-2-hydroxy-2-(3-hydroxyphenyl)propanamido)propyl)piperidin-1-yl)nicotinamide | 543.2 |
| 5-22 | 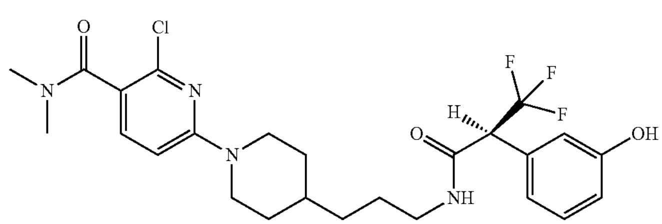 [SMILES: CN(C)C(=O)c1ccc(N2CCC(CCCNC(=O)[C@H](c3cccc(O)c3)C(F)(F)F)CC2)nc1Cl] | (R)-2-chloro-N,N-dimethyl-6-(4-(3-(3,3,3-trifluoro-2-hydroxy-2-(3-hydroxyphenyl)propanamido)propyl)piperidin-1-yl)nicotinamide | 543.2 |

TABLE 5-continued

| Example | Structure | IUPAC Name | LRMS, found [M + H]+ |
|---|---|---|---|
| 5-23 | 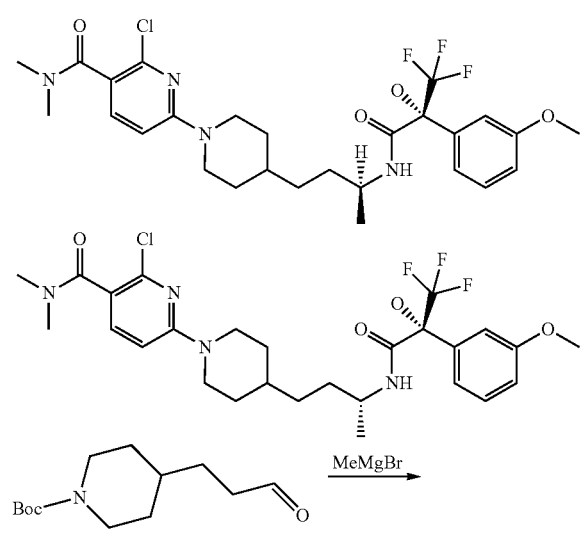 | (R)-2-chloro-N,N-dimethyl-6-(4-(3-(3,3,3-trifluoro-2-hydroxy-2-(3-methoxyphenyl)propanamido)propyl)piperidin-1-yl)nicotinamide | 557.2 |

Example 6-1, 6-2

2-chloro-N,N-dimethyl-6-(4-((S)-3-((R)-3,3,3-trifluoro-2-hydroxy-2-(3-methoxyphenyl)propanamido)butyl)piperidin-1-yl)nicotinamide and 2-chloro-N,N-dimethyl-6-(4-((R)-3-((R)-3,3,3-trifluoro-2-hydroxy-2-(3-methoxyphenyl)propanamido)butyl)piperidin-1-yl)nicotinamide

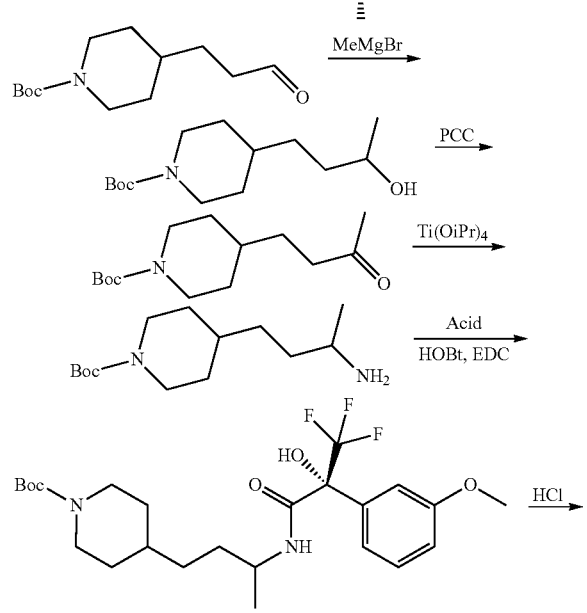

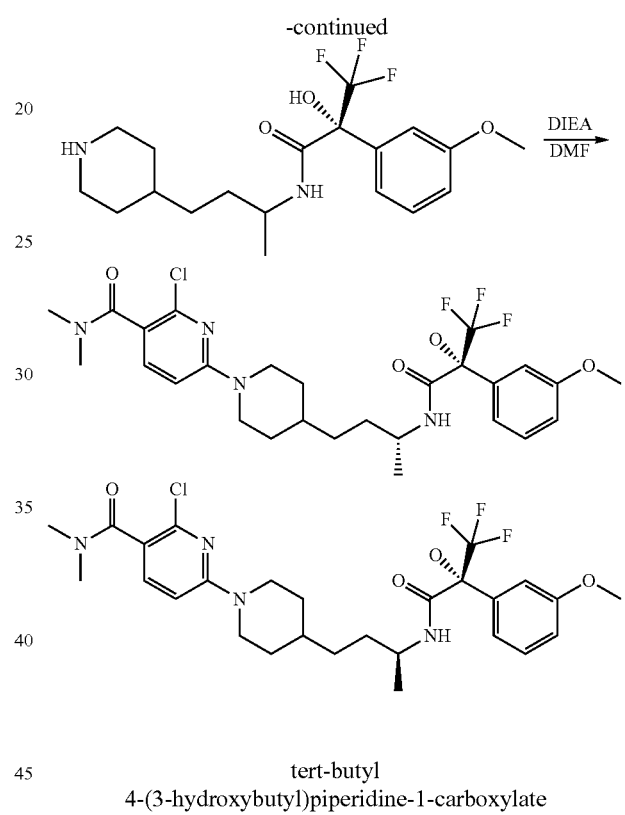

tert-butyl 4-(3-hydroxybutyl)piperidine-1-carboxylate

To a solution of tert-butyl 4-(3-oxopropyl)piperidine-1-carboxylate (1.3 g, 5.4 mmol) in THF (5 mL) at −78° C. was added MeMgBr (8 mL, 8 mmol, 1M in THF). The mixture was stirred for 2 h at −78° C., then quenched with aq. NH$_4$Cl (5 mL), extracted with EtOAc (3×20 mL). The organic layer was dried over anhydrous Na$_2$SO$_4$, concentrated and purified by column chromatography (silica gel: 300-400 mesh, PE/EtOAc=8/1) to afford tert-butyl 4-(3-hydroxybutyl)piperidine-1-carboxylate (1 g, 72.5%). LRMS m/z (M-55) 202.2 found, 202.2 required.

tert-butyl 4-(3-oxobutyl)piperidine-1-carboxylate

A mixture of tert-butyl 4-(3-hydroxybutyl)piperidine-1-carboxylate (1 g, 3.9 mmol) and PCC (1.7 g, 7.8 mmol) in DCM (10 mL) was stirred at rt for 2 h. Then the mixture was concentrated and purified by column chromatography (silica gel: 300-400 mesh, PE/EtOAc=6/1) to afford tert-butyl 4-(3-oxobutyl)piperidine-1-carboxylate (620 mg, 62%). LRMS m/z (M-55) 200.2 found, 200.2 required.

tert-butyl 4-(3-aminobutyl)piperidine-1-carboxylate

A mixture of tert-butyl 4-(3-oxobutyl)piperidine-1-carboxylate (200 mg, 0.8 mmol) and ammonia (4 mL, 8.0 mmol, 2M in dioxane), titanium (IV) isopropoxide (680 mg, 2.4 mmol) in DCE (5 mL) was stirred at rt overnight. Then NaBH(CN)$_3$ (150 mg, 2.4 mmol) was added to the reaction mixture, and the resulting mixture was stirred for another 1 h. The solvent was evaporated under reduced pressure and the residue was purified by reverse-phase HPLC (Mobile phase: methanol/water (10 mM NH$_4$HCO$_3$)) to give tert-butyl 4-(3-aminobutyl)piperidine-1-carboxylate (114 mg, 56%). LRMS m/z (M+H) 257.2 found, 257.2 required.

tert-butyl 4-(3-((R)-3,3,3-trifluoro-2-hydroxy-2-(3-methoxyphenyl)propanamido)butyl)piperidine-1-carboxylate To a solution of tert-butyl 4-(3-aminobutyl)piperidine-1-carboxylate (40 mg, 0.156 mmol) in DMF (0.5 mL) was added (R)-3,3,3-trifluoro-2-hydroxy-2-(3-methoxyphenyl)propanoic acid (47 mg, 0.19 mmol), HOBT (29 mg, 0.19 mmol), EDC (36 mg, 0.19 mmol) and DIEA (0.082 ml, 0.47 mmol). After stirring overnight at 30 C, the mixture was purified by reverse-phase HPLC (Mobile phase: methanol/water (10 mM NH$_4$HCO$_3$)) to afford tert-butyl 4-(3-((R)-3,3,3-trifluoro-2-hydroxy-2-(3-methoxyphenyl)propanamido)butyl)piperidine-1-carboxylate (30 mg, 39% yield). LRMS m/z (M-100) 388.1 found, 388.1 required.

(2R)-3,3,3-trifluoro-2-hydroxy-2-(3-methoxyphenyl)-N-(4-(piperidin-4-yl)butan-2-yl)propanamide A mixture of tert-butyl 4-(3-((R)-3,3,3-trifluoro-2-hydroxy-2-(3-methoxyphenyl)propanamido)butyl)piperidine-1-carboxylate (30 mg, 0.06 mmol) and 4M HCl/dioxane (0.15 mL) in DCM (1 mL) was stirred at rt for 1 h. The mixture was concentrated in vacuo to give (2R)-3,3,3-trifluoro-2-hydroxy-2-(3-methoxyphenyl)-N-(4-(piperidin-4-yl)butan-2-yl)propanamide hydrochloric acid salt (22 mg, 92%). LRMS m/z (M+H) 388.1 found, 388.1 required.

2-chloro-N,N-dimethyl-6-(4-((S)-3-((R)-3,3,3-trifluoro-2-hydroxy-2-(3-methoxyphenyl)propanamido)butyl)piperidin-1-yl)nicotinamide and 2-chloro-N,N-dimethyl-6-(4-((R)-3-((R)-3,3,3-trifluoro-2-hydroxy-2-(3-methoxyphenyl)propanamido)butyl)piperidin-1-yl)nicotinamide A mixture of (2R)-3,3,3-trifluoro-2-hydroxy-2-(3-methoxyphenyl)-N-(4-(piperidin-4-yl)butan-2-yl)propanamide (22 mg, 0.057 mmol), 6-chloro-5-(dimethylcarbamoyl)pyridin-2-yl trifluoromethanesulfonate (19 mg, 0.057 mmol) and DIEA (8 mg, 0.057 mmol) in DMF (1 mL) was stirred at 60° C. for 1 h. Then the mixture was directly purified by Prep-HPLC (Mobile phase: methanol/water (10 mM NH$_4$HCO$_3$)) to afford 2-chloro-N,N-dimethyl-6-(4-((S)-3-((R)-3,3,3-trifluoro-2-hydroxy-2-(3-methoxyphenyl)propanamido)butyl)piperidin-1-yl)nicotinamide (10 mg, 31%, RT=1.94 min) and 2-chloro-N,N-dimethyl-6-(4-((R)-3-((R)-3,3,3-trifluoro-2-hydroxy-2-(3-methoxyphenyl)propanamido)butyl)piperidin-1-yl)nicotinamide (8 mg, 0.014 mmol, 24.74% yield, RT=1.98 min). LRMS m/z (M+H) 571.1 found, 571.1 required.

Example 7-1

2-chloro-N,N-dimethyl-4-(1-(2-((S)-3,3,3-trifluoro-2-hydroxy-N-methyl-2-phenylpropanamido)ethyl)-6-azaspiro[2.5]octan-6-yl)benzamide

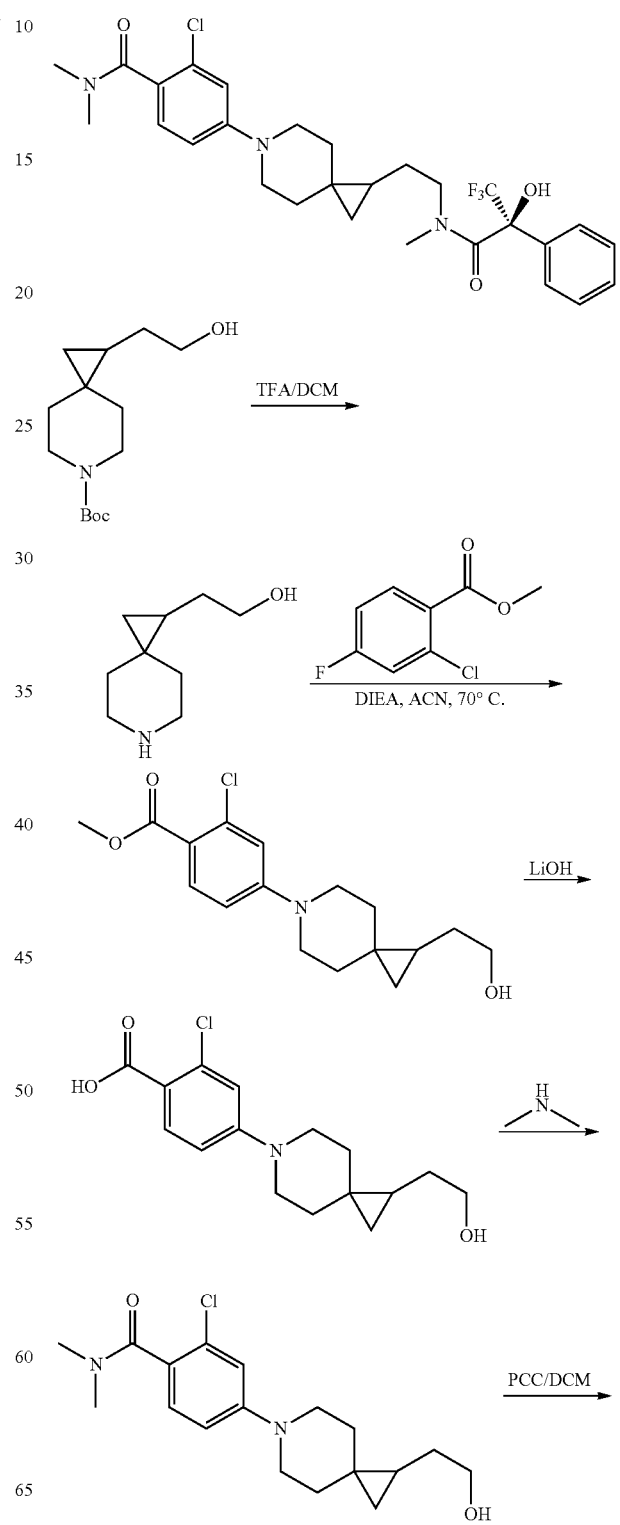

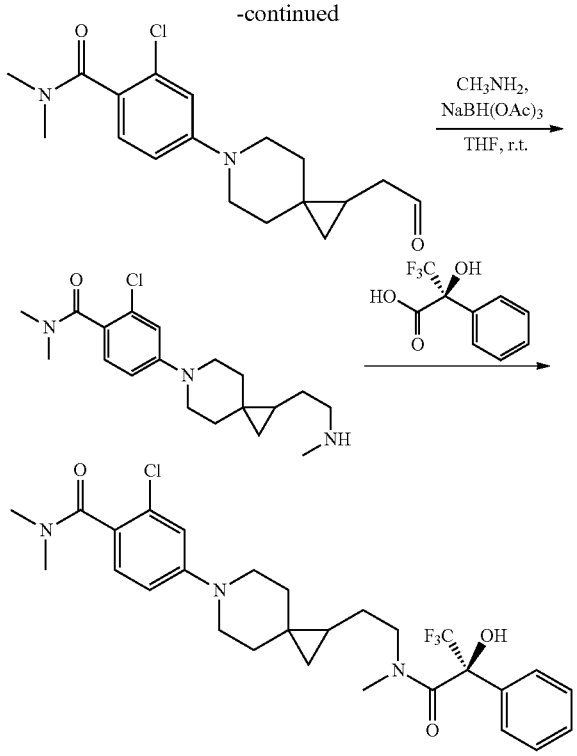

2-(6-azaspiro[2.5]octan-1-yl)ethanol

A mixture of tert-butyl 1-(2-hydroxyethyl)-6-azaspiro[2.5]octane-6-carboxylate (1.5 g, 5.9 mmol) and TFA (2 mL) in DCM (10.0 mL) was stirred at rt for 12 h. The solvent was removed and the residue was dissolved EtOAc (200 mL) and the organic phase was washed with sat. NaHCO$_3$ (30 mL×2) and brine (20 mL), dried over anhydrous Na$_2$SO$_4$, filtered and concentrated in vacuo to give 2-(6-azaspiro[2.5]octan-1-yl)ethanol (810 mg, 89%). LRMS m/z 156.1 found, 156.1 required.

methyl 2-chloro-4-(1-(2-hydroxyethyl)-6-azaspiro[2.5]octan-6-yl)benzoate

A mixture of 2-(6-azaspiro[2.5]octan-1-yl)ethanol (350 mg, 2.26 mmol), methyl 2-chloro-4-fluorobenzoate (510 mg, 2.7 mmol) and DIEA (1.2 mL, 7.2 mmol) in CH$_3$CN (15 mL) was stirred at 70° C. for 5 h. The solvent was removed under reduced pressure and the residue was purified by Prep-TLC (EtOAc/PE=1/1) to get methyl 2-chloro-4-(1-(2-hydroxyethyl)-6-azaspiro[2.5]octan-6-yl)benzoate (385 mg, 53%). LRMS m/z 324.0 found, 324.1 required.

2-chloro-4-(1-(2-hydroxyethyl)-6-azaspiro[2.5]octan-6-yl)benzoic acid

A mixture of methyl 2-chloro-4-(1-(2-hydroxyethyl)-6-azaspiro[2.5]octan-6-yl)benzoate (380 mg, 1.2 mmol) and lithium hydroxide monohydrate (493 mg, 11.8 mmol) in THF/water (1 mL, 1/1) was stirred at rt for 24 h. The mixture was acidified with 2N HCl to pH=3 and extracted with EtOAc (50 mL×3). The organic phase was washed with sat. NaHCO$_3$ (30 mL×2) and brine (20 mL), dried over anhydrous Na$_2$SO$_4$, filtered and concentrated in vacuo to 2-chloro-4-(1-(2-hydroxyethyl)-6-azaspiro[2.5]octan-6-yl)benzoic acid (305 mg, 84%). LRMS m/z 310.0 found, 310.1 required.

2-chloro-4-(1-(2-hydroxyethyl)-6-azaspiro[2.5]octan-6-yl)-N,N-dimethylbenzamide

A mixture of 2-chloro-4-(1-(2-hydroxyethyl)-6-azaspiro[2.5]octan-6-yl)benzoic acid (305 mg, 1.0 mmol), dimethylamine hydrochloride (90 mg, 1.1 mmol), HATU (570 mg, 1.5 mmol) and DIEA (0.83 mL, 5.0 mmol) in DMF (4 mL) was stirred at rt overnight. The mixture was poured into sat. NH$_4$Cl (50 mL) and extracted with EtOAc (50 mL×3). The organic phase was washed with brine (10 mL), dried over anhydrous Na$_2$SO$_4$, filtered and concentrated. The residue was purified by Prep-TLC (EtOAc/PE=4/1) to afford 2-chloro-4-(1-(2-hydroxyethyl)-6-azaspiro[2.5]octan-6-yl)-N,N-dimethylbenzamide (318 mg, 95%). LRMS m/z 337.2 found, 337.2 required.

2-chloro-N,N-dimethyl-4-(1-(2-oxoethyl)-6-azaspiro[2.5]octan-6-yl)benzamide

A mixture of 2-chloro-4-(1-(2-hydroxyethyl)-6-azaspiro[2.5]octan-6-yl)-N,N-dimethylbenzamide (300 mg, 0.89 mmol) and PCC (690 mg, 2.76 mmol) in DCM (15 mL) was stirred at rt for 5 h. The mixture was concentrated under reduced pressure and the residue was directly purified by silica gel chromatography (EtOAc/PE=1/4 to 1/1) to give 2-chloro-N,N-dimethyl-4-(1-(2-oxoethyl)-6-azaspiro[2.5]octan-6-yl)benzamide (90 mg, 30%). LRMS m/z 335.2 found, 335.2 required.

2-chloro-N,N-dimethyl-4-(1-(2-(methylamino)ethyl)-6-azaspiro[2.5]octan-6-yl)benzamide To a mixture of 2-chloro-N,N-dimethyl-4-(1-(2-oxoethyl)-6-azaspiro[2.5]octan-6-yl)benzamide (60 mg, 0.18 mmol) and methylamine (0.9 mL, 1.8 mmol, 2M in THF) in THF (5 mL) was added HOAc (2 drops) at rt. The resulting mixture was then stirred at rt for 5 h before NaBH(OAc)$_3$ (72 mg, 0.36 mmol) was added. The mixture was then allowed to stir for another 5 h and quenched with sat. NaHCO$_3$ (15 mL), extracted with EtOAc (15 mL×6). The organic phase was washed with brine (10 mL), dried over anhydrous Na$_2$SO$_4$, filtered and concentrated. The residue was purified by Prep-TLC (methanol/DCM=6/94) to afford 2-chloro-N,N-dimethyl-4-(1-(2-(methylamino)ethyl)-6-azaspiro[2.5]octan-6-yl)benzamide (32 mg, 51%). LRMS m/z 350.2 found, 350.2 required.

2-chloro-N,N-dimethyl-4-(1-(2-((S)-3,3,3-trifluoro-2-hydroxy-N-methyl-2-phenylpropanamido)ethyl)-6-azaspiro[2.5]octan-6-yl)benzamide A mixture of 2-chloro-N,N-dimethyl-4-(1-(2-(methylamino)ethyl)-6-azaspiro[2.5]octan-6-yl)benzamide (20 mg, 0.057 mmol), (S)-3,3,3-trifluoro-2-hydroxy-2-phenylpropanoic acid (15.0 mg, 0.069 mmol), HATU (35 mg, 0.086 mmol) and DIEA (0.050 mL, 0.29 mmol) in DMF (2 mL) was stirred at rt overnight. The mixture was directly purified by Prep-HPLC (Mobile phase: acetonitrile/water (0.05% TFA)) to afford 2-chloro-N,N-dimethyl-4-(1-(2-((S)-3,3,3-trifluoro-2-hydroxy-N-methyl-2-phenylpropanamido)ethyl)-6-azaspiro[2.5]octan-6-yl)benzamide (24 mg, 75%). LRMS m/z 552.2 found, 552.2 required.

Using the procedure described in Example 7-1, but replacing (S)-3,3,3-trifluoro-2-hydroxy-2-phenylpropanoic acid with (R)-3,3,3-trifluoro-2-hydroxy-2-phenylpropanoic acid at the third step, or replacing tert-butyl 1-(hydroxymethyl)-6-azaspiro[2.5]octane-6-carboxylate with (S)-tert-butyl 1-(hydroxymethyl)-6-azaspiro[2.5]octane-6-carboxylate or (R)-tert-butyl 1-(hydroxymethyl)-6-azaspiro[2.5]octane-6-carboxylate at first step, or replacing methyl 2-chloro-4-fluorobenzoate with methyl 2-chloro-6-(trifluoromethylsulfonyloxy)nicotinate at fifth step, or replacing dimethylamine hydrochloric acid with the appropriate amine at the sixth step, or replacing (S)-3,3,3-trifluoro-2-hydroxy-2-phenylpropanoic acid with the appropriate acid or replacing dimethylamine hydrochloric acid with N-methylpropan-2-amine at the fourth step, replacing methylamine with ammonia dioxane solution at the sixth step and replacing (S)-3,3,3-trifluoro-2-hydroxy-2-phenylpropanoic acid with (R)-3,3,3-trifluoro-2-hydroxy-2-(3-methoxyphenyl)propanoic acid at the last step or methylamine with ammonia dioxane solution at the sixth step and replacing (S)-3,3,3-trifluoro-2-hydroxy-2-phenylpropanoic acid with (R)-3,3,3-trifluoro-2-hydroxy-2-(3-methoxyphenyl)propanoic acid at the last step, or methylamine with ammonia dioxane solution at the sixth step and replacing (S)-3,3,3-trifluoro-2-hydroxy-2-phenylpropanoic acid with (R)-3,3,3-trifluoro-2-hydroxy-2-(3-methoxyphenyl)propanoic acid at the last step, or replacing tert-butyl 1-(2-hydroxyethyl)-6-azaspiro[2.5]octane-6-carboxylate with tert-butyl 1-(3-hydroxypropyl)-6-azaspiro[2.5]octane-6-carboxylate at the first step and replacing (S)-3,3,3-trifluoro-2-hydroxy-2-phenylpropanoic acid with (R)-3,3,3-trifluoro-2-hydroxy-2-phenylpropanoic acid and 2-methyl-2-phenylpropanoic acid at the last step, or replacing tert-butyl 1-(2-hydroxyethyl)-6-azaspiro[2.5]octane-6-carboxylate with tert-butyl 1-(3-hydroxypropyl)-6-azaspiro[2.5]octane-6-carboxylate at the first step, replacing methylamine with ammonia dioxane solution at the sixth step and replacing (S)-3,3,3-trifluoro-2-hydroxy-2-phenylpropanoic acid with (R)-3,3,3-trifluoro-2-hydroxy-2-phenylpropanoic acid and 2-methyl-2-phenylpropanoic acid at last step the examples in Table 7 was prepared.

TABLE 7

| Example | Structure | IUPAC Name | LRMS, found [M + H]+ |
|---|---|---|---|
| 7-1 | 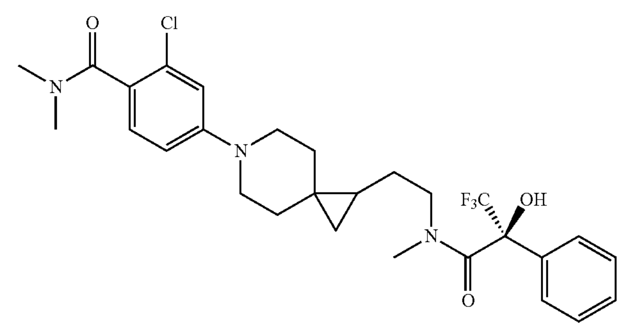 [SMILES: CN(C)C(=O)c1ccc(N2CCC3(CC2)CC3CCN(C)C(=O)[C@@](O)(c2ccccc2)C(F)(F)F)cc1Cl] | 2-chloro-N,N-dimethyl-4-(1-(2-((S)-3,3,3-trifluoro-2-hydroxy-N-methyl-2-phenylpropanamido)ethyl)-6-azaspiro[2.5]octan-6-yl)benzamide | 552.2 |
| 7-2 | 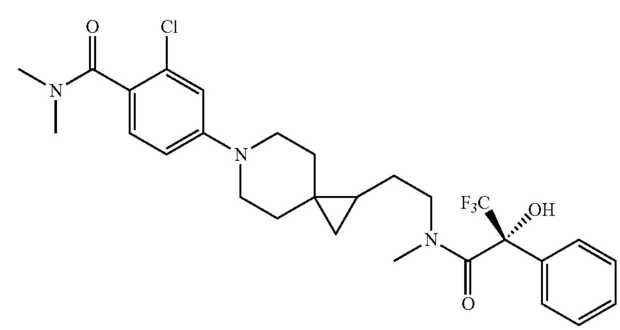 [SMILES: CN(C)C(=O)c1ccc(N2CCC3(CC2)CC3CCN(C)C(=O)[C@](O)(c2ccccc2)C(F)(F)F)cc1Cl] | 2-chloro-N,N-dimethyl-4-(1-(2-((R)-3,3,3-trifluoro-2-hydroxy-N-methyl-2-phenylpropanamido)ethyl)-6-azaspiro[2.5]octan-6-yl)benzamide | 552.2 |
| 7-3 | 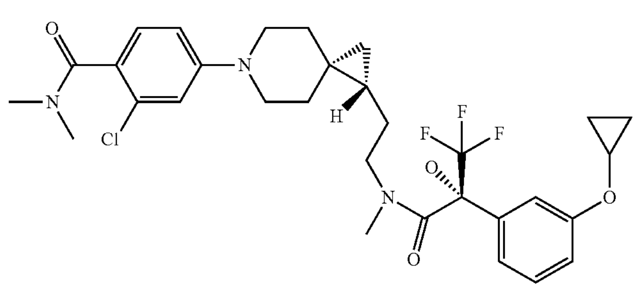 | 2-chloro-4-((R)-1-(2-((R)-2-(3-cyclopropoxyphenyl)-3,3,3-trifluoro-2-hydroxy-N-methylpropanamido)ethyl)-6-azaspiro[2.5]octan-6-yl)-N,N-dimethylbenzamide | 608.2 |

TABLE 7-continued

| Example | Structure | IUPAC Name | LRMS, found [M + H]+ |
|---|---|---|---|
| 7-4 | 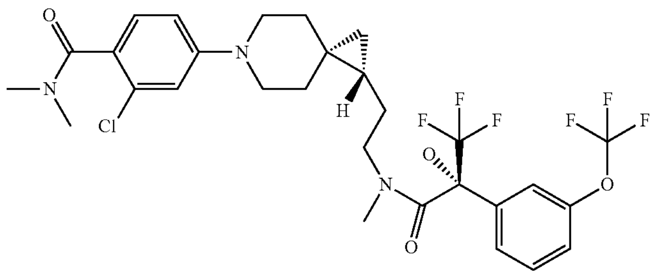 | 2-chloro-N,N-dimethyl-4-((R)-1-(2-((R)-3,3,3-trifluoro-2-hydroxy-N-methyl-2-(3-(trifluoromethoxy)phenyl)propanamido)ethyl)-6-azaspiro[2.5]octan-6-yl)benzamide | 636.2 |
| 7-5 | 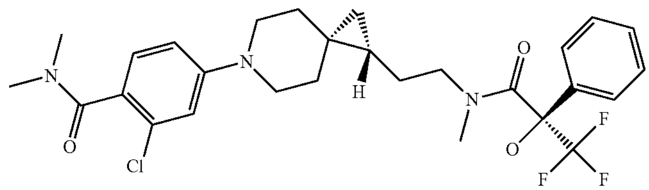 | 2-chloro-N,N-dimethyl-4-((R)-1-(2-((R)-3,3,3-trifluoro-2-hydroxy-N-methyl-2-phenylpropanamido)ethyl)-6-azaspiro[2.5]octan-6-yl)benzamide | 552.2 |
| 7-6 | 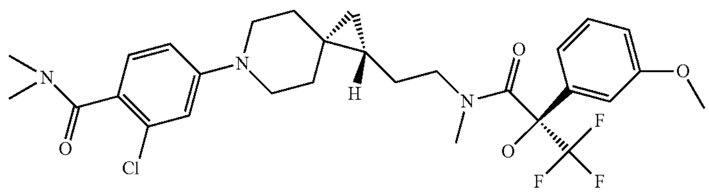 | 2-chloro-N,N-dimethyl-4-((R)-1-(2-((R)-3,3,3-trifluoro-2-hydroxy-2-(3-methoxyphenyl)-N-methylpropanamido)ethyl)-6-azaspiro[2.5]octan-6-yl)benzamide | 582.2 |
| 7-7 | 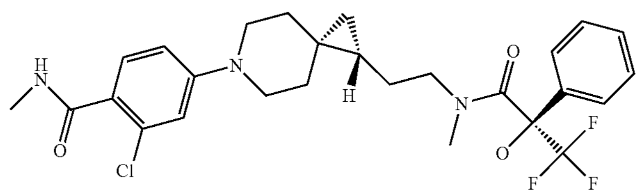 | 2-chloro-N-methyl-4-((R)-1-(2-((R)-3,3,3-trifluoro-2-hydroxy-N-methyl-2-phenylpropanamido)ethyl)-6-azaspiro[2.5]octan-6-yl)benzamide | 538.1 |
| 7-8 | 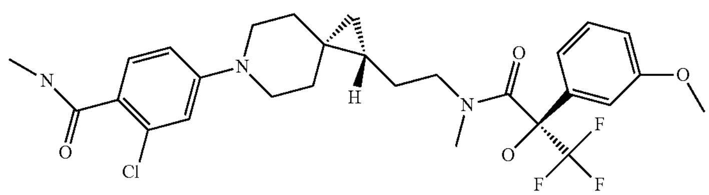 | 2-chloro-N-methyl-4-((R)-1-(2-((R)-3,3,3-trifluoro-2-hydroxy-2-(3-methoxyphenyl)-N-methylpropanamido)ethyl)-6-azaspiro[2.5]octan-6-yl)benzamide | 568.2 |
| 7-9 | 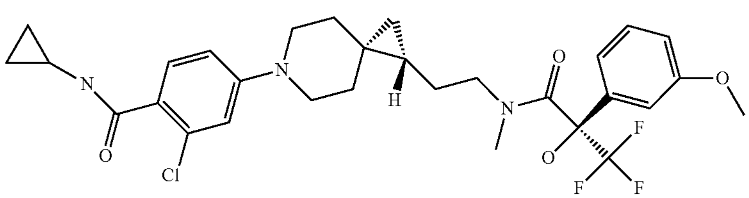 | 2-chloro-N-cyclopropyl-4-((R)-1-(2-((R)-3,3,3-trifluoro-2-hydroxy-2-(3-methoxyphenyl)-N-methylpropanamido)ethyl)-6-azaspiro[2.5]octan-6-yl)benzamide | 594.2 |
| 7-10 | 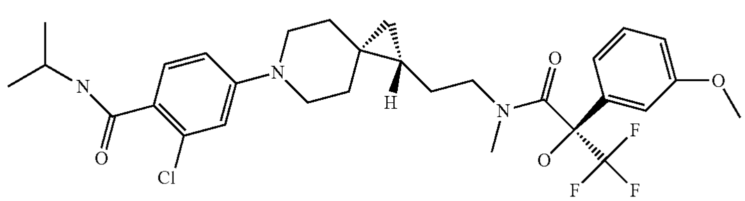 | 2-chloro-N-isopropyl-4-((R)-1-(2-((R)-3,3,3-trifluoro-2-hydroxy-2-(3-methoxyphenyl)-N-methylpropanamido)ethyl)-6-azaspiro[2.5]octan-6-yl)benzamide | 596.2 |

TABLE 7-continued

| Example | Structure | IUPAC Name | LRMS, found [M + H]+ |
|---|---|---|---|
| 7-11 | 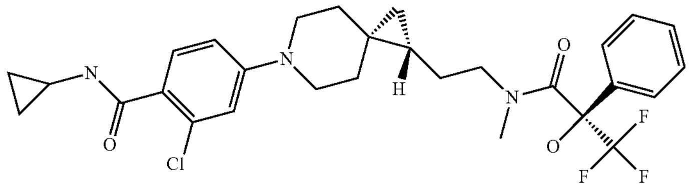 | 2-chloro-N-cyclopropyl-4-((R)-1-(2-((R)-3,3,3-trifluoro-2-hydroxy-N-methyl-2-phenylpropanamido)ethyl)-6-azaspiro[2.5]octan-6-yl)benzamide | 564.2 |
| 7-12 | 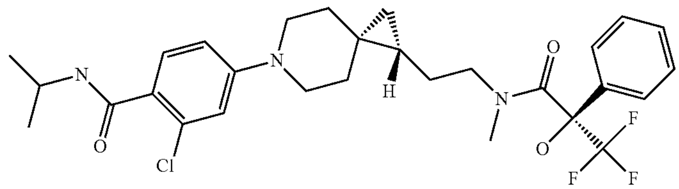 | 2-chloro-N-isopropyl-4-((R)-1-(2-((R)-3,3,3-trifluoro-2-hydroxy-N-methyl-2-phenylpropanamido)ethyl)-6-azaspiro[2.5]octan-6-yl)benzamide | 566.2 |
| 7-13 | 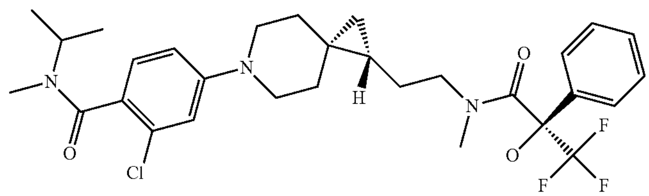 | 2-chloro-N-isopropyl-N-methyl-4-((R)-1-(2-((R)-3,3,3-trifluoro-2-hydroxy-N-methyl-2-phenylpropanamido)ethyl)-6-azaspiro[2.5]octan-6-yl)benzamide | 580.2 |
| 7-14 | 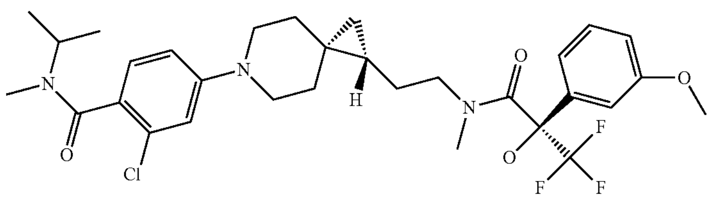 | 2-chloro-N-isopropyl-N-methyl-4-((R)-1-(2-((R)-3,3,3-trifluoro-2-hydroxy-2-(3-methoxyphenyl)-N-methylpropanamido)ethyl)-6-azaspiro[2.5]octan-6-yl)benzamide | 610.3 |
| 7-15 | 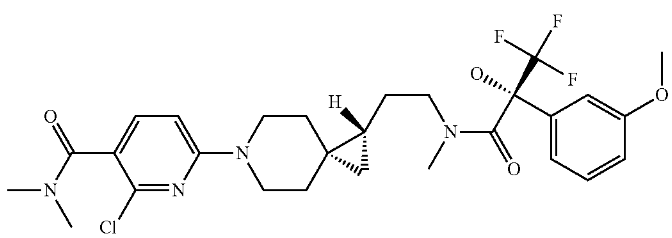 | 2-chloro-N,N-dimethyl-6-((R)-1-(2-((R)-3,3,3-trifluoro-2-hydroxy-2-(3-methoxyphenyl)-N-methylpropanamido)ethyl)-6-azaspiro[2.5]octan-6-yl)nicotinamide | 583.1 |
| 7-16 | 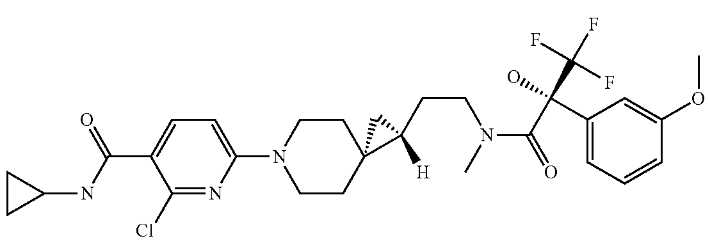 | 2-chloro-N-cyclopropyl-6-((R)-1-(2-((R)-3,3,3-trifluoro-2-hydroxy-2-(3-methoxyphenyl)-N-methylpropanamido)ethyl)-6-azaspiro[2.5]octan-6-yl)nicotinamide | 595.2 |
| 7-17 | 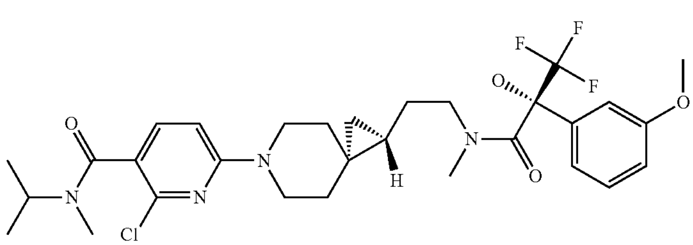 | 2-chloro-N-isopropyl-N-methyl-6-((R)-1-(2-((R)-3,3,3-trifluoro-2-hydroxy-2-(3-methoxyphenyl)-N-methylpropanamido)ethyl)-6-azaspiro[2.5]octan-6-yl)nicotinamide | 611.2 |

TABLE 7-continued

| Example | Structure | IUPAC Name | LRMS, found [M + H]+ |
|---|---|---|---|
| 7-18 | 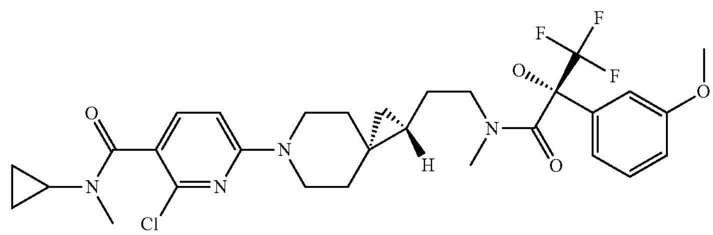 | 2-chloro-N-cyclopropyl-N-methyl-6-((R)-1-(2-((R)-3,3,3-trifluoro-2-hydroxy-2-(3-methoxyphenyl)-N-methylpropanamido)ethyl)-6-azaspiro[2.5]octan-6-yl)nicotinamide | 609.1 |
| 7-19 | 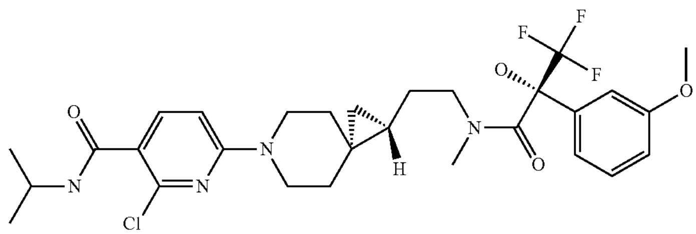 | 2-chloro-N-isopropyl-6-((R)-1-(2-((R)-3,3,3-trifluoro-2-hydroxy-2-(3-methoxyphenyl)-N-methylpropanamido)ethyl)-6-azaspiro[2.5]octan-6-yl)nicotinamide | 597.1 |
| 7-20 | 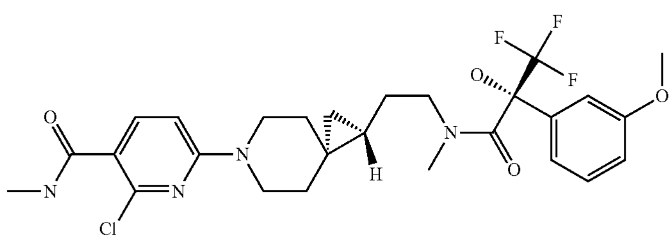 | 2-chloro-N-methyl-6-((R)-1-(2-((R)-3,3,3-trifluoro-2-hydroxy-2-(3-methoxyphenyl)-N-methylpropanamido)ethyl)-6-azaspiro[2.5]octan-6-yl)nicotinamide | 569.2 |
| 7-21 | 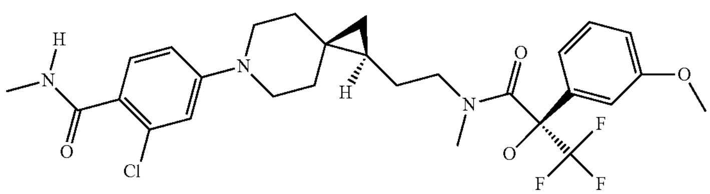 | 2-chloro-N-methyl-4-((S)-1-(2-((R)-3,3,3-trifluoro-2-hydroxy-2-(3-methoxyphenyl)-N-methylpropanamido)ethyl)-6-azaspiro[2.5]octan-6-yl)benzamide | 568.2 |
| 7-22 | 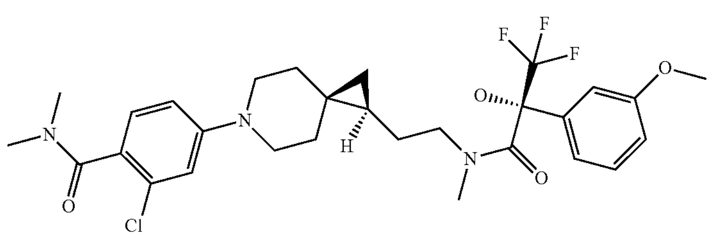 | 2-chloro-N,N-dimethyl-4-((S)-1-(2-((R)-3,3,3-trifluoro-2-hydroxy-2-(3-methoxyphenyl)-N-methylpropanamido)ethyl)-6-azaspiro[2.5]octan-6-yl)benzamide | 582.1 |
| 7-23 | 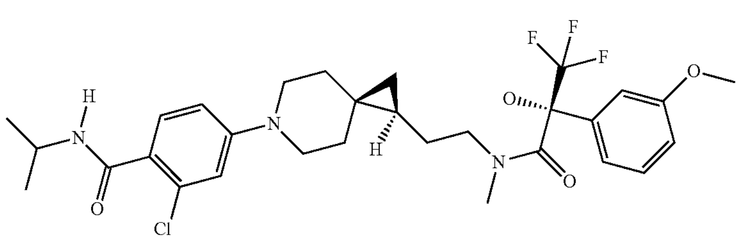 | 2-chloro-N-isopropyl-4-((S)-1-(2-((R)-3,3,3-trifluoro-2-hydroxy-2-(3-methoxyphenyl)-N-methylpropanamido)ethyl)-6-azaspiro[2.5]octan-6-yl)benzamide | 596.2 |

TABLE 7-continued

| Example | Structure | IUPAC Name | LRMS, found [M + H]+ |
|---|---|---|---|
| 7-24 | 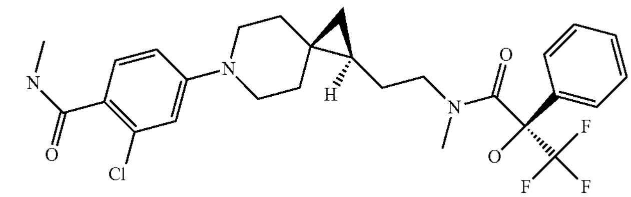 | 2-chloro-N-methyl-4-((S)-1-(2-((R)-3,3,3-trifluoro-2-hydroxy-N-methyl-2-phenylpropanamido)ethyl)-6-azaspiro[2.5]octan-6-yl)benzamide | 538.1 |
| 7-25 | 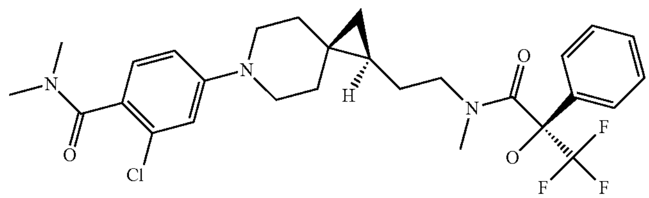 | 2-chloro-N,N-dimethyl-4-((S)-1-(2-((R)-3,3,3-trifluoro-2-hydroxy-N-methyl-2-phenylpropanamido)ethyl)-6-azaspiro[2.5]octan-6-yl)benzamide | 552.2 |
| 7-26 | 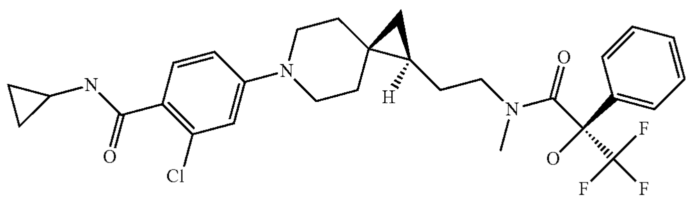 | 2-chloro-N-cyclopropyl-4-((S)-1-(2-((R)-3,3,3-trifluoro-2-hydroxy-N-methyl-2-phenylpropanamido)ethyl)-6-azaspiro[2.5]octan-6-yl)benzamide | 564.2 |
| 7-27 | 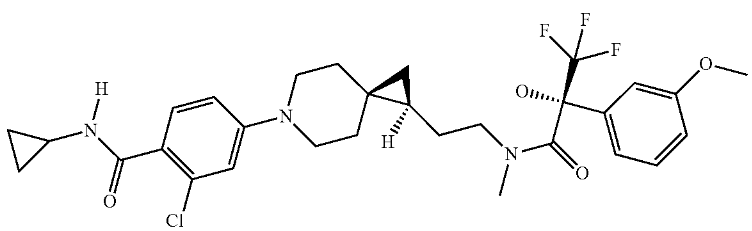 | 2-chloro-N-cyclopropyl-4-((S)-1-(2-((R)-3,3,3-trifluoro-2-hydroxy-2-(3-methoxyphenyl)-N-methylpropanamido)ethyl)-6-azaspiro[2.5]octan-6-yl)benzamide | 594.1 |
| 7-28 | 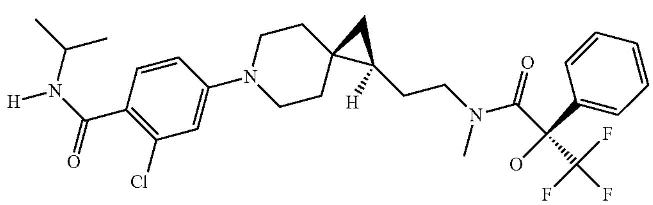 | 2-chloro-N-isopropyl-4-((S)-1-(2-((R)-3,3,3-trifluoro-2-hydroxy-N-methyl-2-phenylpropanamido)ethyl)-6-azaspiro[2.5]octan-6-yl)benzamide | 566.2 |
| 7-29 | 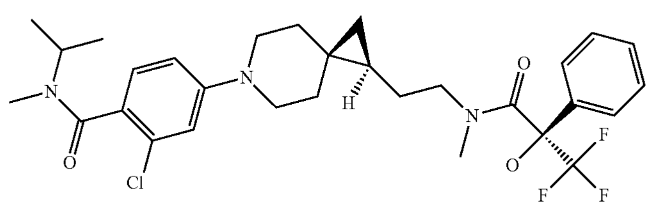 | 2-chloro-N-isopropyl-N-methyl-4-((S)-1-(2-((R)-3,3,3-trifluoro-2-hydroxy-N-methyl-2-phenylpropanamido)ethyl)-6-azaspiro[2.5]octan-6-yl)benzamide | 580.2 |
| 7-30 | 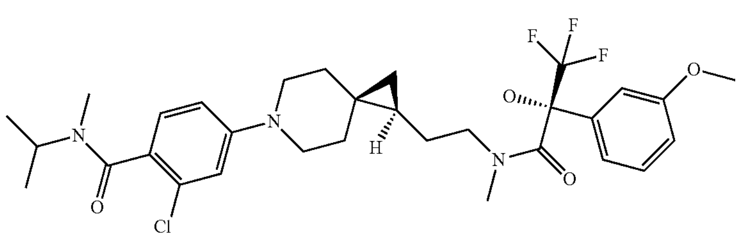 | 2-chloro-N-isopropyl-N-methyl-4-((S)-1-(2-((R)-3,3,3-trifluoro-2-hydroxy-2-(3-methoxyphenyl)-N-methyl-propanamido)ethyl)-6-azaspiro[2.5]octan-6-yl)benzamide | 610.2 |

TABLE 7-continued

| Example | Structure | IUPAC Name | LRMS, found [M + H]+ |
|---|---|---|---|
| 7-31 | 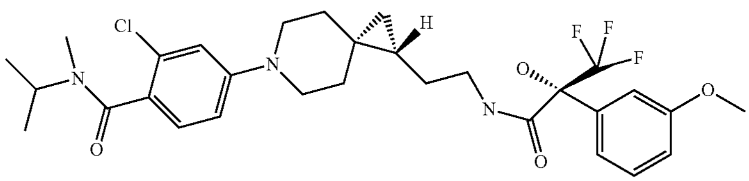 | 2-chloro-N-isopropyl-N-methyl-4-((R)-1-(2-((R)-3,3,3-trifluoro-2-hydroxy-2-(3-methoxyphenyl)propanamido)ethyl)-6-azaspiro[2.5]octan-6-yl)benzamide | 596.2 |
| 7-32 | 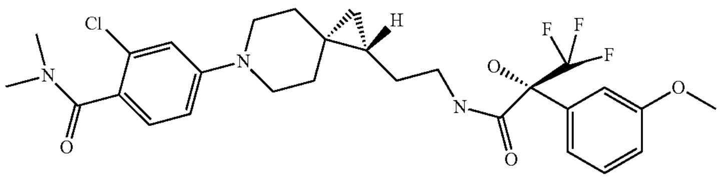 | 2-chloro-N,N-dimethyl-4-((R)-1-(2-((R)-3,3,3-trifluoro-2-hydroxy-2-(3-methoxyphenyl)propanamido)ethyl)-6-azaspiro[2.5]octan-6-yl)benzamide | 568.2 |
| 7-33 | 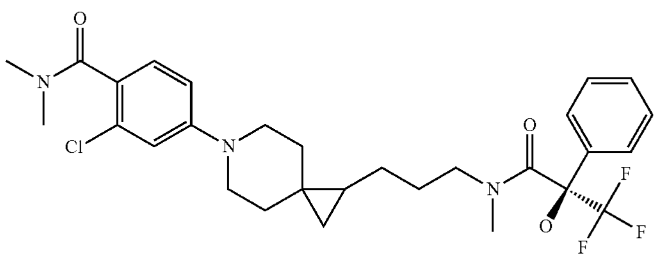 [SMILES: CN(C)C(=O)c1ccc(N2CCC3(CC2)CC3CCCN(C)C(=O)[C@](O)(c2ccccc2)C(F)(F)F)cc1Cl] | 2-chloro-N,N-dimethyl-4-(1-(3-((R)-3,3,3-trifluoro-2-hydroxy-N-methyl-2-phenylpropanamido)propyl)-6-azaspiro[2.5]octan-6-yl)benzamide | 566.2 |
| 7-34 | 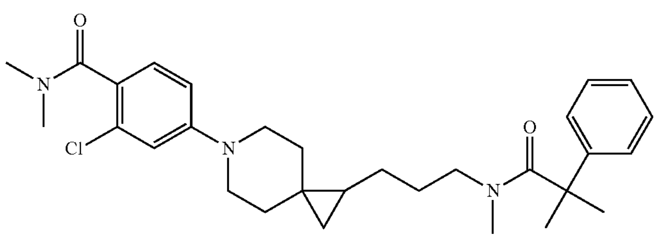 [SMILES: CN(C)C(=O)c1ccc(N2CCC3(CC2)CC3CCCN(C)C(=O)C(C)(C)c2ccccc2)cc1Cl] | 2-chloro-4-(1-(3-(N,2-dimethyl-2-phenylpropanamido)propyl)-6-azaspiro[2.5]octan-6-yl)-N,N-dimethylbenzamide | 510.3 |
| 7-35 | 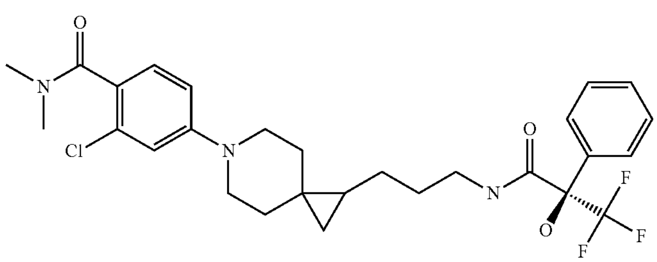 [SMILES: CN(C)C(=O)c1ccc(N2CCC3(CC2)CC3CCCNC(=O)[C@](O)(c2ccccc2)C(F)(F)F)cc1Cl] | 2-chloro-N,N-dimethyl-4-(1-(3-((R)-3,3,3-trifluoro-2-hydroxy-2-phenylpropanamido)propyl)-6-azaspiro[2.5]octan-6-yl)benzamide | 552.2 |
| 7-36 | 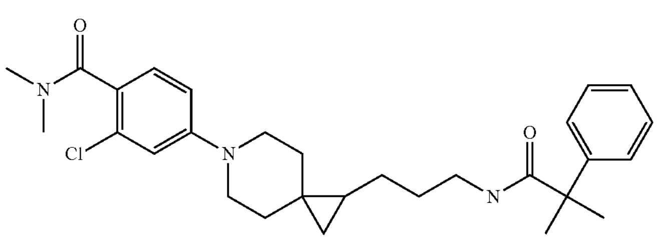 [SMILES: CN(C)C(=O)c1ccc(N2CCC3(CC2)CC3CCCNC(=O)C(C)(C)c2ccccc2)cc1Cl] | 2-chloro-N,N-dimethyl-4-(1-(3-(2-methyl-2-phenylpropanamido)propyl)-6-azaspiro[2.5]octan-6-yl)benzamide | 496.2 |

Example 8-1

(R)-2-chloro-N,N-dimethyl-6-(4-(2-(1-(3,3,3-trifluoro-2-hydroxy-2-(3-methoxyphenyl)propanamido)cyclopropyl)ethyl)piperidin-1-yl)nicotinamide

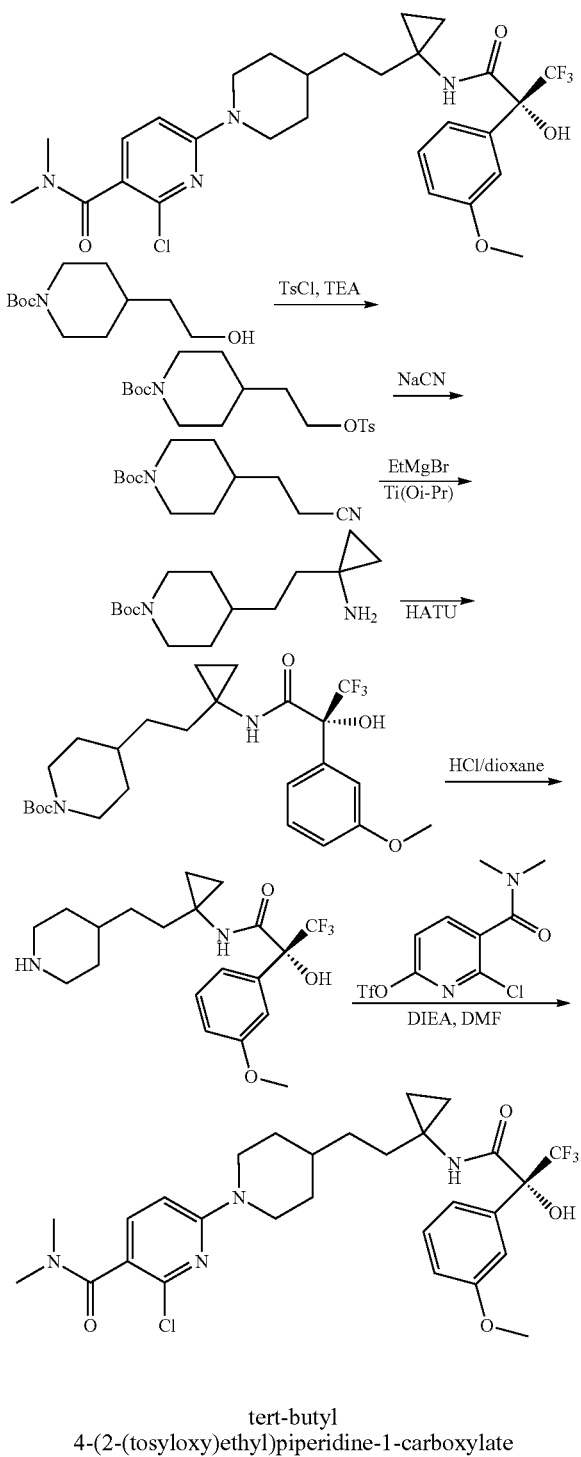

tert-butyl 4-(2-(tosyloxy)ethyl)piperidine-1-carboxylate 4-methylbenzene-1-sulfonyl chloride (585 mg, 3.08 mmol) was added to a mixture of tert-butyl 4-(2-hydroxyethyl)piperidine-1-carboxylate (500 mg, 2.2 mmol) and TEA (577 mg, 5.72 mmol) in DCM (6 mL) at rt. The resulting mixture was stirred at rt overnight and diluted with DCM (20 mL). The organic phase was washed with $H_2O$ (15 mL×2), dried over anhydrous $Na_2SO_4$, filtered and concentrated. The crude product was purified by column chromatography (silica gel: 300-400 mesh, PE/EtOAc=40/1 to 8/1) to give tert-butyl 4-(2-(tosyloxy)ethyl)piperidine-1-carboxylate (674 mg, 80%). LRMS m/z (M+H) 384.1 found, 384.2 required.

tert-butyl 4-(2-cyanoethyl)piperidine-1-carboxylate

To a solution of tert-butyl 4-(2-(tosyloxy)ethyl)piperidine-1-carboxylate (674 mg, 1.76 mmol) in $CH_3CN$ (7 mL) was added sodium cyanide (172 mg, 3.52 mmol) at rt. After stirring at 70° C. overnight, the reaction was diluted with EtOAc (40 mL). The organic phase was washed with water (30 mL×3), brine (10 mL×3) and dried over anhydrous $Na_2SO_4$. The organic phase was concentrated and the residue was purified by column chromatography (silica gel: 300-400 mesh, PE/EtOAc=20/1 to 5/1) to afford tert-butyl 4-(2-cyanoethyl)piperidine-1-carboxylate (390 mg, 93%). LRMS m/z (M+Na) 261.1 found, 261.2 required.

tert-butyl 4-(2-(1-aminocyclopropyl)ethyl)piperidine-1-carboxylate

To a solution of tert-butyl 4-(2-cyanoethyl)piperidine-1-carboxylate (88 mg, 0.37 mmol) in ether (3 mL) was added successively titanium(IV) isopropoxide (116 mg, 0.41 mmol) and ethyl magnesium bromide (0.37 mL, 0.75 mmol, 2M in THF) at rt. After stirring for 0.5 h, boron trifluoride diethyl ether complex (106 mg, 0.746 mmol) was added at once. The resulting mixture was stirred over a period of 10 min and a solution of 10% NaOH (Ca. 1 mL) was added to the mixture. The mixture was extracted with ether (50 mL×2). The combined ether layers were dried over anhydrous sodium sulfate, filtered and concentrated. The residue was purified by column chromatography (silica gel: 300-400 mesh, PE/EtOAc=20/1 to 2/1) to afford tert-butyl 4-(2-(1-aminocyclopropyl)ethyl)piperidine-1-carboxylate (40 mg, 40%). LRMS m/z (M+H) 269.1 found, 269.2 required.

(R)-tert-butyl 4-(2-(1-(3,3,3-trifluoro-2-hydroxy-2-(3-methoxyphenyl)propanamido)cyclopropyl)ethyl)piperidine-1-carboxylate A mixture of tert-butyl 4-(2-(1-aminocyclopropyl)ethyl)piperidine-1-carboxylate (40 mg, 0.15 mmol), (R)-3,3,3-trifluoro-2-hydroxy-2-(3-methoxyphenyl)propanoic acid (56 mg, 0.225 mmol), HATU (85 mg, 0.225 mmol) and TEA (45 mg, 0.45 mmol) in THF (2 mL) was stirred at rt overnight. The mixture was directly purified by reverse-phase HPLC (mobile phase: methanol/water (10 mM $NH_4HCO_3$)) to afford (R)-tert-butyl 4-(2-(1-(3,3,3-trifluoro-2-hydroxy-2-(3-methoxyphenyl)propanamido)cyclopropyl)ethyl)piperidine-1-carboxylate (38 mg, 50.6%). LRMS m/z (M+H) 501.2 found, 501.2 required.

(R)-3,3,3-trifluoro-2-hydroxy-2-(3-methoxyphenyl)-N-(1-(2-(piperidin-4-yl)ethyl)cyclopropyl)propanamide hydrochloride A solution of (R)-tert-butyl 4-(2-(1-(3,3,3-trifluoro-2-hydroxy-2-(3-methoxyphenyl)propanamido)cyclopropyl)ethyl)piperidine-1-carboxylate (38 mg, 0.076 mmol) in 4M HCl/dioxane (4 mL) was stirred at rt for 4 h. The mixture was concentrated in vacuo to afford the crude (R)-3,3,3- trifluoro-2-hydroxy-2-(3-methoxyphenyl)-N-(1-(2-(piperidin-4-yl)ethyl)cyclopropyl)propanamide hydrochloride (33 mg, 100%). LRMS m/z (M+H) 401.2 found, 401.2 required.

(R)-2-chloro-N,N-dimethyl-6-(4-(2-(1-(3,3,3-trifluoro-2-hydroxy-2-(3-methoxyphenyl)propanamido)cyclopropyl)ethyl)piperidin-1-yl)nicotinamide To a solution of benzyl (R)-3,3,3-trifluoro-2-hydroxy-2-(3-methoxyphenyl)-N-(1-(2-(piperidin-4-yl)ethyl)cyclopropyl)propanamide hydrochloride (22 mg, 0.05 mmol) in DMF (2 mL) was added DIEA (20 mg, 0.15 mmol) and 6-chloro-5-(dimethylcarbamoyl)pyridin-2-yl trifluoromethanesulfonate (16.6 mg, 0.05 mmol). After stirring at 80° C. for 3 h, the mixture was directly purified by reverse-phase HPLC (mobile phase: methanol/water (10 mM NH$_4$HCO$_3$)) to afford (R)-2-chloro-N,N-dimethyl-6-(4-(2-(1-(3,3,3-trifluoro-2-hydroxy-2-(3-methoxyphenyl)propanamido)cyclopropyl)ethyl)piperidin-1-yl)nicotinamide (10 mg, 34.3%). LRMS m/z (M+H) 583.1 found, 583.2 required.

Example 9-1

(R)-2-chloro-N,N-dimethyl-6-(4-methyl-4-(3-(3,3,3-trifluoro-2-hydroxy-2-(3-methoxyphenyl)-N-methylpropanamido)propyl)piperidin-1-yl)nicotinamide

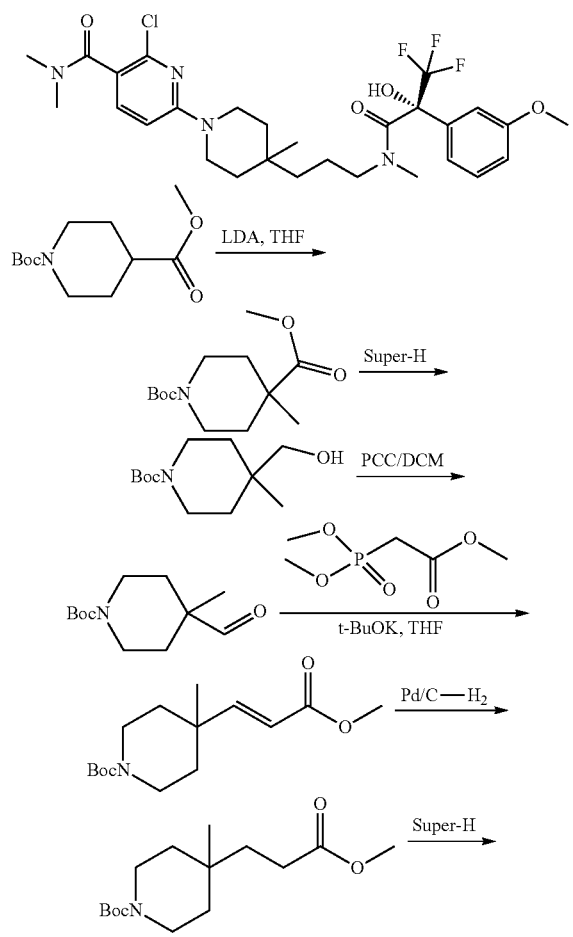

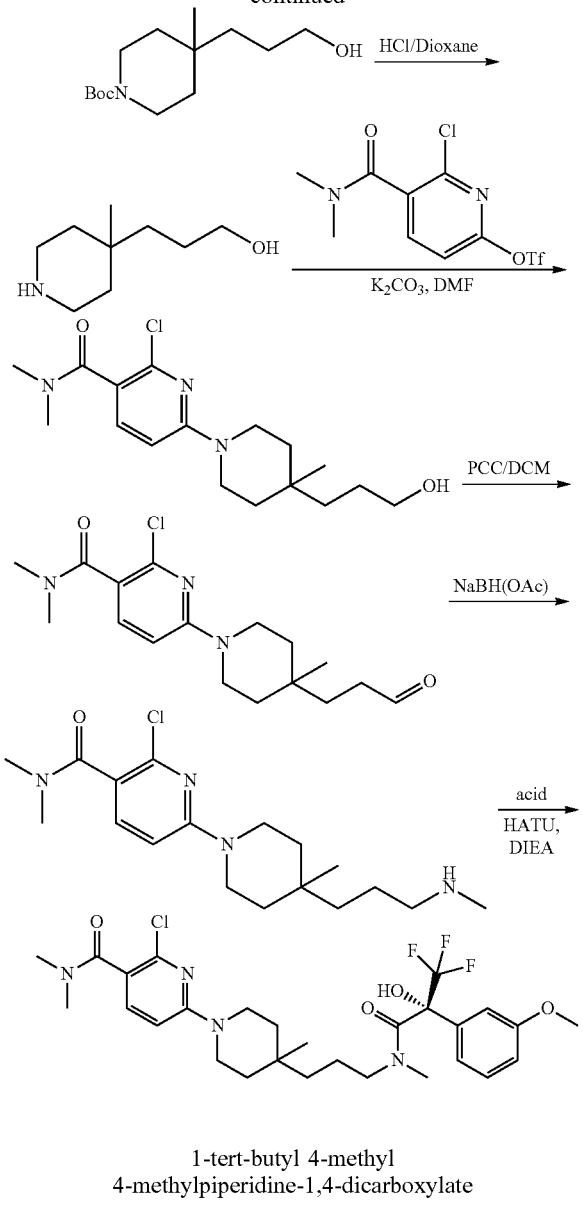

1-tert-butyl 4-methyl 4-methylpiperidine-1,4-dicarboxylate

To a solution of 1-tert-butyl 4-methyl piperidine-1,4-dicarboxylate (11 g, 45 mmol) in THF (200 mL) was added LDA (34 mL, 68 mmol, 2M in THF/heptane/ethylbenzene) at −78° C. under N$_2$. After stirring at −78° C. for 3 h, a solution of iodomethane (10 g, 70 mmol) in THF (10 mL) was added to the mixture at −78° C. under N$_2$. And then the resulting mixture was gradually warmed to rt and stirred overnight, quenched with aq. NH$_4$Cl (200 mL) carefully. The mixture was extracted with DCM/MeOH (10/1, 300 mL×3). And the organic phase was dried over anhydrous Na$_2$SO$_4$, filtered, concentrated and purified by column chromatography (silica gel: 300-400 mesh, PE/EtOAc=20/1 to 5/1) to give 1-tert-butyl 4-methyl 4-methylpiperidine-1,4-dicarboxylate (9.7 g, 83%). LRMS m/z (M-55) 202.2 found, 202.1 required.

tert-butyl 4-(hydroxymethyl)-4-methylpiperidine-1-carboxylate

Super-hydride (105 mL, 105 mmol, 1M in THF) was added to the solution of 1-tert-butyl 4-methyl 4-methylpiperidine-1,4-dicarboxylate (9 g, 35 mmol) in THF (100 mL) at 0° C. The resulting mixture was stirred for 1 h at 0° C., and then quenched with MeOH (200 mL) carefully. The solvent was removed under reduced pressure and the residue was dissolved with aq. NH$_4$Cl (300 mL) and extracted with EtOAc (200 mL×3). The organic phase was dried over anhydrous Na$_2$SO$_4$, filtered and concentrated. The crude compound was purified by column chromatography (silica gel: 300-400 mesh, PE/EtOAc=20/1 to 5/1) to give tert-butyl 4-(hydroxymethyl)-4-methylpiperidine-1-carboxylate (7.8 g, 97%). LRMS m/z (M-55) 174.2 found, 174.1 required.

tert-butyl 4-formyl-4-methylpiperidine-1-carboxylate

A mixture of tert-butyl 4-(hydroxymethyl)-4-methylpiperidine-1-carboxylate (7.8 g, 34 mmol) and PCC (22 g, 102 mmol) in DCM (100 mL) was stirred at rt for 2 h. Then the mixture was concentrated and the residue was purified by column chromatography (silica gel:300-400 mesh, PE/EtOAc=50/1 to 15/1) to obtain tert-butyl 4-formyl-4-methylpiperidine-1-carboxylate (7 g, 90%). LRMS m/z (M-55) 172.2 found, 172.1 required.

(E)-tert-butyl 4-(3-methoxy-3-oxoprop-1-enyl)-4-methylpiperidine-1-carboxylate

A mixture of methyl 2-(dimethoxyphosphoryl)acetate (1.82 g, 10 mmol) and t-BuOK (1.2 g, 10 mmol) in dry THF (15 mL) was stirred at 0° C. for 2 h under N$_2$. Then a solution of tert-butyl 4-formyl-4-methylpiperidine-1-carboxylate (2.2 g, 9 mmol) was added to the mixture at 0° C. under N$_2$. And the resulting mixture was stirred at rt overnight, quenched with aq. NH$_4$Cl (100 mL) and extracted with EtOAc (100 mL×3). The organic phase was dried over anhydrous Na$_2$SO$_4$, filtered and concentrated. The crude compound was purified by column chromatography (silica gel: 300-400 mesh, PE/EtOAc=20/1 to 5/1) to give (E)-tert-butyl 4-(3-methoxy-3-oxoprop-1-enyl)-4-methylpiperidine-1-carboxylate (2 g, 78%). LRMS m/z (M-55) 228.2 found, 228.1 required.

tert-butyl 4-(3-methoxy-3-oxopropyl)-4-methylpiperidine-1-carboxylate

A mixture of (E)-tert-butyl 4-(3-methoxy-3-oxoprop-1-enyl)-4-methylpiperidine-1-carboxylate (2 g, 7 mmol) and 10% Pd/C (630 mg) in MeOH (20 mL) was degassed and backfilled with H$_2$ (three times). The mixture was stirred at rt overnight under H$_2$ balloon. The catalyst was filtered off and the filtrate was concentrated to get tert-butyl 4-(3-methoxy-3-oxopropyl)-4-methylpiperidine-1-carboxylate (2 g, 100%). LRMS m/z (M-55) 230.2 found, 230.1 required.

tert-butyl 4-(3-hydroxypropyl)-4-methylpiperidine-1-carboxylate

Super-hydride (25 mL, 25 mmol, 1M in THF) was added to the solution of tert-butyl 4-(3-methoxy-3-oxopropyl)-4-methylpiperidine-1-carboxylate (2 g, 7 mmol) in THF (10 mL) at 0° C. The resulting mixture was stirred for 1 h at 0° C., and then quenched with MeOH (200 mL) carefully. The solvent was removed under reduced pressure and the residue was dissolved with aq. NH$_4$Cl (300 mL) and extracted with EtOAc (200 mL×3). The organic phase was dried over anhydrous Na$_2$SO$_4$, filtered and concentrated. The crude compound was purified by column chromatography (silica gel: 300-400 mesh, PE:EtOAc=20/1 to 5/1) to afford tert-butyl 4-(3-hydroxypropyl)-4-methylpiperidine-1-carboxylate (1.6 g, 89%). LRMS m/z (M-55) 202.2 found, 202.1 required.

3-(4-methylpiperidin-4-yl)propan-1-ol

A mixture of tert-butyl 4-(3-hydroxypropyl)-4-methylpiperidine-1-carboxylate (500 mg, 1.9 mmol) and 4M HCl/dioxane (10 mL) was stirred at rt for 2 h. Then the mixture was concentrated in vacuo to give the crude 3-(4-methylpiperidin-4-yl)propan-1-ol hydrochloric acid salt (339 mg, 90%) which was used in next step without purification. LRMS m/z (M+H) 158.2 found, 158.2 required.

2-chloro-6-(4-(3-hydroxypropyl)-4-methylpiperidin-1-yl)-N,N-dimethylnicotinamide A mixture of 3-(4-methylpiperidin-4-yl)propan-1-ol (339 mg, 1.7 mmol), 6-chloro-5-(dimethylcarbamoyl)pyridin-2-yl trifluoromethanesulfonate (630 mg, 1.9 mmol) and DIEA (735 mg, 5.7 mmol) in DMF (9 mL) was irradiated by a CEM Microwave Reactor at 60° C. for 1 h. Then the resulting mixture was directly purified by reverse-phase HPLC (mobile phase: methanol/water (10 mM NH$_4$HCO$_3$) to give the 2-chloro-6-(4-(3-hydroxypropyl)-4-methylpiperidin-1-yl)-N,N-dimethylnicotinamide (570 mg, 96%). LRMS m/z (M+H) 340.2 found, 340.2 required.

2-chloro-N,N-dimethyl-6-(4-methyl-4-(3-oxopropyl) piperidin-1-yl)nicotinamide

A mixture of 2-chloro-6-(4-(3-hydroxypropyl)-4-methylpiperidin-1-yl)-N,N-dimethylnicotinamide (570 mg, 1.7 mmol) and Dess-Martin Perioxidinane (1 g, 2.4 mmol) in DCM (10 mL) was stirred at rt for 1 h. Then the mixture was concentrated, and purified by column chromatography (silica gel: 300-400 mesh, PE/EtOAc=20/1 to 5/1) to give 2-chloro-N,N-dimethyl-6-(4-methyl-4-(3-oxopropyl)piperidin-1-yl)nicotinamide (420 mg, 74%). LRMS m/z (M+H) 338.2 found, 338.2 required.

2-chloro-N,N-dimethyl-6-(4-methyl-4-(3-(methylamino)propyl)piperidin-1-yl)nicotinamide A mixture of 2-chloro-N,N-dimethyl-6-(4-methyl-4-(3-oxopropyl)piperidin-1-yl)nicotinamide (420 mg, 1.2 mmol), methylamine (12 mL, 12 mmol, 1M in THF), and titanium (IV) isopropoxide (708 mg, 2.5 mmol) was stirred at 0° C. for 4 h under N$_2$. Then NaBH$_4$ (142 mg, 3.7 mmol) was added to the mixture at rt under N$_2$ and the resulting mixture was stirred overnight at rt. The reaction mixture was poured into 6N HCl (20 mL) 0° C. carefully and stirred for another 2 h. The aqueous phase was basified with aqueous NaOH (60 mL, 2M) and extracted with DCM/MeOH (10/1, 50 mL×3). The combined organic layers were dried over anhydrous Na$_2$SO$_4$ and concentrated to give the crude 2-chloro-N,N-dimethyl-6-(4-methyl-4-(3-(methylamino)propyl)piperidin-1-yl)nicotinamide (340 mg, 78%) which was used in next step without purification. LRMS m/z (M+H) 353.2 found, 353.2 required.

(R)-2-chloro-N,N-dimethyl-6-(4-methyl-4-(3-(3,3,3-trifluoro-2-hydroxy-2-(3-methoxyphenyl)-N-methyl-propanamido)propyl)piperidin-1-yl)nicotinamide A mixture of 2-chloro-N,N-dimethyl-6-(4-methyl-4-(3-(methylamino)propyl)piperidin-1-yl)nicotinamide (30 mg, 0.09 mmol), (R)-3,3,3-trifluoro-2-hydroxy-2-(3-methoxyphenyl)propanoic acid (31 mg, 0.12 mmol), HATU (49 mg, 0.13 mmol) and DIEA (49 mg, 0.38 mmol) in THF (2 mL) was stirred at rt overnight. Then the mixture was directly purified by reverse-phase HPLC (mobile phase: methanol/water (10 mM NH$_4$HCO$_3$) to give the (R)-2-chloro-N,N-dimethyl-6-(4-methyl-4-(3-(3,3,3-trifluoro-2-hydroxy-2-(3-methoxyphenyl)-N-methylpropanamido)propyl)piperidin-1-yl)nicotinamide (15 mg, 30%). LRMS m/z (M+H) 585.2 found, 585.2 required.

Using the procedure described in Example 9-1, but replacing (R)-3,3,3-trifluoro-2-hydroxy-2-(3-methoxyphenyl)propanoic acid with the appropriate acid, the examples in Table 9 were prepared.

TABLE 9

| Example | Structure | IUPAC Name | LRMS, found M + H]+ |
|---|---|---|---|
| 9-1 | 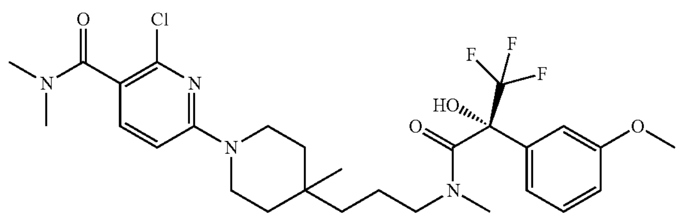 | (R)-2-chloro-N,N-dimethyl-6-(4-methyl-4-(3-(3,3,3-trifluoro-2-hydroxy-2-(3-methoxyphenyl)-N-methylpropanamido)propyl)piperidin-1-yl)nicotinamide | 585.2 |
| 9-2 | 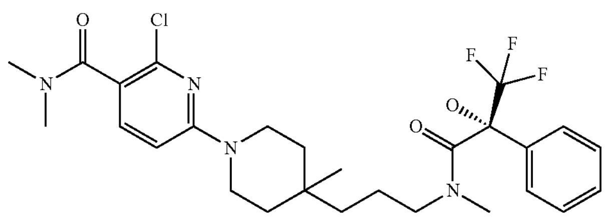 [SMILES: CN(C)C(=O)c1ccc(N2CCC(C)(CCCN(C)C(=O)[C@](O)(c3ccccc3)C(F)(F)F)CC2)nc1Cl] | (R)-2-chloro-N,N-dimethyl-6-(4-methyl-4-(3-(3,3,3-trifluroo-2-hydroxy-N-methyl-2-phenylpropanamido)propyl)piperidin-1-yl)nicotinamide | 555.2 |
| 9-3 | 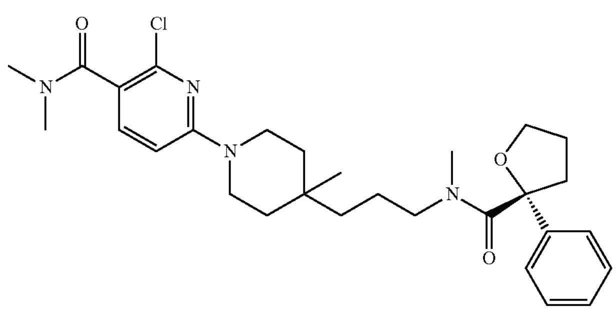 [SMILES: CN(C)C(=O)c1ccc(N2CCC(C)(CCCN(C)C(=O)[C@]3(c4ccccc4)CCCO3)CC2)nc1Cl] | (R)-2-chloro-N,N-dimethyl-6-(4-methyl-4-(3-(N-methyl-2-phenyltetrahydrofuran-2-carboxamido)propyl)piperidin-1-yl)nicotinamide | 527.3 |
| 9-4 | 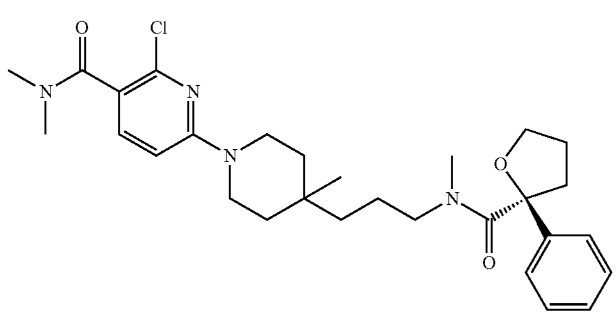 [SMILES: CN(C)C(=O)c1ccc(N2CCC(C)(CCCN(C)C(=O)[C@@]3(c4ccccc4)CCCO3)CC2)nc1Cl] | (S)-2-chloro-N,N-dimethyl-6-(4-methyl-4-(3-(N-methyl-2-phenyltetrahydrofuran-2-carboxamido)propyl)piperidin-1-yl)nicotinamide | 527.3 |

TABLE 9-continued

| Example | Structure | IUPAC Name | LRMS, found M + H]+ |
|---|---|---|---|
| 9-5 | 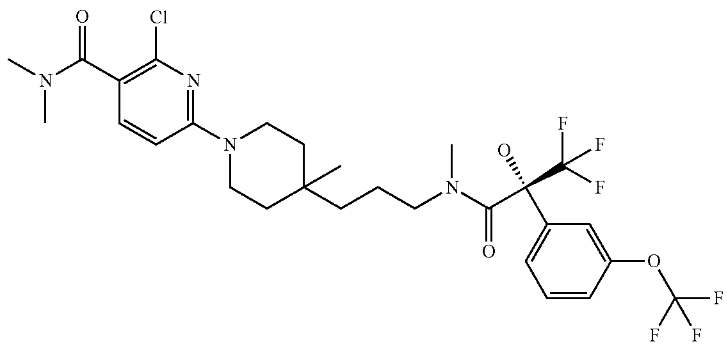 [SMILES: CN(C)C(=O)c1ccc(N2CCC(C)(CCCN(C)C(=O)[C@](O)(c3cccc(OC(F)(F)F)c3)C(F)(F)F)CC2)nc1Cl] | (R)-2-chloro-N,N-dimethyl-6-(4-methyl-4-(3-(3,3,3-trifluoro-2-hydroxy-N-methyl-2-(3-(trifluoromethoxy)phenyl)propanamido)propyl)piperidin-1-yl)nicotinamide | 639.2 |
| 9-6 | 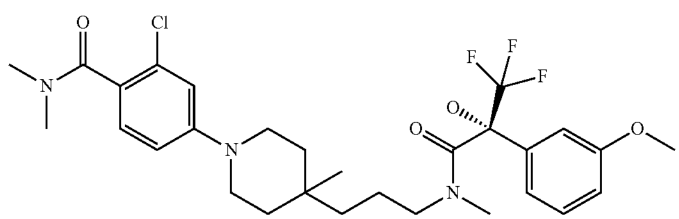 | (R)-2-chloro-N,N-dimethyl-4-(4-methyl-4-(3-(3,3,3-trifluoro-2-hydroxy-2-(3-methoxyphenyl)-N-methylpropanamido)propyl)piperidin-1-yl)benzamide | 584.2 |
| 9-7 | 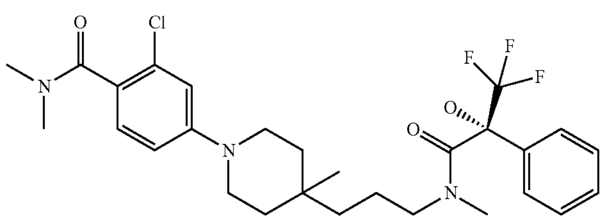 [SMILES: CN(C)C(=O)c1ccc(N2CCC(C)(CCCN(C)C(=O)[C@](O)(c3ccccc3)C(F)(F)F)CC2)cc1Cl] | (R)-2-chloro-N,N-dimethyl-4-(4-methyl-4-(3-(3,3,3-trifluoro-2-hydroxy-N-methyl-2-phenylpropanamido)propyl)piperidin-1-yl)benzamide | 554.2 |

Example 10-1

(R)-2-chloro-N,N-dimethyl-6-(4-(4-(3,3,3-trifluoro-2-hydroxy-2-(3-methoxyphenyl)propanamido)phenyl)piperidin-1-yl)nicotinamide

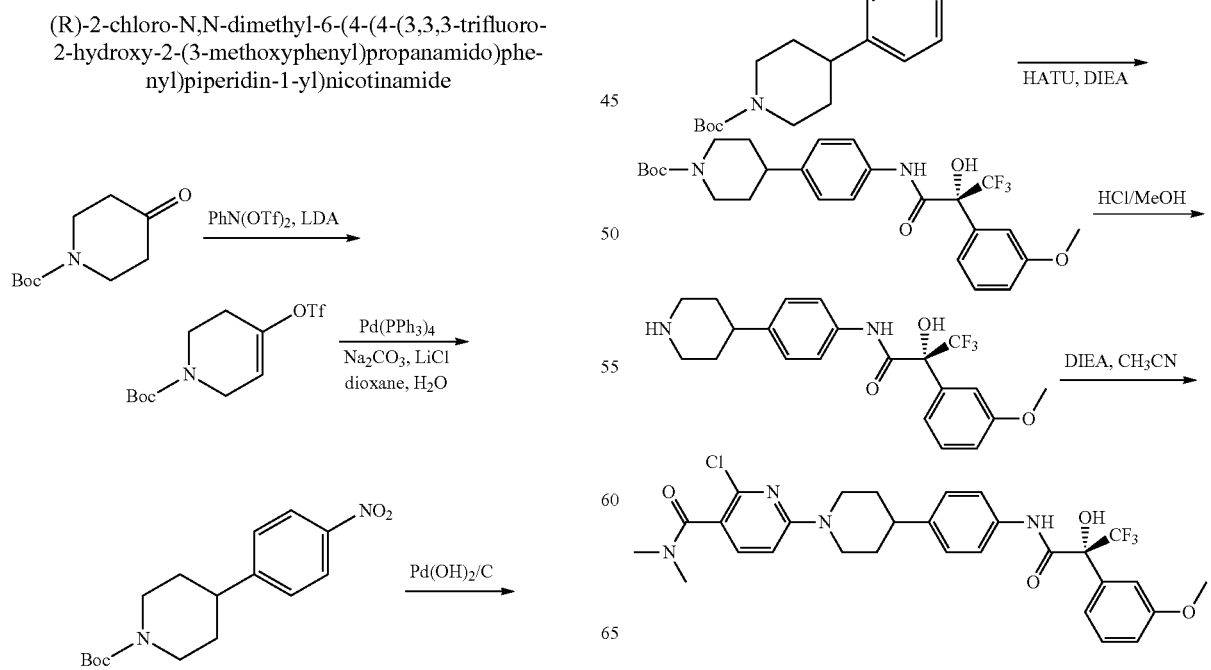

tert-butyl 4-(((trifluoromethyl)sulfonyl)oxy)-5,6-dihydropyridine-1(2H)-carboxylate To a solution of tert-butyl 4-oxopiperidine-1-carboxylate (5 g, 25.09 mmol) in THF (40 mL) was added LDA (25.09 mL, 50.2 mmol, 2M in THF/heptane/ethylbenzene) at −78° C. After stirring at −78° C. for 1 h, N,N-bis(trifluoromethylsulfonyl)aniline (10.76 g, 30.1 mmol) was added to the mixture. The resulting mixture was stirred at rt overnight, quenched with aq NH$_4$Cl (30 mL) and extracted with EtOAc (30 mL×3). The combined organic layer was washed with brine (15 mL), dried over anhydrous Na$_2$SO$_4$, filtered, concentrated and purified by silica gel chromatography (PE/EtOAc=20/1 to 10/1) to afford the tert-butyl 4-(((trifluoromethyl)sulfonyl)oxy)-5,6-dihydropyridine-1(2H)-carboxylate (5.6 g, 16.90 mmol, 67.4%). LRMS m/z (M-55) 276.0 found, 276.1 required.

tert-butyl 4-(4-nitrophenyl)-5,6-dihydropyridine-1(2H)-carboxylate

A mixture of tert-butyl 4-(((trifluoromethyl)sulfonyl)oxy)-5,6-dihydropyridine-1(2H)-carboxylate (1324 mg, 4.00 mmol), (4-nitrophenyl)boronic acid (667 mg, 4.00 mmol), Pd(Ph$_3$P)$_4$ (231 mg, 0.200 mmol), Na$_2$CO$_3$ (1271 mg, 11.99 mmol), LiCl (508 mg, 11.99 mmol), 1,4-dioxane (15 mL) and water (6 mL) was degassed and backfilled with N$_2$ three times. The mixture was heated to 100° C. overnight, and then the solvent was removed under reduced pressure and the residue was dissolved with water (30 mL), extracted with EtOAc (30 mL×3). The combined organic layer was washed with brine (15 mL), dried over anhydrous Na$_2$SO$_4$, filtered, concentrated and purified by silica gel chromatography (PE/EtOAc=30/1 to 10/1) to afford the tert-butyl 4-(4-nitrophenyl)-5,6-dihydropyridine-1(2H)-carboxylate (500 mg, 1.561 mmol, 39.1%). LRMS m/z (M-55) 249.2 found, 249.2 required.

tert-butyl 4-(4-aminophenyl)piperidine-1-carboxylate

A mixture of tert-butyl 4-(4-nitrophenyl)-5,6-dihydropyridine-1(2H)-carboxylate (495 mg, 1.626 mmol) and 20% Pd(OH)$_2$/C (50 mg, 0.071 mmol) in MeOH (20 mL) was degassed and backfilled with H$_2$ three times. The resulting mixture was stirred at rt under H$_2$ balloon overnight. The catalyst was filtered off and the filtrate was concentrated in vacuo to afford the tert-butyl 4-(4-aminophenyl)piperidine-1-carboxylate (409 mg, 1.480 mmol, 91%). LRMS m/z (M-55) 221.2 found, 221.2 required.

(R)-tert-butyl-4-(4-(3,3,3-trifluoro-2-hydroxy-2-(3-methoxyphenyl)propanamido)phenyl)piperidine-1-carboxylate A mixture of tert-butyl 4-(4-aminophenyl)piperidine-1-carboxylate (110 mg, 0.398 mmol), (R)-3,3,3-trifluoro-2-hydroxy-2-(3-methoxyphenyl)propanoic acid (100 mg, 0.398 mmol), HATU (227 mg, 0.597 mmol) and DIEA (0.209 mL, 1.194 mmol) in DMF (2 mL) was stirred at rt overnight. The crude was directly purified by reverse-phase HPLC (Mobile Phase: methanol/water (10 mM NH$_4$HCO$_3$)) to afford the (R)-tert-butyl 4-(4-(3,3,3-trifluoro-2-hydroxy-2-(3-methoxyphenyl)propanamido)phenyl)piperidine-1-carboxylate (93 mg, 0.172 mmol, 43.2%). LRMS m/z (M-55) 453.3 found, 453.2 required.

(R)-3,3,3-trifluoro-2-hydroxy-2-(3-methoxyphenyl)-N-(4-(piperidin-4-yl)phenyl)propanamide A mixture of (R)-tert-butyl 4-(4-(3,3,3-trifluoro-2-hydroxy-2-(3-methoxyphenyl)propanamido)phenyl)piperidine-1-carboxylate (93 mg, 0.183 mmol) and 4M HCl/MeOH (3 mL, 12.00 mmol) was stirred at rt overnight. The volatile was removed in vacuo to give the crude (R)-3,3,3-trifluoro-2-hydroxy-2-(3-methoxyphenyl)-N-(4-(piperidin-4-yl)phenyl)propanamide (74.7 mg, 0.183 mmol, 100%) which was used in next step without purification. LRMS m/z (M+H) 409.2 found, 409.2 required.

N,N-dimethyl-6-(4-(4-(3,3,3-trifluoro-2-hydroxy-2-(3-methoxyphenyl)propanamido)phenyl)piperidin-1-yl)nicotinamide A mixture of (R)-3,3,3-trifluoro-2-hydroxy-2-(3-methoxyphenyl)-N-(4-(piperidin-4-yl)phenyl)propanamide (37 mg, 0.091 mmol), 6-chloro-5-(dimethylcarbamoyl)pyridin-2-yl trifluoromethanesulfonate (30 mg, 0.091 mmol) and DIEA (0.032 mL, 0.181 mmol) in acetonitrile (2 mL) was stirred at 50° C. overnight. The mixture was directly purified by reverse-phase HPLC (Mobile Phase: methanol/water (10 mM NH$_4$HCO$_3$)) to give (R)-2-chloro-N,N-dimethyl-6-(4-(4-(3,3,3-trifluoro-2-hydroxy-2-(3-methoxyphenyl)propanamido)phenyl)piperidin-1-yl)nicotinamide (20 mg, 0.032 mmol, 35%). LRMS m/z (M+H) 591.0 found, 591.2 required.

Using the same procedure described in Example 10-1, but replacing 6-chloro-5-(dimethylcarbamoyl)pyridin-2-yl trifluoromethanesulfonate with 2-chloro-4-fluoro-N,N-dimethylbenzamide and 2-chloro-4-fluoro-N-methylbenzamide in the last step or replacing (4-nitrophenyl)boronic acid with (3-nitrophenyl)boronic acid and but replacing 6-chloro-5-(dimethylcarbamoyl)pyridin-2-yl trifluoromethanesulfonate with 2-chloro-4-fluoro-N,N-dimethylbenzamide in the last step, the examples in table 10 were prepared.

TABLE 10

| Example | Structure | IUPAC Name | LRMS, found [M + H]+ |
|---|---|---|---|
| 10-1 | 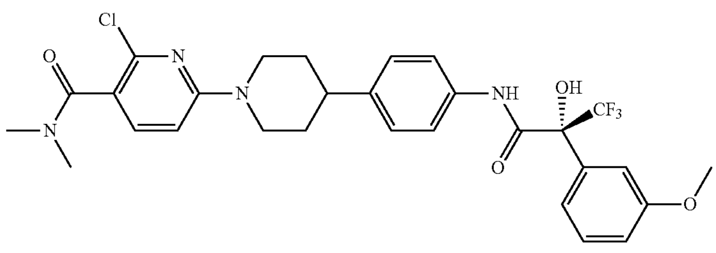 | (R)-2-chloro-N,N-dimethyl-6-(4-(4-(3,3,3-trifluoro-2-hydroxy-2-(3-methoxyphenyl)propanamido)phenyl)piperidin-1-yl)nicotinamide | 591.0 |

TABLE 10-continued

| Example | Structure | IUPAC Name | LRMS, found [M + H]+ |
|---|---|---|---|
| 10-2 | 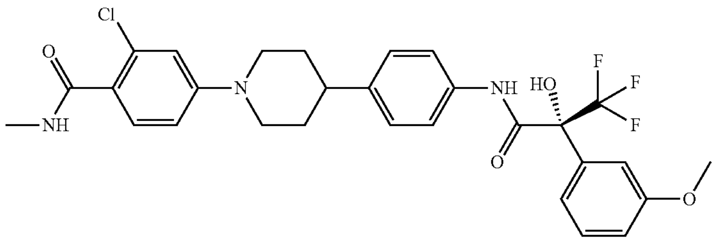 | (R)-2-chloro-N-methyl-4-(4-(4-(3,3,3-trifluoro-2-hydroxy-2-(3-methoxyphenyl)propanamido)phenyl)piperidin-1-yl)benzamide | 576.2 |
| 10-3 | 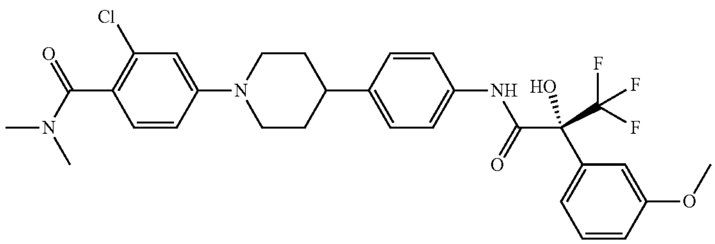 | (R)-2-chloro-N,N-dimethyl-4-(4-(4-(3,3,3-trifluoro-2-hydroxy-2-(3-methoxyphenyl)propanamido)phenyl)piperidin-1-yl)benzamide | 590.2 |
| 10-4 | 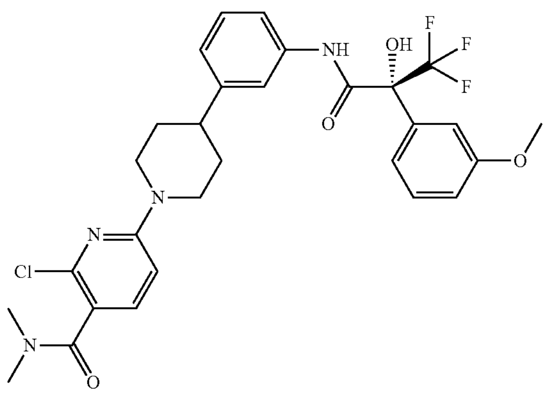 | (R)-2-chloro-N,N-dimethyl-6-(4-(3-(3,3,3-trifluoro-2-hydroxy-2-(3-methoxyphenyl)propanamido)phenyl)piperidin-1-yl)nicotinamide | 591.2 |

Example 11-1

(R)—N,N,2-trimethyl-6-(4-((3-(3,3,3-trifluoro-2-hydroxy-2-(3-methoxyphenyl)-N-methylpropanamido)cyclobutyl)methyl)piperidin-1-yl)nicotinamide

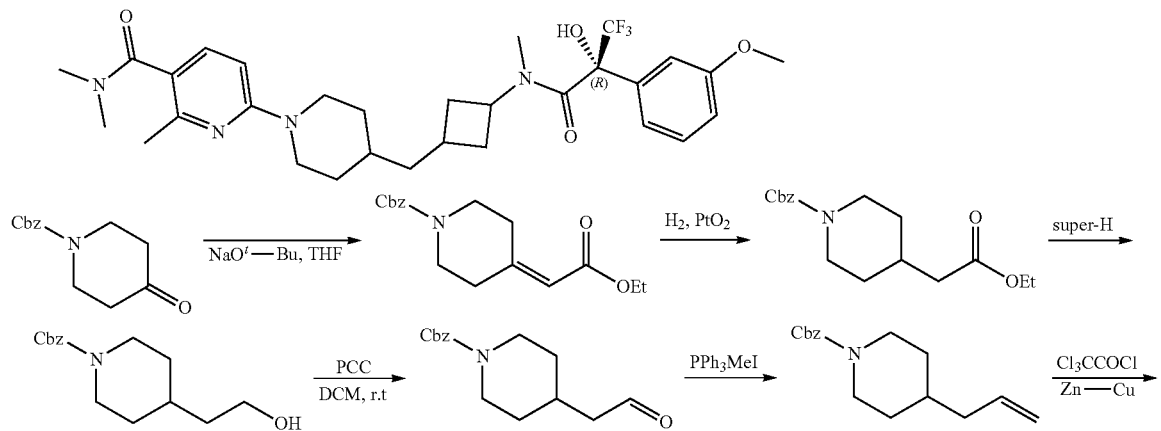

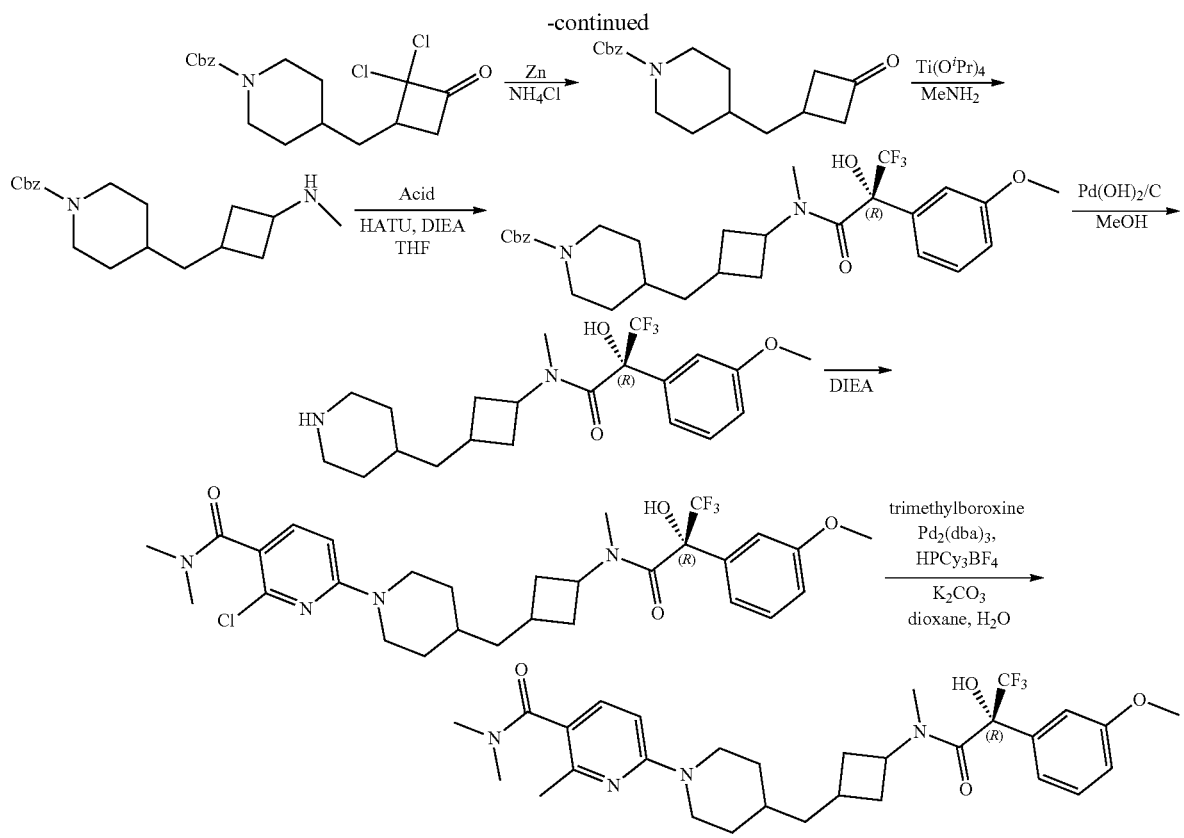

benzyl 4-(2-ethoxy-2-oxoethylidene)piperidine-1-carboxylate

To a solution of ethyl 2-(dimethoxyphosphoryl)acetate (40.4 g, 206 mmol) in THF (200 mL) was added sodium 2-methylpropan-2-olate (24.72 g, 257 mmol) at 0° C. After stirring for 1 h, benzyl 4-oxopiperidine-1-carboxylate (40 g, 171 mmol) was added to the mixture, and then the mixture was stirred for 2 h at rt, quenched with aq $NH_4Cl$ (50 mL) and extracted with EtOAc (3×200 mL). The organic layer was dried over anhydrous $Na_2SO_4$, filtered and concentrated. The crude product was purified by chromatography (PE:EtOAc=10:1) to give the benzyl 4-(2-ethoxy-2-oxoethylidene)piperidine-1-carboxylate (44 g, 145 mmol, 85%). LRMS m/z (M+H) 304.3 found, 304.2 required.

benzyl 4-(2-ethoxy-2-oxoethyl)piperidine-1-carboxylate

A mixture of benzyl 4-(2-ethoxy-2-oxoethylidene)piperidine-1-carboxylate (44 g, 145 mmol) and platinum(IV) oxide (1.647 g, 7.25 mmol) in EtOAc (400 mL) was stirred overnight at rt under $H_2$ atmosphere. The catalyst was filtered off and the filtrate was concentrated to give benzyl 4-(2-ethoxy-2-oxoethyl)piperidine-1-carboxylate (44 g, 144 mmol, 99%) which was directly used in next step. LRMS m/z (M+H) 306.0 found, 306.2 required.

benzyl 4-(2-hydroxyethyl)piperidine-1-carboxylate

To a solution of benzyl 4-(2-ethoxy-2-oxoethyl)piperidine-1-carboxylate (44 g, 144 mmol) in DCM (5 mL) was added Super-H (288 mL, 288 mmol, 1M in THF) at 0° C. The mixture was stirred for 3 h at rt, quenched with aq $NH_4Cl$ (200 mL) and extracted with EtOAc (3×200 mL). The organic layer was dried over anhydrous $Na_2SO_4$, filtered and concentrated. The crude product was purified by chromatography (PE:EtOAc=1:1) to give the benzyl 4-(2-hydroxyethyl)piperidine-1-carboxylate (30 g, 114 mmol, 79%). LRMS m/z (M+H) 264.2 found, 264.2 required.

benzyl 4-(2-oxoethyl)piperidine-1-carboxylate

A mixture of benzyl 4-(2-hydroxyethyl)piperidine-1-carboxylate (27 g, 103 mmol), PCC (44.2 g, 205 mmol) and silica gel (50 g) in DCM (500 mL) was stirred for 3 h at rt. The solid was filtered off and the filtrate was washed with water (100 mL). The aqueous layer was extracted with $Et_2O$ (3×2000 mL). The organic layer was dried over anhydrous $Na_2SO_4$, filtered and concentrated to give benzyl 4-(2-oxoethyl)piperidine-1-carboxylate (21 g, 80 mmol, 78%) which was used in next step without purification. LRMS m/z (M+H) 262.2 found, 262.2 required.

benzyl 4-allylpiperidine-1-carboxylate

To a solution of iodo(methyl)triphenylphosphorane (16.24 g, 40.2 mmol) in THF (100 mL) was added potassium 2-methylpropan-2-olate (6.01 g, 53.6 mmol) at 0° C. After stirring for 1 h at 0° C., benzyl 4-(2-oxoethyl)piperidine-1-carboxylate (7 g, 26.8 mmol) was added to the mixture. The resulting mixture was stirred for 2 h at rt, quenched with aq $NH_4Cl$ (50 mL) and extracted with EtOAc (3×200 mL). The organic layer was dried over anhydrous $Na_2SO_4$, filtered and concentrated. The crude product was purified by chromatography (PE:EtOAc=40:1) to give the benzyl 4-allylpiperidine-1-carboxylate (4.8 g, 18.51 mmol, 69%). LRMS m/z (M+H) 260.1 found, 260.2 required.

benzyl 4-((2,2-dichloro-3-oxocyclobutyl)methyl) piperidine-1-carboxylate

To a mixture of benzyl 4-allylpiperidine-1-carboxylate (3 g, 11.57 mmol) and zinc-copper couple (7.5 g, 58.2 mmol) in $Et_2O$ (300 mL) was added 2,2,2-trichloroacetyl chloride (11 g, 60.5 mmol). After stirring at rt for 2 h, the mixture was poured into saturated $NaHCO_3$ (200 mL) and the solid was filtered off. The filtrate was extracted with EtOAc (300 mL×3). The organic phase was washed with brine (30 mL), dried and concentrated to give benzyl 4-((2,2-dichloro-3-oxocyclobutyl)methyl)piperidine-1-carboxylate (3.8 g, 88%) which was used in next step directly. LRMS m/z (M+H) 370.1 found, 370.2 required.

benzyl 4-((3-oxocyclobutyl)methyl)piperidine-1-carboxylate

A mixture of benzyl 4-((2,2-dichloro-3-oxocyclobutyl)methyl)piperidine-1-carboxylate (3.8 g, 10.26 mmol), Zn (3.76 g, 57.8 mmol) and $NH_4Cl$ (2.74 g, 51.3 mmol) in MeOH (200 mL) was stirred at rt overnight. The solid was filtered off and the filtrate was concentrated and purified by column chromatography (PE/EtOAc=20:1 to 10:1) to give benzyl 4-((3-oxocyclobutyl)methyl)piperidine-1-carboxylate (2 g, 6.64 mmol, 64.7% yield). LRMS m/z (M+H) 302.1 found, 302.2 required.

benzyl 4-((3-(methylamino)cyclobutyl)methyl)piperidine-1-carboxylate

A mixture of benzyl 4-((3-oxocyclobutyl)methyl)piperidine-1-carboxylate (150 mg, 0.5 mmol), $MeNH_2$ (2.5 mL, 5 mmol, 2M in THF) and titanium isopropoxide (284 mg, 1 mmol) in DCE (10 mL) was stirred at rt overnight. NaBH(OAc)$_3$ (1.06 g, 5 mmol) was added to the mixture and the resulting mixture was stirred overnight. The reaction was quenched with aq NH4Cl (20 mL) and extracted with EtOAc (30 mL×3). The organic phase was washed with brine (10 mL), dried over anhydrous $Na_2SO_4$, filtered and concentrated to give benzyl 4-((3-(methylamino)cyclobutyl) methyl)piperidine-1-carboxylate (158 mg, 100%) which was used in next step without purification. LRMS m/z (M+H) 317.3 found, 317.2 required.

(R)-benzyl-4-((3-(3,3,3-trifluoro-2-hydroxy-2-(3-methoxyphenyl)-N-methylpropanamido)cyclobutyl) methyl)piperidine-1-carboxylate A mixture of benzyl 4-((3-(methylamino)cyclobutyl) methyl)piperidine-1-carboxylate (260 mg, 0.82 mmol), (R)-3,3,3-trifluoro-2-hydroxy-2-(3-methoxyphenyl)propanoic acid (205 mg, 0.82 mmol), HATU (467 mg, 1.23 mmol) and DIEA (317 mg, 2.46 mmol) in THF (4 mL) was stirred at rt for 1 h. The crude was directly purified by reverse-phase HPLC (Mobile Phase: methanol/water (10 mM NH$_4$HCO$_3$)) to afford the (R)-benzyl 4-((3-(3,3,3-trifluoro-2-hydroxy-2-(3-methoxyphenyl)-N-methylpropanamido)cyclobutyl) methyl)piperidine-1-carboxylate (110 mg, 24%). LRMS m/z (M-55) 549.3 found, 549.2 required.

(R)-3,3,3-trifluoro-2-hydroxy-2-(3-methoxyphenyl)-N-methyl-N-(3-(piperidin-4-ylmethyl)cyclobutyl) propanamide A mixture of (R)-benzyl 4-((3-(3,3,3-trifluoro-2-hydroxy-2-(3-methoxyphenyl)-N-methylpropanamido)cyclobutyl) methyl)piperidine-1-carboxylate (110 mg, 0.2 mmol) and 20% Pd(OH)$_2$/C (11 mg) in MeOH (2 mL) was degassed and backfilled with $H_2$ three times. The resulting mixture was stirred at rt under $H_2$ balloon for 4 h. The catalyst was filtered off and the filtrate was concentrated in vacuo to afford (R)-3,3,3-trifluoro-2-hydroxy-2-(3-methoxyphenyl)-N-methyl-N-(3-(piperidin-4-ylmethyl)cyclobutyl)propanamide (70 mg, 84%). LRMS m/z (M+H) 415.3 found, 415.2 required.

(R)-2-chloro-N,N-dimethyl-6-(4-((3-(3,3,3-trifluoro-2-hydroxy-2-(3-methoxyphenyl)-N-methylpropanamido)cyclobutyl)methyl)piperidin-1-yl)nicotinamide A mixture of (R)-3,3,3-trifluoro-2-hydroxy-2-(3-methoxyphenyl)-N-methyl-N-(3-(piperidin-4-ylmethyl)cyclobutyl)propanamide (48 mg, 0.144 mmol), 6-chloro-5-(dimethylcarbamoyl)pyridin-2-yl trifluoromethanesulfonate (50 mg, 0.12 mmol) and DIEA (31 mg, 0.24 mmol) in acetonitrile (2 mL) was stirred at 60° C. for 4 h. The mixture was directly purified by reverse-phase HPLC (Mobile Phase: methanol/water (10 mM NH$_4$HCO$_3$)) to give (R)-2-chloro-N,N-dimethyl-6-(4-((3-(3,3,3-trifluoro-2-hydroxy-2-(3-methoxyphenyl)-N-methylpropanamido)cyclobutyl)methyl) piperidin-1-yl)nicotinamide (50 mg, 69%). LRMS m/z (M+H) 597.3 found, 597.2 required.

(R)—N,N,2-trimethyl-6-(4-((3-(3,3,3-trifluoro-2-hydroxy-2-(3-methoxyphenyl)-N-methylpropanamido)cyclobutyl)methyl)piperidin-1-yl)nicotinamide A microwave tube was charged with (R)-2-chloro-N,N-dimethyl-6-(4-((3-(3,3,3-trifluoro-2-hydroxy-2-(3-methoxyphenyl)-N-methylpropanamido)cyclobutyl)methyl) piperidin-1-yl)nicotinamide (50 mg, 0.084 mmol), trimethylboroxin (31 mg, 0.25 mmol), Pd$_2$(dba)$_3$ (6 mg, 0.0084 mmol), HP(Cy)$_3$BF$_4$ (6 mg, 0.0168 mmol), K$_2$CO$_3$ (23 mg, 0.168 mmol), dioxane (2 mL), H$_2$O (0.2 mL) and stirred bar. The mixture was bubbled with a stream of $N_2$ for 3 min and the tube was sealed and heated to 100° C. for 1.5 h in CEM Microwave Reactor. The mixture was purified by Prep-HPLC (mobile phase: acetonitrile/water (10 mM NH$_4$HCO$_3$)) to afford the 2 isomers (cis and trans) (15 mg each, 31%, RT=1.95 min, 1.98 min). LRMS m/z (M+H) 577.3 found, 577.3 required. Cyclobutane stereochemistry not established and first eluting peak not active.

Using the procedure described in Example 11-1, but replacing methylamine with ammonia dioxane solution in the eighth step, or replacing methylamine with ammonia dioxane solution in the eighth step, replacing (R)-3,3,3-trifluoro-2-hydroxy-2-(3-methoxyphenyl)propanoic acid with (R)-3,3,3-trifluoro-2-hydroxy-2-(3-methoxyphenyl) propanoic acid and (R)-3,3,3-trifluoro-2-hydroxy-2-phenyl-propanoic acid in the ninth step and replacing 6-chloro-5-(dimethylcarbamoyl)pyridin-2-yl trifluoromethanesulfonate with 2-chloro-4-fluoro-N,N-dimethylbenzamide and 2-chloro-4-fluoro-N-methylbenzamide, the examples of Table 11 were prepared.

TABLE 11

| Example | Structure | IUPAC Name | LRMS, found [M + H]+ |
|---|---|---|---|
| 11-1 | 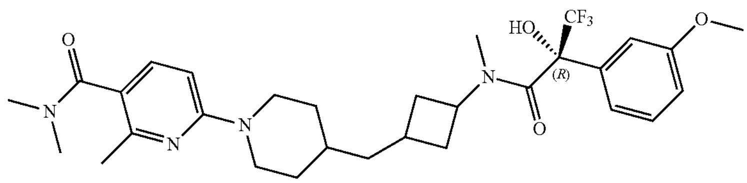 | (R)-N,N,2-trimethyl-6-(4-((3-(3,3,3-trifluoro-2-hydroxy-2-(3-methoxyphenyl)-N-methyl-propanamido)cyclobutyl)meth-yl)piperidin-1-yl)nicotinamide | 577.3 |
| 11-2 | 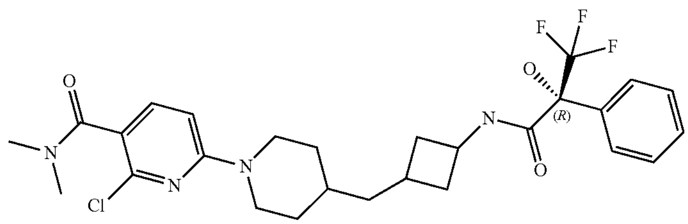 | (R)-2-chloro-N,N-dimethyl-6-(4-((3-(3,3,3-trifluoro-2-hydroxy-2-phenylpropanamido)cyclo-butyl)methyl)piperidin-1-yl)nicotinamide | 553.2 |
| 11-3 | 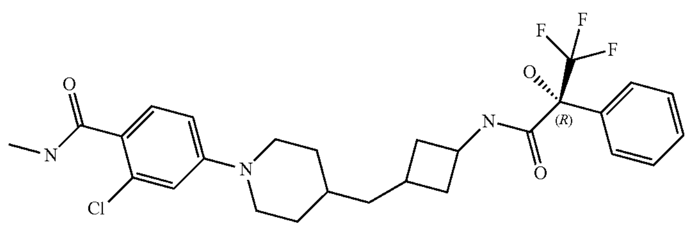 | (R)-2-chloro-N-methyl-4-(4-((3-(3,3,3-trifluoro-2-hydroxy-2-phenylpropanamido)cyclobutyl)methyl)piperidin-1-yl)benzamide | 538.2 |
| 11-4 | 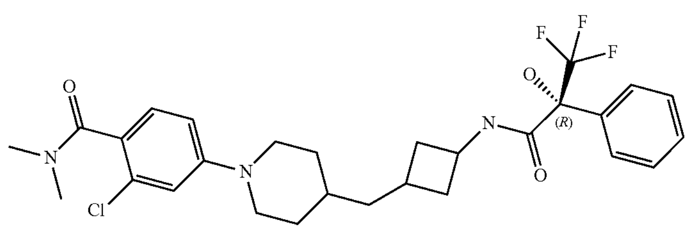 | (R)-2-chloro-N,N-dimethyl-4-(4-((3-(3,3,3-trifluoro-2-hydroxy-2-phenylpropanamido)cyclo-butyl)methyl)piperidin-1-yl)benz-amide | 552.2 |
| 11-5 | 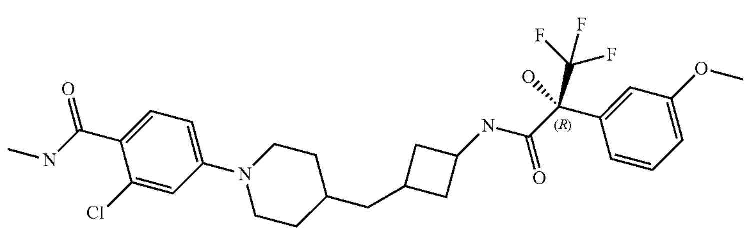 | (R)-2-chloro-N-methyl-4-(4-((3-(3,3,3-trifluoro-2-hydroxy-2-(3-methoxyphenyl)propanamido)cyclobutyl)methyl)piperidin-1-yl)benzamide | 568.2 |
| 11-6 | 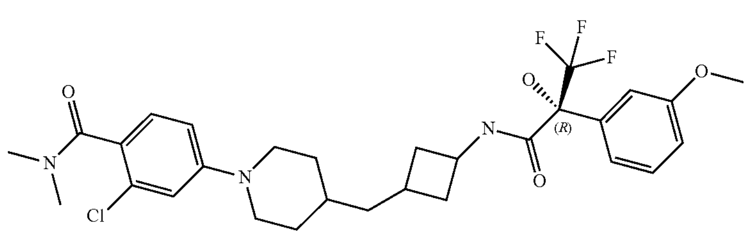 | (R)-2-chloro-N,N-dimethyl-4-(4-((3-(3,3,3-trifluoro-2-hydroxy-2-(3-methoxy-phenyl)propanamido)cyclo-butyl)methyl)piperidin-1-yl)benzamide | 582.2 |

Example 12-1

(R)-2-chloro-4-(4-fluoro-4-(3-(3,3,3-trifluoro-2-hydroxy-N-methyl-2-phenylpropanamido)propyl)piperidin-1-yl)-N,N-dimethylbenzamide

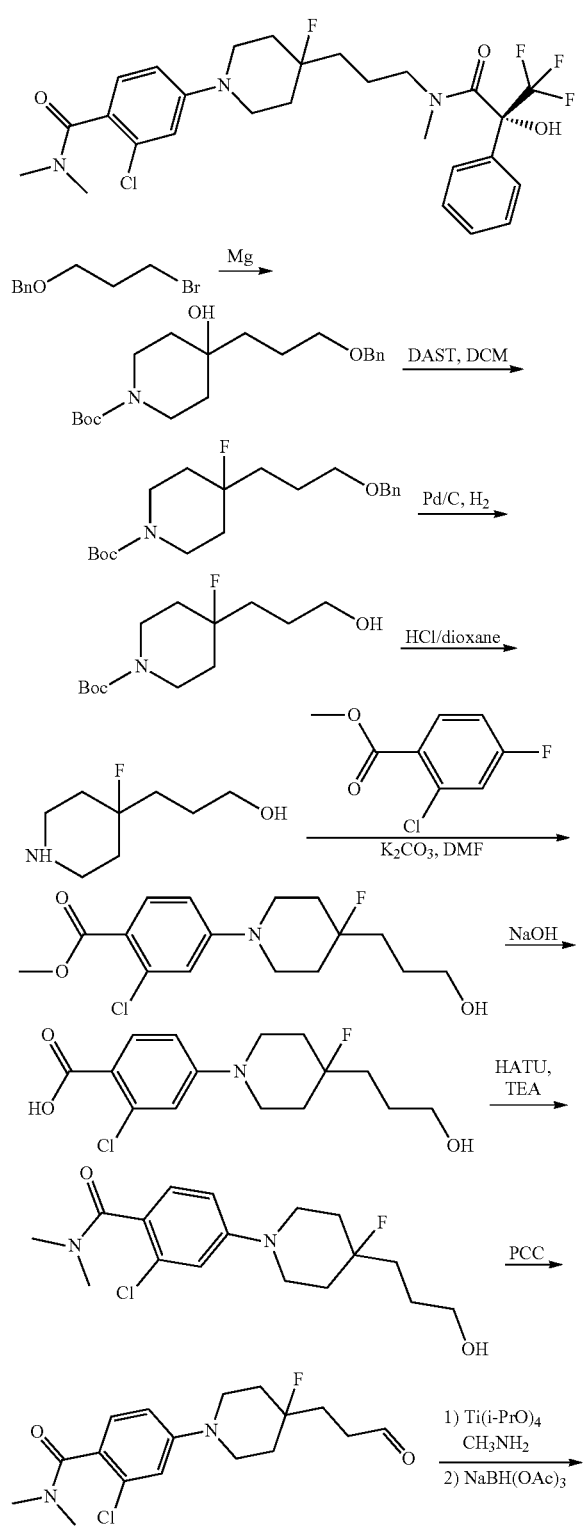

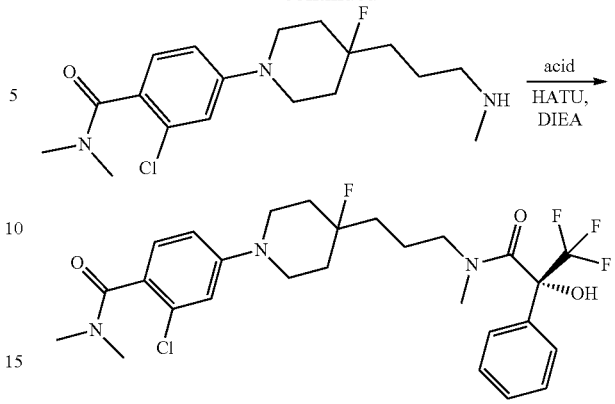

tert-butyl 4-(3-(benzyloxy)propyl)-4-hydroxypiperidine-1-carboxylate

To a mixture of ((3-bromopropoxy)methyl)benzene (5.5 g, 24 mmol) and Mg (672 mg, 28 mmol) in THF (25 mL) was added a solution of $I_2$ (30 mg, 0.12 mmol) in THF (5 mL) at rt. The mixture was stirred at rt for 3 h to give a solution, to which was added tert-butyl 4-oxopiperidine-1-carboxylate (4 g, 20 mmol) in THF (10 mL) at −78° C. The resulting mixture was stirred for another 1 h at rt. The mixture was quenched by 50 mL sat. $NH_4Cl$, extracted with EtOAc (200 mL×2), concentrated under reduced pressure to give the crude product. The crude product was purified by column chromatography (silica gel: 300-400 mesh, PE/EtOAc=10/1 to 5/1) to give pure tert-butyl 4-(3-(benzyloxy)propyl)-4-hydroxypiperidine-1-carboxylate (4.67 g, 70%). LRMS m/z (M+Na) 372.2 found, 372.2 required.

tert-butyl 4-(3-(benzyloxy)propyl)-4-fluoropiperidine-1-carboxylate

To a solution of tert-butyl 4-(3-(benzyloxy)propyl)-4-hydroxypiperidine-1-carboxylate (2.2 g, 6.3 mmol) in 12 mL of DCM was added DAST (2.78 g, 12.6 mmol, 50% in THF) at −78° C. The resulting mixture was stirred for 1 h, quenched by 20 mL sat. $NaHCO_3$, extracted with DCM (40 mL×3). The combined organic phase was dried over $Na_2SO_4$, filtered, and concentrated to give tert-butyl 4-(3-(benzyloxy)propyl)-4-fluoropiperidine-1-carboxylate (1.37 g, 62%). LRMS m/z (M+Na) 374.2 found, 374.2 required.

tert-butyl 4-fluoro-4-(3-hydroxypropyl)piperidine-1-carboxylate

A mixture of tert-butyl 4-(3-(benzyloxy)propyl)-4-fluoropiperidine-1-carboxylate (1.37 g, 3.9 mmol) and dry 10% Pd/C (150 mg) in ethanol (30 mL) was degassed and backfilled with $H_2$ (three times). The mixture was stirred under $H_2$ balloon at rt overnight. The catalyst was filtered off and the filtrate was concentrated to afford crude tert-butyl 4-fluoro-4-(3-hydroxypropyl)piperidine-1-carboxylate (1.23 g, 89%). LRMS m/z (M+Na) 284.2 found, 284.2 required.

3-(4-fluoropiperidin-4-yl)propan-1-ol

A solution of tert-butyl 4-fluoro-4-(3-hydroxypropyl)piperidine-1-carboxylate (450 mg, 1.72 mmol) in 4M HCl/1,4-dioxane (5 mL) was stirred for 2 h at rt. Then the mixture was concentrated under reduced pressure to give crude 3-(4-fluoropiperidin-4-yl)propan-1-ol (320 mg, 94%). LRMS m/z (M+H) 162.1 found, 162.1 required.

methyl 2-chloro-4-(4-fluoro-4-(3-hydroxypropyl) piperidin-1-yl)benzoate

A mixture of 3-(4-fluoropiperidin-4-yl)propan-1-ol (286 mg, 1.6 mmol), methyl 2-chloro-4-fluorobenzoate (360 mg, 1.9 mmol), K$_2$CO$_3$ (662 mg, 4.8 mmol) in 8 mL of DMF was stirred at 90° C. for 16 h. The resulting mixture was poured into 50 mL of water, extracted with EtOAc (30 mL×2), and the combined organic phase was concentrated. The crude compound was purified by reverse-phase HPLC (mobile phase: methanol/water (10 mM NH$_4$HCO$_3$)) to afford methyl 2-chloro-4-(4-fluoro-4-(3-hydroxypropyl)piperidin-1-yl)benzoate (293 mg, 62%). LRMS m/z (M+H) 330.1 found, 330.1 required.

2-chloro-4-(4-fluoro-4-(3-hydroxypropyl)piperidin-1-yl)benzoic acid

A solution of methyl 2-chloro-4-(4-fluoro-4-(3-hydroxypropyl)piperidin-1-yl)benzoate (293 mg, 0.89 mmol) in 2N NaOH (4 mL) and methanol (4 mL) was stirred at 50° C. for 1 h. The solution was acidified with 6N HCl to pH=2-4, extracted with EtOAc (20 mL×3), dried over anhydrous Na$_2$SO$_4$, filtered and concentrated to give the 2-chloro-4-(4-fluoro-4-(3-hydroxypropyl)piperidin-1-yl)benzoic acid (256 mg, 91%). LRMS m/z (M+H) 316.1 found, 316.1 required.

2-chloro-4-(4-fluoro-4-(3-hydroxypropyl)piperidin-1-yl)-N,N-dimethylbenzamide

A mixture of 2-chloro-4-(4-fluoro-4-(3-hydroxypropyl) piperidin-1-yl)benzoic acid (256 mg, 0.81 mmol), dimethylamine hydrochloride (140 mg, 1.42 mmol), Et$_3$N (282 mg, 2.8 mmol), HATU (616 mg, 1.62 mmol) in DMF (8 mL) was stirred at rt for 16 h. The mixture was directly purified by reverse-phase HPLC (mobile phase: methanol/water (10 mM NH$_4$HCO$_3$)) to afford 2-chloro-4-(4-fluoro-4-(3-hydroxypropyl)piperidin-1-yl)-N,N-dimethylbenzamide (266 mg, 96%). LRMS m/z (M+H) 343.2 found, 343.2 required.

2-chloro-4-(4-fluoro-4-(3-oxopropyl)piperidin-1-yl)-N,N-dimethylbenzamide

To a solution of 2-chloro-4-(4-fluoro-4-(3-hydroxypropyl)piperidin-1-yl)-N,N-dimethylbenzamide (234 mg, 0.68 mmol) in DCM (8 mL) was added PCC (232 mg, 1.07 mmol). The mixture was stirred at 30° C. for 4 h. The mixture was concentrated and the crude product was directly purified by reverse-phase HPLC (mobile phase: methanol/water (10 mM NH$_4$HCO$_3$)) to afford 2-chloro-4-(4-fluoro-4-(3-oxopropyl)piperidin-1-yl)-N,N-dimethylbenzamide (80 mg, 34%). LRMS m/z (M+H) 341.1 found, 341.1 required.

2-chloro-4-(4-fluoro-4-(3-(methylamino)propyl) piperidin-1-yl)-N,N-dimethylbenzamide Titanium tetraisopropanolate (130 mg, 0.46 mmol) was added to a solution of methylamine (2 mL, 4 mmol, 2M in THF) followed by the addition of 2-chloro-4-(4-fluoro-4-(3-oxopropyl)piperidin-1-yl)-N,N-dimethylbenzamide (80 mg, 0.23 mmol) in 1 mL of THF. After stirring at rt for 5 h, sodium triacetoxyborohydride (97 mg, 0.46 mmol was added and the resulting mixture was further stirred for another 4 h. The reaction was quenched with 1N NaOH (10 mL), and the precipitate was filtered off and the filtrate was concentrated. The crude compound was purified by reverse-phase HPLC (mobile phase: methanol/water (10 mM NH$_4$HCO$_3$)) to afford 2-chloro-4-(4-fluoro-4-(3-(methylamino)propyl)piperidin-1-yl)-N,N-dimethylbenzamide (24 mg, 30%). LRMS m/z (M+H) 356.2 found, 356.2 required.

(R)-2-chloro-4-(4-fluoro-4-(3-(3,3,3-trifluoro-2-hydroxy-N-methyl-2-phenylpropanamido)propyl)piperidin-1-yl)-N,N-dimethylbenzamide A mixture of (R)-3,3,3-trifluoro-2-hydroxy-2-phenylpropanoic acid (15 mg, 0.067 mmol), Et$_3$N (10 mg, 0.1 mmol), HATU (25 mg, 0.067 mmol), 2-chloro-4-(4-fluoro-4-(3-(methylamino)propyl)piperidin-1-yl)-N,N-dimethylbenzamide (12 mg, 0.034 mmol) in THF (3 mL) was stirred at rt overnight. The mixture was directly purified by reverse-phase HPLC (mobile phase: methanol/water (10 mM NH$_4$HCO$_3$)) to afford (R)-2-chloro-4-(4-fluoro-4-(3-(3,3,3-trifluoro-2-hydroxy-N-methyl-2-phenylpropanamido)propyl)piperidin-1-yl)-N,N-dimethylbenzamide (12 mg, 63%). LRMS m/z (M+H) 558.2 found, 558.2 required.

Using the procedure described in Example 12-1, but replacing (R)-3,3,3-trifluoro-2-hydroxy-2-phenylpropanoic acid with (R)-3,3,3-trifluoro-2-hydroxy-2-(3-methoxyphenyl)propanoic acid in last step, or replacing methyl 2-chloro-4-fluorobenzoate with methyl 2-chloro-6-(trifluoromethylsulfonyloxy)nicotinate in the fifth step, the examples of Table 12 were prepared.

TABLE 12

| Example | Structure | IUPAC Name | LRMS, found [M + H] |
|---|---|---|---|
| 12-1 | 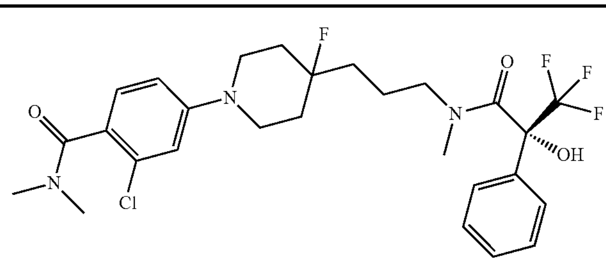 | (R)-2-chloro-4-(4-fluoro-4-(3-(3,3,3-trifluoro-2-hydroxy-N-methyl-2-phenylpropanamido)propyl)piperidin-1-yl)-N,N-dimethylbenzamide | 558.2 |

TABLE 12-continued

| Example | Structure | IUPAC Name | LRMS, found [M + H] |
|---|---|---|---|
| 12-2 | 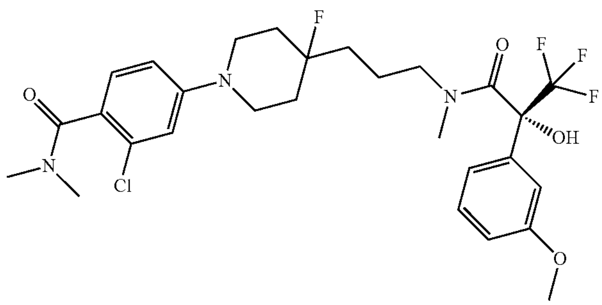 [SMILES: COc1cccc([C@@](O)(C(=O)N(C)CCCC2(F)CCN(c3ccc(C(=O)N(C)C)c(Cl)c3)CC2)C(F)(F)F)c1] | (R)-2-chloro-4-(4-fluoro-4-(3-(3,3,3-trifluoro-2-hydroxy-2-(3-methoxyphenyl)-N-methylpropanamido)propyl)piperidin-1-yl)-N,N-dimethylbenzamide | 588.2 |
| 12-3 | 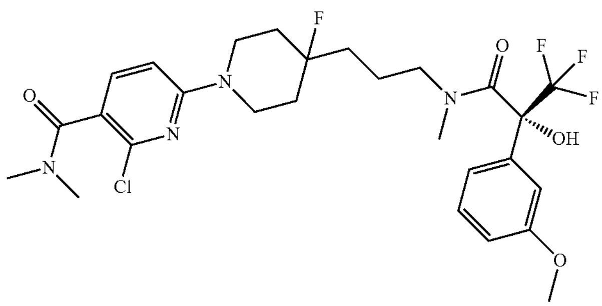 [SMILES: COc1cccc([C@@](O)(C(=O)N(C)CCCC2(F)CCN(c3ccc(C(=O)N(C)C)c(Cl)n3)CC2)C(F)(F)F)c1] | (R)-2-chloro-6-(4-fluoro-4-(3-(3,3,3-trifluoro-2-hydroxy-2-(3-methoxyphenyl)-N-methylpropanamido)propyl)piperidin-1-yl)-N,N-dimethylnicotinamide | 589.2 |
| 12-4 | 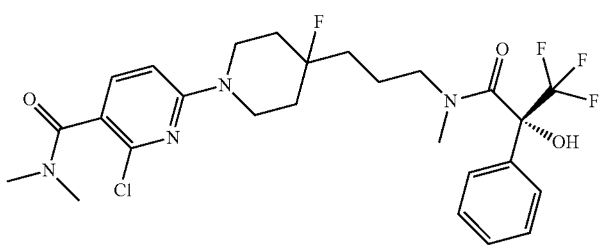 [SMILES: CN(C)C(=O)c1ccc(N2CCC(F)(CCCN(C)C(=O)[C@](O)(c3ccccc3)C(F)(F)F)CC2)nc1Cl] | (R)-2-chloro-6-(4-fluoro-4-(3-(3,3,3-trifluoro-2-hydroxy-N-methyl-2-phenylpropanamido)propyl)piperidin-1-yl)-N,N-dimethylnicotinamide | 559.2 |

Example 13-1

2-chloro-N,N-dimethyl-6-(2-(2-((R)-3,3,3-trifluoro-2-hydroxy-N-methyl-2-phenylpropanamido)ethyl)-7-azaspiro[3.5]nonan-7-yl)nicotinamide

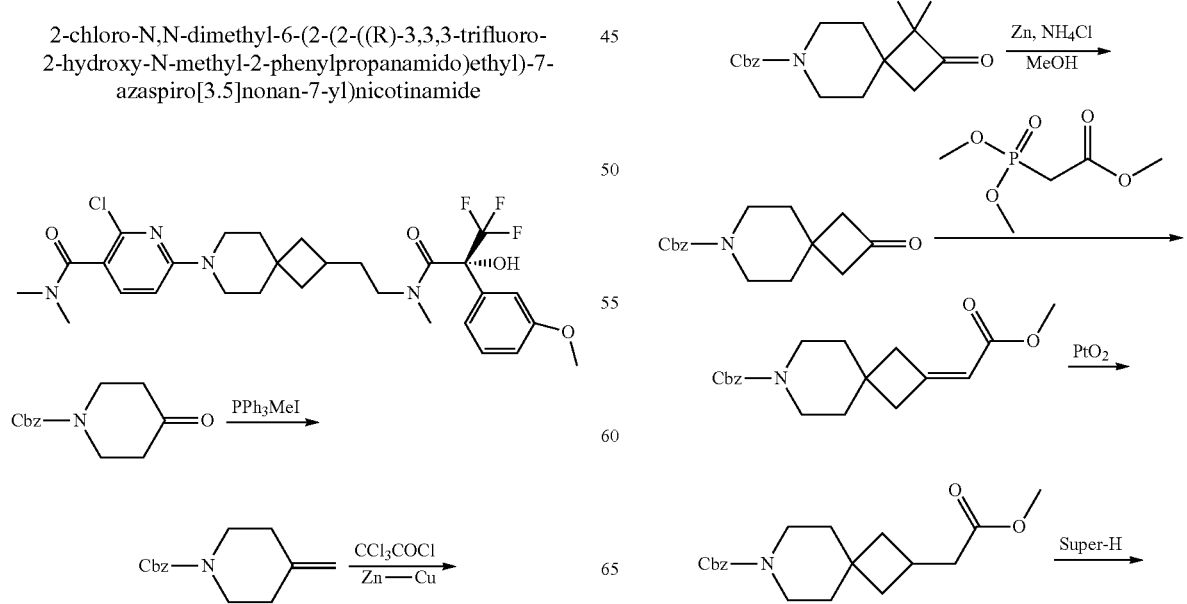

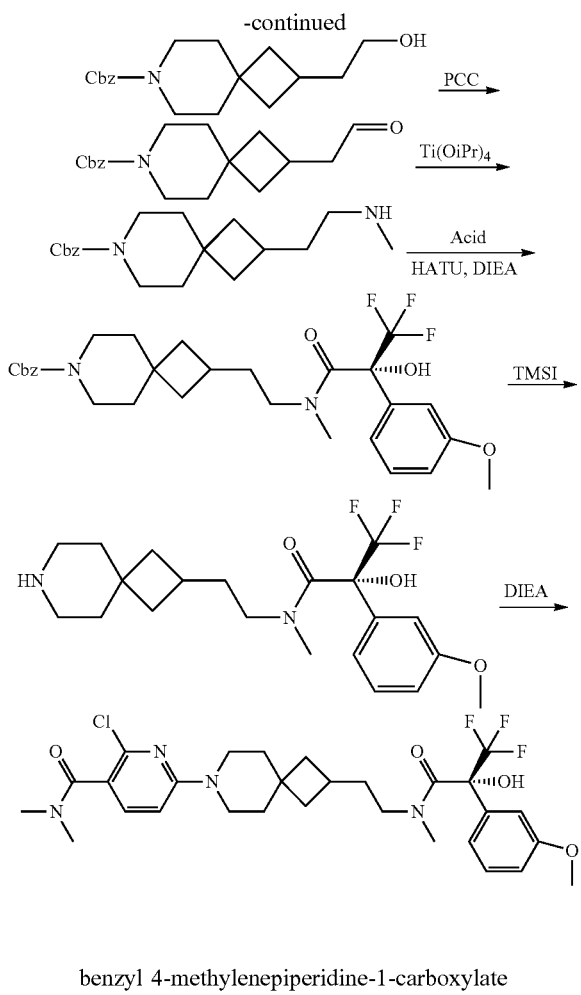

benzyl 4-methylenepiperidine-1-carboxylate

To a solution of iodo(methyl)triphenylphosphorane (5.20 g, 12.86 mmol) in THF (20 mL) was added potassium 2-methylpropan-2-olate (1.924 g, 17.15 mmol) at 0° C. After stirring for 1 h at 0° C., benzyl 4-oxopiperidine-1-carboxylate (2 g, 8.57 mmol) was added to the mixture. And then the mixture was stirred for 2 h at rt, quenched with aq NH₄Cl (10 mL) and extracted with EtOAc (3×20 mL). The organic layer was dried over anhydrous Na₂SO₄, filtered and concentrated. The crude product was purified by chromatography (PE:EtOAc=40:1) to give benzyl 4-methylenepiperidine-1-carboxylate (1.6 g, 6.92 mmol, 81% yield). LRMS m/z (M+H) 232.1 found, 232.1 required.

benzyl 1,1-dichloro-2-oxo-7-azaspiro[3.5]nonane-7-carboxylate

To the mixture of benzyl 4-methylenepiperidine-1-carboxylate (1.6 g, 6.92 mmol) and zinc-copper couple (8.92 g, 69.2 mmol) in ether (20 mL) was added 2,2,2-trichloroacetyl chloride (6.29 g, 34.6 mmol). The mixture was stirred at rt for 2 h. Then the reaction mixture was poured into saturated NaHCO₃ (50 mL) and the solid was filtered off and the filtrate was extracted with EtOAc (30 mL×2). The organic layer was washed with brine (30 mL), dried and concentrated to give benzyl 1,1-dichloro-2-oxo-7-azaspiro[3.5]nonane-7-carboxylate (1.8 g, 5.26 mmol, 76%) which was used in next step directly. LRMS m/z (M+H) 342.2 found, 342.1 required.

benzyl 2-oxo-7-azaspiro[3.5]nonane-7-carboxylate

To a mixture of benzyl 1,1-dichloro-2-oxo-7-azaspiro[3.5]nonane-7-carboxylate (1.8 g, 5.26 mmol) in saturated ammonium chloride in MeOH (10 mL) was added Zn (1.719 g, 26.3 mmol). The resulting mixture was stirred at rt overnight. The Zn powder was filtered off and the filtrate was evaporated. The residue was purified by silica gel chromatography (PE:EtOAc=10:1) to give benzyl 2-oxo-7-azaspiro[3.5]nonane-7-carboxylate (1.2 g, 4.39 mmol, 83%). LRMS m/z (M+H) 274.3 found, 274.1 required.

benzyl 2-(2-methoxy-2-oxoethylidene)-7-azaspiro[3.5]nonane-7-carboxylate

A mixture of methyl 2-(dimethoxyphosphoryl)acetate (1.2 g, 6.6 mmol) and sodium 2-methylpropan-2-olate (740 mg, 7.7 mmol) in THF (20 mL) was stirred at 0° C. for 1 h. Benzyl 2-oxo-7-azaspiro[3.5]nonane-7-carboxylate (1.2 g, 4.4 mmol) was added to the mixture. The resulting mixture was stirred for 2 h at rt, quenched with aq NH₄Cl (10 mL) and extracted with EtOAc (3×20 mL). The organic layer was dried over anhydrous Na₂SO₄, filtered and concentrated. The crude product was purified by chromatography (PE:EtOAc=8:1) to give the benzyl 2-(2-methoxy-2-oxoethylidene)-7-azaspiro[3.5]nonane-7-carboxylate (1.1 g, 3.34 mmol, 76%). LRMS m/z (M+H) 330.2 found, 330.2 required.

benzyl 2-(2-methoxy-2-oxoethyl)-7-azaspiro[3.5]nonane-7-carboxylate

A mixture of benzyl 4-(2-ethoxy-2-oxoethylidene)piperidine-1-carboxylate (1.1 g, 3.3 mmol) and platinum(IV) oxide (100 mg) in EtOAc (10 mL) was stirred overnight at rt under atmosphere of hydrogen. The catalyst was filtered and the filtrate was concentrated to afford benzyl 2-(2-methoxy-2-oxoethyl)-7-azaspiro[3.5]nonane-7-carboxylate (1.1 g, 99%) which was used in next step without purification. LRMS m/z (M+H) 332.2 found, 332.2 required.

benzyl 2-(2-hydroxyethyl)-7-azaspiro[3.5]nonane-7-carboxylate

To a solution of benzyl 2-(2-methoxy-2-oxoethyl)-7-azaspiro[3.5]nonane-7-carboxylate (1.1 g, 3.3 mmol) in DCM (5 mL) was added Super-H (10 mL, 10 mmol, 1M in THF) at 0° C. The mixture was stirred for 3 h at rt, quenched with aq NH₄Cl (15 mL) and extracted with EtOAc (3×20 mL). The organic layer was dried over anhydrous Na₂SO₄, filtered and concentrated. The crude product was purified by silica gel column chromatography (PE:EtOAc=1:1) to give benzyl 2-(2-hydroxyethyl)-7-azaspiro[3.5]nonane-7-carboxylate (750 mg, 75%). LRMS m/z (M+H) 304.2 found, 304.2 required.

benzyl 2-(2-oxoethyl)-7-azaspiro[3.5]nonane-7-carboxylate

A mixture of benzyl 2-(2-hydroxyethyl)-7-azaspiro[3.5]nonane-7-carboxylate (750 mg, 2.5 mmol) and PCC (1.0 g, 4.6 mmol) in DCM (10 mL) was stirred for 2 h at rt. Then the mixture was concentrated and purified by column chromatography (silica gel: 300-400 mesh, PE/EtOAc=5/1) to afford benzyl 2-(2-oxoethyl)-7-azaspiro[3.5]nonane-7-carboxylate (480 mg, 64%). LRMS m/z (M+H) 302.2 found, 302.2 required.

benzyl 2-(2-(methylamino)ethyl)-7-azaspiro[3.5]nonane-7-carboxylate

A mixture of benzyl 2-(2-oxoethyl)-7-azaspiro[3.5]nonane-7-carboxylate (200 mg, 0.66 mmol) and methylamine (7 mL, 7 mmol, 1M in THF), titanium(IV) isopropoxide (560 mg, 1.97 mmol) in DCE (5 mL) was stirred overnight at rt. Then sodium cyanoborohydride (125 mg, 1.98 mmol) was added to the reaction mixture, and stirred for another 1 h at rt. The solvent was evaporated under reduced pressure and the residue was purified by reverse-phase HPLC (mobile phase: MeOH/Water (10 mM NH$_4$HCO$_3$)) to give benzyl 2-(2-(methylamino)ethyl)-7-azaspiro[3.5]nonane-7-carboxylate (120 mg, 57.4%). LRMS m/z (M+H) 317.2 found, 317.2 required.

benzyl 2-(2-((R)-3,3,3-trifluoro-2-hydroxy-N-methyl-2-phenylpropanamido)ethyl)-7-azaspiro[3.5]nonane-7-carboxylate A mixture of benzyl 2-(2-(methylamino)ethyl)-7-azaspiro[3.5]nonane-7-carboxylate (120 mg, 0.38 mmol), (R)-3,3,3-trifluoro-2-hydroxy-2-(3-methoxyphenyl)propanoic acid (120 mg, 0.48 mmol), HATU (188 mg, 0.49 mmol) and DIEA (147 mg, 1.14 mmol) in DMF (3 mL) was stirred at rt overnight. The mixture was directly purified by reverse-phase HPLC (mobile phase: methanol/water (10 mM NH$_4$HCO$_3$)) to afford benzyl 2-(2-((R)-3,3,3-trifluoro-2-hydroxy-N-methyl-2-phenylpropanamido)ethyl)-7-azaspiro[3.5]nonane-7-carboxylate (100 mg, 51.0%). LRMS m/z (M+H) 549.3 found, 549.2 required.

(2R)—N-(2-(7-azaspiro[3.5]nonan-2-yl)ethyl)-3,3,3-trifluoro-2-hydroxy-2-(3-methoxyphenyl)-N-methylpropanamide To a solution of 2-(2-((R)-3,3,3-trifluoro-2-hydroxy-N-methyl-2-phenylpropanamido)ethyl)-7-azaspiro[3.5]nonane-7-carboxylate (100 mg, 0.18 mmol) in DCM (5 mL) was added iodotrimethylsilane (70 mg, 0.35 mmol). The resulting mixture was stirred for 1 h at rt, quenched with MeOH (1 mL). The mixture was concentrated and purified by reverse-phase HPLC (mobile phase: methanol/water (10 mM NH$_4$HCO$_3$)) to give (2R)—N-(2-(7-azaspiro[3.5]nonan-2-yl)ethyl)-3,3,3-trifluoro-2-hydroxy-2-(3-methoxyphenyl)-N-methylpropanamide (50 mg, 66.2%). LRMS m/z (M+H) 415.1 found, 415.2 required.

2-chloro-N,N-dimethyl-6-(2-(2-((R)-3,3,3-trifluoro-2-hydroxy-2-(3-methoxyphenyl)-N-methylpropanamido)ethyl)-7-azaspiro[3.5]nonan-7-yl)nicotinamide A mixture of (2R)—N-(2-(7-azaspiro[3.5]nonan-2-yl)ethyl)-3,3,3-trifluoro-2-hydroxy-2-(3-methoxyphenyl)-N-methylpropanamide (15 mg, 0.036 mmol), 6-chloro-5-(dimethylcarbamoyl)pyridin-2-yltrifluoromethanesulfonate (12 mg, 0.036 mmol) and DIEA (14 mg, 0.108 mmol) in DMF (1 mL) was stirred for 1 h at 60° C. Then the mixture was purified by reverse-phase HPLC (mobile phase: methanol/water (10 mM NH$_4$HCO$_3$)) to afford 2-chloro-N,N-dimethyl-6-(2-(2-((R)-3,3,3-trifluoro-2-hydroxy-2-(3-methoxyphenyl)-N-methylpropanamido)ethyl)-7-azaspiro[3.5]nonan-7-yl)nicotinamide (12 mg, 60%). LRMS m/z (M+H) 597.2 found, 597.2 required.

Using the procedure described in Example 13-1, but replacing 6-chloro-5-(dimethylcarbamoyl)pyridin-2-yltrifluoromethanesulfonate with 6-chloro-5-(methylcarbamoyl)pyridin-2-yl trifluoromethanesulfonate and 6-chloro-5-(cyclopropylcarbamoyl)pyridin-2-yl trifluoromethanesulfonate in last step, the examples of Table 13 were prepared.

TABLE 13

| Example | Structure | IUPAC Name | LRMS, found [M + H] |
|---|---|---|---|
| 13-1 | 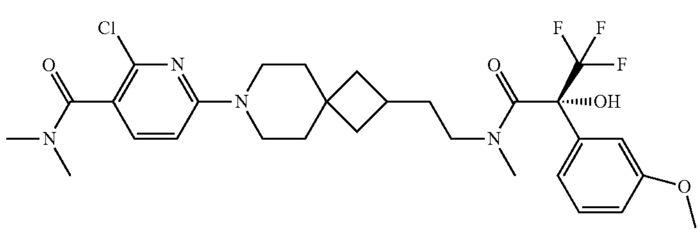 | 2-chloro-N,N-dimethyl-6-(2-(2-((R)-3,3,3-trifluoro-2-hydroxy-N-methyl-2-phenylpropanamido)ethyl)-7-azaspiro[3.5]nonan-7-yl)nicotinamide | 597.2 |
| 13-2 | 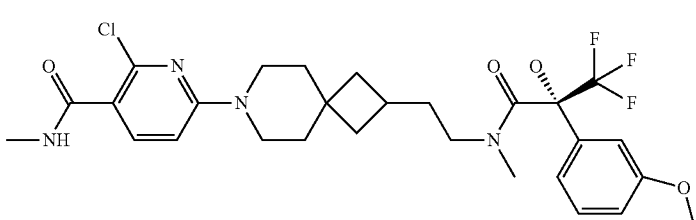 | 2-chloro-N-methyl-6-(2-(2-((R)-3,3,3-trifluoro-2-hydroxy-2-(3-methoxyphenyl)-N-methylpropanamido)ethyl)-7-azaspiro[3.5]nonan-7-yl)nicotinamide | 583.2 |

TABLE 13-continued

| Example | Structure | IUPAC Name | LRMS, found [M + H] |
|---|---|---|---|
| 13-3 | 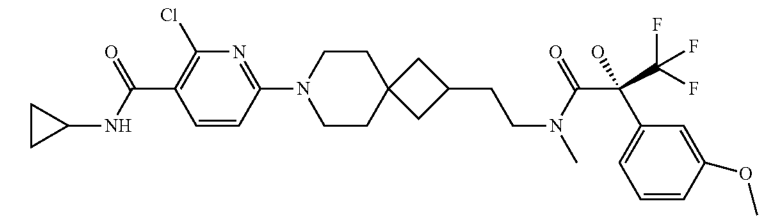 [SMILES: COc1cccc([C@@](O)(C(=O)N(C)CCC2CC3(CCN(c4ccc(C(=O)NC5CC5)c(Cl)n4)CC3)C2)C(F)(F)F)c1] | 2-chloro-N-cyclopropyl-6-(2-(2-(((R)-3,3,3-trifluoro-2-hydroxy-2-(3-methoxyphenyl)-N-methylpropanamido)ethyl)-7-azaspiro[3.5]nonan-7-yl)nicotinamide | 609.2 |

Example 14-1

2-chloro-N,N-dimethyl-6-(2-(((R)-3,3,3-trifluoro-2-hydroxy-2-(3-methoxyphenyl)-N-methylpropanamido)methyl)-7-azaspiro[3.5]nonan-7-yl)nicotinamide

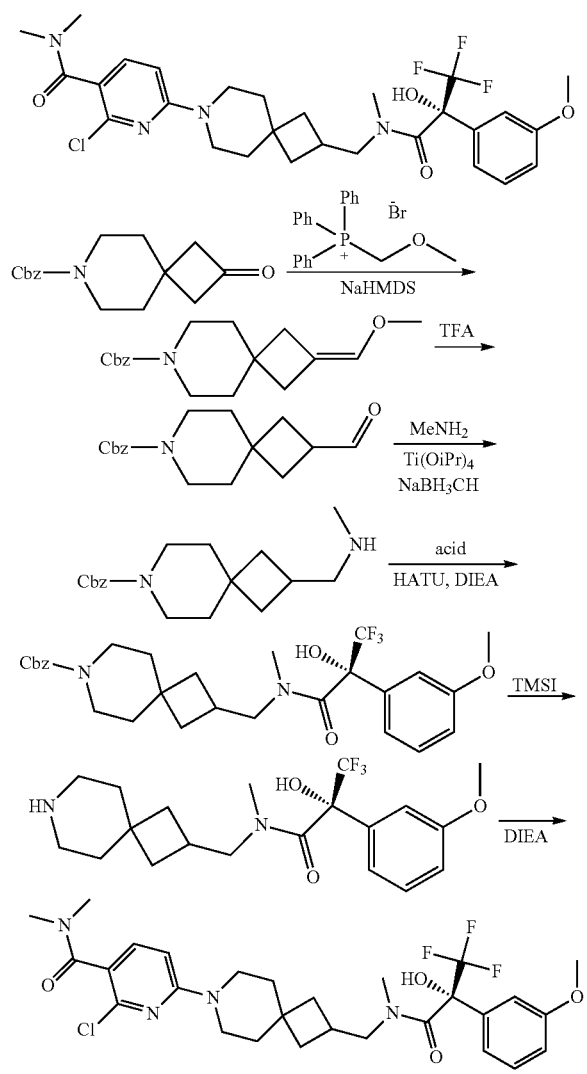

benzyl 2-(methoxymethylene)-7-azaspiro[3.5]nonane-7-carboxylate

To a solution (methoxymethyl)triphenylphosphonium bromide (338 mg, 0.87 mmol) in THF (5 mL) was added NaHMDS (1 mL, 1 mmol, 1M in THF) at 0° C. After stirring for 1 h at 0° C., benzyl 2-oxo-7-azaspiro[3.5]nonane-7-carboxylate (200 mg, 0.73 mmol) was added to the mixture, then the resulting mixture was stirred for 2 h at rt. The reaction was quenched with aq NH$_4$Cl (5 mL) and extracted with EtOAc (3×10 mL). The organic layer was dried over anhydrous Na$_2$SO$_4$, filtered and concentrated. The crude product was purified by reverse-phase HPLC (mobile phase: methanol/water (10 mM NH$_4$HCO$_3$)) to give benzyl 2-(methoxymethylene)-7-azaspiro[3.5]nonane-7-carboxylate (180 mg, 81.8%). LRMS m/z (M+H) 302.2 found, 302.2 required.

benzyl 2-formyl-7-azaspiro[3.5]nonane-7-carboxylate

A mixture of benzyl 2-(methoxymethylene)-7-azaspiro[3.5]nonane-7-carboxylate (180 mg, 0.60 mmol) and TFA (2 mL) in DCM (2 mL) was stirred for 30 min at rt. Then the mixture was diluted with EtOAc (30 mL) and washed with water (10 mL) and brine (10 mL). The organic layer was dried over Na$_2$SO$_4$, concentrated to give benzyl 2-formyl-7-azaspiro[3.5]nonane-7-carboxylate (150 mg, 87.4%). LRMS m/z (M+H) 288.2 found, 288.2 required.

benzyl 2-((methylamino)methyl)-7-azaspiro[3.5]nonane-7-carboxylate

A mixture benzyl 2-formyl-7-azaspiro[3.5]nonane-7-carboxylate (150 mg, 0.52 mmol) and methylamine (5 mL, 5 mmol, 1M in THF), titanium(IV) isopropoxide (440 mg, 1.54 mmol) in DCE (5 mL) was stirred overnight at rt. Then sodium cyanoborohydride (100 mg, 1.58 mmol) was added to the reaction mixture, and stirred for 1 h at rt. The reaction mixture was quenched with methanol (1 mL) and solvent was evaporated under reduced pressure. The residue was purified by reverse-phase HPLC (mobile phase: methanol/water (10 mM NH$_4$HCO$_3$)) to give benzyl 2-((methylamino)methyl)-7-azaspiro[3.5]nonane-7-carboxylate (100 mg, 63.7%). LRMS m/z (M+H) 303.2 found, 303.2 required.

benzyl 2-(((R)-3,3,3-trifluoro-2-hydroxy-2-(3-methoxyphenyl)-N-methylpropanamido)methyl)-7-azaspiro[3.5]nonane-7-carboxylate A mixture of benzyl 2-((methylamino)methyl)-7-azaspiro[3.5]nonane-7-carboxylate (100 mg, 0.33 mmol), ((R)-3,3,3-trifluoro-2-hydroxy-2-(3-methoxyphenyl)propanoic acid (100 mg, 0.4 mmol), HATU (190 mg, 0.5 mmol) and DIEA (130 mg, 1.0 mmol) in DMF (2 mL) was stirred at rt overnight. The mixture was directly purified by reverse-phase HPLC (mobile phase: methanol/water (10 mM NH₄HCO₃)) to afford benzyl 2-(((R)-3,3,3-trifluoro-2-hydroxy-2-(3-methoxyphenyl)-N-methylpropanamido)methyl)-7-azaspiro[3.5]nonane-7-carboxylate (80 mg, 45.4%). LRMS m/z (M+H) 535.2 found, 535.2 required.

ethylcarbamoyl)pyridin-2-yltrifluoromethanesulfonate (18 mg, 0.05 mmol) and DIEA (20 mg, 0.16 mmol) in DMF (1 mL) was stirred for 1 h at 60° C. Then the mixture was purified by reverse-phase HPLC (mobile phase: methanol/water (10 mM NH₄HCO₃)) to afford 2-chloro-N,N-dimethyl-6-(2-(((R)-3,3,3-trifluoro-2-hydroxy-2-(3-methoxyphenyl)-N-methylpropanamido)methyl)-7-azaspiro[3.5]nonan-7-yl)nicotinamide (18 mg, 62.0%). LRMS m/z (M+H) 583.2 found, 583.2 required.

Using the procedure described in Example 14-1, but replacing 6-chloro-5-(dimethylcarbamoyl)pyridin-2-yltrifluoromethanesulfonate with 6-chloro-5-(methylcarbamoyl)pyridin-2-yl trifluoromethanesulfonate in last step, the examples of Table 14 was prepared.

TABLE 14

| Example | Structure | IUPAC Name | LRMS, found [M + H] |
|---|---|---|---|
| 14-1 | 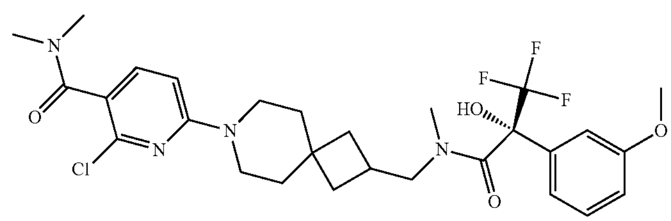 | 2-chloro-N,N-dimethyl-6-(2-(((R)-3,3,3-trifluoro-2-hydroxy-2-(3-methoxyphenyl)-N-methylpropanamido)methyl)-7-azaspiro[3.5]nonan-7-yl)nicotinamide | 583.2 |
| 14-2 | 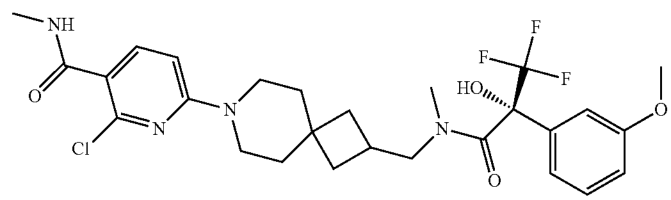 | 2-chloro-N-methyl-6-(2-(((R)-3,3,3-trifluoro-2-hydroxy-2-(3-methoxyphenyl)-N-methylpropanamido)methyl)-7-azaspiro[3.5]nonan-7-yl)nicotinamide | 569.2 |

(2R)—N-(7-azaspiro[3.5]nonan-2-ylmethyl)-3,3,3-trifluoro-2-hydroxy-2-(3-methoxyphenyl)-N-methylpropanamide To a solution of benzyl 2-(((R)-3,3,3-trifluoro-2-hydroxy-2-(3-methoxyphenyl)-N-methylpropanamido)methyl)-7-azaspiro[3.5]nonane-7-carboxylate (80 mg, 0.15 mmol) in DCM (5 mL) was added iodotrimethylsilane (60 mg, 0.30 mmol). The mixture was stirred for 1 h at rt, quenched with methanol (1 mL) and concentrated. The residue was purified by reverse-phase HPLC (mobile phase: methanol/water (10 mM NH₄HCO₃)) to afford (2R)—N-(7-azaspiro[3.5]nonan-2-ylmethyl)-3,3,3-trifluoro-2-hydroxy-2-(3-methoxyphenyl)-N-methylpropanamide (40 mg, 66.6%). LRMS m/z (M+H) 401.2 found, 401.2 required.

2-chloro-N,N-dimethyl-6-(2-(((R)-3,3,3-trifluoro-2-hydroxy-2-(3-methoxyphenyl)-N-methylpropanamido)methyl)-7-azaspiro[3.5]nonan-7-yl)nicotinamide A mixture of (2R)—N-(7-azaspiro[3.5]nonan-2-ylmethyl)-3,3,3-trifluoro-2-hydroxy-2-(3-methoxyphenyl)-N-methylpropanamide (20 mg, 0.05 mmol), 6-chloro-5-(dim- Example 15-1

2-chloro-6-(4-((1R,2R)-2-(((R)-2-(3-ethoxyphenyl)-3,3,3-trifluoro-2-hydroxy-N-methylpropanamido)methyl)cyclopropyl)piperidin-1-yl)-N,N-dimethylnicotinamide

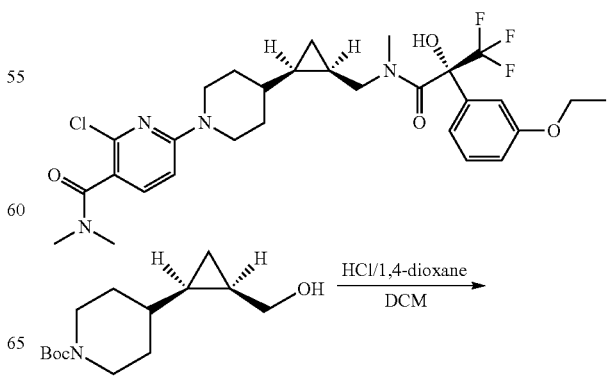

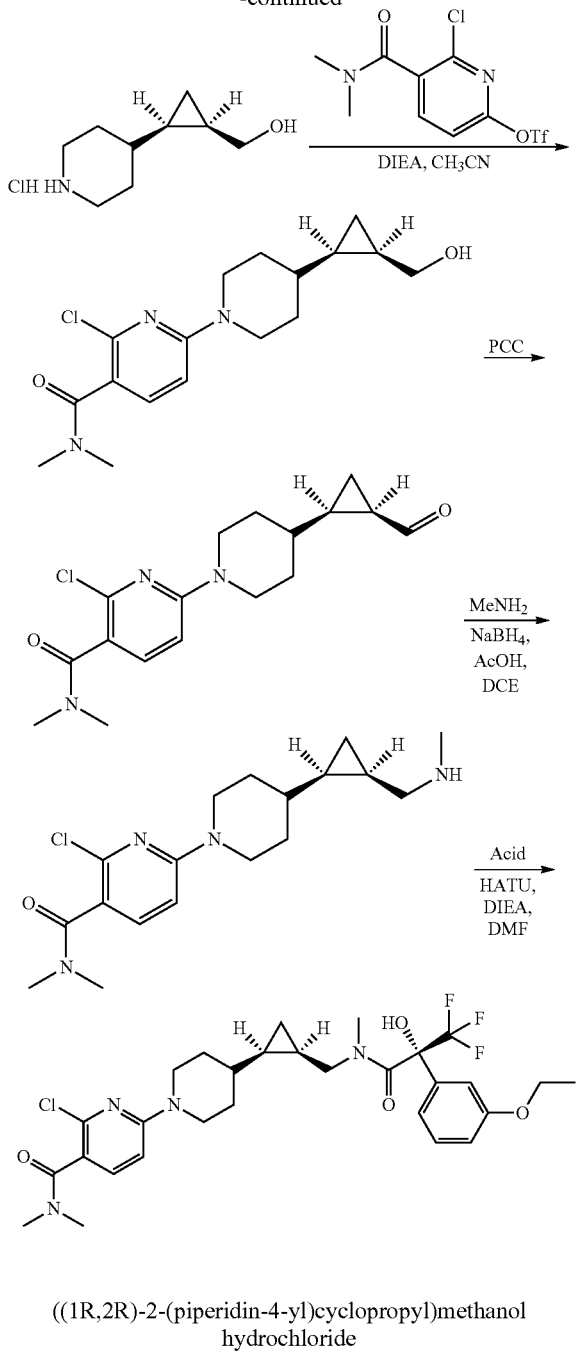

(((1R,2R)-2-(piperidin-4-yl)cyclopropyl)methanol hydrochloride

To a solution of tert-butyl 4-((1R,2R)-2-(hydroxymethyl)cyclopropyl)piperidine-1-carboxylate (300 mg, 1.175 mmol, 1.0 eq) in DCM (6 mL) was added 4M HCl/dioxane (6 mL, 24 mmol, 4M in 1,4-dioxane) at rt. After stirring for 2 h, the reaction mixture was concentrated to afford ((1R,2R)-2-(piperidin-4-yl)cyclopropyl)methanol hydrochloride (350 mg, 155%), which was directly used in next step without further purification.

2-chloro-6-(4-((1R,2R)-2-(hydroxymethyl)cyclopropyl)piperidin-1-yl)-N,N-dimethylnicotinamide The reaction mixture of ((1R,2R)-2-(piperidin-4-yl)cyclopropyl)methanol hydrochloride (350 mg, 1.17 mmol), 6-chloro-5-(dimethylcarbamoyl)pyridin-2-yl trifluoromethanesulfonate (392 mg, 1.179 mmol) and DIEA (2.00 mL, 11.45 mmol, 9.71 eq) in acetonitrile (30 mL) was refluxed under nitrogen atmosphere for 1 h. The reaction mixture was filtered, and the filtrate was purified by reverse-phase HPLC (mobile phase: methanol/water (10 mM $NH_4HCO_3$)) to give 2-chloro-6-(4-((1R,2R)-2-(hydroxymethyl)cyclopropyl)piperidin-1-yl)-N,N-dimethylnicotinamide (316 mg, 72%). LRMS m/z (M+H) 338.2 found, 338.2 required.

2-chloro-6-(4-((1R,2R)-2-formylcyclopropyl)piperidin-1-yl)-N,N-dimethylnicotinamide To a solution of 2-chloro-6-(4-((1R,2R)-2-(hydroxymethyl)cyclopropyl)piperidin-1-yl)-N,N-dimethylnicotinamide (350 mg, 0.942 mmol, 1.0 eq) in DCM (100 mL) was added PCC (410 mg, 1.902 mmol, 2.0 eq). After stirring at ambient temperature for 3 h, the reaction mixture was filtered through a short kieselgur and washed with ether (500 mL). The solution was washed with water (35 mL×5), brine (35 mL) and dried over anhydrous $Na_2SO_4$. The organic phase was concentrated to afford 2-chloro-6-(4-((1R,2R)-2-formylcyclopropyl)piperidin-1-yl)-N,N-dimethylnicotinamide (247 mg, 78% yield), which was used in next step without further purification. LRMS m/z (M+H) 336.1 found, 336.1 required.

2-chloro-N,N-dimethyl-6-(4-((1R,2R)-2-((methylamino)methyl)cyclopropyl)piperidin-1-yl)nicotinamide To a solution of 2-chloro-6-(4-((1R,2R)-2-formylcyclopropyl)piperidin-1-yl)-N,N-dimethylnicotinamide (247 mg, 0.563 mmol, 1.0 eq), and methylamine (50 mL, 100 mmol, 2M in THF) in DCE (10 mL) was added acetic acid (0.6 mL, 10.48 mmol, 18.6 eq) at rt. Then the mixture was stirred at 20° C. for 13 h under nitrogen atmosphere. Sodium borohydride (213 mg, 5.63 mmol, 10.0 eq) was added, and stirred at 30° C. for 3 h. The reaction was quenched with MeOH (300 mL), concentrated to give a solid. The crude product was purified by column chromatography (silica gel: 300-400 mesh, PE/EtOAc=20/1, V/V) to afford an oil, which was purified by reverse-phase HPLC (mobile phase: acetonitrile/water (10 mM $NH_4HCO_3$)) to afford 2-chloro-N,N-dimethyl-6-(4-((1R,2R)-2-((methylamino)methyl)cyclopropyl)piperidin-1-yl)nicotinamide (180 mg, 91%). LRMS m/z (M+H) 351.1 found, 351.2 required.

2-chloro-6-(4-((1R,2R)-2-(((R)-2-(3-ethoxyphenyl)-3,3,3-trifluoro-2-hydroxy-N-methylpropanamido)methyl)cyclopropyl)piperidin-1-yl)-N,N-dimethylnicotinamide To a solution of 2-chloro-N,N-dimethyl-6-(4-((1R,2R)-2-((methylamino)methyl)cyclopropyl)piperidin-1-yl)nicotinamide (20 mg, 0.057 mmol, 1.0 eq), (R)-2-(3-ethoxyphenyl)-3,3,3-trifluoro-2-hydroxypropanoic acid (16 mg, 0.061 mmol, 1.1 eq), and HATU (44 mg, 0.116 mmol, 2.0 eq) in THF (4.5 mL) was added DIEA (0.04 mL, 0.016 mmol, 4.0 eq) at rt. And the reaction mixture was stirred at rt for 17 h. The mixture was directly purified by reverse-phase HPLC (mobile phase: methanol/water (10 mM $NH_4HCO_3$)) to afford 2-chloro-6-(4-((1R,2R)-2-(((R)-2-(3-ethoxyphenyl)-3,3,3-trifluoro-2-hydroxy-N-methylpropanamido)methyl)cyclopropyl)piperidin-1-yl)-N,N-dimethylnicotinamide (11 mg, 30%). LRMS m/z (M+H) 597.0 found, 597.2 required.

Using the procedure described in Example 15-1, but replacing (R)-2-(3-ethoxyphenyl)-3,3,3-trifluoro-2-hydroxypropanoic acid with the appropriate acid in the last step or replacing methylamine with ammonia dioxane solution in the fourth step and replacing (R)-2-(3-ethoxyphenyl)-3,3,3-trifluoro-2-hydroxypropanoic acid with the appropriate acid in last step or replacing 6-chloro-5-(dimethylcarbamoyl)pyridin-2-yl trifluoromethanesulfonate with 6-chloro-5-(methylcarbamoyl)pyridin-2-yl trifluoromethanesulfonate in the second step, replacing methylamine with ammonia dioxane solution in the fourth step and replacing (R)-2-(3-ethoxyphenyl)-3,3,3-trifluoro-2-hydroxypropanoic acid with th appropriate acid in last step or replacing tert-butyl 4-((1R,2R)-2-(hydroxymethyl)cyclopropyl)piperidine-1-carboxylate with tert-butyl 4-((1S,2R)-2-(hydroxymethyl)cyclopropyl)piperidine-1-carboxylate in the first step and replacing (R)-2-(3-ethoxyphenyl)-3,3,3-trifluoro-2-hydroxypropanoic acid with the appropriate acid, or replacing tert-butyl 4-((1R,2R)-2-(hydroxymethyl)cyclopropyl)piperidine-1-carboxylate with tert-butyl 4-((1S,2R)-2-(hydroxymethyl)cyclopropyl)piperidine-1-carboxylate in the first step, replacing methylamine with ammonia dioxane solution in the fourth step and replacing (R)-2-(3-ethoxyphenyl)-3,3,3-trifluoro-2-hydroxypropanoic acid with the appropriate acid in last step, or replacing tert-butyl 4-((1R,2R)-2-(hydroxymethyl)cyclopropyl)piperidine-1-carboxylate with tert-butyl 4-((1 S,2R)-2-(hydroxymethyl)cyclopropyl)piperidine-1-carboxylate in the first step replacing 6-chloro-5-(dimethylcarbamoyl)pyridin-2-yl trifluoromethanesulfonate with 2-chloro-4-fluoro-N,N-dimethylbenzamide in the second step and replacing (R)-2-(3-ethoxyphenyl)-3,3,3-trifluoro-2-hydroxypropanoic acid with the appropriate acid in last step, or replacing tert-butyl 4-((1R,2R)-2-(hydroxymethyl)cyclopropyl)piperidine-1-carboxylate with tert-butyl 4-((1S,2R)-2-(hydroxymethyl)cyclopropyl)piperidine-1-carboxylate in the first step, replacing 6-chloro-5-(dimethylcarbamoyl)pyridin-2-yl trifluoromethanesulfonate with 2-chloro-4-fluoro-N,N-dimethylbenzamide in the second step, replacing methylamine with ammonia dioxane solution in the fourth step and replacing (R)-2-(3-ethoxyphenyl)-3,3,3-trifluoro-2-hydroxypropanoic acid with the appropriate acid in last step the examples in Table 15 were prepared.

TABLE 15

| Example | Structure | IUPAC Name | LRMS, found [M + H]+ |
|---|---|---|---|
| 15-1 | 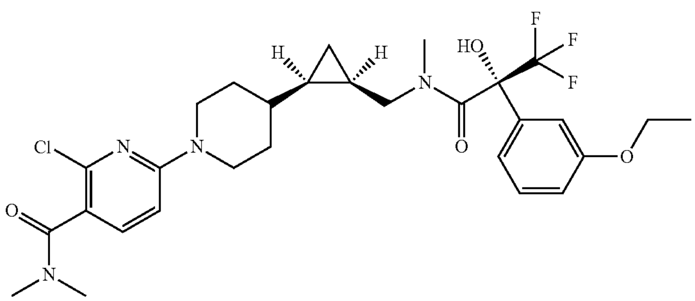 [SMILES: CCOc1cccc([C@@](O)(C(=O)N(C)C[C@@H]2C[C@@H]2C2CCN(c3ccc(C(=O)N(C)C)c(Cl)n3)CC2)C(F)(F)F)c1] | 2-chloro-6-(4-((1R,2R)-2-(((R)-2-(3-ethoxyphenyl)-3,3,3-trifluoro-2-hydroxy-N-methylpropanamido)methyl)cyclopropyl)piperidin-1-yl)-N,N-dimethylnicotinamide | 597.0 |
| 15-2 | 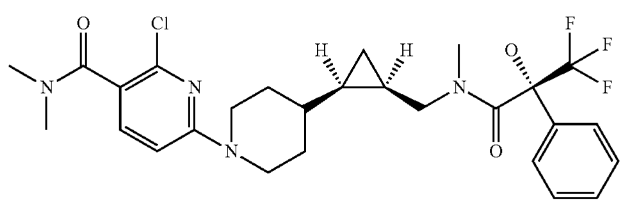 [SMILES: CN(C)C(=O)c1ccc(N2CCC([C@H]3C[C@H]3CN(C)C(=O)[C@](O)(c3ccccc3)C(F)(F)F)CC2)nc1Cl] | 2-chloro-N,N-dimethyl-6-(4-((1R,2R)-2-(((R)-3,3,3-trifluroo-2-hydroxy-N-methyl-2-phenylpropanamido)methyl)cyclopropyl)piperidin-1-yl)nicotinamide | 553.2 |
| 15-3 | 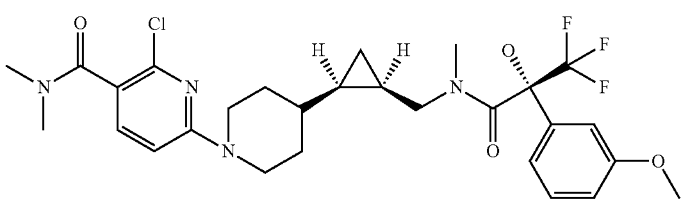 | 2-chloro-N,N-dimethyl-6-(4-((1R,2R)-2-(((R)-3,3,3-trifluoro-2-hydroxy-2-(3-methoxyphenyl)-N-methylpropanamido)methyl)cyclopropyl)piperidin-1-yl)nicotinamide | 582.2 |
| 15-4 | 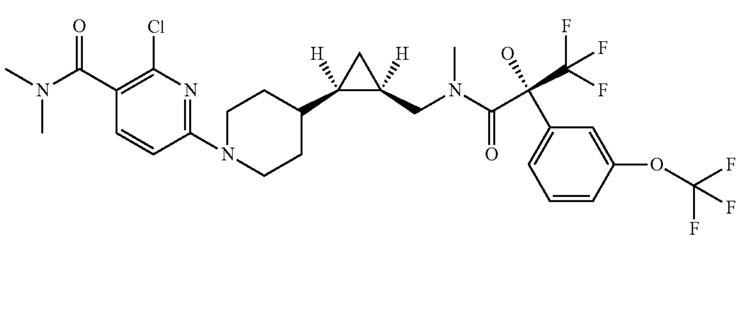 [SMILES: CN(C)C(=O)c1ccc(N2CCC([C@H]3C[C@H]3CN(C)C(=O)[C@](O)(c3cccc(OC(F)(F)F)c3)C(F)(F)F)CC2)nc1Cl] | 2-chloro-N,N-dimethyl-6-(4-((1R,2R)-2-(((R)-3,3,3-trifluoro-2-hydroxy-N-methyl-2-(3-(trifluoromethoxy)phenyl)propanamido)methyl)cyclopropyl)piperidin-1-yl)nicotinamide | 637.1 |

TABLE 15-continued

| Example | Structure | IUPAC Name | LRMS, found [M + H]+ |
|---|---|---|---|
| 15-5 | 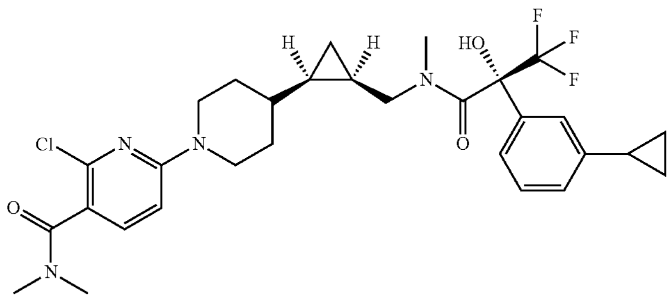 [SMILES: CN(C)C(=O)c1ccc(N2CCC([C@H]3C[C@H]3CN(C)C(=O)[C@](O)(c3cccc(C4CC4)c3)C(F)(F)F)CC2)nc1Cl] | 2-chloro-6-(4-((1R,2R)-2-(((R)-2-(3-cyclopropylphenyl)-3,3,3-trifluoro-2-hydroxy-N-methylpropanamido)methyl)cyclopropyl)piperidin-1-yl)-N,N-dimethylnicotinamide | 593.3 |
| 15-6 | 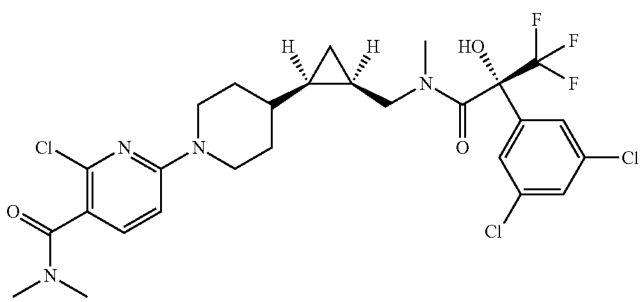 [SMILES: CN(C)C(=O)c1ccc(N2CCC([C@H]3C[C@H]3CN(C)C(=O)[C@](O)(c3cc(Cl)cc(Cl)c3)C(F)(F)F)CC2)nc1Cl] | 2-chloro-6-(4-((1R,2R)-2-(((R)-2-(3,5-dichlorophenyl)-3,3,3-trifluoro-2-hydroxy-N-methylpropanamido)methyl)cyclopropyl)piperidin-1-yl)-N,N-dimethylnicotinamdie | 623.2 |
| 15-7 | 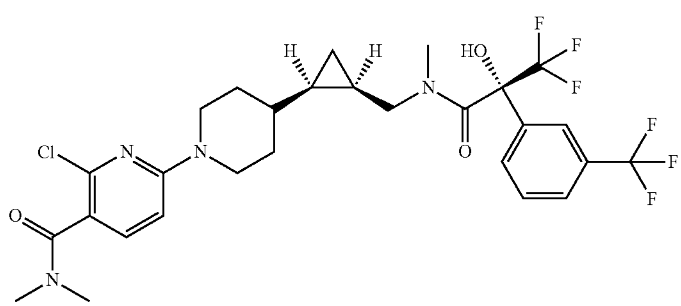 [SMILES: CN(C)C(=O)c1ccc(N2CCC([C@H]3C[C@H]3CN(C)C(=O)[C@](O)(c3cccc(C(F)(F)F)c3)C(F)(F)F)CC2)nc1Cl] | 2-chloro-N,N-dimethyl-6-(4-((1R,2R)-2-(((R)-3,3,3-trifluoro-2-hydroxy-N-methyl-2-(3-(trifluoromethyl)phenyl)rpropanamido)methyl)cyclopropyl)piperidin-1-yl)nicotinamide | 621.3 |
| 15-8 | 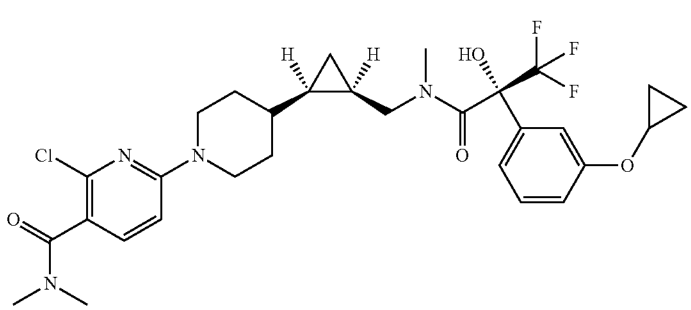 [SMILES: CN(C)C(=O)c1ccc(N2CCC([C@H]3C[C@H]3CN(C)C(=O)[C@](O)(c3cccc(OC4CC4)c3)C(F)(F)F)CC2)nc1Cl] | 2-chloro-6-(4-((1R,2R)-2-(((R)-2-(3-cyclopropoxyphenyl)-3,3,3-trifluoro-2-hydroxy-N-methylpropanamido)methyl)cyclopropyl)piperidin-1-yl)-N,N-dimethylnicotinamide | 609.1 |
| 15-9 | 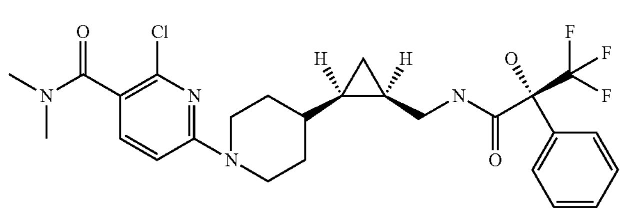 [SMILES: CN(C)C(=O)c1ccc(N2CCC([C@H]3C[C@H]3CNC(=O)[C@](O)(c3ccccc3)C(F)(F)F)CC2)nc1Cl] | 2-chloro-N,N-dimethyl-6-(4-((1R,2R)-2-((R)-3,3,3-trifluoro-2-hydroxy-2-phenylpropanamido)methyl)cyclopropyl)piperidin-1-yl)nicotinamide | 539.2 |

TABLE 15-continued

| Example | Structure | IUPAC Name | LRMS, found [M + H]+ |
|---|---|---|---|
| 15-10 | 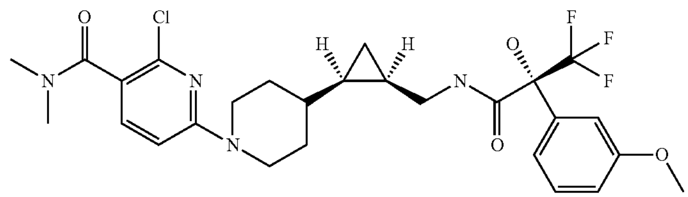 | 2-chloro-N,N-dimethyl-6-(4-((1R,2R)-2-(((R)-3,3-trifluoro-2-hydroxy-2-(3-methoxyphenyl)propanamido)methyl)cyclopropyl)piperidin-1-yl)nicotinamide | 569.2 |
| 15-11 | 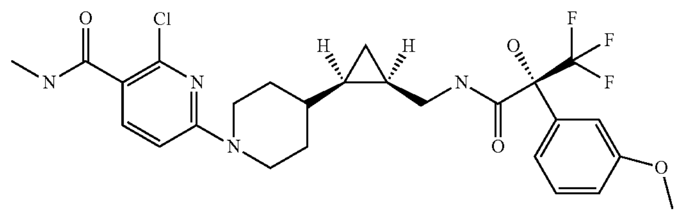 | 2-chloro-N-methyl-6-(4-((1R,2R)-2-(((R)-3,3-trifluoro-2-hydroxy-2-(3-methoxyphenyl)propanamido)methyl)cyclopropyl)piperidin-1-yl)nicotinamide | 555.2 |
| 15-12 | 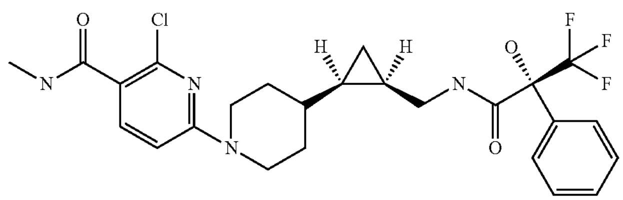 [SMILES: CNC(=O)c1ccc(N2CCC([C@H]3C[C@H]3CNC(=O)[C@](O)(c3ccccc3)C(F)(F)F)CC2)nc1Cl] | 2-chloro-N-methyl-6-(4-((1R,2R)-2-(((R)-3,3-trifluoro-2-hydroxy-2-phenylpropanamido)methyl)cyclopropyl)piperidin-1-yl)nicotinamide | 525.2 |
| 15-13 | 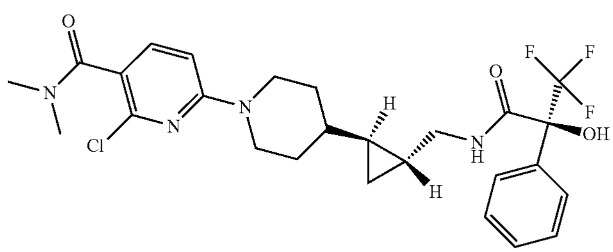 [SMILES: CN(C)C(=O)c1ccc(N2CCC([C@@H]3C[C@H]3CNC(=O)[C@@](O)(c3ccccc3)C(F)(F)F)CC2)nc1Cl] | 2-chloro-N,N-dimethyl-6-(4-((1S,2R)-2-(((S)-3,3-trifluoro-2-hydroxy-2-phenylpropanamido)methyl)cyclopropyl)piperidin-1-yl)nicotinamide | 539.2 |
| 15-14 | 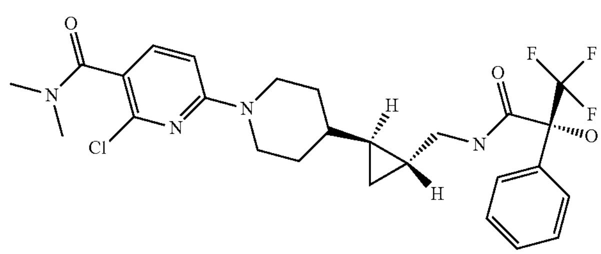 [SMILES: CN(C)C(=O)c1ccc(N2CCC([C@@H]3C[C@H]3CNC(=O)[C@](O)(c3ccccc3)C(F)(F)F)CC2)nc1Cl] | 2-chloro-N,N-dimethyl-6-(4-((1S,2R)-2-(((R)-3,3-trifluoro-2-hydroxy-2-phenylpropanamido)methyl)cyclopropyl)piperidin-1-yl)nicotinamide | 539.2 |
| 15-15 | 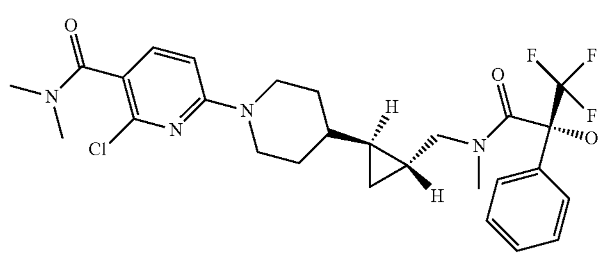 [SMILES: CN(C)C(=O)c1ccc(N2CCC([C@@H]3C[C@H]3CN(C)C(=O)[C@](O)(c3ccccc3)C(F)(F)F)CC2)nc1Cl] | 2-chloro-N,N-dimethyl-6-(4-((1S,2R)-2-((R)-3,3-trifluoro-2-hydroxy-N-methyl-2-phenylpropanamido)methyl)cyclopropyl)piperidin-1-yl)nicotinamide | 553.2 |

TABLE 15-continued

| Example | Structure | IUPAC Name | LRMS, found [M + H]+ |
|---|---|---|---|
| 15-16 | 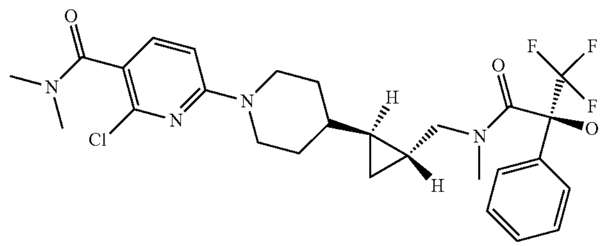 [SMILES: CN(C)C(=O)c1ccc(N2CCC([C@@H]3C[C@H]3CN(C)C(=O)[C@@](O)(c3ccccc3)C(F)(F)F)CC2)nc1Cl] | 2-chloro-N,N-dimethyl-6-(4-((1S,2R)-2-(((S)-3,3,3-trifluoro-2-hydroxy-N-methyl-2-phenylpropanamido)methyl)cyclopropyl)piperidin-1-yl)nicotinamide | 553.2 |
| 15-17 | 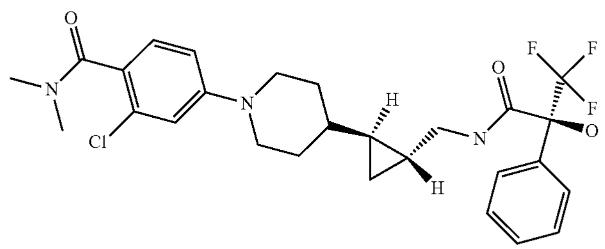 [SMILES: CN(C)C(=O)c1ccc(N2CCC([C@@H]3C[C@H]3CNC(=O)[C@@](O)(c3ccccc3)C(F)(F)F)CC2)cc1Cl] | 2-chloro-N,N-dimethyl-4-(4-((1S,2R)-2-(((S)-3,3,3-trifluoro-2-hydroxy-2-phenylpropanamido)methyl)cyclopropyl)piperidin-1-yl)benzamide | 538.2 |
| 15-18 | 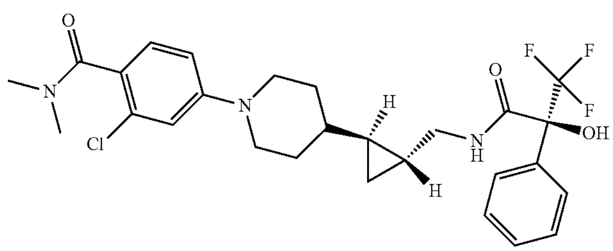 [SMILES: CN(C)C(=O)c1ccc(N2CCC([C@@H]3C[C@H]3CNC(=O)[C@@](O)(c3ccccc3)C(F)(F)F)CC2)cc1Cl] | 2-chloro-N,N-dimethyl-4-(4-((1S,2R)-2-(((S)-3,3,3-trifluoro-2-hydroxy-2-phenylpropanamido)methyl)cyclopropyl)piperidin-1-yl)benzamide | 538.2 |
| 15-19 | 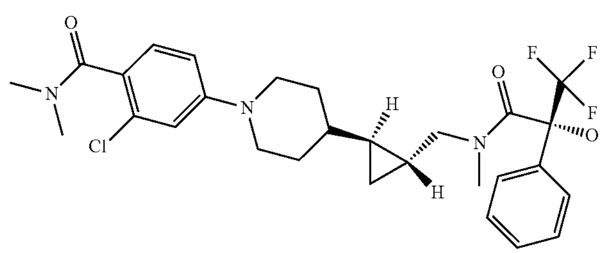 [SMILES: CN(C)C(=O)c1ccc(N2CCC([C@@H]3C[C@H]3CN(C)C(=O)[C@](O)(c3ccccc3)C(F)(F)F)CC2)cc1Cl] | 2-chloro-N,N-dimethyl-4-(4-((1S,2R)-2-(((R)-3,3,3-trifluoro-2-hydroxy-N-methyl-2-phenylpropanamido)methyl)cyclopropyl)piperidin-1-yl)benzamide | 552.2 |
| 15-20 | 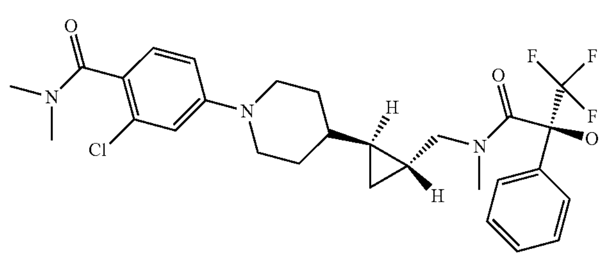 [SMILES: CN(C)C(=O)c1ccc(N2CCC([C@@H]3C[C@H]3CN(C)C(=O)[C@@](O)(c3ccccc3)C(F)(F)F)CC2)cc1Cl] | 2-chloro-N,N-dimethyl-4-(4-((1S,2R)-2-(((S)-3,3,3-trifluoro-2-hydroxy-N-methyl-2-phenylpropanamido)methyl)cyclopropyl)piperidin-1-yl)benzamide | 552.2 |

Example 16-1

(R)-2-chloro-N,N-dimethyl-6-(4-(3-((3,3,3-trifluoro-2-hydroxy-2-(3-methoxyphenyl)-N-methylpropanamido)methyl)cyclobutyl)piperidin-1-yl)nicotinamide

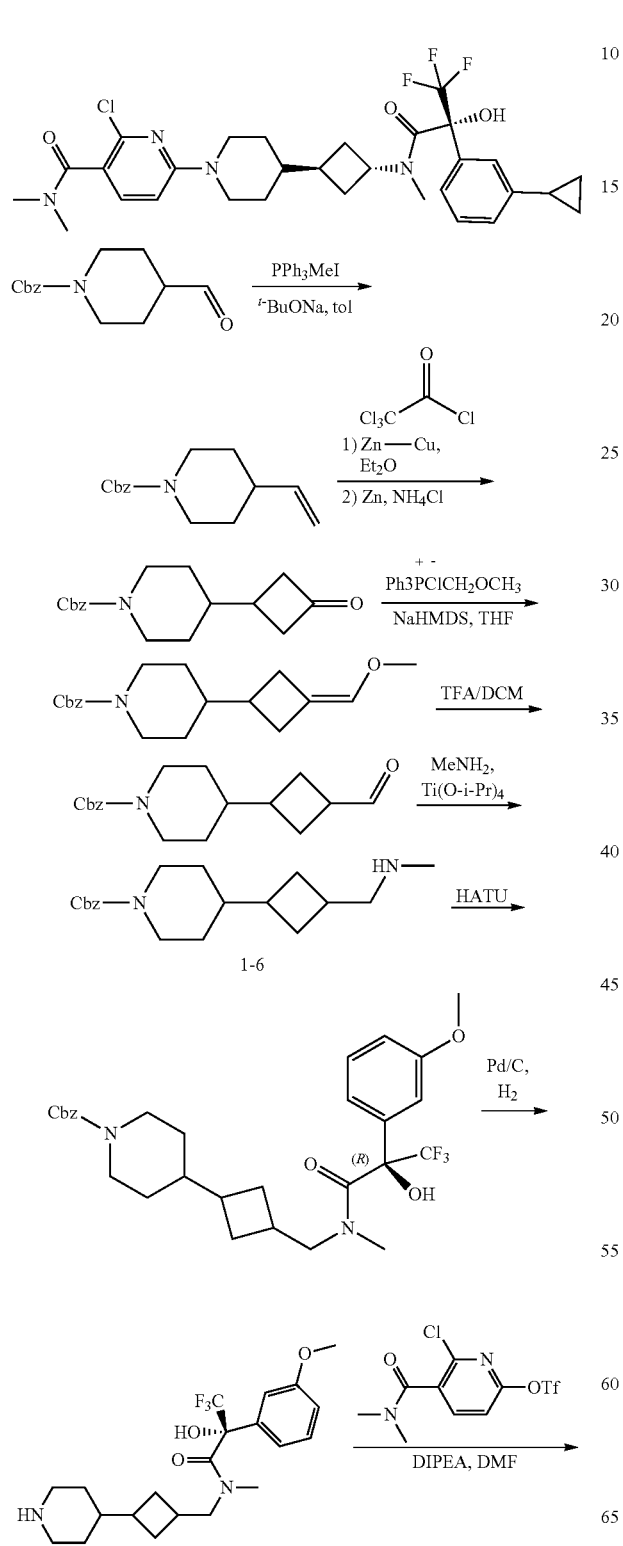

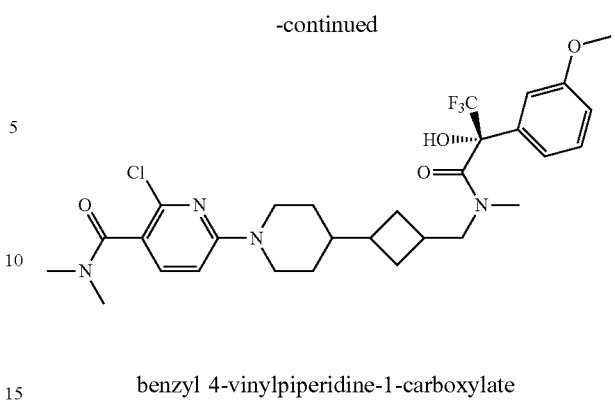

benzyl 4-vinylpiperidine-1-carboxylate

To a solution of methyltriphenylphosphonium iodide (12.2 g, 30.3 mmol) in THF (50 mL) was added sodium tert-butoxide (2.9 g, 30.3 mmol). The resulting mixture was stirred at rt for 1 h and a solution of benzyl 4-formylpiperidine-1-carboxylate (5 g, 20.2 mmol) in THF (10 mL) was added. The reaction solution was stirred at rt overnight, diluted with aq NH$_4$Cl (50 mL) and the organic phase was washed with water (100 mL×3), brine (10 mL×3) and dried over anhydrous Na$_2$SO$_4$ and concentrated. The crude product was purified by column chromatography (silica gel: 300-400 mesh, PE/EtOAc=50/1 to 10/1) to get pure benzyl 4-vinylpiperidine-1-carboxylate (3.1 g, 62.6%). LRMS m/z (M+H) 246.0 found, 246.1 required.

benzyl 4-(3-oxocyclobutyl)piperidine-1-carboxylate

To a suspension of zinc-copper couple (3.9 g, 61 mmol), benzyl 4-vinylpiperidine-1-carboxylate (1.5 g, 6.1 mmol) and POCl$_3$ (1 g, 6.7 mmol) in Et$_2$O (50 mL) was added trichloroacetyl chloride (5.5 g, 30.5 mmol) dropwise at rt under a nitrogen atmosphere. After stirring at rt for 12 h, the reaction mixture was poured into an aqueous solution of NaHCO$_3$ (100 mL) at 0° C., and the precipitation was filtered off. The filtrate was extracted with EtOAc (100 mL×3). The extract was washed with brine (20 mL), dried, and concentrated. The residue was passed though silica gel (20% EtOAc-hexane) to afford 2.7 g of the crude dichloroketone as an oil. The crude product was dissolved in saturated NH$_4$Cl-MeOH (50 mL) and zinc (1.98 g, 30.5 mmol) was added. The reaction mixture was stirred at rt for 8 h, and then the zinc was filtered off. The filtrate was concentrated in vacuo and the residue was purified by chromatography (silica gel, 20% EtOAc-hexane) to give benzyl 4-(3-oxocyclobutyl)piperidine-1-carboxylate (0.9 g, 51.4%). LRMS m/z (M+H) 288.2 found, 288.1 required.

benzyl 4-(3-(methoxymethylene)cyclobutyl)piperidine-1-carboxylate

To a solution of (methoxymethyl)triphenylphosphonium chloride (181 mg, 0.53 mmol) in THF (30 mL) was added NaHMDS (0.53 mL, 0.53 mmol, 1M in THF) at 0° C. The resulting mixture was stirred at 0° C. for 1 h and a solution of benzyl 4-(3-oxocyclobutyl)piperidine-1-carboxylate (100 mg, 0.35 mmol) in THF (1 mL) was added. The reaction solution was stirred at rt overnight, and diluted with EtOAc (200 mL). The organic phase was washed with water (100 mL×2), brine (50 mL×1) and dried over anhydrous Na$_2$SO$_4$ and concentrated. The crude product was purified by column chromatography (silica gel: 300-400 mesh, PE/EtOAc=50/1 to 10/1) to get pure benzyl 4-(3-(methoxymethylene)cyclobutyl)piperidine-1-carboxylate (78 mg, 70.7%). LRMS m/z (M+H) 316.2 found, 316.1 required.

benzyl 4-(3-formylcyclobutyl)piperidine-1-carboxylate

To a solution of 4-(3-(methoxymethylene)cyclobutyl)piperidine-1-carboxylate (78 mg, 0.24 mmol) in DCM (2 mL) was added TFA (2 mL) at 0° C. The resulting mixture was stirred at 0° C. for 1 h. The organic layer was concentrated in vacuo to afford the crude product. The crude product was neutralized with sat. NaHCO$_3$ (3 mL), extracted with EtOAc (4 mL×2) and dried over anhydrous Na$_2$SO$_4$. The organic layer was concentrated in vacuo to afford benzyl 4-(3-formylcyclobutyl)piperidine-1-carboxylate (70 mg, 96.8%) which was used in next step without purification. LRMS m/z (M+H) 302.2 found, 302.1 required.

benzyl 4-(3-((methylamino)methyl)cyclobutyl)piperidine-1-carboxylate

To a solution of benzyl 4-(3-formylcyclobutyl)piperidine-1-carboxylate (70 mg, 0.23 mmol) in DCE (2 mL) was added MeNH$_2$ (1.0 mL, 2 mmol, 2M in THF), titanium isopropoxide (196 mg, 0.69 mmol). The mixture was stirred at rt for 3 h and then NaHB(OAc)$_3$ (147 mg, 0.69 mmol, 3.0 eq) was added. The resulting mixture stirred at rt overnight. The mixture was directly purified by reverse-phase HPLC (mobile phase: methanol/water (10 mM NH$_4$HCO$_3$) to afford benzyl 4-(3-((methylamino)methyl)cyclobutyl)piperidine-1-carboxylate (55 mg, 75.6%). LRMS m/z (M+H) 317.3 found, 317.2 required.

(R)-benzyl-4-(3-((3,3,3-trifluoro-2-hydroxy-2-(3-methoxyphenyl)-N-methylpropanamido)methyl)cyclobutyl)piperidine-1-carboxylate A mixture of benzyl 4-(3-((methylamino)methyl)cyclobutyl)piperidine-1-carboxylate (55 mg, 0.17 mmol), (R)-3,3,3-trifluoro-2-hydroxy-2-(3-methoxyphenyl)propanoic acid (56 mg, 0.225 mmol), HATU (85 mg, 0.225 mmol) and TEA (45 mg, 0.45 mmol) in THF (2 mL) was stirred at rt overnight. The mixture was directly purified by reverse-phase HPLC (mobile phase: methanol/water (10 mM NH$_4$HCO$_3$)) to afford (R)-benzyl 4-(3-((3,3,3-trifluoro-2-hydroxy-2-(3-methoxyphenyl)-N-methylpropanamido)methyl)cyclobutyl)piperidine-1-carboxylate (42 mg, 45%). LRMS m/z (M+H) 549.2 found, 549.2 required.

(R)-3,3,3-trifluoro-2-hydroxy-2-(3-methoxyphenyl)-N-methyl-N-((3-(piperidin-4-yl)cyclobutyl)methyl)propanamide The solution of (R)-benzyl 4-(3-((3,3,3-trifluoro-2-hydroxy-2-(3-methoxyphenyl)-N-methylpropanamido)methyl)cyclobutyl)piperidine-1-carboxylate (42 mg, 0.076 mmol), 10% Pd/C (15 mg) in MeOH (2 mL) was stirred overnight at rt under H$_2$ balloon. The mixture was filtered though a celite pad, and the filtrate was concentrated to give the (R)-3,3,3-trifluoro-2-hydroxy-2-(3-methoxyphenyl)-N-methyl-N-((3-(piperidin-4-yl)cyclobutyl)methyl)propanamide (30 mg, 95%). LRMS m/z (M+H) 415.2 found, 415.2 required.

(R)-2-chloro-N,N-dimethyl-6-(4-(3-((3,3,3-trifluoro-2-hydroxy-2-(3-methoxyphenyl)-N-methylpropanamido)methyl)cyclobutyl)piperidin-1-yl)nicotinamide To a solution of (R)-3,3,3-trifluoro-2-hydroxy-2-(3-methoxyphenyl)-N-methyl-N-((3-(piperidin-4-yl)cy-clobutyl)methyl)propanamide (30 mg, 0.072 mmol) in DMF (2 mL) was added DIEA (20 mg, 0.15 mmol) and 6-chloro-5-(dimethylcarbamoyl)pyridin-2-yl trifluoromethanesulfonate (24 mg, 0.072 mmol). After stirring at 80° C. for 3 h, the mixture was directly purified by reverse-phase HPLC (mobile phase: methanol/water (10 mM NH$_4$HCO$_3$)) to afford (R)-2-chloro-N,N-dimethyl-6-(4-(3-((3,3,3-trifluoro-2-hydroxy-2-(3-methoxyphenyl)-N-methylpropanamido)methyl)cyclobutyl)piperidin-1-yl)nicotinamide (14 mg, 32.5%). LRMS m/z (M+H) 597.3 found, 597.2 required.

Example 17-1

2-chloro-6-(4-((1R,3r)-3-((R)-2-(3-cyclopropylphenyl)-3,3,3-trifluoro-2-hydroxy-N-methylpropanamido)cyclobutyl)piperidin-1-yl)-N,N-dimethylnicotinamide

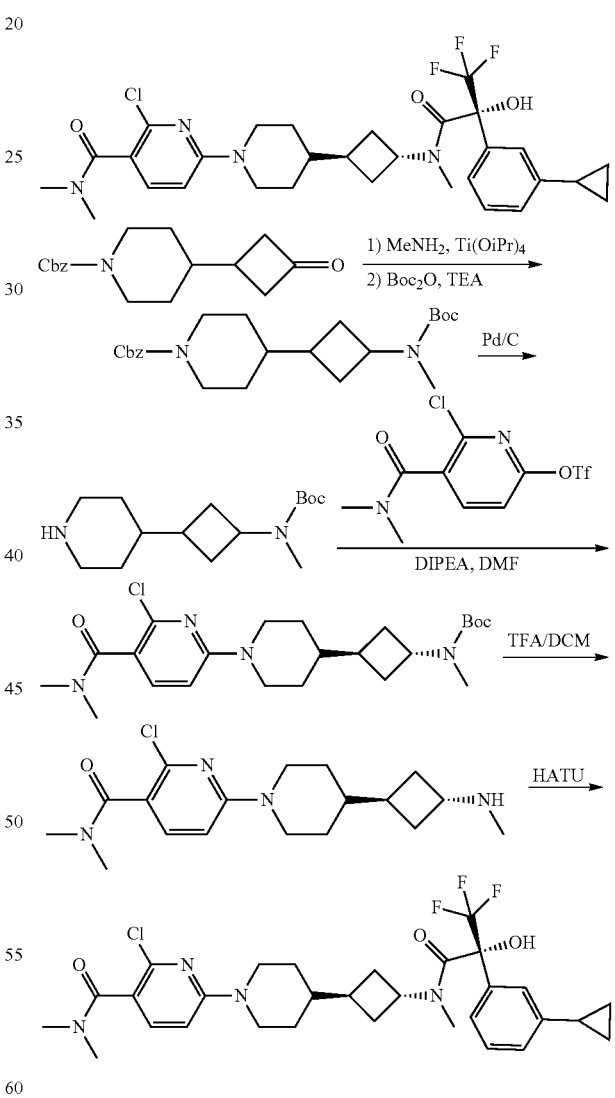

benzyl 4-(3-(tert-butoxycarbonyl(methyl)amino)cyclobutyl)piperidine-1-carboxylate To a solution of benzyl 4-(3-oxocyclobutyl)piperidine-1-carboxylate (500 mg, 1.74 mmol) in DCE (5 mL) was added MeNH$_2$ (4 ml, 8 mmol, 2M in THF), Ti(O$^i$Pr)$_4$ (741 mg, 2.61 mmol). The mixture was stirred at rt for 3 h and then NaBH₃CN (219 mg, 3.48 mmol, 3.0 eq) was added to the mixture. The resulting mixture stirred at rt overnight, diluted with DCM (40 mL).

The organic phase was washed with water (30 mL×3), brine (10 mL×1) and dried over anhydrous Na₂SO₄, filtered and concentrated in vacuo to afford the crude product. To a solution of this crude product in DCM (8 mL) was added TEA (351 mg, 3.48 mmol) and Boc₂O (453 mg, 2.1 mmol) at rt. The reaction mixture was stirred at rt for 8 h. The reaction solution was concentrated and the residue was purified by column chromatography (PE/EtOAc=20/1 to 5/1) to afford benzyl 4-(3-(tert-butoxycarbonyl(methyl)amino)cyclobutyl)piperidine-1-carboxylate (550 mg, 78.6%). LRMS m/z (M+H) 403.1 found, 403.2 required.

tert-butyl methyl(3-(piperidin-4-yl)cyclobutyl)carbamate

To a solution of benzyl 4-(3-(tert-butoxycarbonyl(methyl)amino)cyclobutyl)piperidine-1-carboxylate (760 mg, 1.89 mmol) in MeOH (10 mL) was added Pd/C (100 mg, 10% in carbon). The mixture was stirred at rt for 2 h under hydrogen atmosphere. The catalyst was filtered off and the filtrate was concentrated in vacuo to afford tert-butyl methyl(3-(piperidin-4-yl)cyclobutyl)carbamate (500 mg, 98.62%) which was used in next step directly. LRMS m/z (M+H) 269.4 found, 269.2 required.

tert-butyl-3-(1-(6-chloro-5-(dimethylcarbamoyl)pyridin-2-yl)piperidin-4-yl)cyclobutyl(methyl)carbamate To a solution of tert-butyl methyl(3-(piperidin-4-yl)cyclobutyl)carbamate (470 mg, 1.76 mmol) in DMF (5 mL) was added 6-chloro-5-(dimethylcarbamoyl)pyridin-2-yl trifluoromethanesulfonate (699 mg, 2.1 mmol) and DIEA (453 mg, 3.5 mmol). The mixture was stirred at 60° C. for 30 min under microwave. The mixture was directly purified by reverse-phase HPLC (mobile phase: methanol/water (10 mM NH₄HCO₃)) to afford tert-butyl 3-(1-(6-chloro-5-(dimethylcarbamoyl)pyridin-2-yl)piperidin-4-yl)cyclobutyl (methyl)carbamate (500 mg, 63.37%). The product was resolved by Chiral-HPLC (column: AD-H (250*4.6 mm 5 um); mobile phase: SFC—CO₂:MeOH=65:35; flow: 2.5 mL/min; temperature: 37.9° C.) to afford the isomer A (130 mg, 0.29 mmol, 26.0% yield) (RT=3.3 min) and trans-isomer B (240 mg, 0.53 mmol, 48.0% yield) (RT=4.44 min). LRMS m/z (M-56+H) 395.0 found, 395.2 required.

Trans-2-chloro-N,N-dimethyl-6-(4-(3-(methylamino)cyclobutyl)piperidin-1-yl)nicotinamide To a solution of trans-tert-butyl 3-(1-(6-chloro-5-(dimethylcarbamoyl)pyridin-2-yl)piperidin-4-yl)cyclobutyl (methyl)carbamate (isomer B) (240 mg, 0.53 mmol) in DCM (4 mL) was added TFA (1 mL). The mixture was stirred at rt for 30 min and concentrated in vacuo to afford trans-2-chloro-N,N-dimethyl-6-(4-(3-(methylamino)cyclobutyl)piperidin-1-yl)nicotinamide (190 mg, 100%). LRMS m/z (M+H) 351.1 found, 351.2 required.

Trans-2-chloro-6-(4-(-3-((R)-2-(3-cyclopropylphenyl)-3,3,3-trifluoro-2-hydroxy-N-methylpropanamido)cyclobutyl)piperidin-1-yl)-N,N-dimethylnicotinamide A mixture of trans-2-chloro-N,N-dimethyl-6-(4-(-3-(methylamino)cyclobutyl)piperidin-1-yl)nicotinamide (40 mg, 0.114 mmol), (R)-3,3,3-trifluoro-2-hydroxy-2-(3-methoxyphenyl)propanoic acid (42.7 mg, 0.171 mmol), HATU (65 mg, 0.171 mmol) and TEA (35 mg, 0.342 mmol) in THF (2 mL) was stirred at rt overnight. The mixture was directly purified by reverse-phase HPLC (mobile phase: methanol/water (10 mM NH₄HCO₃)) to afford trans-2-chloro-6-(4-(-3-((R)-2-(3-cyclopropylphenyl)-3,3,3-trifluoro-2-hydroxy-N-methylpropanamido)cyclobutyl)piperidin-1-yl)-N,N-dimethylnicotinamide (18 mg, 26.6%). LRMS m/z (M+H) 593.2 found, 593.2 required.

Using the procedure described in Example 17-1, but replacing replacing isomer B with isomer A in the fourth step and replacing (R)-3,3,3-trifluoro-2-hydroxy-2-(3-methoxyphenyl)propanoic acid with the appropriate acid in the last step, the examples of Table 17 were prepared.

TABLE 17

| Example | Structure | IUPAC Name | LRMS, found [M + H]+ |
|---|---|---|---|
| 17-1 | 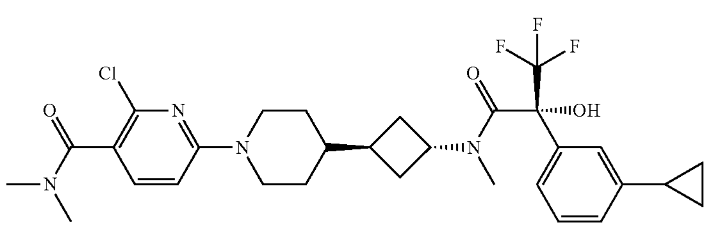 [SMILES: CN(C)C(=O)c1ccc(N2CCC([C@H]3C[C@H](N(C)C(=O)[C@](O)(c4cccc(C5CC5)c4)C(F)(F)F)C3)CC2)nc1Cl] | 2-chloro-6-(4-((1R,3r)-3-((R)-2-(3-cyclopropylphenyl)-3,3,3-trifluoro-2-hydroxy-N-methyl-propanamido)cyclobutylpiperidin-1-yl)-N,N-dimethylnicotinamide | 593.2 |
| 17-2 | 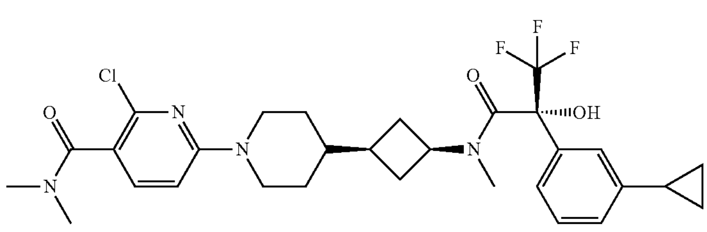 [SMILES: CN(C)C(=O)c1ccc(N2CCC([C@H]3C[C@@H](N(C)C(=O)[C@](O)(c4cccc(C5CC5)c4)C(F)(F)F)C3)CC2)nc1Cl] | cis-2-chloro-6-(4-(-3-((R)-2-(3-cyclopropylphenyl)-3,3,3-trifluoro-2-hydroxy-N-methyl-propanamido)cyclobutyl)piperidin-1-yl)-N,N-dimethylnicotinamide | 593.2 |

TABLE 17-continued

| Example | Structure | IUPAC Name | LRMS, found [M + H]+ |
|---|---|---|---|
| 17-3 | 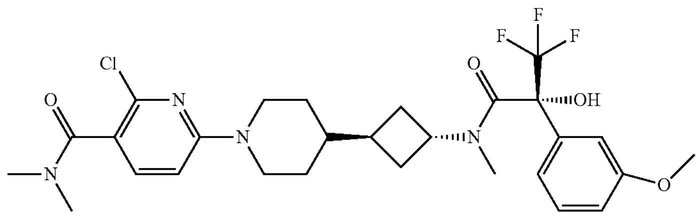 | Trans-2-chloro-N,N-dimethyl-6-(4-(-3-((R)-3,3,3-trifluoro-2-hydroxy-2-(3-methoxyphenyl)-N-methyl-propanamido)cyclobutyl)piperidin-1-yl)nicotinamide | 583.2 |
| 17-4 | 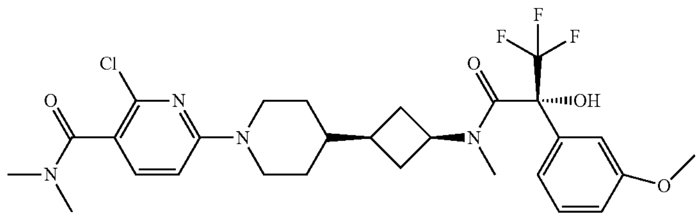 | cis-2-chloro-N,N-dimethyl-6-(4-(-3-((R)-3,3,3-trifluoro-2-hydroxy-2-(3-methoxyphenyl)-N-methyl-propanamido)cyclobutyl)piperidin-1-yl)nicotinamide | 583.2 |
| 17-5 | 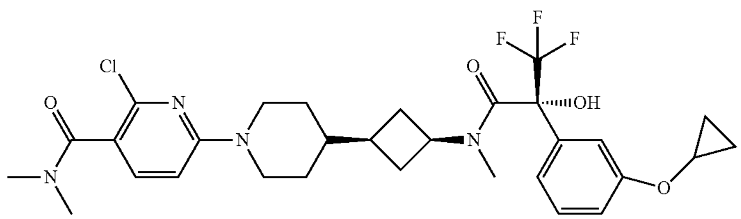 [SMILES: CN(C)C(=O)c1ccc(N2CCC([C@H]3C[C@@H](N(C)C(=O)[C@](O)(c4cccc(OC5CC5)c4)C(F)(F)F)C3)CC2)nc1Cl] | Cis-2-chloro-6-(4-(-3-((R)-2-(3-cyclopropoxyphenyl)-3,3,3-trifluoro-2-hydroxy-N-methyl-propanamido)cyclobutyl)piperidin-1-yl)-N,N-dimethylnicotinamide | 609.3 |

Example 18-1

2-chloro-N,N-dimethyl-6-(4-(((1S,2R)-2-(((R)-3,3,3-trifluoro-2-hydroxy-N-methyl-2-phenylpropanamido)methyl)cyclopropyl)methyl)piperidin-1-yl)nicotinamide

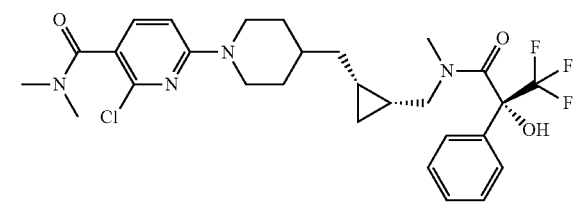

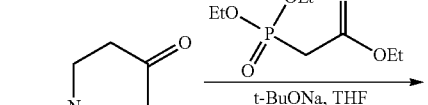

-continued

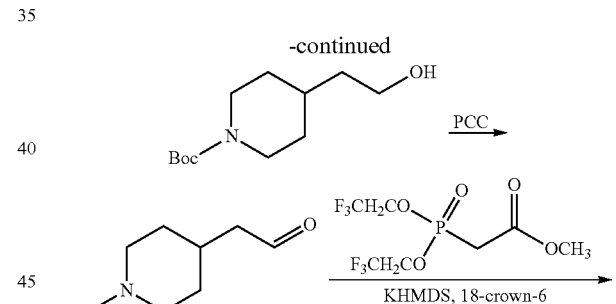

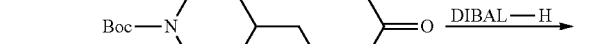

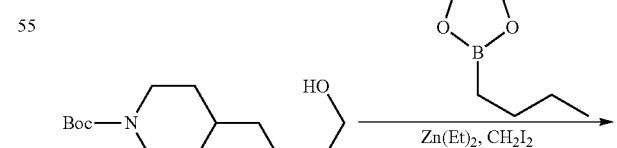

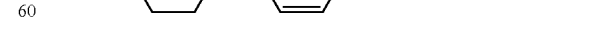

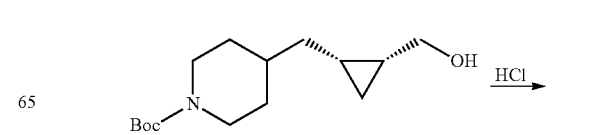

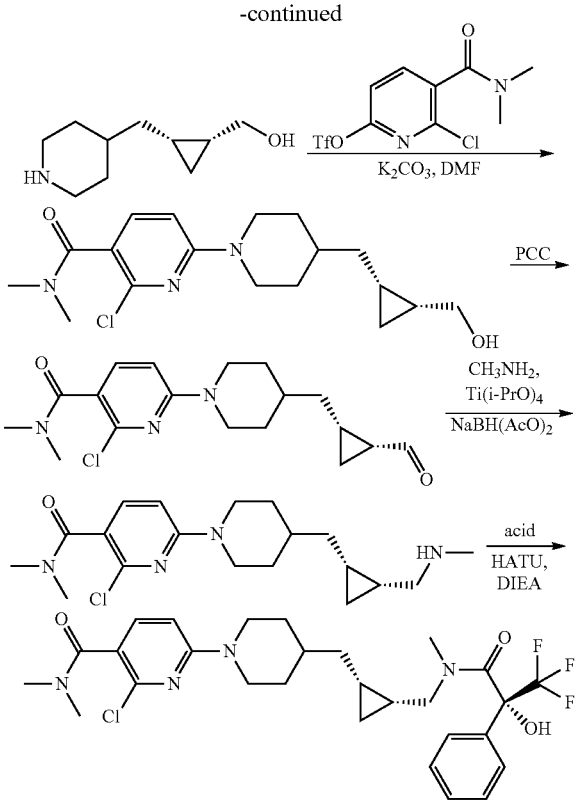

tert-butyl 4-(2-ethoxy-2-oxoethylidene)piperidine-1-carboxylate

To a solution of t-BuOK (11.52 g, 120 mmol) in dry THF (200 mL) was added ethyl 2-(diethoxyphosphoryl)acetate (23.6 g, 105 mmol) at 0° C. After stirring for 1 h at 0° C., tert-butyl 4-oxopiperidine-1-carboxylate (20 g, 100 mmol) in 50 mL of dry THF was added dropwise to the mixture, and the resulting solution was stirred at rt for 2 h. The reaction mixture was quenched with saturated aqueous NH$_4$Cl (50 mL), extracted with EtOAc (200 mL×3). The organic layer was collected, washed with saturated aqueous solution of Na$_2$CO$_3$ (50 mL) and dried over anhydrous Na$_2$SO$_4$. The solvent was evaporated under reduced pressure and the residue was purified by silica gel chromatography (silica gel: 300-400 mesh, PE/EtOAc=20/1) to afford tert-butyl 4-(2-ethoxy-2-oxoethylidene)piperidine-1-carboxylate (22 g, 81%). LRMS m/z (M-100) 170.1 found, 170.1 required.

tert-butyl 4-(2-ethoxy-2-oxoethyl)piperidine-1-carboxylate

A mixture of tert-butyl 4-(2-ethoxy-2-oxoethylidene)piperidine-1-carboxylate (22 g, 81.8 mmol) and wet 10% Pd/C (2.2 g) in ethanol (160 mL) was degassed and backfilled with H$_2$ (three times). The mixture was stirred under H$_2$ balloon at rt for 2 h. The catalyst was filtered off and the filtrate was concentrated to afford tert-butyl 4-(2-ethoxy-2-oxoethyl)piperidine-1-carboxylate (22.5 g, 100%). LRMS m/z (M-100) 172.1 found, 172.1 required.

tert-butyl 4-(2-hydroxyethyl)piperidine-1-carboxylate

To a solution of tert-butyl 4-(2-ethoxy-2-oxoethyl)piperidine-1-carboxylate (22 g, 81 mmol) in dry THF (100 mL) at −78° C. under N$_2$ atmosphere was added Super-H (200 mL, 200 mmol, 1M in THF). The resulting mixture was stirred at rt for 1 h and then treated with MeOH (10 mL) and saturated aqueous NH$_4$Cl (100 mL) at 0° C. The mixture was stirred at rt for 1 h and extracted with EtOAc (200 mL×3). The organic layer was concentrated under reduced pressure and the residue was purified by silica gel chromatography (silica gel: 300-400 mesh, PE/EtOAc=5/1 to 2/1) to afford tert-butyl 4-(2-hydroxyethyl)piperidine-1-carboxylate (17 g, 91%). LRMS m/z (M-100) 130.1 found, 130.1 required.

tert-butyl 4-(2-oxoethyl)piperidine-1-carboxylate

To a solution of tert-butyl 4-(2-hydroxyethyl)piperidine-1-carboxylate (6.87 g, 30 mmol) in DCM (100 mL) was added PCC (9.72 g, 45 mmol) at 0° C. The reaction mixture was allowed to stir at rt for 2 h and then concentrated under reduced pressure to give crude product which was purified by column chromatography (silica gel: 300-400 mesh, PE/EtOAc=20/1 to 5/1) to afford tert-butyl 4-(2-oxoethyl)piperidine-1-carboxylate (4.5 g, 66%). LRMS m/z (M-100) 128.1 found, 128.1 required.

(Z)-tert-butyl 4-(4-methoxy-4-oxobut-2-enyl)piperidine-1-carboxylate

To a solution of methyl 2-(bis(2,2,2-trifluoroethoxy)phosphoryl)acetate (1.9 g, 6 mmol) and 18-crown-6 (3.96 g, 15 mmol) in dry THF (70 mL) at −78° C. was dropwise added KHMDS (15 mL, 7.5 mmol, 0.5 M in toluene). After stirring at −78° C. for 0.5 h, tert-butyl 4-(2-oxoethyl)piperidine-1-carboxylate (1.14 g, 5 mmol) in dry THF (5 mL) was added to the mixture at −78° C. and the resulting mixture stirred at rt for 0.5 h. The reaction was quenched with saturated aqueous NH$_4$Cl (100 mL) and extracted with DCM (100 mL×3). The combined organic layers was washed with brine (50 mL), dried over anhydrous Na$_2$SO$_4$ and concentrated. The residue was purified by chromatography (silica gel: 300-400 mesh, PE/EtOAc=40/1 to 20/1) to afford (Z)-tert-butyl 4-(4-methoxy-4-oxobut-2-enyl)piperidine-1-carboxylate (1.1 g, 78%). LRMS m/z (M-100) 184.1 found, 184.1 required.

(Z)-tert-butyl 4-(4-hydroxybut-2-enyl)piperidine-1-carboxylate

To a solution of (Z)-tert-butyl 4-(4-methoxy-4-oxobut-2-enyl)piperidine-1-carboxylate (800 mg, 2.8 mmol) in dry DCM (5 mL) was added DIBAL-H (6.2 mL, 6.2 mmol, 1M in hexane) at 0° C. After stirring for 2 h, the mixture was quenched with methanol (10 mL) and 2 N NaOH (1 mL) and stirred at rt for 20 min, filtered off the precipitate. The organic phase was concentrated under reduced pressure to give crude product, which was purified by column chromatography (silica gel: 300-400 mesh, PE/EtOAc=5/1) to give the (Z)-tert-butyl 4-(4-hydroxybut-2-enyl)piperidine-1-carboxylate (560 mg, 78%). LRMS m/z (M-100) 156.1 found, 156.1 required.

tert-butyl 4-(((1S,2R)-2-(hydroxymethyl)cyclopropyl)methyl)piperidine-1-carboxylate To a solution of Zn(Et)$_2$ (7 mL, 7.7 mmol, 1.1 M in toluene) in dry DCM (10 mL) was added CH$_2$I$_2$ (2.25 g, 8.4 mmol) at 10° C. After stirring for 1 h, the (4S,5S)-2-butyl-N$^4$,N$^4$,N$^5$,N$^5$-tetramethyl-1,3,2-dioxaborolane-4,5-dicarboxamide (450 mg, 1.68 mmol) and (Z)-tert-butyl 4-(4- hydroxybut-2-enyl)piperidine-1-carboxylate (360 mg, 1.4 mmol) in dry DCM (4 mL) was added to the solution. The resulting mixture was stirred for another 2 h at rt and quenched with saturated aqueous NH₄Cl (10 mL), extracted with DCM (50 mL×3). The organic phase was concentrated under reduced pressure to give crude product, which was purified by column chromatography (silica gel: 300-400 mesh, PE/EtOAc=10/1 to 3/1) to afford tert-butyl 4-(((1S,2R)-2-(hydroxymethyl)cyclopropyl)methyl)piperidine-1-carboxylate (300 mg, 79%). (ee %=90%). LRMS m/z (M-100) 170.1 found, 170.1 required.

((1R,2S)-2-(piperidin-4-ylmethyl)cyclopropyl)methanol

A solution of ((1R,2S)-2-(piperidin-4-ylmethyl)cyclopropyl)methanol (300 mg, 1.12 mmol) in 4M HCl/1,4-dioxane (4 mL) was stirred for 1 h at rt. Then the mixture was concentrated in vacuo to give crude ((1R,2S)-2-(piperidin-4-ylmethyl)cyclopropyl)methanol (180 mg, 96%). LRMS m/z (M+H) 170.1 found, 170.1 required.

2-chloro-6-(4-(((1S,2R)-2-(hydroxymethyl)cyclopropyl)methyl)piperidin-1-yl)-N,N-dimethylnicotinamide A mixture of 6-chloro-5-(dimethylcarbamoyl)pyridin-2-yl trifluoromethanesulfonate (332 mg, 1 mmol), ((1R,2S)-2-(piperidin-4-ylmethyl)cyclopropyl)methanol (169 mg, 1 mmol), K₂CO₃ (336 mg, 2.43 mmol) in DMF (5 mL) was stirred at CEM Microwave Reactor at 60° C. for 0.5 h. The mixture was directly purified by reverse-phase HPLC (mobile phase: methanol/water (10 mM NH₄HCO₃)) to afford 2-chloro-6-(4-(((1S,2R)-2-(hydroxymethyl)cyclopropyl)methyl)piperidin-1-yl)-N,N-dimethylnicotinamide (180 mg, 51%). LRMS m/z (M+H) 352.2 found, 352.2 required.

2-chloro-6-(4-(((1S,2R)-2-formylcyclopropyl)methyl)piperidin-1-yl)-N,N-dimethylnicotinamide A mixture of 2-chloro-6-(4-(((1S,2R)-2-(hydroxymethyl)cyclopropyl)methyl)piperidin-1-yl)-N,N-dimethylnicotinamide (170 mg, 0.5 mmol) and PCC (162 mg, 0.75 mmol) in DCM (3 mL) was stirred at rt for 1 h. The mixture was concentrated under reduced pressure and the crude compound was purified by reverse-phase HPLC (mobile phase: methanol/water (10 mM NH₄HCO₃)) to afford 2-chloro-6-(4-(((1S,2R)-2-formylcyclopropyl)methyl)piperidin-1-yl)-N,N-dimethylnicotinamide (104 mg, 68%). LRMS m/z (M+H) 350.2 found, 350.2 required.

2-chloro-N,N-dimethyl-6-(4-(((1S,2R)-2-((methylamino)methyl)cyclopropyl)methyl)piperidin-1-yl)nicotinamide A mixture of 2-chloro-6-(4-(((1S,2R)-2-formylcyclopropyl)methyl)piperidin-1-yl)-N,N-dimethylnicotinamide (104 mg, 0.3 mmol), CH₃NH₂ (1 mL, 2 mmol, 2 M in THF) and titanium tetraisopropanolate (114 mg, 0.4 mmol) was stirred for 3 h at rt. And then NaBH(OAc)₃ (85 mg, 0.4 mmol) was added to the mixture and the resulting mixture was stirred for 1 h at rt. The mixture solution was quenched with 1N NaOH (1 mL), filtered off the white solid, and the filtrate was concentrated. The crude was purified by reverse-phase HPLC (mobile phase: methanol/water (10 mM NH₄HCO₃)) to afford 2-chloro-N,N-dimethyl-6-(4-(((1S,2R)-2-((methylamino)methyl)cyclopropyl)methyl)piperidin-1-yl)nicotinamide (60 mg, 66%). LRMS m/z (M+H) 365.2 found, 365.2 required.

2-chloro-N,N-dimethyl-6-(4-(((1S,2R)-2-(((R)-3,3,3-trifluoro-2-hydroxy-N-methyl-2-phenylpropanamido)methyl)cyclopropyl)methyl)piperidin-1-yl)nicotinamide A mixture of (R)-3,3,3-trifluoro-2-hydroxy-2-phenylpropanoic acid (18 mg, 0.08 mmol), DIPEA (21 mg, 0.16 mmol), HATU (38 mg, 0.1 mmol), 2-chloro-N,N-dimethyl-6-(4-(((1S,2R)-2-((methylamino)methyl)cyclopropyl)methyl)piperidin-1-yl)nicotinamide (18 mg, 0.05 mmol) in dry THF (1 mL) was stirred at rt for 4 h. The mixture was directly purified by reverse-phase HPLC (mobile phase: methanol/water (10 mM NH₄HCO₃)) to afford 2-chloro-N,N-dimethyl-6-(4-(((1 S,2R)-2-(((R)-3,3,3-trifluoro-2-hydroxy-N-methyl-2-phenylpropanamido)methyl)cyclopropyl)methyl)piperidin-1-yl)nicotinamide (10 mg, 30%). LRMS m/z (M+H) 567.3 found, 567.2 required.

Using the same procedure described in Example 18-1 but replacing (R)-3,3,3-trifluoro-2-hydroxy-2-phenylpropanoic acid with (R)-3,3,3-trifluoro-2-hydroxy-2-(3-methoxyphenyl)propanoic acid and (S)-3,3,3-trifluoro-2-hydroxy-2-(3-methoxyphenyl)propanoic acid in last step, or replacing methyl 2-(bis(2,2,2-trifluoroethoxy)phosphoryl)acetate with methyl 2-(diethoxyphosphoryl)acetate and replacing KHMDS with NaOᵗBu in the fifth step, the examples in Table 18 were prepared.

TABLE 18

| Example | Structure | IUPAC Name | LRMS, found [M + H]+ |
|---|---|---|---|
| 18-1 | 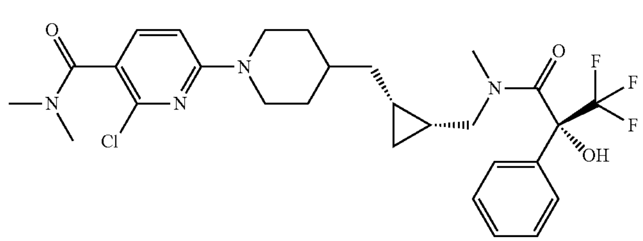 [SMILES: CN(C)C(=O)c1ccc(N2CCC(C[C@H]3C[C@H]3CN(C)C(=O)[C@](O)(c3ccccc3)C(F)(F)F)CC2)nc1Cl] | 2-chloro-N,N-dimethyl-6-(4-(((1S,2R)-2-(((R)-3,3,3-trifluoro-2-hydroxy-N-methyl-2-phenylpropanamido)methyl)cyclopropyl)methyl)piperidin-1-yl)nicotinamide | 567.3 |

TABLE 18-continued

| Example | Structure | IUPAC Name | LRMS, found [M + H]+ |
|---|---|---|---|
| 18-2 | 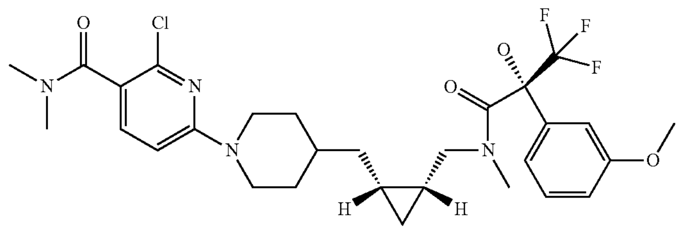 | 2-chloro-N,N-dimethyl-6-(4-(((1S,2R)-2-(((R)-3,3,3-trifluoro-2-hydroxy-2-(3-methoxyphenyl)-N-methylpropanamido)methyl)cyclopropyl)methyl)piperidin-1-yl)nicotinamdie | 597.2 |
| 18-3 | 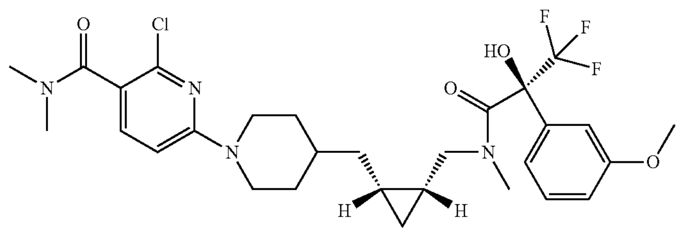 | 2-chloro-N,N-dimethyl-6-(4-(((1S,2R)-2-(((S)-3,3,3-trifluoro-2-hydroxy-2-(3-methoxyphenyl)-N-methylpropanamido)methyl)cyclopropyl)methyl)piperidin-1-yl)nicotinamide | 597.3 |
| 18-4 | 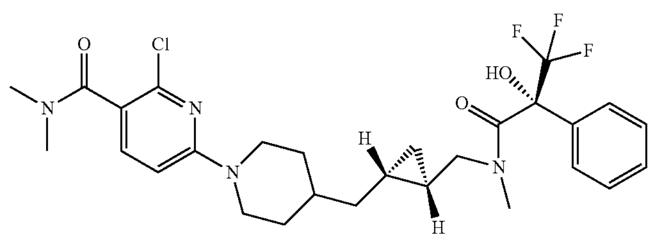 | 2-chloro-N,N-dimethyl-6-(4-(((1R,2R)-2-(((R)-3,3,3-trifluoro-2-hydroxy-N-methyl-2-phenylpropanamido)methyl)cyclopropyl)methyl)piperidin-1-yl)nicotinamide | 567.2 |

Biological Assays

Potency (Inflection Point, IP) and efficacy (Emax) are evaluated via compound-induced co-activator recruitment to glutathione-S-transferase (GST) tagged LXRbeta and LXRalpha LBD (ligand binding domain) proteins in relation to reference dual agonist compound T0901317 (N-(2,2,2-Trifluoroethyl)-N-[4-[2,2,2-trifluoro-1-hydroxy-1-(trifluoromethyl)ethyl]phenyl]benzenesulfonamide) using the LanthaScreen™ TR-FRET Liver X Receptor Coactivator Assays according to manufacturer's instructions (Invitrogen catalog number pv4658.pps and pv4655). While running the LanthaScreen™ TR-FRET Liver X Receptor Coactivator Assay, LXR alpha-LBD or LXR beta-LBD was added to ligand test compounds followed by addition of a mixture of a fluorescein-labelled coactivator peptide and terbium-conjugated anti-GST antibody. After an incubation period at room temperature, TR-FRET (time-resolved fluorescence resonance energy transfer) was measured using a filter-based instrument capable of TR-FRET, e.g. PerkinElmer Envision. When the terbium label on the anti-GST antibody was excited at 340 nm, energy was transferred to the fluorescein label on the coactivator peptide and detected as emission at 520 nm, providing an indication of ligand binding that enables ligand-dependent recruitment of coactivator peptide, and the ratio of 520 nm:495 nm is calculated and is used to determine the ligands potencies and efficacies from appropriate dose response curves of the compound. IP and % Emax values for each of the example compounds of the invention were measured in accordance with the above and are provided in the Table below.

| Example | LXR beta IP (nM) | LXR beta actiivty at max dose (%) | LXR alpha IP (nM) | LXR alpha actiivty at max dose (%) |
|---|---|---|---|---|
| 1-1 | 38 | 78 | 752 | 27 |
| 1-2 | 259 | 68 | No IP | 16 |
| 1-3 | 159 | 102 | 1782 | 40 |
| 1-4 | 82 | 92 | 1183 | 52 |
| 1-5 | 55 | 82 | No IP | 6 |
| 1-6 | 64 | 80 | 1461 | 27 |
| 1-7 | 144 | 94 | 2524 | 57 |
| 1-8 | 106 | 81 | 1769 | 51 |
| 1-9 | 46 | 69 | No IP | 4 |
| 1-10 | 72 | 71 | No IP | 9 |
| 1-11 | 453 | 59 | No IP | 0 |
| 1-12 | 13 | 78 | 372 | 23 |
| 1-13 | 148 | 63 | No IP | 0 |
| 1-14 | 366 | 19 | No IP | 0 |
| 1-15 | 76 | 55 | No IP | 0 |
| 1-16 | 179 | 54 | No IP | 1 |
| 1-17 | 290 | 55 | No IP | 7 |
| 1-18 | 564 | 41 | No IP | 13 |
| 1-19 | 1038 | 41 | 17450 | 38 |
| 1-20 | 508 | 32 | No IP | 6 |
| 1-21 | 330 | 60 | No IP | 9 |
| 1-22 | 64 | 94 | No IP | 9 |
| 1-23 | 64 | 90 | 1764 | 39 |
| 1-24 | 351 | 59 | No IP | 12 |
| 1-25 | 110 | 71 | 3362 | 26 |
| 1-26 | 910 | 51 | No IP | 6 |
| 1-27 | 603 | 53 | No IP | 3 |
| 1-28 | 67 | 39 | No IP | 0 |
| 1-29 | 396 | 51 | No IP | 8 |
| 1-30 | 237 | 47 | No IP | 1 |
| 1-31 | 163 | 56 | No IP | 0 |
| 1-32 | 95 | 48 | No IP | 0 |

-continued

| Example | LXR beta IP (nM) | LXR beta actiivty at max dose (%) | LXR alpha IP (nM) | LXR alpha actiivty at max dose (%) |
|---|---|---|---|---|
| 1-33 | 17 | 70 | No IP | 0 |
| 1-34 | 261 | 49 | No IP | 16 |
| 1-35 | 437 | 46 | No IP | 14 |
| 1-36 | 78 | 63 | No IP | 0 |
| 1-37 | 35 | 44 | No IP | 0 |
| 1-38 | 156 | 78 | 1924 | 18 |
| 1-39 | 567 | 53 | 11140 | 34 |
| 1-40 | 52 | 63 | No IP | 0 |
| 1-41 | 105 | 44 | No IP | 0 |
| 1-42 | 92 | 64 | No IP | 11 |
| 1-43 | 110 | 54 | No IP | 11 |
| 1-44 | 822 | 39 | No IP | 0 |
| 1-45 | 45 | 82 | 2512 | 32 |
| 1-46 | 412 | 37 | No IP | 0 |
| 1-47 | 100 | 56 | No IP | 11 |
| 1-48 | 333 | 43 | No IP | 2 |
| 1-49 | 54 | 50 | No IP | 0 |
| 1-50 | 62 | 63 | No IP | 18 |
| 1-51 | 546 | 55 | 5531 | 23 |
| 1-52 | 5042 | 46 | No IP | 11 |
| 1-53 | 580 | 43 | No IP | 0 |
| 1-54 | 579 | 49 | No IP | 15 |
| 1-55 | 856 | 48 | No IP | 16 |
| 1-56 | 168 | 80 | 2612 | 43 |
| 1-57 | 268 | 48 | No IP | 0 |
| 1-58 | 37 | 86 | 2775 | 37 |
| 1-59 | 118 | 80 | 2863 | 24 |
| 1-60 | 60 | 93 | 1453 | 33 |
| 1-61 | 1380 | 23 | No IP | 0 |
| 1-62 | 694 | 28 | No IP | 0 |
| 1-63 | 368 | 40 | No IP | 0 |
| 1-64 | 285 | 26 | No IP | 0 |
| 1-65 | 217 | 74 | No IP | 14 |
| 1-66 | 138 | 82 | No IP | 7 |
| 2-1 | 686 | 51 | No IP | 18 |
| 2-2 | 688 | 44 | No IP | 7 |
| 2-3 | 107 | 42 | No IP | 0 |
| 2-4 | 24 | 61 | No IP | 0 |
| 2-5 | 28 | 63 | 705 | 23 |
| 2-6 | 126 | 50 | No IP | 0 |
| 2-7 | 420 | 43 | No IP | 4 |
| 2-8 | 11 | 47 | 690 | 40 |
| 2-9 | 9 | 65 | 164 | 45 |
| 2-10 | 134 | 43 | No IP | 0 |
| 2-11 | 524 | 60 | No IP | 13 |
| 2-12 | 11 | 62 | 95 | 40 |
| 2-13 | 195 | 60 | No IP | 11 |
| 2-14 | 83 | 67 | No IP | 14 |
| 2-15 | 272 | 49 | No IP | 0 |
| 2-16 | 296 | 54 | No IP | 12 |
| 2-17 | 5729 | 22 | No IP | 0 |
| 2-18 | 523 | 47 | No IP | 0 |
| 2-19 | 128 | 76 | 2607 | 23 |
| 2-20 | 271 | 64 | No IP | 0 |
| 2-21 | 1907 | 30 | 5938 | 26 |
| 2-22 | 1122 | 32 | No IP | 2 |
| 3-1 | 25 | 70 | No IP | 16 |
| 3-2 | 53 | 81 | No IP | 0 |
| 3-3 | 373 | 49 | No IP | 6 |
| 3-4 | 134 | 87 | No IP | 19 |
| 3-5 | 156 | 57 | 2892 | 22 |
| 3-6 | 961 | 38 | No IP | 7 |
| 3-7 | 425 | 94 | No IP | 13 |
| 4-1 | 247 | 59 | No IP | 8 |
| 4-2 | 217 | 49 | No IP | 0 |
| 4-3 | 67 | 53 | No IP | 0 |
| 4-4 | 45 | 59 | 1581 | 14 |
| 4-5 | 229 | 50 | No IP | 8 |
| 4-6 | 77 | 73 | 677 | 15 |
| 4-7 | 369 | 48 | No IP | 12 |
| 4-8 | 471 | 73 | 3352 | 23 |
| 4-9 | 72 | 40 | No IP | 0 |
| 4-10 | 162 | 67 | No IP | 10 |
| 4-11 | 120 | 40 | No IP | 0 |
| 5-1 | 610 | 95 | 3508 | 14 |
| 5-2 | 686 | 80 | No IP | 11 |
| 5-3 | 380 | 118 | 1673 | 27 |
| 5-4 | 561 | 72 | No IP | 16 |
| 5-5 | 1505 | 39 | No IP | 0 |
| 5-6 | 267 | 105 | 3702 | 23 |
| 5-7 | 636 | 106 | No IP | 27 |
| 5-8 | 105 | 104 | 5137 | 28 |
| 5-9 | 165 | 101 | 2281 | 9 |
| 5-10 | 343 | 58 | No IP | 3 |
| 5-11 | 349 | 46 | No IP | -8 |
| 5-12 | 1013 | 40 | 13250 | 40 |
| 5-13 | 187 | 54 | No IP | 9 |
| 5-14 | 207 | 44 | No IP | 0 |
| 5-15 | 215 | 83 | 2734 | 22 |
| 5-16 | 235 | 83 | 5223 | 26 |
| 5-17 | 401 | 43 | No IP | 0 |
| 5-18 | 990 | 66 | No IP | 7 |
| 5-19 | 160 | 104 | 2339 | 36 |
| 5-20 | 230 | 69 | No IP | 17 |
| 5-21 | 314 | 91 | 8721 | 36 |
| 5-22 | 1190 | 101 | 10280 | 31 |
| 5-23 | 275 | 73 | No IP | 16 |
| 6-1 | 379 | 25 | No IP | 0 |
| 6-2 | 98 | 116 | 2438 | 29 |
| 7-1 | 342 | 54 | 4087 | 10 |
| 7-2 | 14 | 73 | 534 | 44 |
| 7-3 | 32 | 61 | 601 | 24 |
| 7-4 | 20 | 64 | 826 | 26 |
| 7-5 | 11 | 68 | 381 | 55 |
| 7-6 | 21 | 76 | 439 | 33 |
| 7-7 | 22 | 64 | 504 | 42 |
| 7-8 | 82 | 56 | 1275 | 33 |
| 7-9 | 109 | 52 | 775 | 25 |
| 7-10 | 100 | 58 | 1065 | 35 |
| 7-11 | 81 | 60 | 1152 | 42 |
| 7-12 | 79 | 64 | 765 | 47 |
| 7-13 | 14 | 55 | 158 | 32 |
| 7-14 | 18 | 55 | No IP | 6 |
| 7-15 | 12 | 58 | 680 | 37 |
| 7-16 | 101 | 54 | 1788 | 40 |
| 7-17 | 12 | 59 | 160 | 36 |
| 7-18 | 45 | 57 | No IP | 16 |
| 7-19 | 76 | 58 | 688 | 27 |
| 7-20 | 36 | 60 | 1184 | 40 |
| 7-21 | 1550 | 36 | No IP | 12 |
| 7-22 | 572 | 43 | No IP | 3 |
| 7-23 | 2065 | 32 | No IP | 7 |
| 7-24 | 1414 | 37 | No IP | 16 |
| 7-25 | 473 | 46 | 3102 | 22 |
| 7-26 | 1017 | 31 | 6103 | 32 |
| 7-27 | 1875 | 32 | No IP | 5 |
| 7-28 | 1620 | 31 | No IP | 6 |
| 7-29 | 611 | 40 | No IP | 5 |
| 7-30 | 557 | 27 | No IP | 0 |
| 7-31 | 304 | 49 | No IP | 1 |
| 7-32 | 284 | 69 | No IP | 17 |
| 7-33 | 136 | 44 | No IP | 0 |
| 7-34 | 264 | 23 | No IP | 0 |
| 7-35 | 435 | 46 | No IP | 0 |
| 7-36 | 525 | 57 | No IP | 0 |
| 8-1 | 201 | 82 | No IP | 16 |
| 9-1 | 16 | 37 | No IP | 0 |
| 9-2 | 18 | 47 | 441 | 21 |
| 9-3 | 14 | 94 | 198 | 31 |
| 9-4 | 63 | 67 | No IP | 14 |
| 9-5 | 43 | 38 | No IP | 0 |
| 9-6 | 136 | 20 | No IP | 0 |
| 9-7 | 78 | 42 | 921 | 19 |
| 10-1 | 1348 | 65 | No IP | 0 |
| 10-2 | 3729 | 40 | No IP | 0 |
| 10-3 | 1326 | 67 | No IP | 18 |
| 10-4 | 649 | 49 | No IP | 0 |
| 11-1 | 727 | 42 | No IP | 0 |
| 11-2 | 273 | 118 | 2388 | 28 |
| 11-3 | 508 | 93 | 6008 | 22 |

-continued

| Example | LXR beta IP (nM) | LXR beta actiivty at max dose (%) | LXR alpha IP (nM) | LXR alpha actiivty at max dose (%) |
|---|---|---|---|---|
| 11-4 | 270 | 85 | No IP | 14 |
| 11-5 | 653 | 53 | No IP | 7 |
| 11-6 | 561 | 54 | No IP | 3 |
| 12-1 | 266 | 44 | No IP | 12 |
| 12-2 | 218 | 25 | No IP | 4 |
| 12-3 | 151 | 58 | No IP | 12 |
| 12-4 | 266 | 46 | No IP | 0 |
| 13-1 | 34 | 50 | 472 | 26 |
| 13-2 | 142 | 49 | No IP | 1 |
| 13-3 | 654 | 35 | No IP | 1 |
| 14-1 | 35 | 42 | No IP | 5 |
| 14-2 | 473 | 30 | No IP | 8 |
| 15-1 | 34 | 66 | No IP | 9 |
| 15-2 | 10 | 64 | 289 | 25 |
| 15-3 | 17 | 58 | No IP | 10 |
| 15-4 | 23 | 50 | 623 | 15 |
| 15-5 | 16 | 75 | No IP | 18 |
| 15-6 | 9 | 29 | No IP | 4 |
| 15-7 | 26 | 53 | No IP | 11 |
| 15-8 | 74 | 59 | No IP | 0 |
| 15-9 | 393 | 54 | 4225 | 39 |
| 15-10 | 442 | 38 | No IP | 4 |
| 15-11 | 4439 | 36 | No IP | 1 |
| 15-12 | 1330 | 39 | 3781 | 29 |
| 15-13 | 542 | 84 | No IP | 17 |
| 15-14 | 264 | 69 | No IP | 3 |
| 15-15 | 186 | 75 | 6066 | 23 |
| 15-16 | 583 | 58 | No IP | 0 |
| 15-17 | 505 | 79 | No IP | 0 |
| 15-18 | 763 | 66 | No IP | 8 |
| 15-19 | 127 | 72 | No IP | 0 |
| 15-20 | 403 | 65 | No IP | 12 |
| 16-1 | 47 | 64 | 1405 | 36 |
| 17-1 | 18 | 76 | No IP | 14 |
| 17-2 | 33 | 43 | No IP | 10 |
| 17-3 | 27 | 65 | No IP | 12 |
| 17-4 | 53 | 39 | No IP | 13 |
| 17-5 | 148 | 20 | No IP | 0 |
| 18-1 | 131 | 56 | No IP | 12 |
| 18-2 | 124 | 44 | No IP | 0 |
| 18-3 | 518 | 25 | No IP | 0 |
| 18-4 | 66 | 57 | No IP | 15 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A compound having the structural Formula (I):

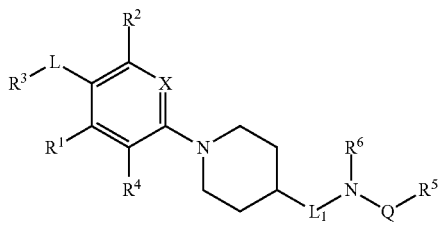

(I)

or a pharmaceutically acceptable salt thereof, wherein:
X is selected from —N— and —CH—;
$R^1$ is selected from H, methyl, and halogen;
$R^2$ is selected from H, halogen, cyano, cyclopropyl, —$CH_3$, and —$OCH_3$;
$R^4$ is selected from H, halogen, and methyl;
-L- is a divalent moiety —C(O)—;
$R^3$ is —N($R^{N1}$)($R^{N2}$), wherein:
  $R^{N1}$ is selected from H and —($C_1$-$C_6$)alkyl; and
  $R^{N2}$ is selected from H, —($C_1$-$C_6$)alkyl, cyclopropyl, —O—($C_1$-$C_6$)alkyl, —OH, halogen, —CN, and —($C_1$-$C_6$)alkyl which is substituted with 1 or 2 groups independently selected from:
    —OH, halogen, —CN,
    optionally substituted phenyl, (wherein said optional substitutents on said phenyl are 1 to 3 groups independently selected from OH, CN, —($C_1$-$C_4$)alkyl, —($C_1$-$C_4$)alkoxyl),
    optionally substituted heteroaryl, (wherein said optional substituents on said heteroaryl are 1 to 3 groups independently selected from —($C_1$-$C_6$)alkyl, —($C_1$-$C_4$)alkoxyl, and cyclopropyl),
    optionally substituted cyclopropyl (wherein said optional substituents on said cyclopropyl are 1 to 3 groups independently selected from —($C_1$-$C_6$)alkyl), and
    optionally substituted heterocycloalkyl (wherein said optional substitutents on said heterocycloalkyl are 1 to 3 groups independently selected from halogen, —OH, oxo, CN, and —($C_1$-$C_6$)alkyl,
  or, alternatively, $R^{N1}$ and $R^{N2}$ are taken together with the nitrogen atom to which they are shown attached to form a 4-, 5-, or 6-membered fully saturated heterocyclic ring comprising (including the nitrogen atom) 1, 2, or 3 ring heteroatoms selected from N, N-oxide, O, S, and S-oxide,
    wherein said heterocyclic ring is unsubstituted or substituted with 1, 2, or 3 substituents independently selected from halogen, —OH, oxo, CN, —($C_1$-$C_6$)alkyl, amino-substituted —($C_1$-$C_6$)alkyl (wherein said amino is 1, 2, or 3 groups independently selected from —$NH_2$, —N($C_1$-$C_4$alkyl)$_2$, and —NH($C_1$-$C_4$alkyl)), —O—($C_1$-$C_6$)alkyl, —($C_1$-$C_6$)alkyl-OH, —($C_1$-$C_6$)haloalkyl, —C(O)O—($C_1$-$C_6$)alkyl, cyclopropyl, spirocyclopropyl, —$CH_2$—NHC(O)O—($C_1$-$C_6$)alkyl, —$CH_2$—N($CH_3$)C(O)O—($C_1$-$C_6$)alkyl, phenyl, benzyl, —NHC(O)-phenyl, heteroaryl, —($C_1$-$C_4$)alkylheteroaryl, and heterocycloalkyl;
-$L_1$- is a divalent moiety selected from:

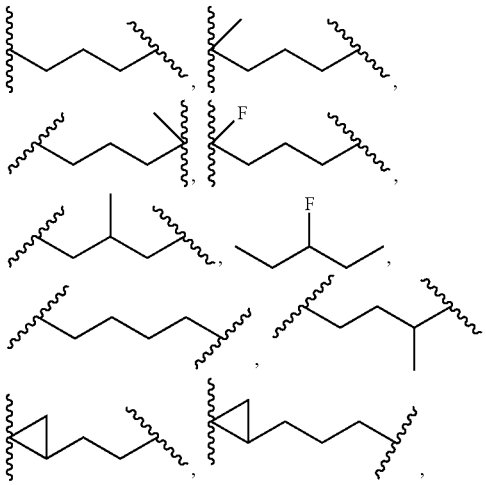

-continued

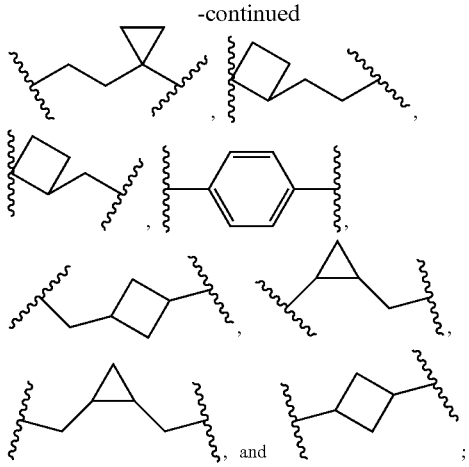

wherein the wavy line ~~ indicates point of attachment for L1 to the rest of the compound;

Q is a bond or a divalent moiety selected from —C(O)—, and —C(O)O—; and

R⁵ is selected from:

—C(R⁵ᴬ)(R⁵ᴮ)(R⁵ᶜ), wherein:
each of R⁵ᴬ, R⁵ᴮ and R⁵ᶜ is independently selected from: H, halogen, NH₂, NHCH₃, OH, —(C₁-C₆)alkyl, —(C₁-C₆)haloalkyl, —(C₁-C₆)alkenyl, —(C₁-C₆)alkynyl, —(C₃-C₆)cycloalkyl, —(C₃-C₆)cycloalkyl substituted with —(C₁-C₆)alkyl, —(C₁-C₆)alkenyl, —(C₁-C₆)alkynyl, phenyl, phenyl substituted with from 1 to 3 groups independently selected from halogen, OH, —NH₂, —(C₁-C₆)alkyl, —O—(C₁-C₆)alkyl, cyclopropyl, —O—(C₁-C₆)haloalkyl, —O-cyclopropyl, and —C(O)O—(C₁-C₆)alkyl,

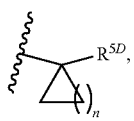

wherein n is an integer from 1 to 4;

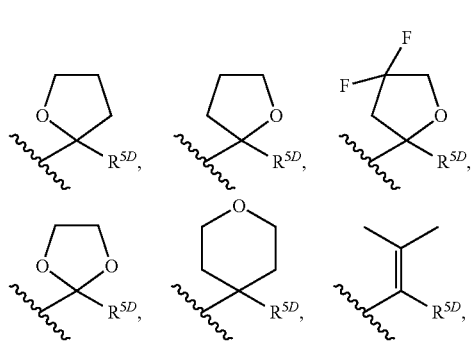

wherein R⁵ᴰ is selected from H, —(C₁-C₆)alkyl, —(C₁-C₆)haloalkyl, phenyl, and phenyl substituted with from 1 to 3 groups independently selected from OH, halogen, —(C₁-C₆)alkyl, and —O—(C₁-C₆)alkyl, and phenyl, wherein:
said phenyl is unsubstituted or substituted with 1, 2, or 3 groups independently selected from halogen, CN, —(C₁-C₆)alkyl, and —(C₁-C₆)haloalkyl; and R⁶ is H or CH₃.

2. The compound of claim 1, or a pharmaceutically acceptable salt thereof, wherein X is N.

3. The compound of claim 1, or a pharmaceutically acceptable salt thereof, wherein X is CH.

4. The compound of claim 1, or a pharmaceutically acceptable salt thereof, wherein R¹ is selected from H, methyl, F, and Cl.

5. The compound of claim 4, or a pharmaceutically acceptable salt thereof, wherein R² is selected from H, Cl, cyano, cyclopropyl, —CH₃, and —OCH₃.

6. The compound of claim 5, or a pharmaceutically acceptable salt thereof, wherein R⁴ is H, —CH₃, or chloro.

7. The compound of claim 6, or a pharmaceutically acceptable salt thereof, wherein L is —C(O)—.

8. The compound of claim 7, or a pharmaceutically acceptable salt thereof, wherein R³ is —N(Rᴺ¹)(Rᴺ²), wherein:
Rᴺ¹ is selected from H and —(C₁-C₆)alkyl; and
Rᴺ² is selected from H, —(C₁-C₆)alkyl, cyclopropyl, —O—(C₁-C₆)alkyl, —OH, halogen, —CN, and —(C₁-C₆)alkyl which is substituted with 1 or 2 groups independently selected from:
—OH, halogen, —CN,
optionally substituted phenyl, (wherein said optional substitutents on said phenyl are 1 to 3 groups independently selected from OH, CN, —(C₁-C₄)alkyl, —(C₁-C₄)alkoxyl),
optionally substituted heteroaryl, (wherein said optional substituents on said heteroaryl are 1 to 3 groups independently selected from —(C₁-C₆)alkyl, —(C₁-C₄)alkoxyl, and cyclopropyl),
optionally substituted cyclopropyl (wherein said optional substituents on said cyclopropyl are 1 to 3 groups independently selected from —(C₁-C₆)alkyl), and
optionally substituted heterocycloalkyl (wherein said optional substitutents on said heterocycloalkyl are 1 to 3 groups independently selected from halogen, —OH, oxo, CN, and —(C₁-C₆)alkyl.

9. The compound of claim 8, or a pharmaceutically acceptable salt thereof, wherein:
R³ is —N(Rᴺ¹)(Rᴺ²), wherein:
Rᴺ¹ is selected from H, methyl, and ethyl; and
Rᴺ² is H, methyl, ethyl, —O-methyl, —O-ethyl, OH, fluoro, chloro, —CN, substituted methyl, or substituted ethyl, wherein each said substituent is 1 or 2 groups independently selected from:
OH, fluoro, chloro, —CN,
optionally substituted phenyl, (wherein said optional substitutents on said phenyl are 1 to 3 groups independently selected from OH, CN, methyl, ethyl, —O-methyl, and —O-ethyl),
optionally substituted heteroaryl, (wherein said optional substituents on said heteroaryl are 1 to 3 groups independently selected from methyl, ethyl, —O-methyl, —O-ethyl, and cyclopropyl),
optionally substituted cyclopropyl (wherein said optional substitutents on said cyclopropyl are 1 to 3 groups independently selected from methyl and ethyl,
optionally substituted heterocycloalkyl (wherein said optional substitutents on said heterocycloalkyl are 1 to 3 groups independently selected from halogen, —OH, oxo, CN, methyl, and ethyl,
—O-methyl, —O-ethyl, —OH, F, Cl, and —CN.

10. The compound of claim 9, or a pharmaceutically acceptable salt thereof, wherein:
$R^3$ is —N($R^{N1}$)($R^{N2}$), wherein $R^{N1}$ and $R^{N2}$ are each independently selected from H, methyl, ethyl, n-propyl, i-propyl, —CH$_2$CH$_2$—OH, cyclopropyl, —CH$_2$-oxadiazolyl, —CH$_2$-triazolyl, wherein said oxadiazolyl and said triazolyl are each optionally substituted with methyl or cyclopropyl.

11. The compound of claim 7, or a pharmaceutically acceptable salt thereof, wherein:
L is —C(O)—; and $R^3$ is —N(CH$_3$)$_2$ or —NH(CH$_3$).

12. The compound of claim 7, or a pharmaceutically acceptable salt thereof, wherein:
$R^3$ is —N($R^{N1}$)($R^{N2}$), wherein $R^{N1}$ and $R^{N2}$ are taken together with the nitrogen atom to which they are shown attached to form a 4-, 5-, or 6-membered fully saturated heterocyclic ring comprising (including the nitrogen atom) 1, 2, or 3 ring heteroatoms selected from N, N-oxide, O, S, and S-oxide,
wherein said heterocyclic ring is unsubstituted or substituted with 1, 2, or 3 substituents independently selected from halogen, —OH, oxo, CN, —(C$_1$-C$_6$)alkyl, amino-substituted —(C$_1$-C$_6$)alkyl (wherein said amino is 1, 2, or 3 groups independently selected from —NH$_2$, —N(C$_1$-C$_4$alkyl)$_2$, and —NH(C$_1$-C$_4$alkyl)), —O—(C$_1$-C$_6$)alkyl, —(C$_1$-C$_6$)alkyl-OH, —(C$_1$-C$_6$)haloalkyl, —C(O)O—(C$_1$-C$_6$)alkyl, cyclopropyl, spirocyclopropyl, —CH$_2$—NHC(O)O—(C$_1$-C$_6$)alkyl, —CH$_2$—N(CH$_3$)C(O)O—(C$_1$-C$_6$)alkyl, phenyl, benzyl, —NHC(O)-phenyl, heteroaryl, and —(C$_1$-C$_4$)alkylheteroaryl, heterocycloalkyl.

13. The compound of claim 7, or a pharmaceutically acceptable salt thereof, wherein:
$R^5$ is —C($R^{5A}$)($R^{5B}$)($R^{5C}$),
wherein each of $R^{5A}$, $R^{5B}$ and $R^{5C}$ is independently selected from H, F, Cl, OH, NH$_2$, NHCH$_3$, —(C$_1$-C$_6$)alkyl, —(C$_1$-C$_6$)haloalkyl, —(C$_1$-C$_6$)alkenyl, —(C$_1$-C$_6$)alkynyl, —(C$_3$-C$_6$)cycloalkyl, —(C$_3$-C$_6$)cycloalkyl substituted with —(C$_1$-C$_6$)alkyl, —(C$_1$-C$_6$)alkenyl, —(C$_1$-C$_6$)alkynyl, phenyl, phenyl substituted with from 1 to 3 groups independently selected from F, Cl, —(C$_1$-C$_6$)alkyl, —O—(C$_1$-C$_6$)alkyl, and —C(O)O—(C$_1$-C$_6$)alkyl.

14. The compound of claim 7, or a pharmaceutically acceptable salt thereof, wherein:
$R^5$ is —C($R^{5A}$)($R^{5B}$)($R^{5C}$), wherein:
$R^{5A}$ is OH;
$R^{5B}$ is —(C$_1$-C$_3$)fluoroalkyl; and
$R^{5C}$ is selected from the group consisting of NH$_2$, NHCH$_3$, —(C$_1$-C$_6$)alkyl, —(C$_1$-C$_4$)fluoroalkyl, phenyl, (wherein said phenyl substituted with from 1-3 groups independently selected from halogen —(C$_1$-C$_6$)alkyl, and —(C$_1$-C$_6$)alkoxy), cyclopropyl (wherein said cyclopropyl is optionally substituted with —(C$_1$-C$_6$)alkyl), cyclobutyl, wherein said cyclobutyl is optionally substituted with —(C$_1$-C$_6$)alkyl, ethenyl, and ethynyl.

15. The compound of claim 7, or a pharmaceutically acceptable salt thereof, wherein:
$R^5$ is a moiety selected from

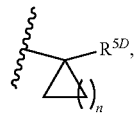

wherein n is an integer from 1 to 4,

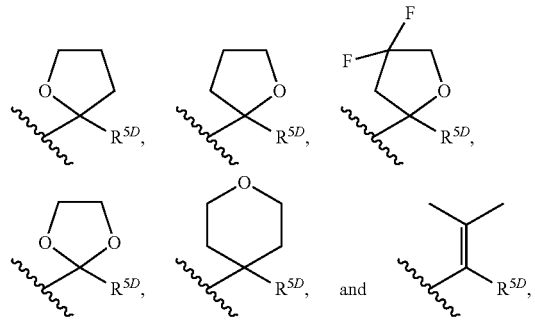

wherein $R^{5D}$ is selected from H, —(C$_1$-C$_6$)alkyl, —(C$_1$-C$_6$)haloalkyl, phenyl, and phenyl substituted with from 1 to 3 groups independently selected from OH, F, Cl, methyl, ethyl, n-propyl, i-propyl, —O-methyl, and —O-ethyl.

16. The compound of claim 7, or a pharmaceutically acceptable salt thereof, wherein:
$R^5$ is phenyl, wherein said phenyl is unsubstituted or substituted with 1, 2, or 3 groups independently selected from halogen, CN, —(C$_1$-C$_6$)alkyl, and —(C$_1$-C$_6$)haloalkyl.

17. The compound of claim 7, or a pharmaceutically acceptable salt thereof, wherein:
Q is selected from a bond, —C(O)—, and —C(O)O—.

18. The compound of claim 1, or a pharmaceutically acceptable salt thereof, said compound selected from:

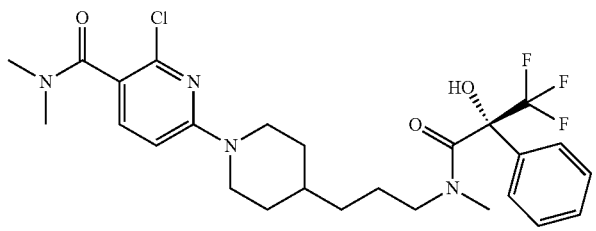

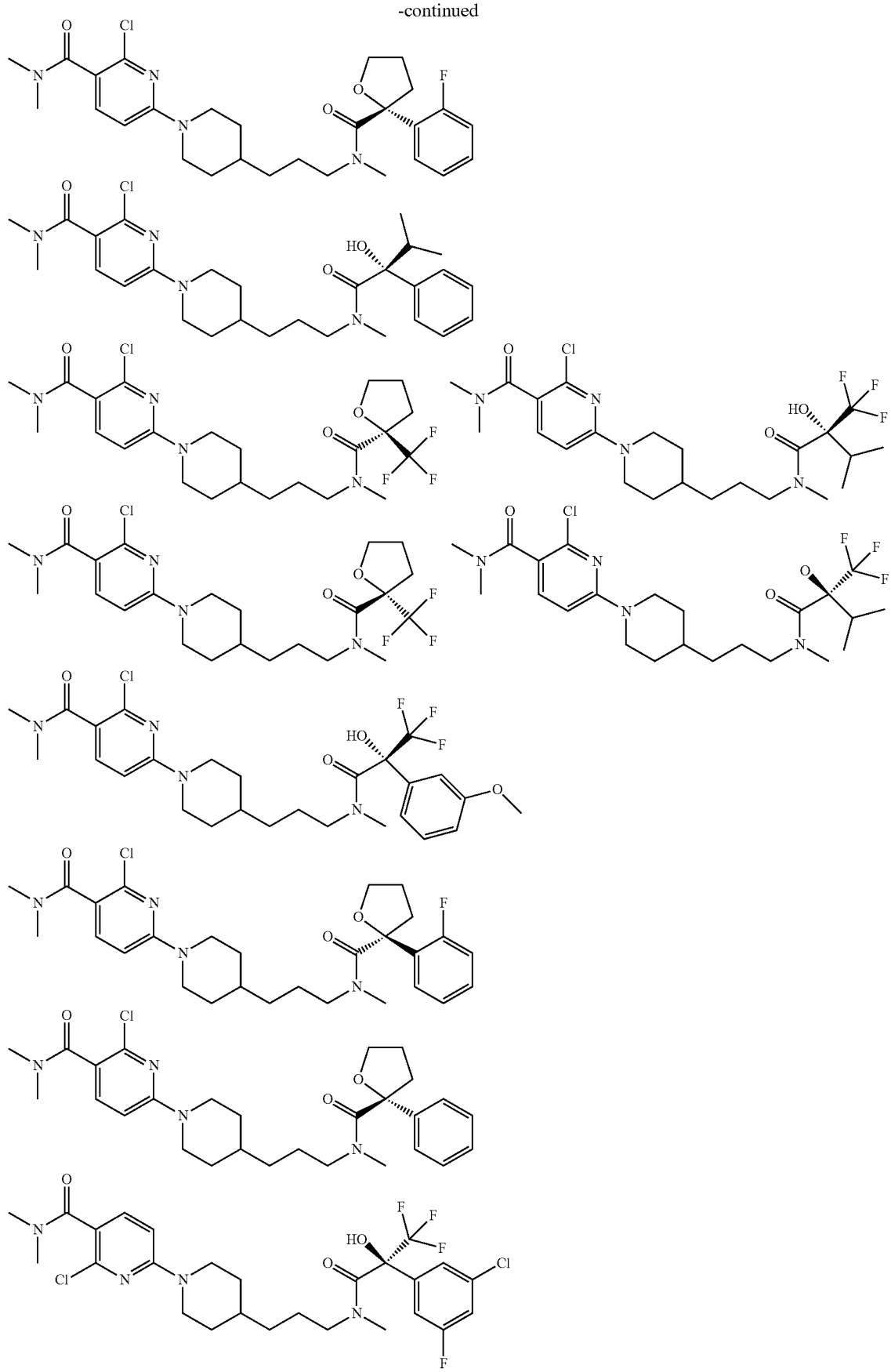

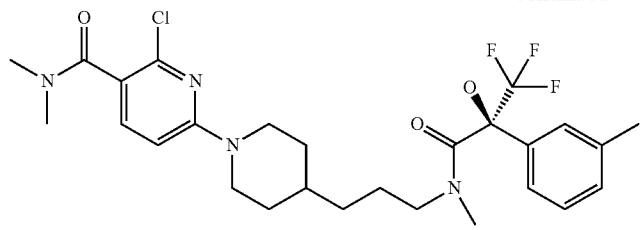
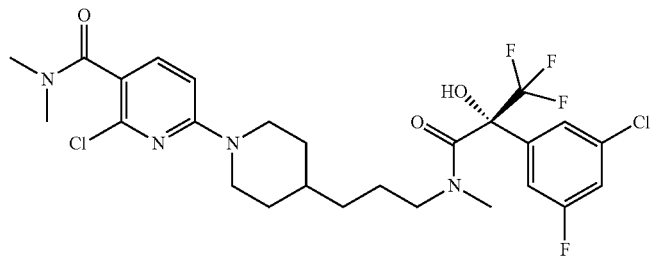
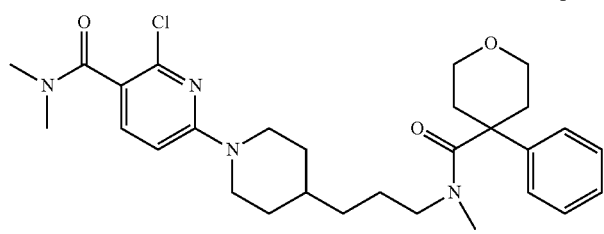
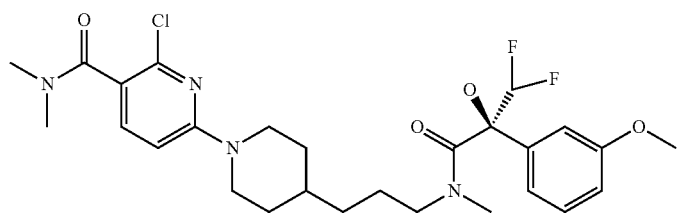
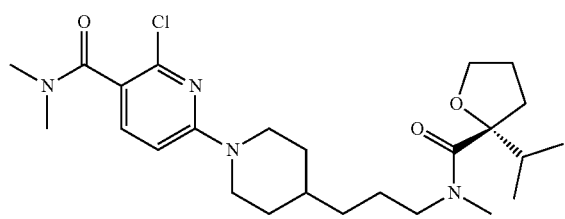
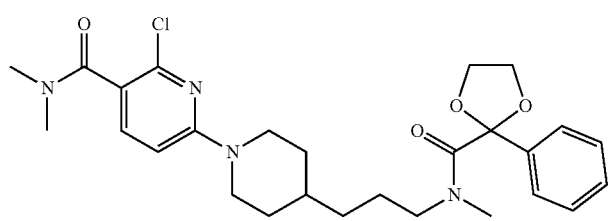
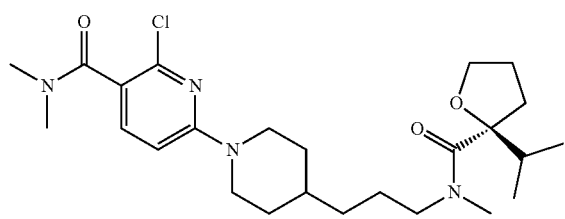

-continued
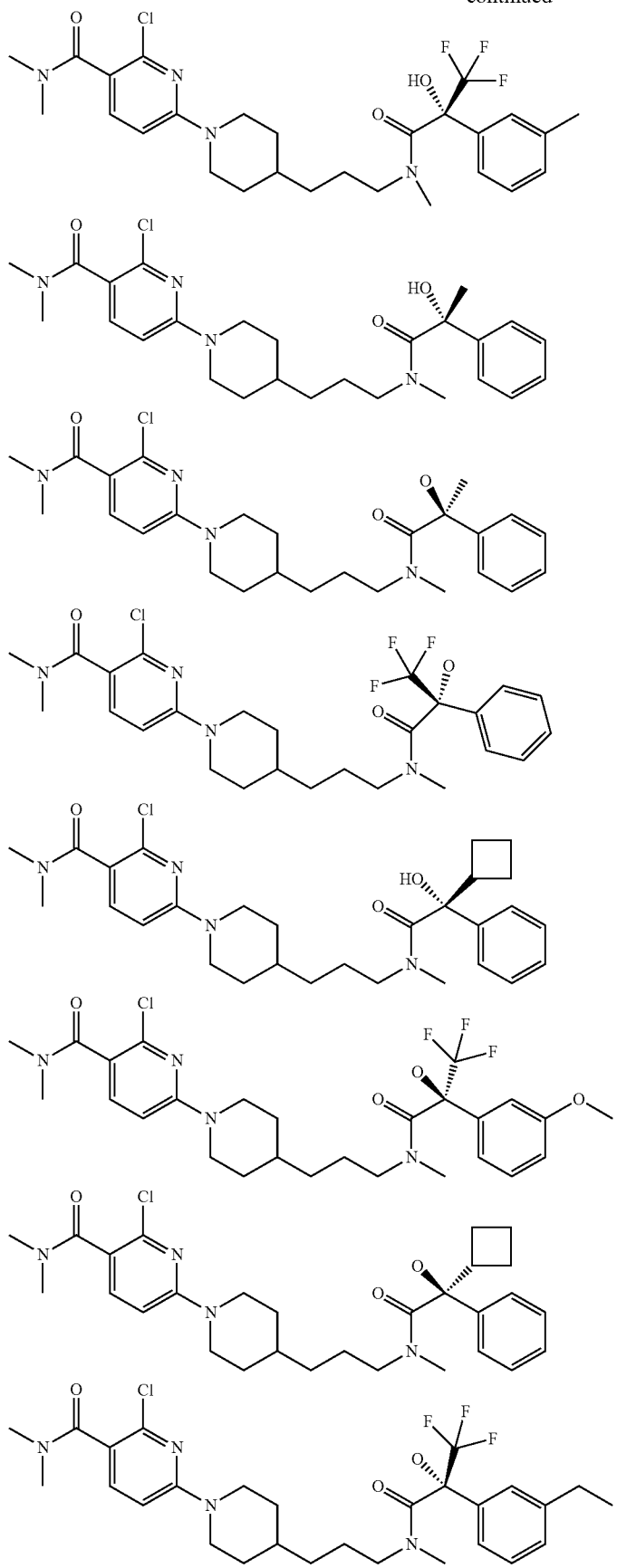

-continued
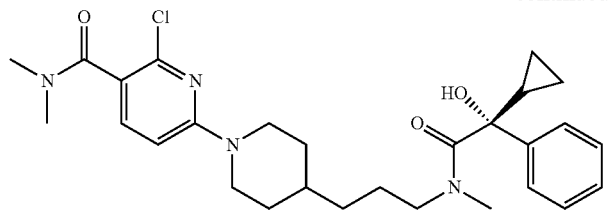
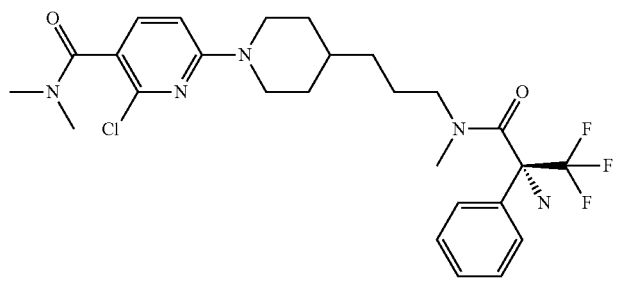
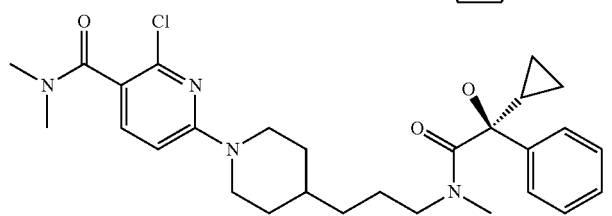
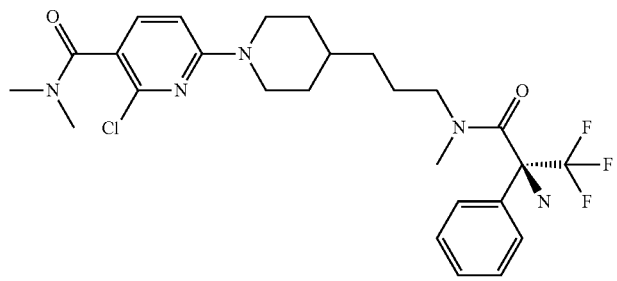
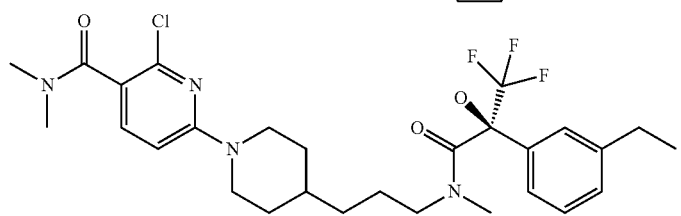
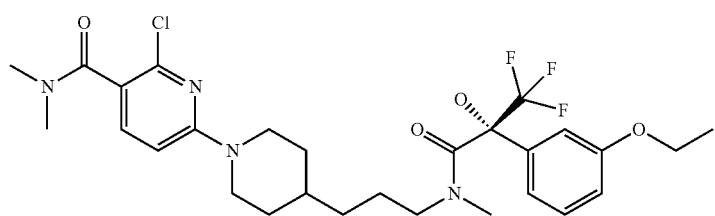
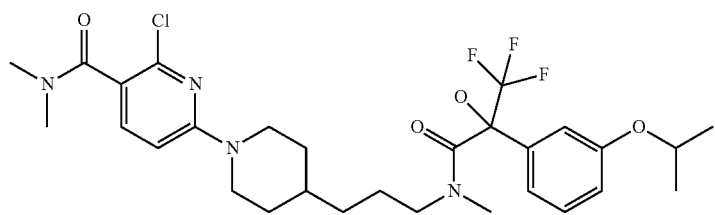

-continued
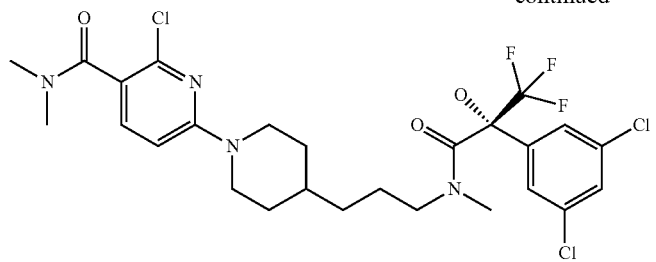
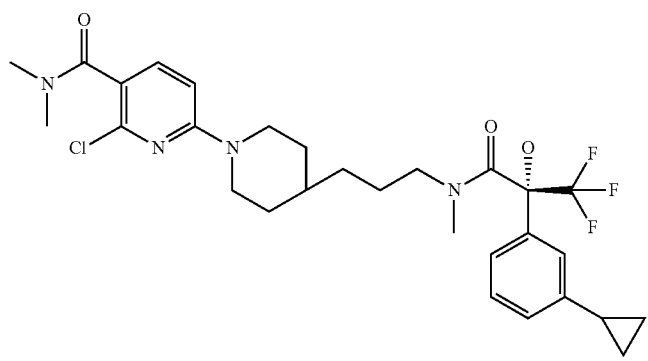
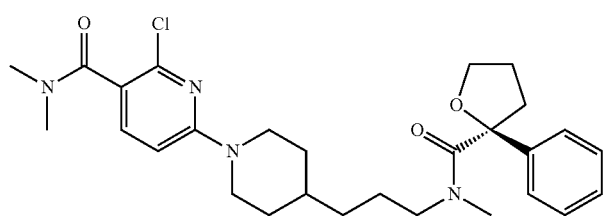
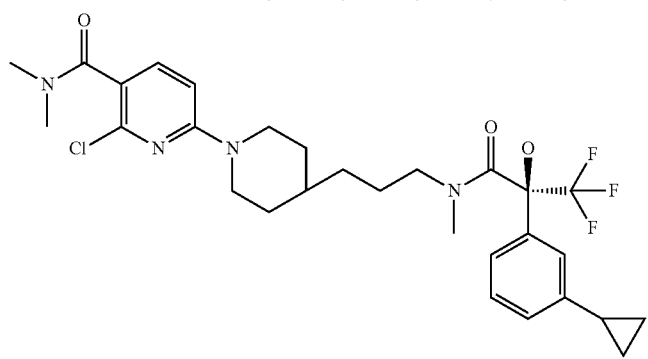
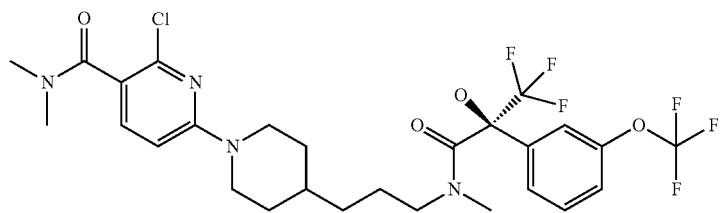
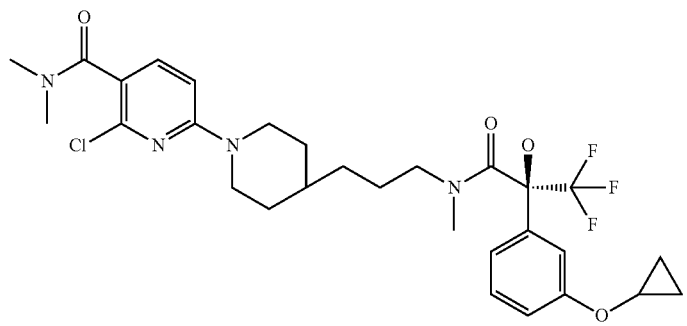

-continued
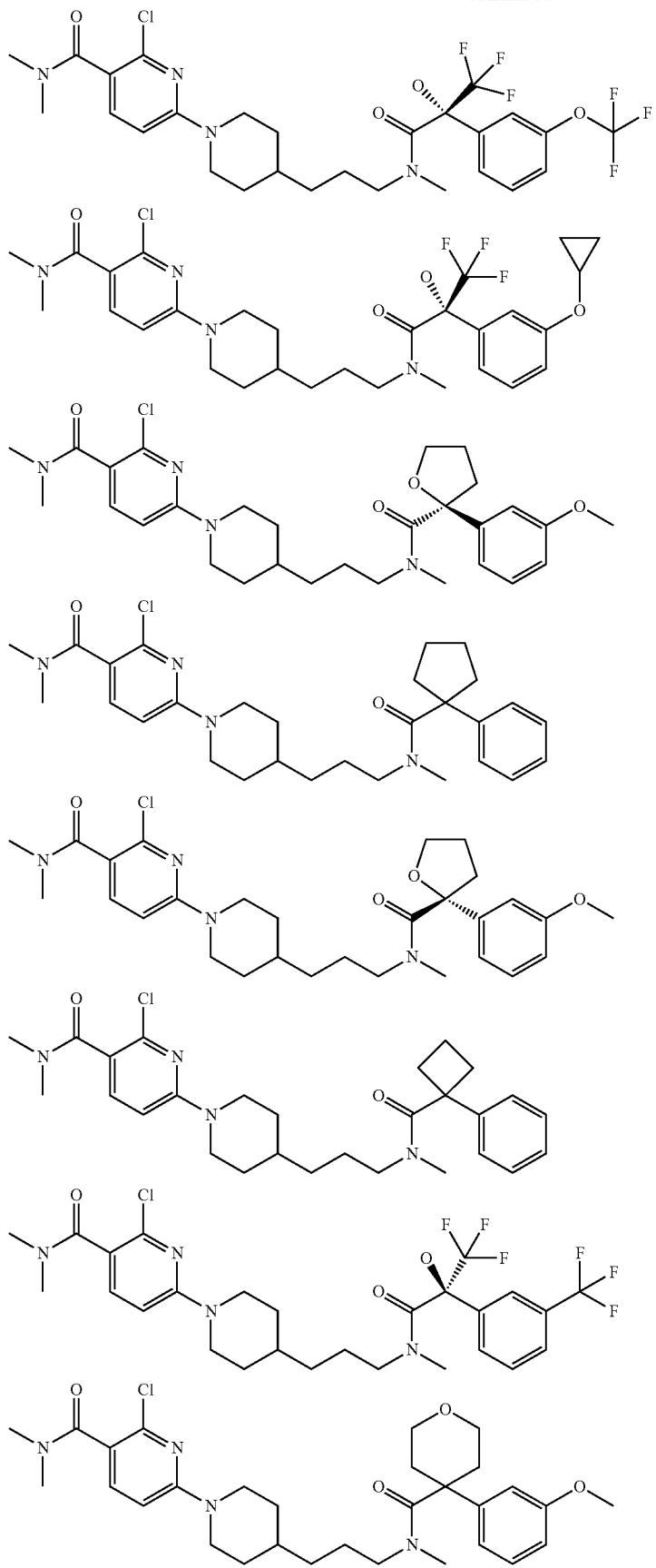

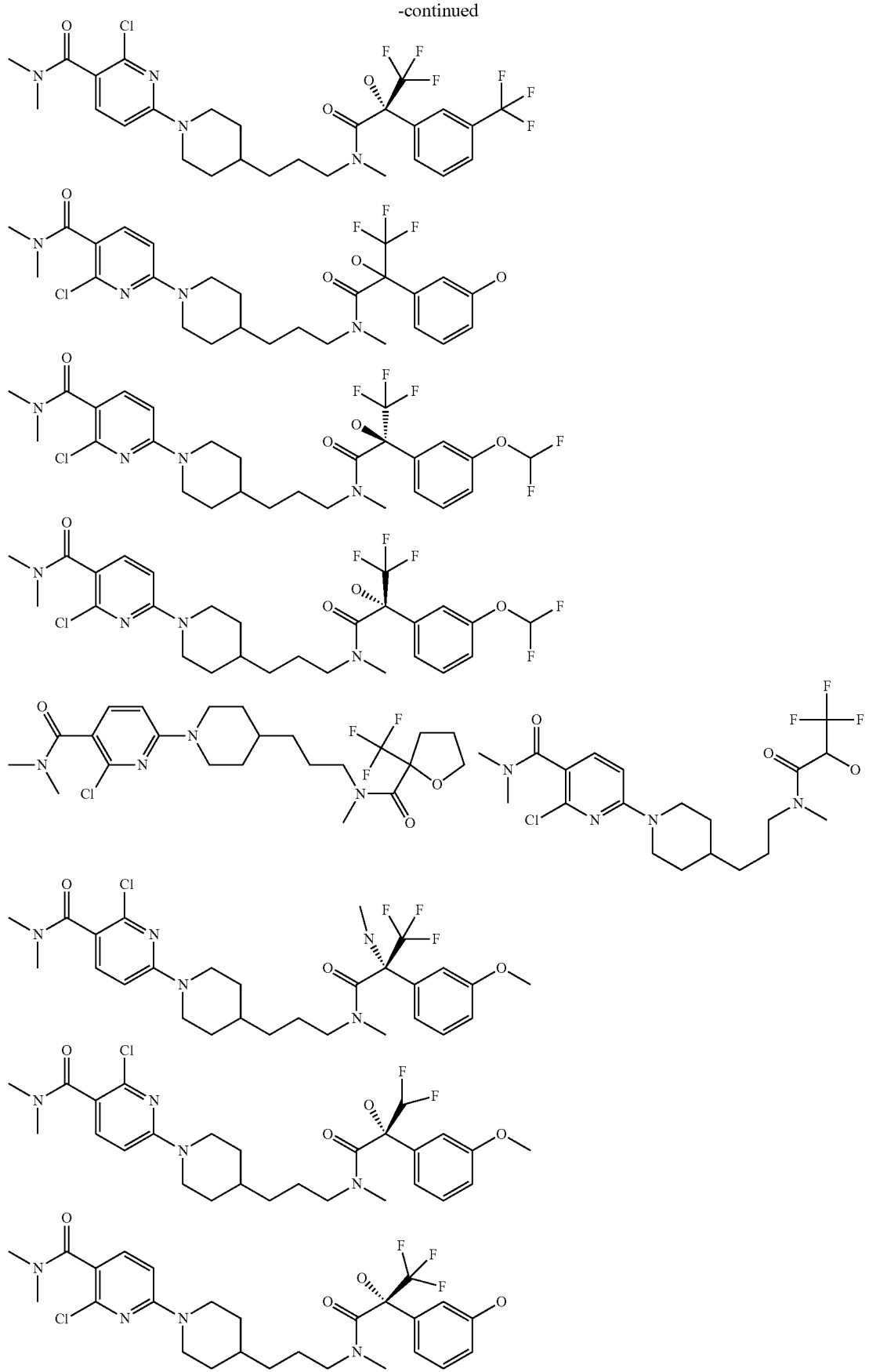

-continued
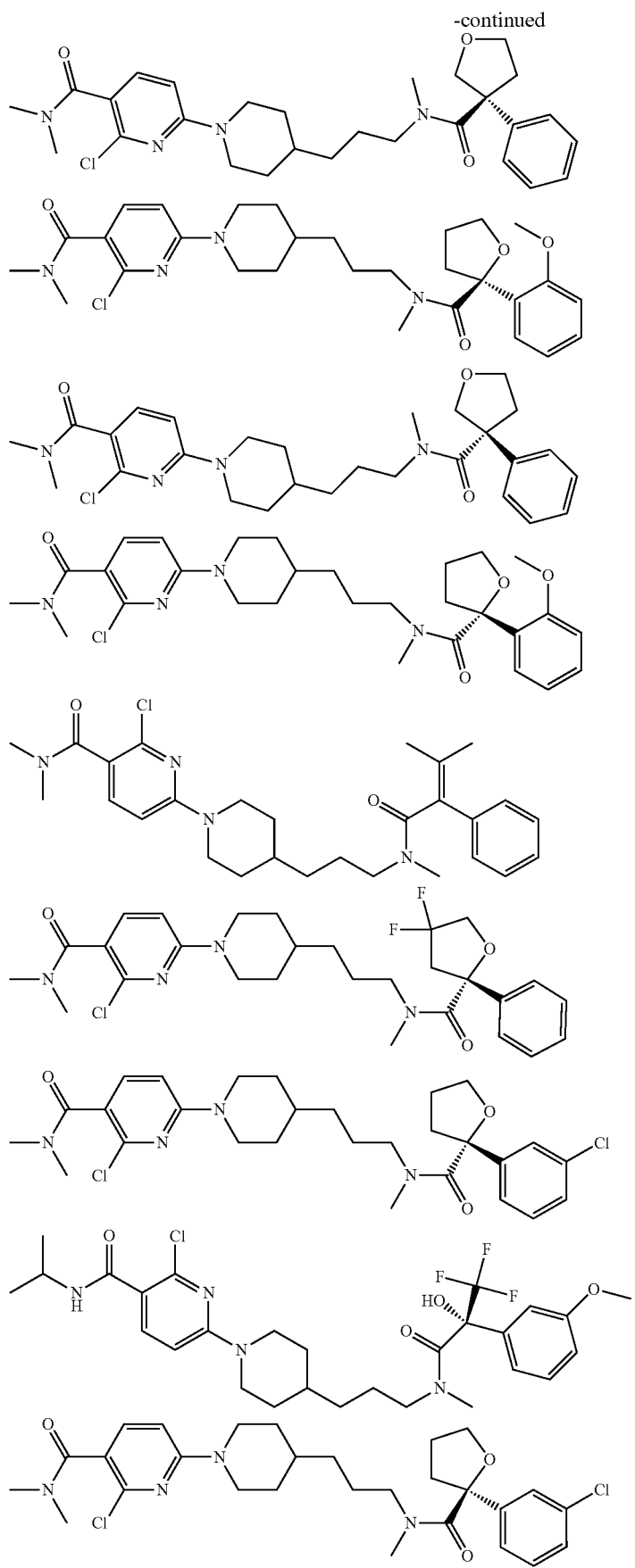

-continued
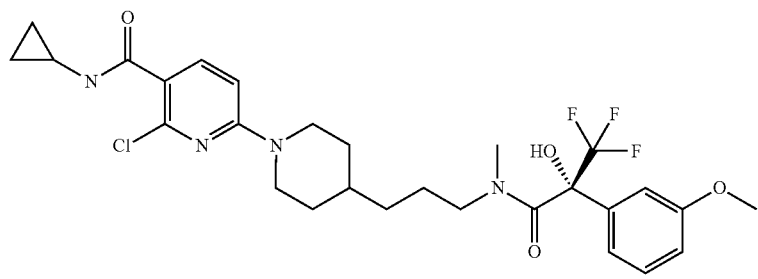
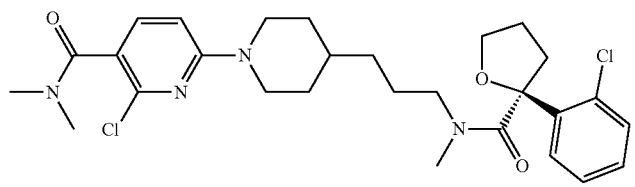
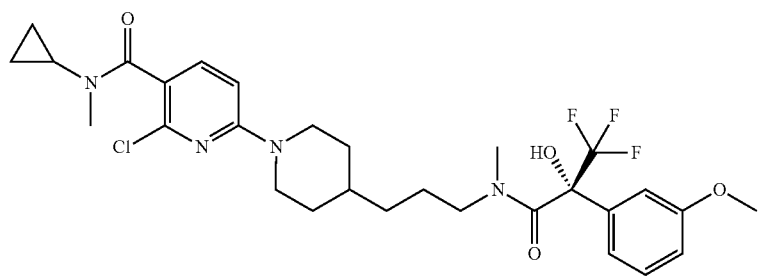
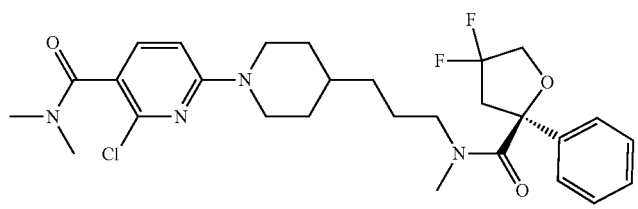
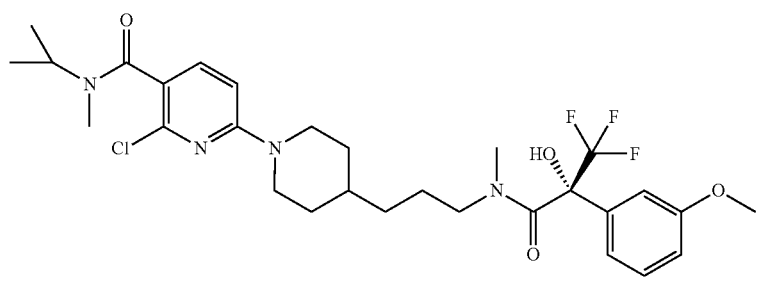
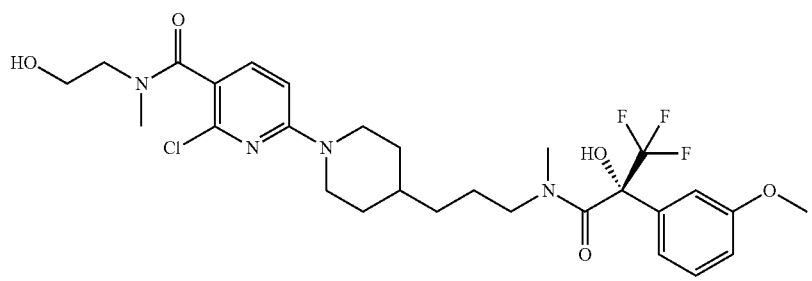

-continued
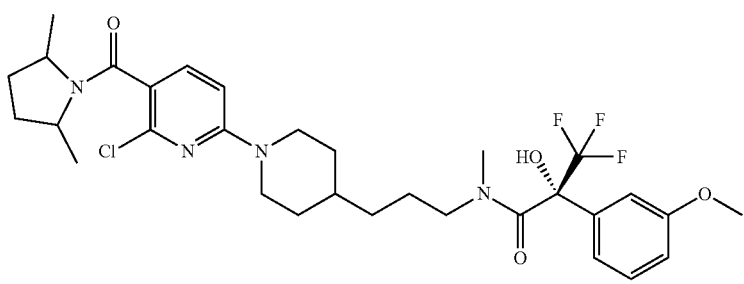
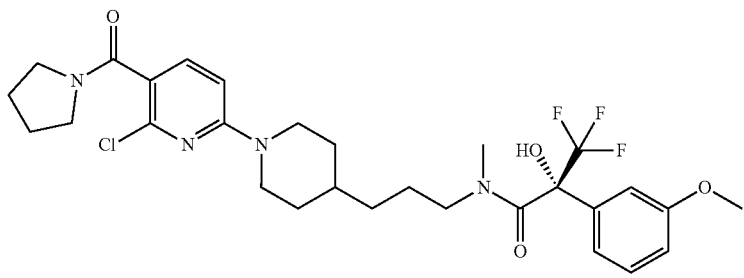
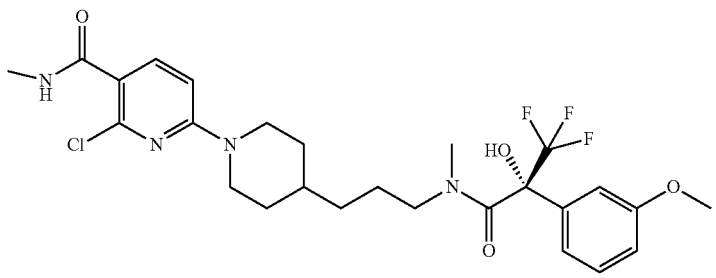
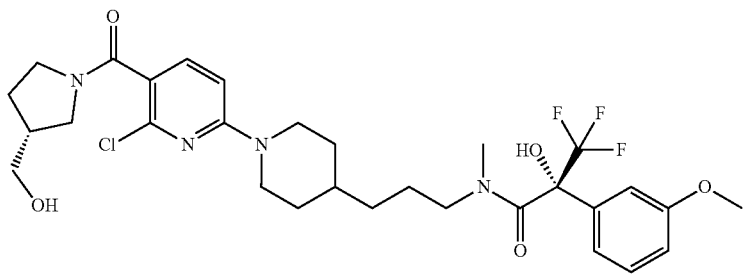
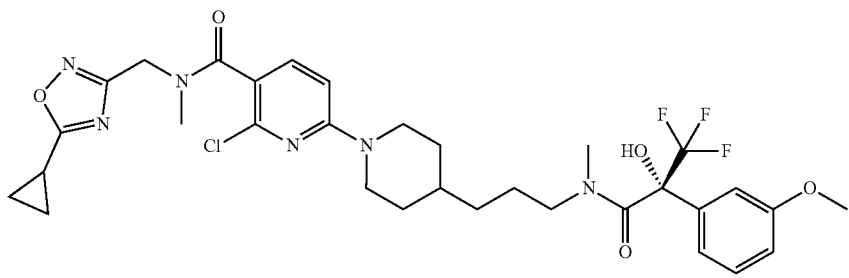
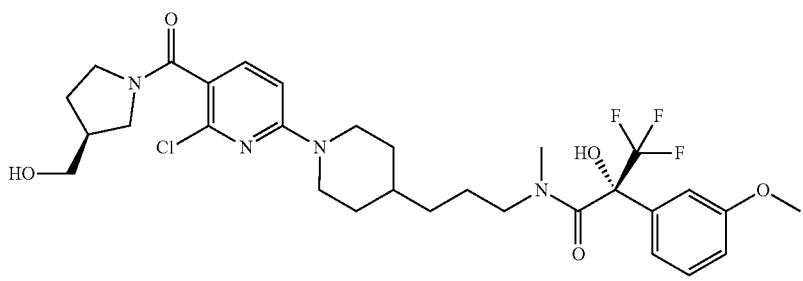

-continued
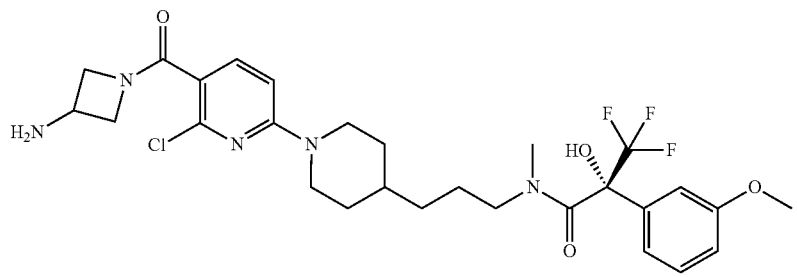
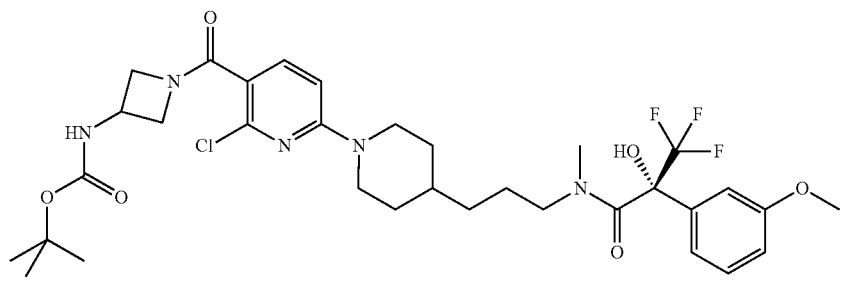
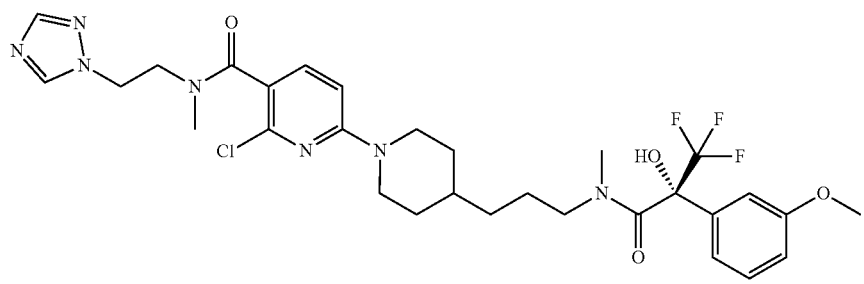
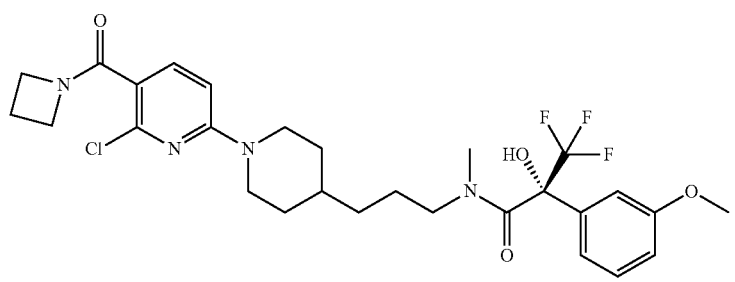
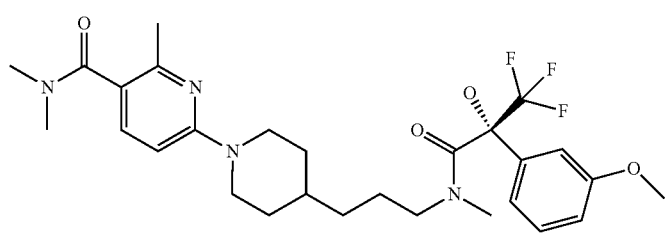
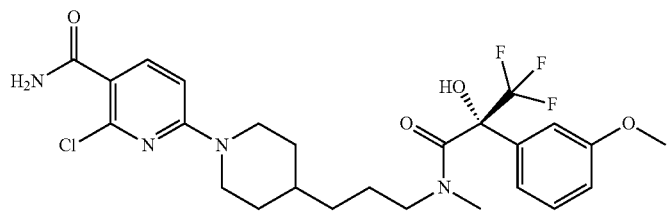

-continued
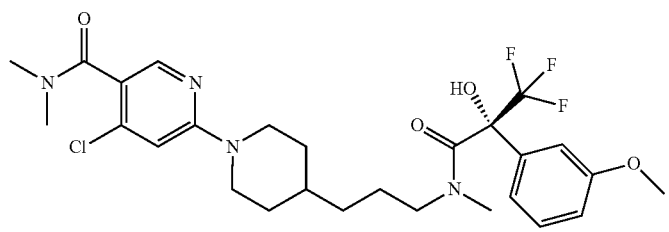
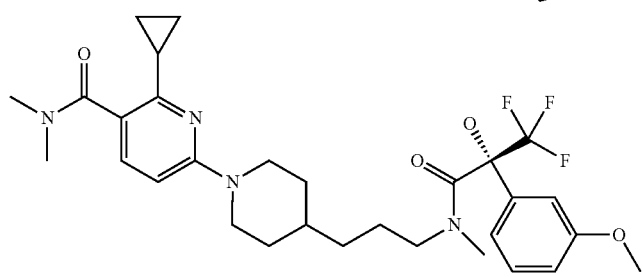
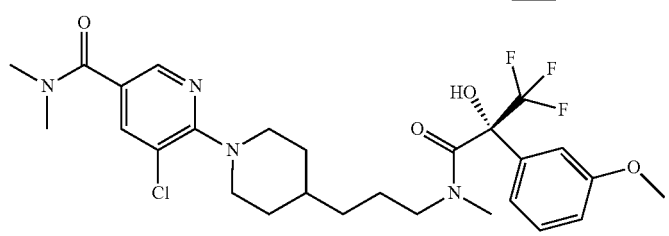
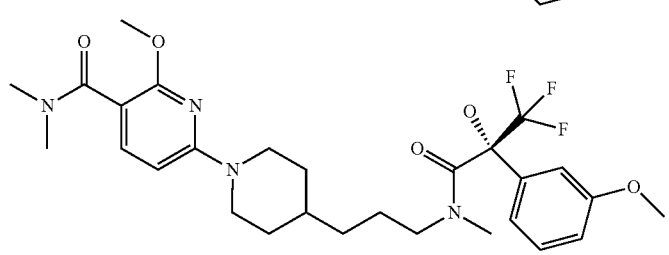
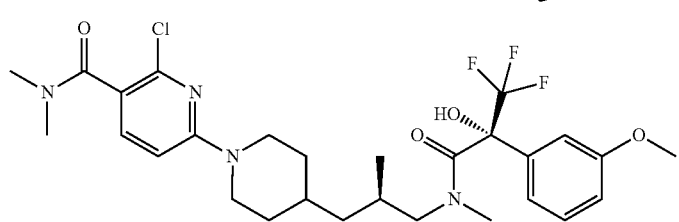
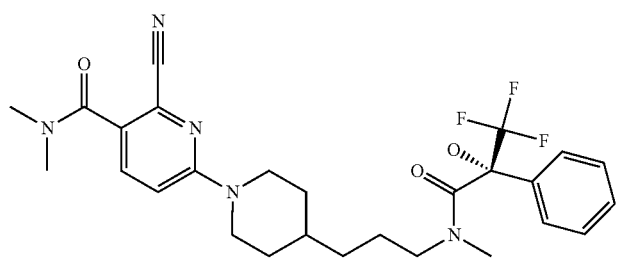
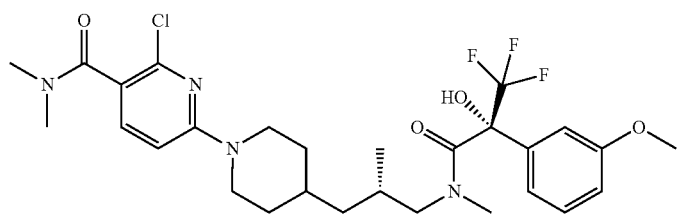

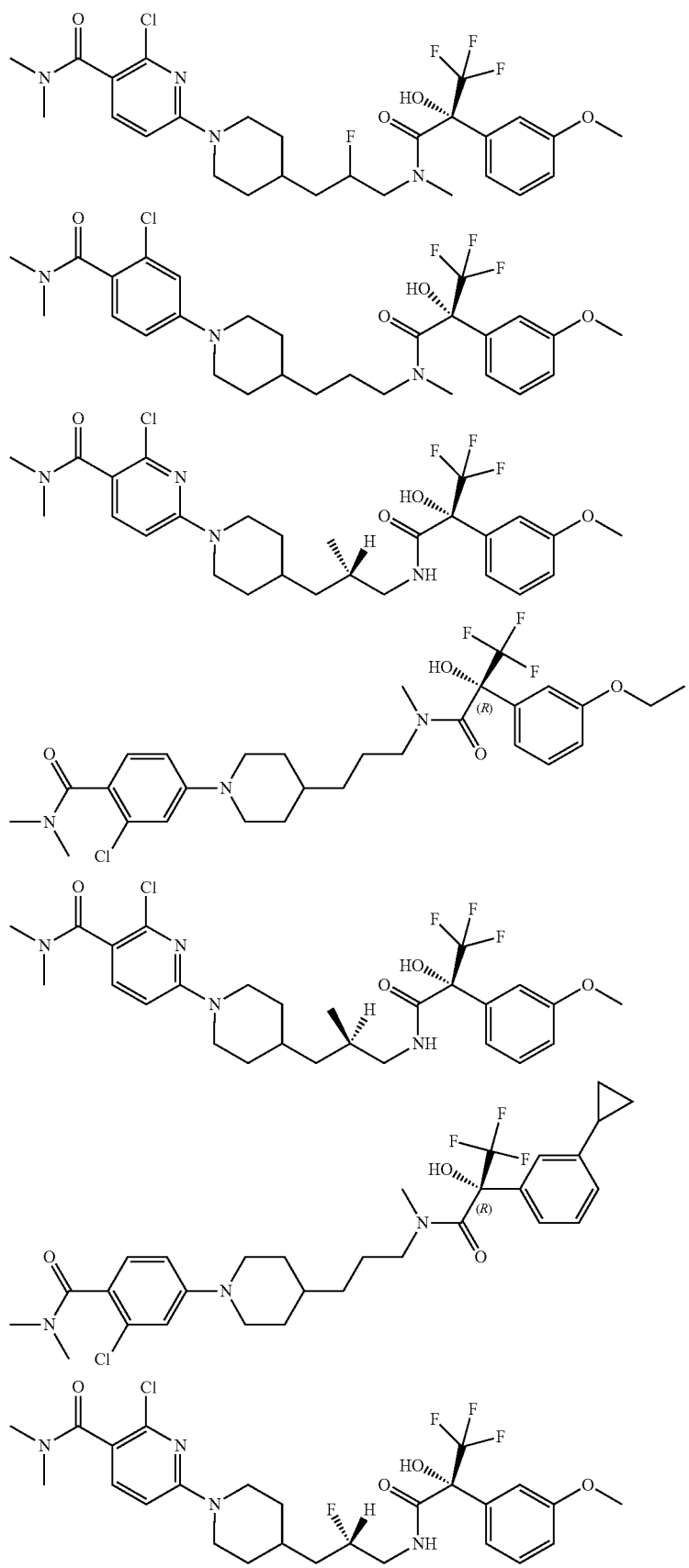

-continued
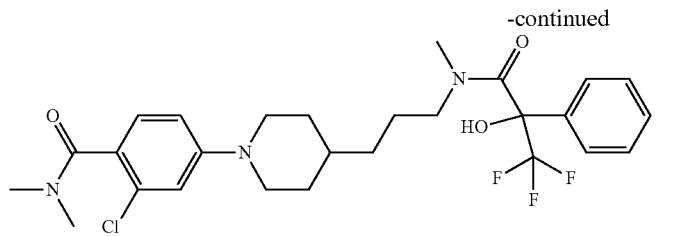
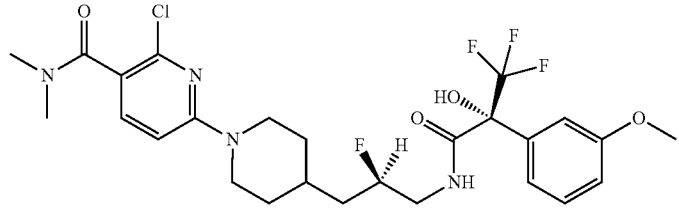
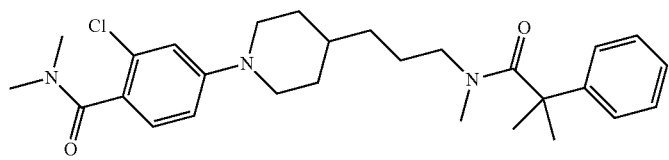
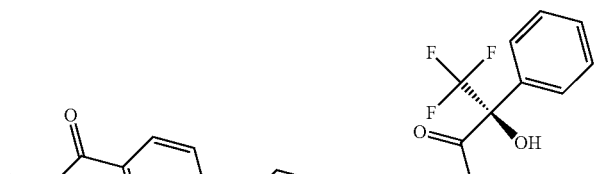
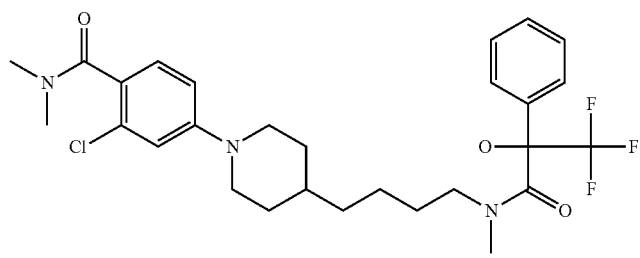
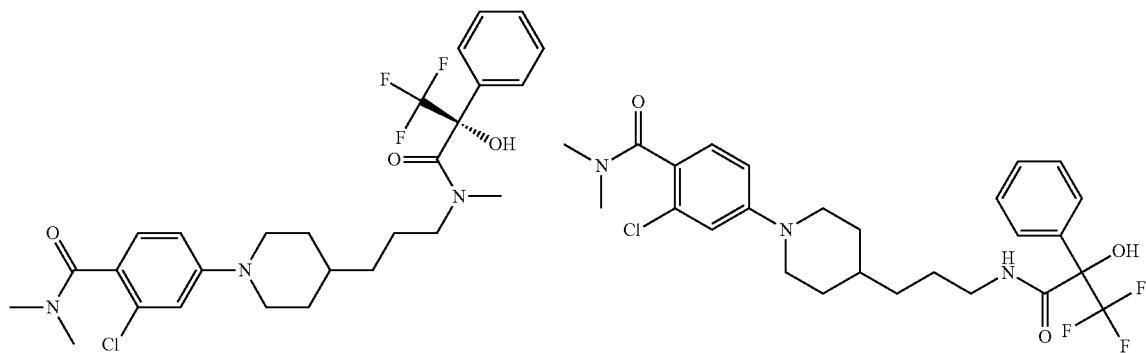
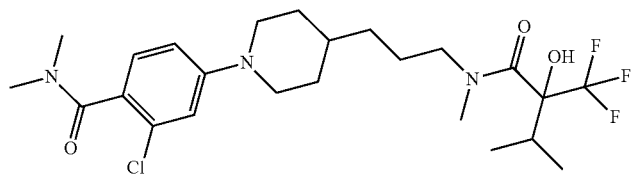

-continued
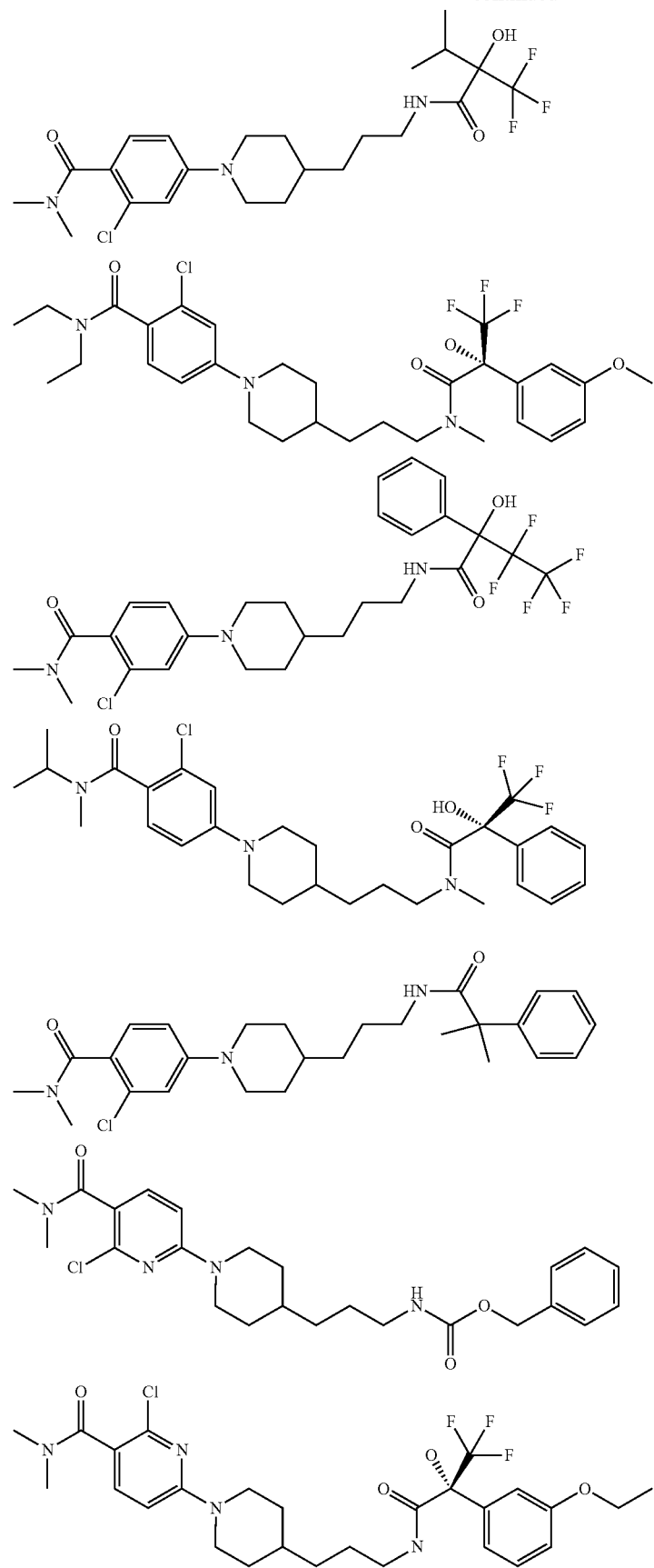

-continued
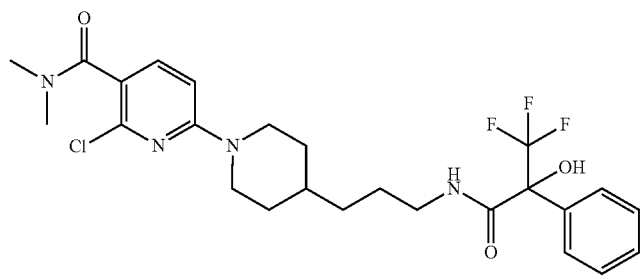
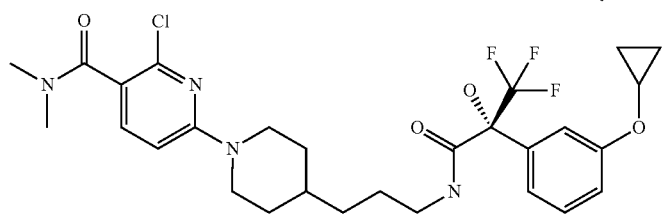
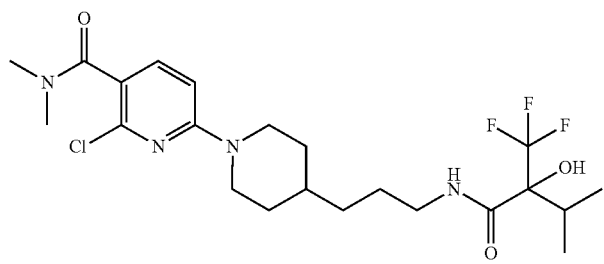
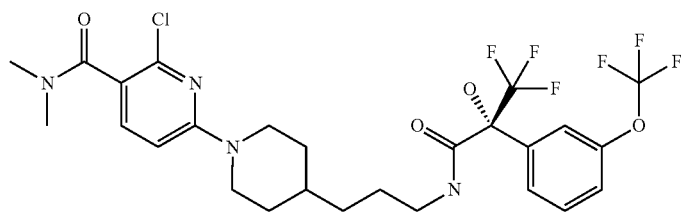
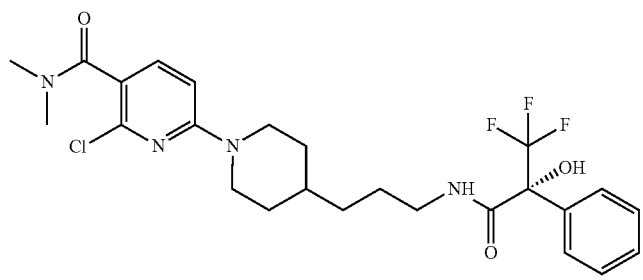
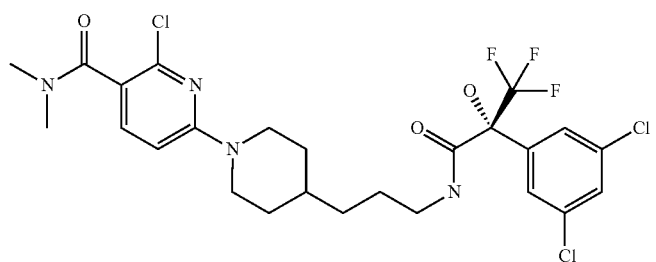

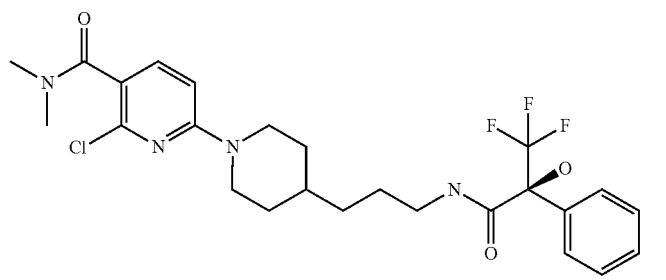
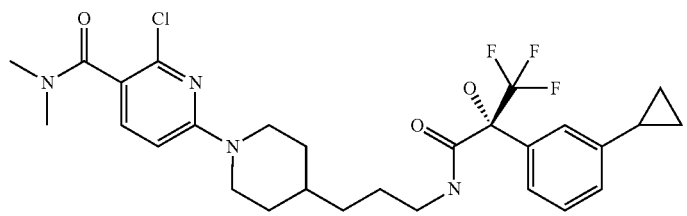
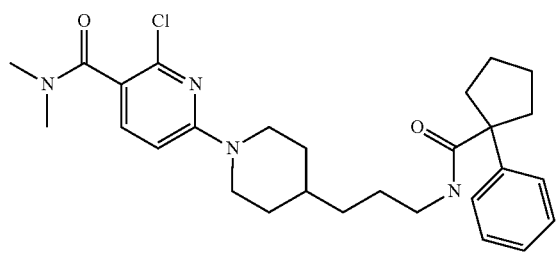
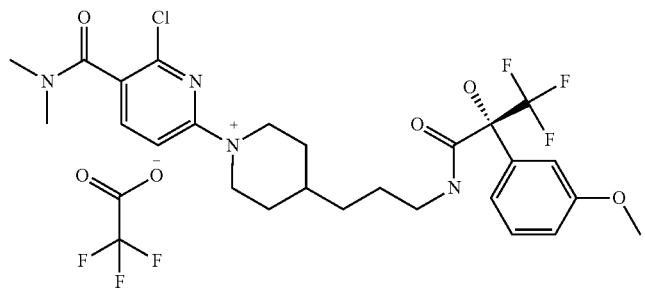
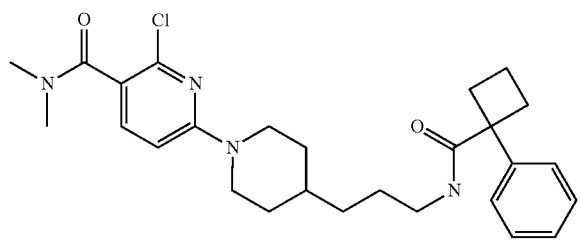
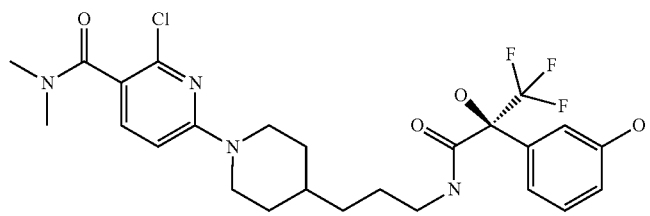
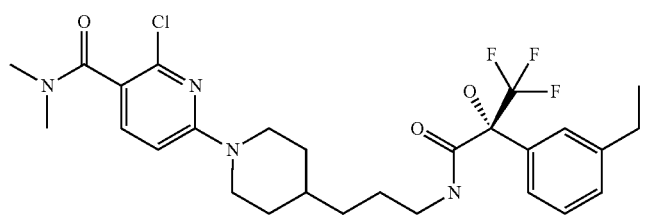

-continued
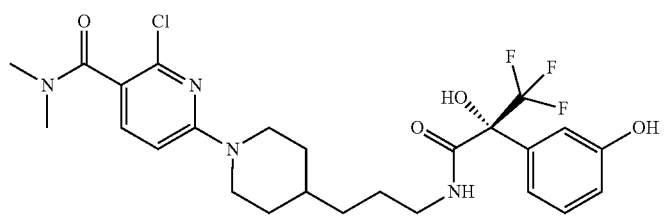
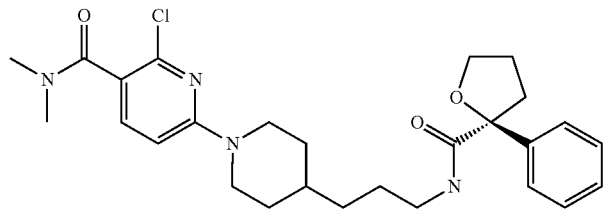
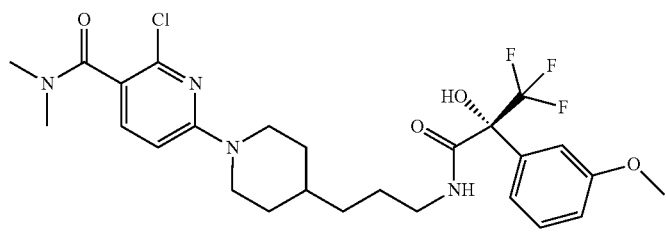
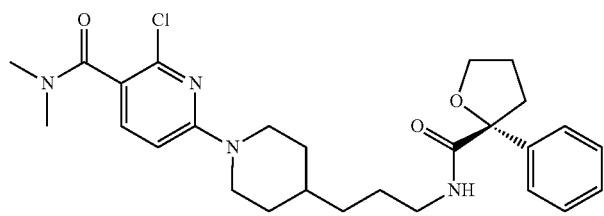
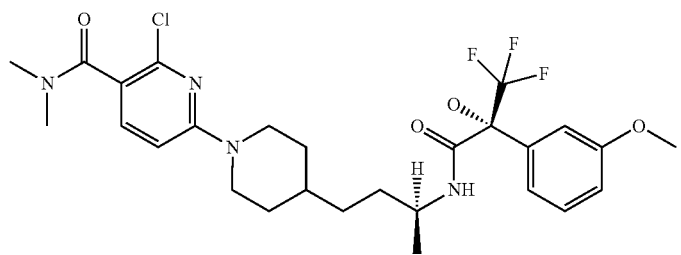
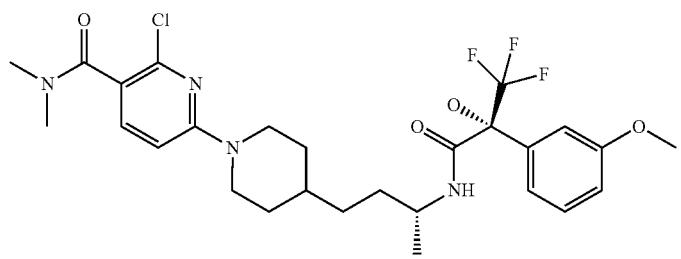
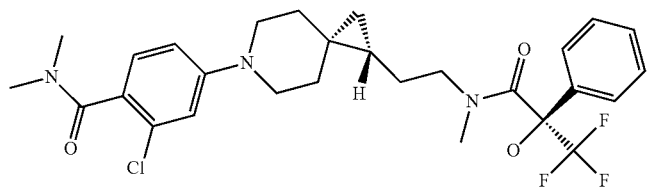

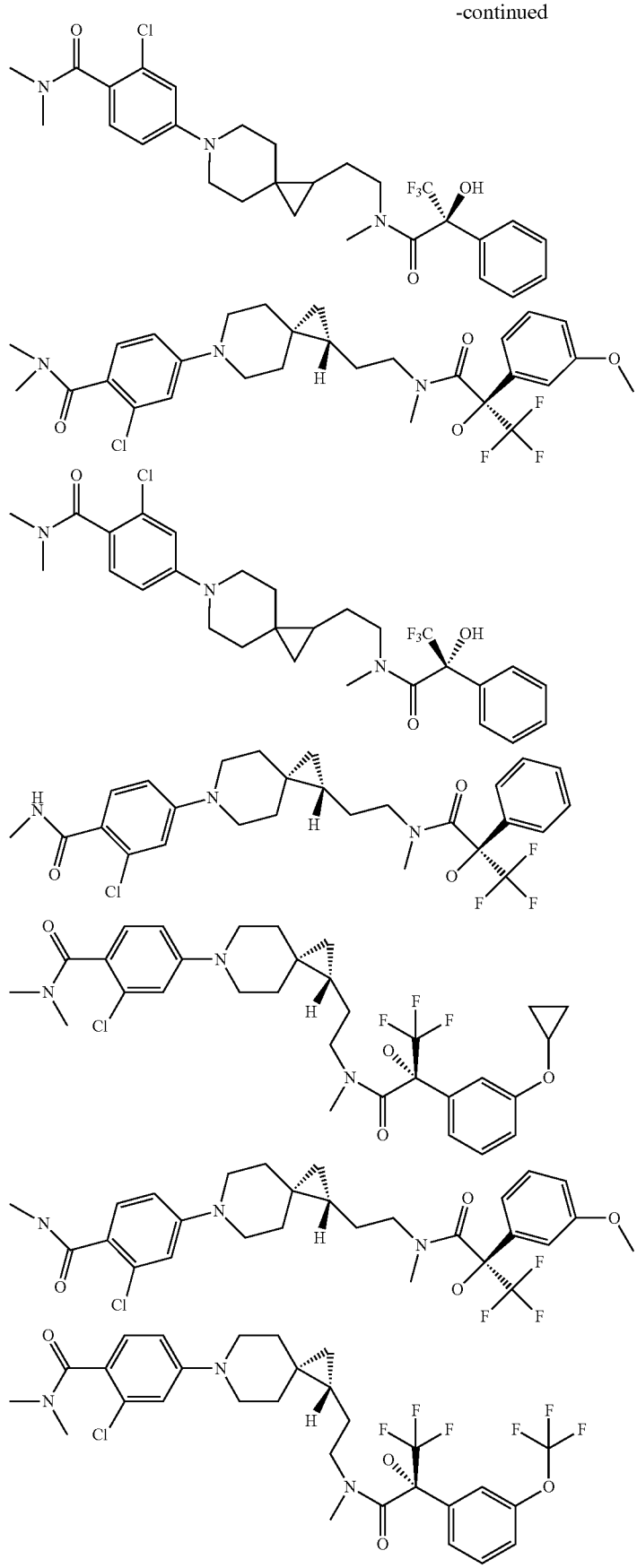

-continued
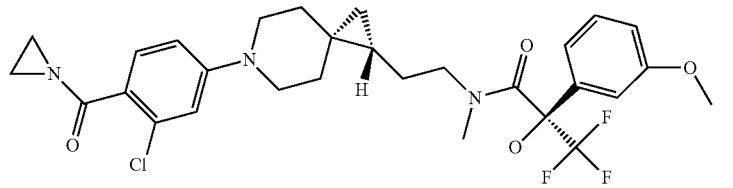
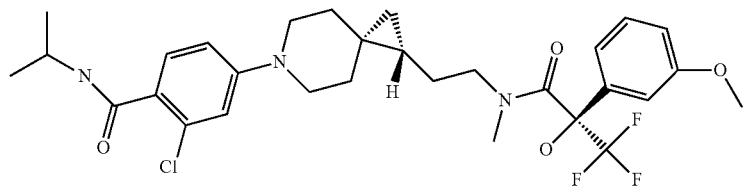
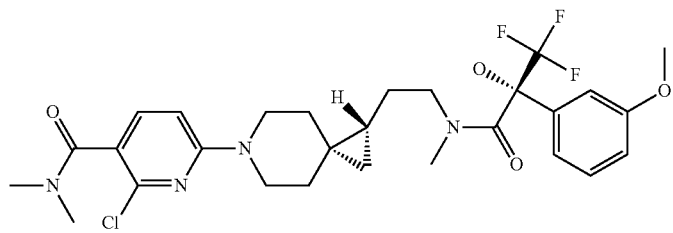
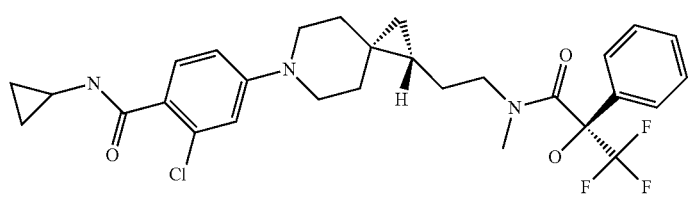
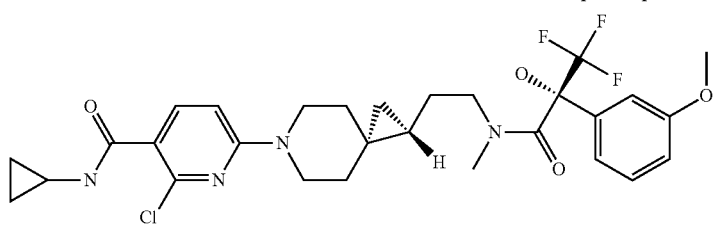
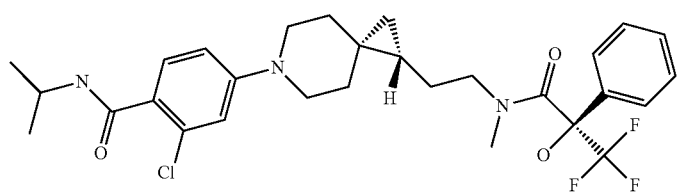
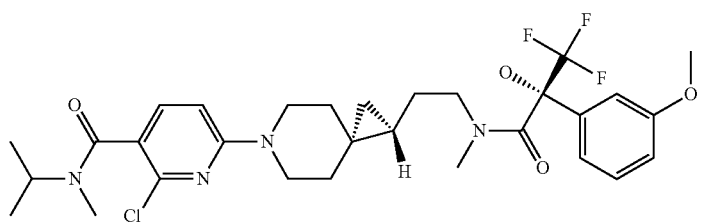
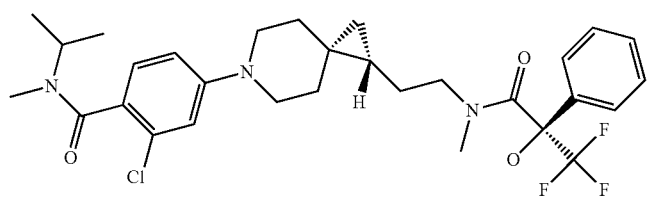

-continued
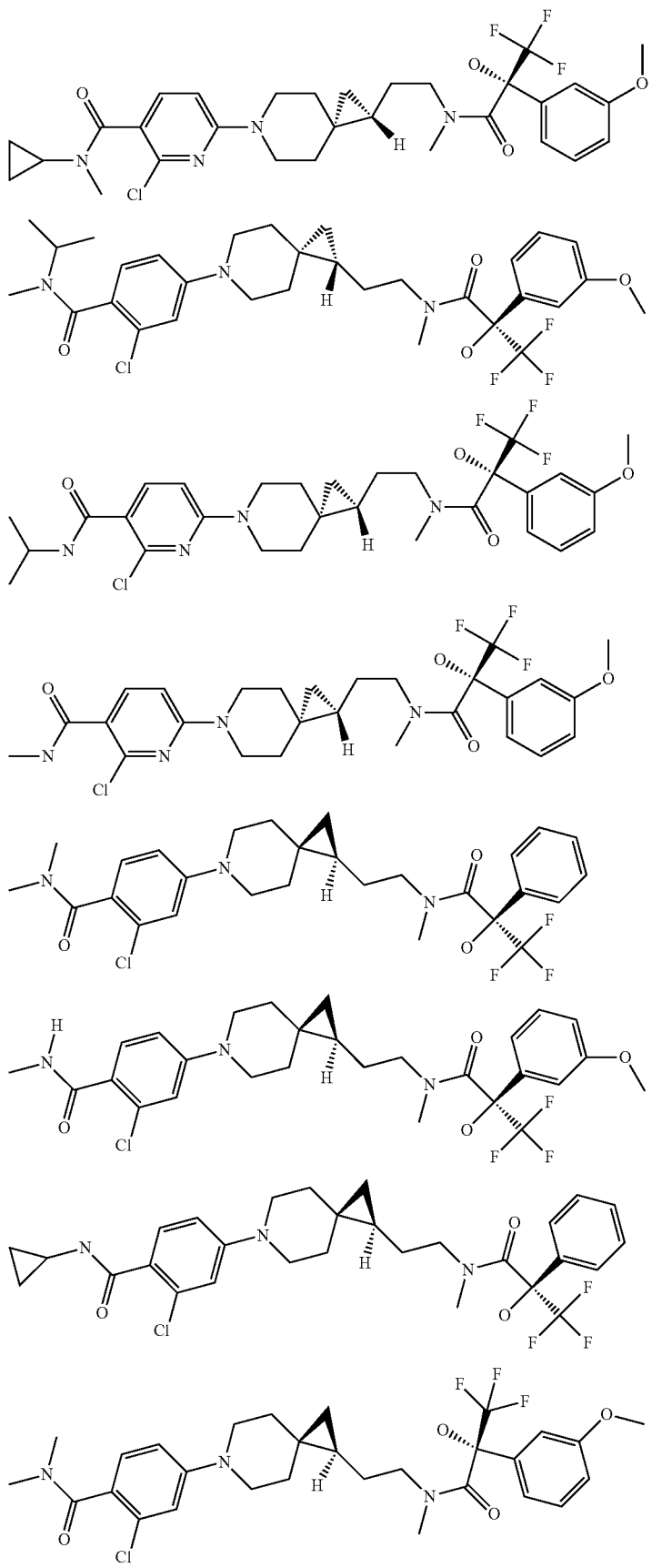

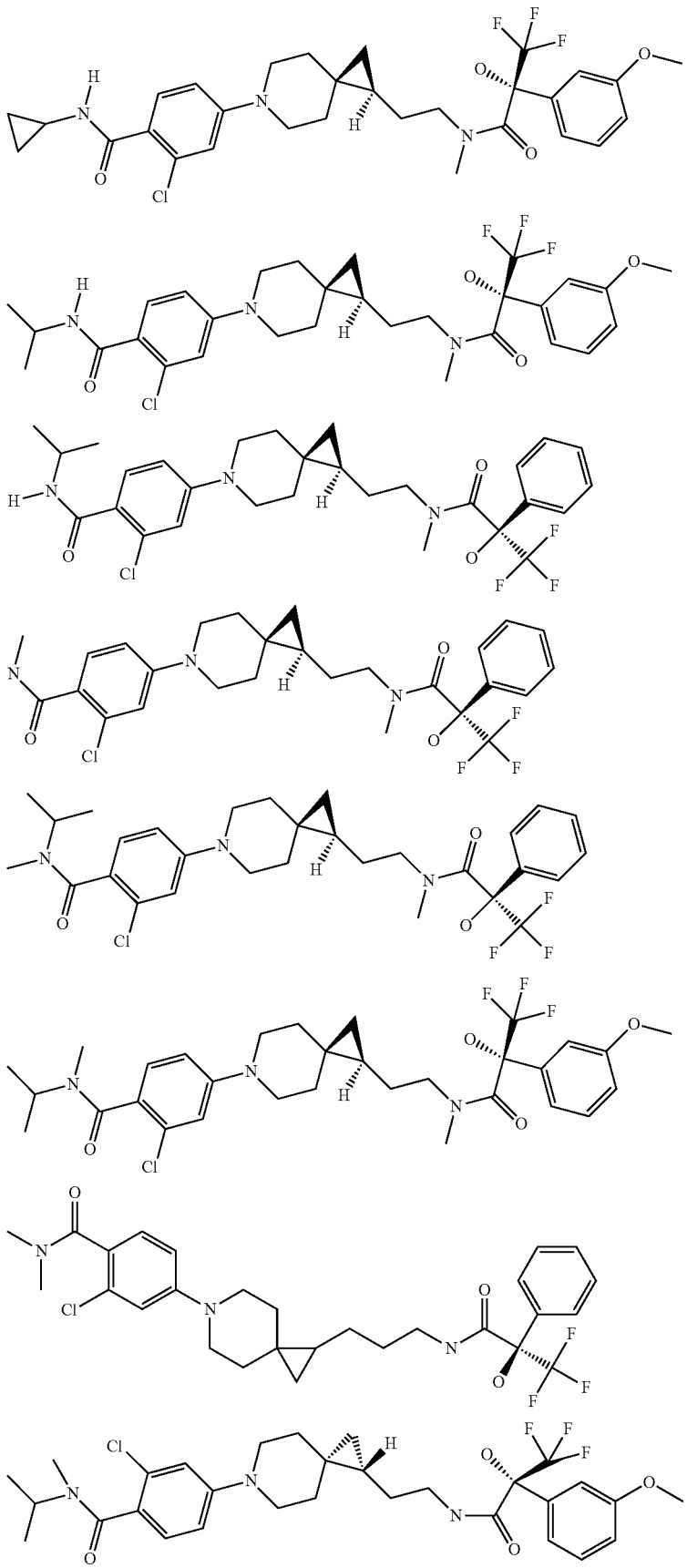

-continued
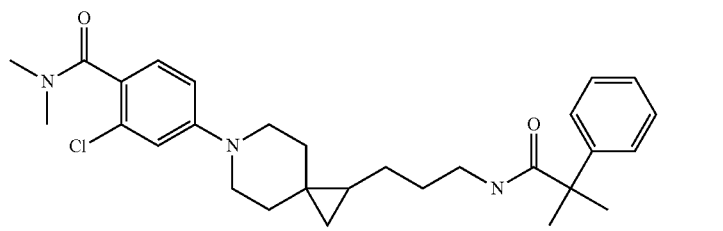
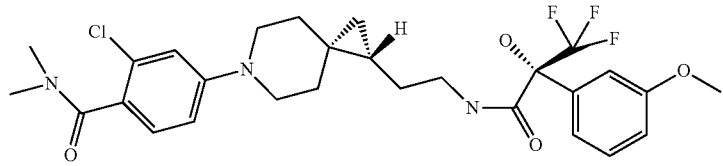
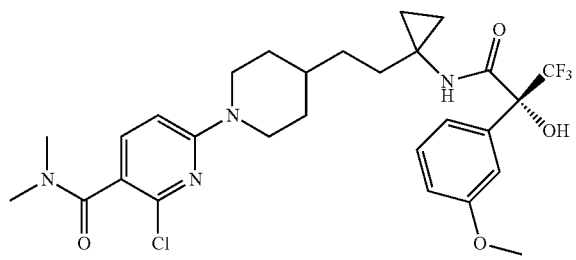
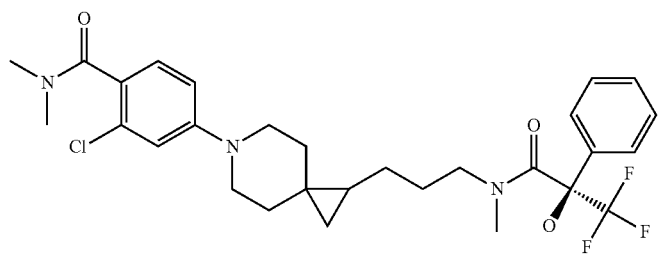
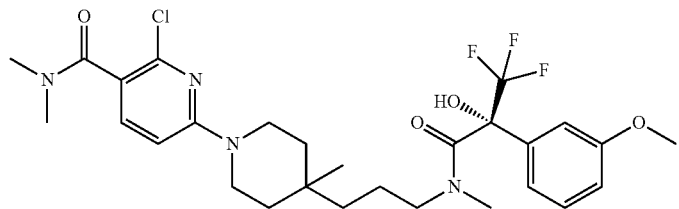
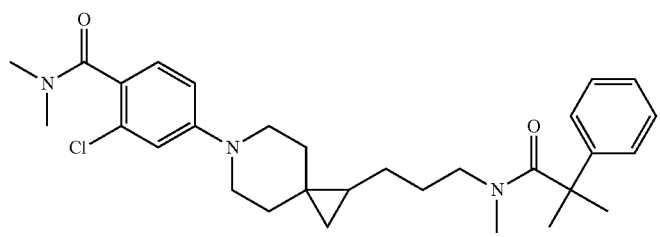
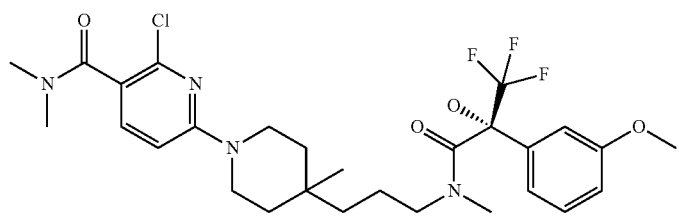

-continued
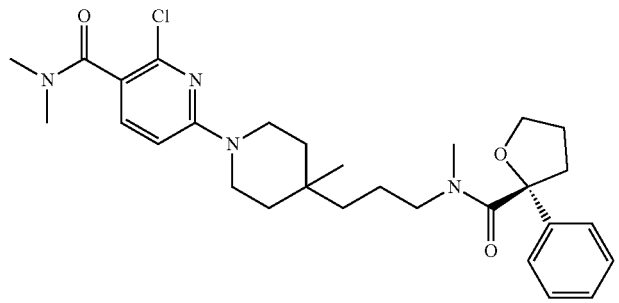
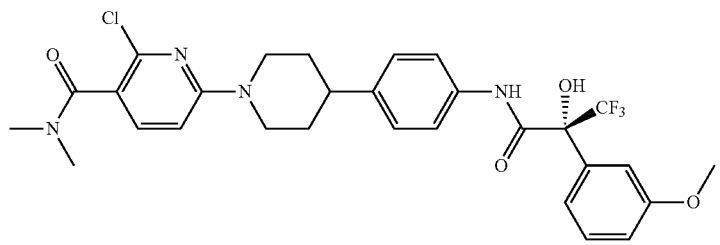
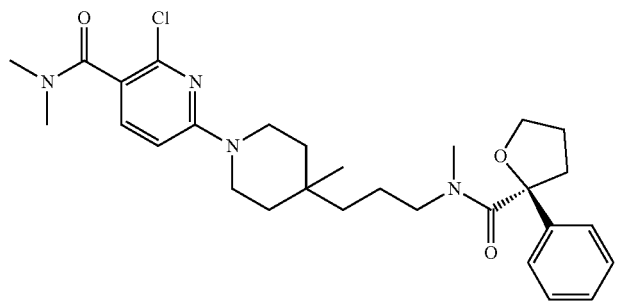
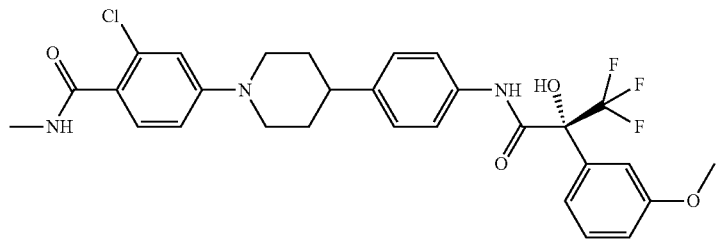
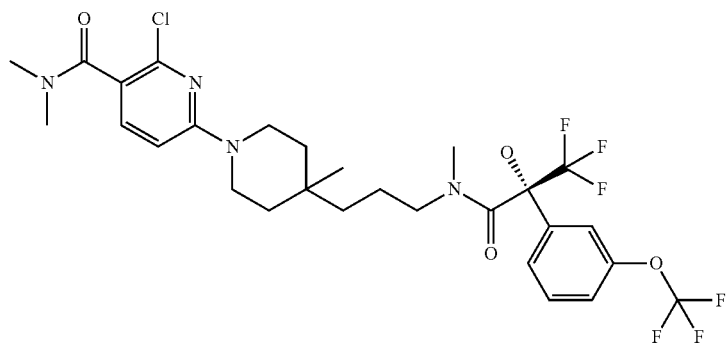
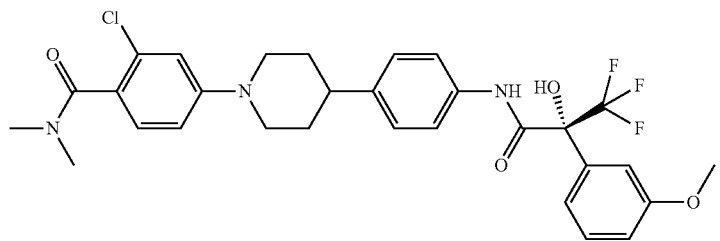

-continued
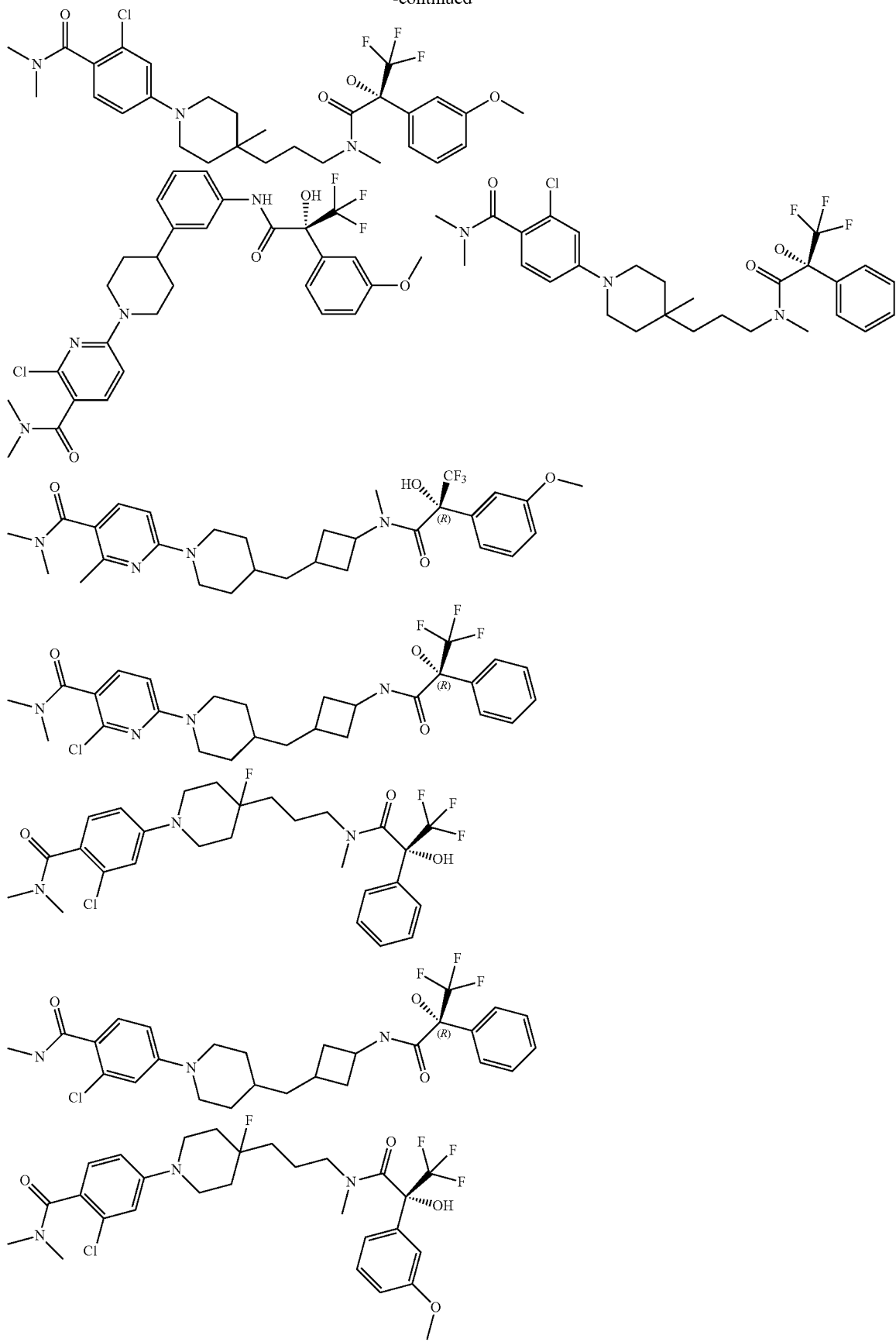

-continued
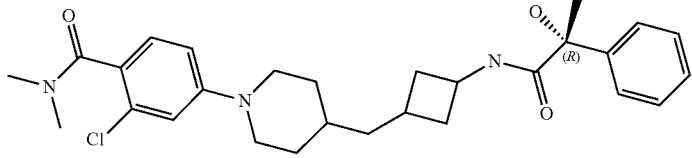
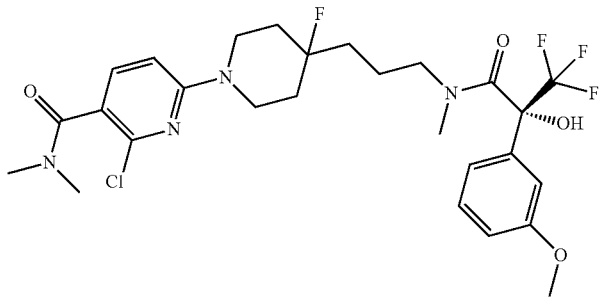
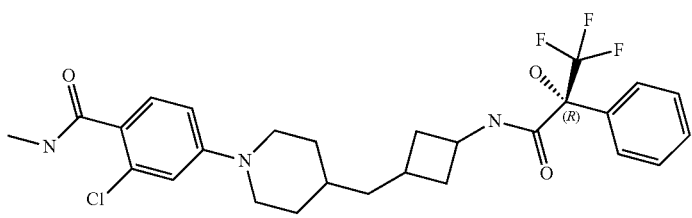
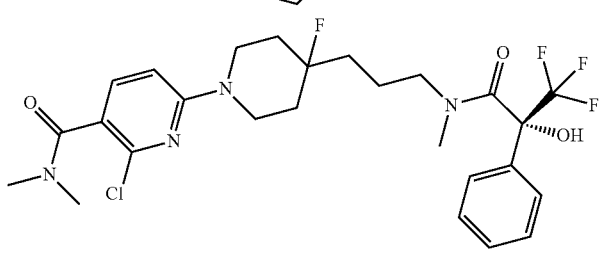
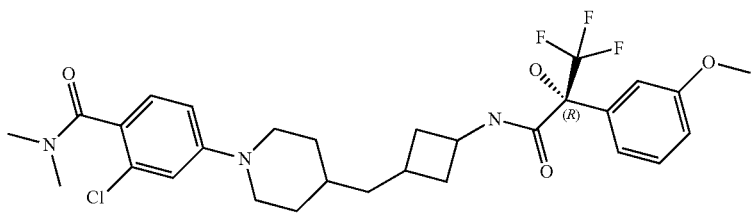
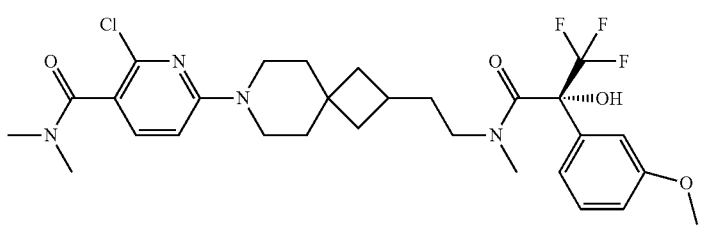
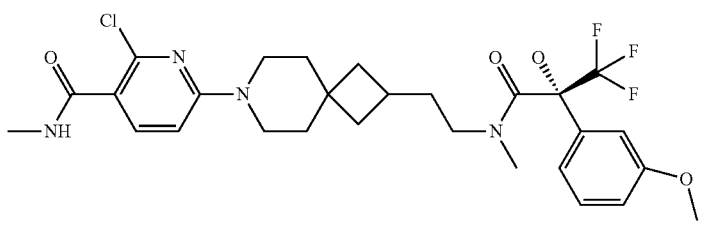

-continued
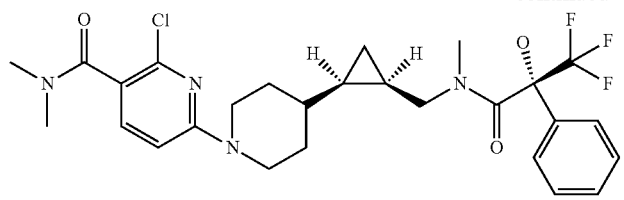
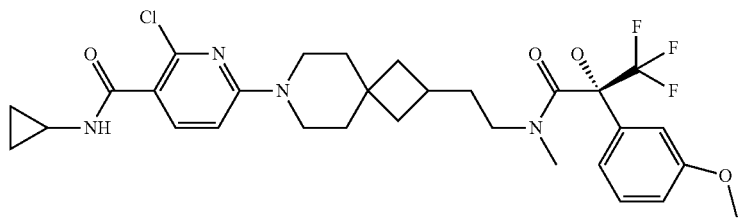
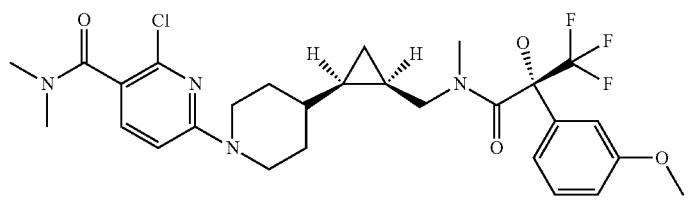
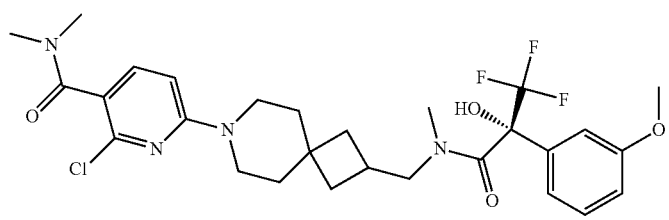
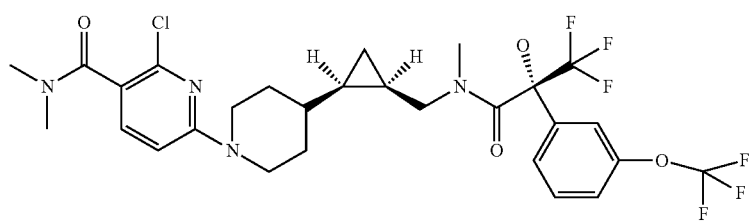
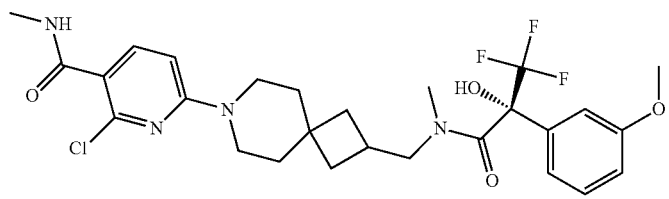
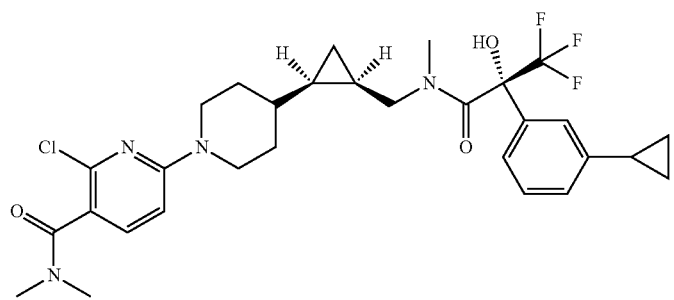

-continued
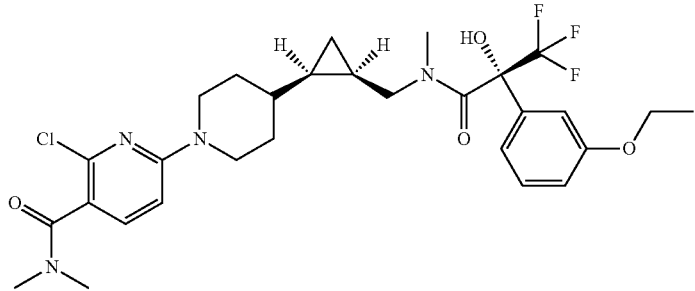
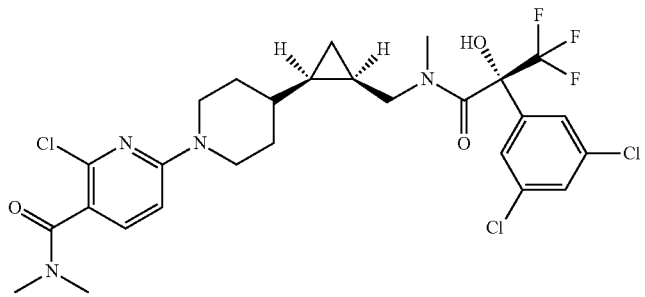
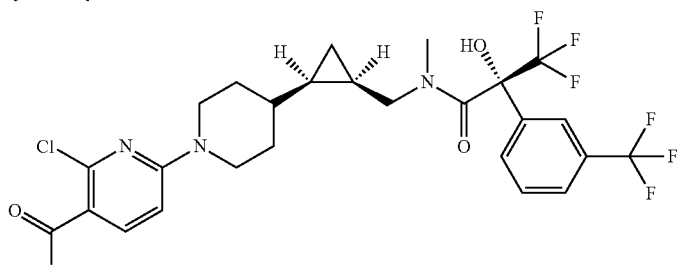
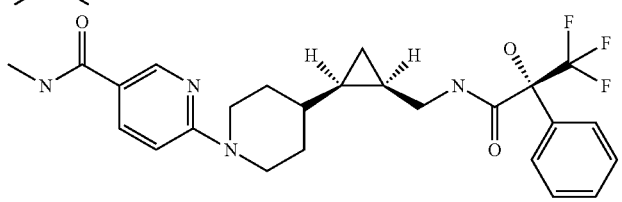
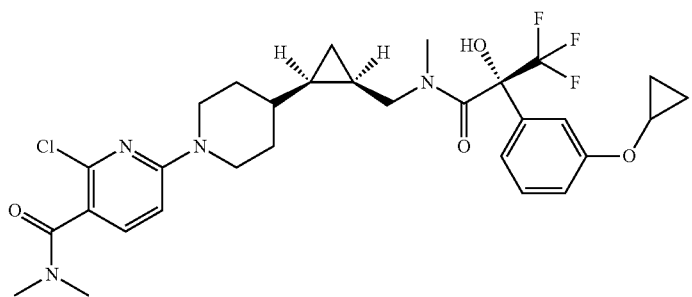
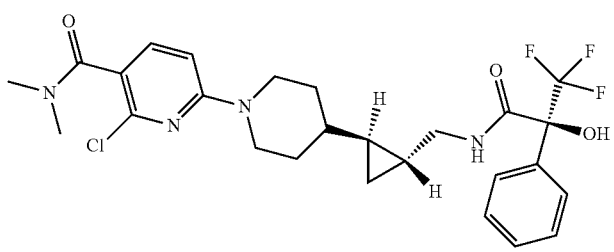

-continued
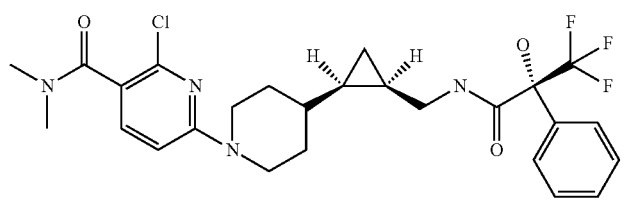
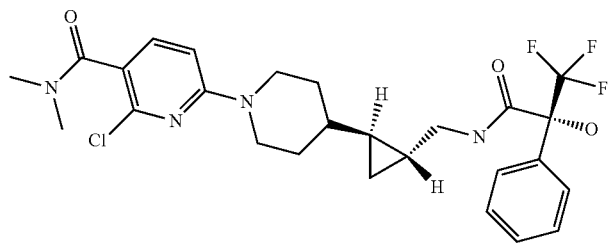
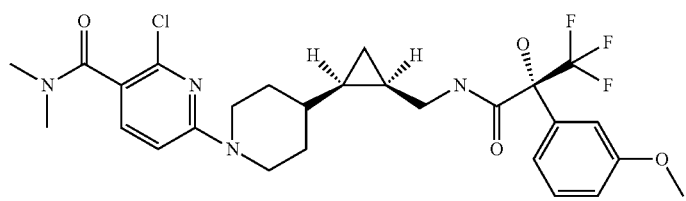
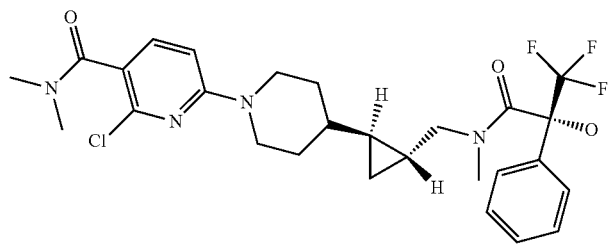
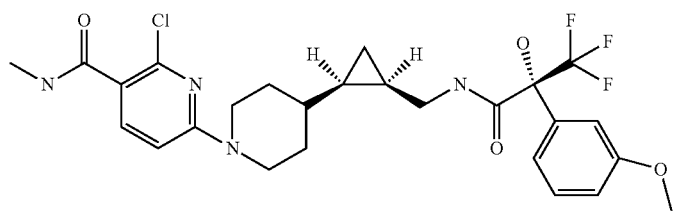
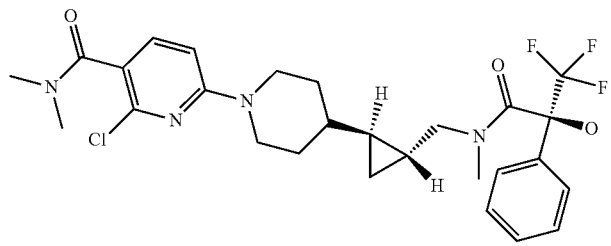
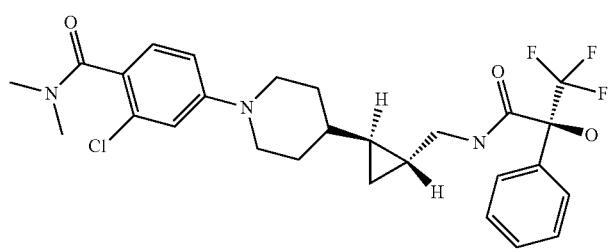

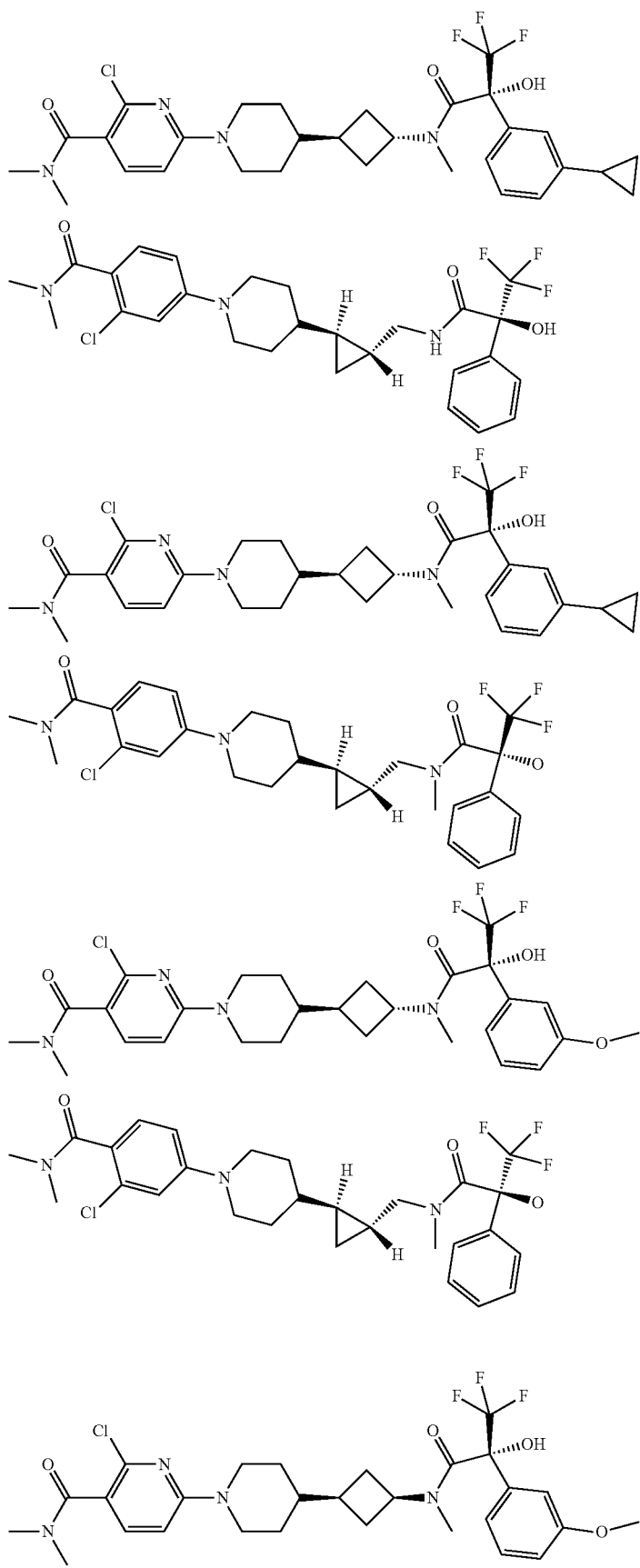

-continued
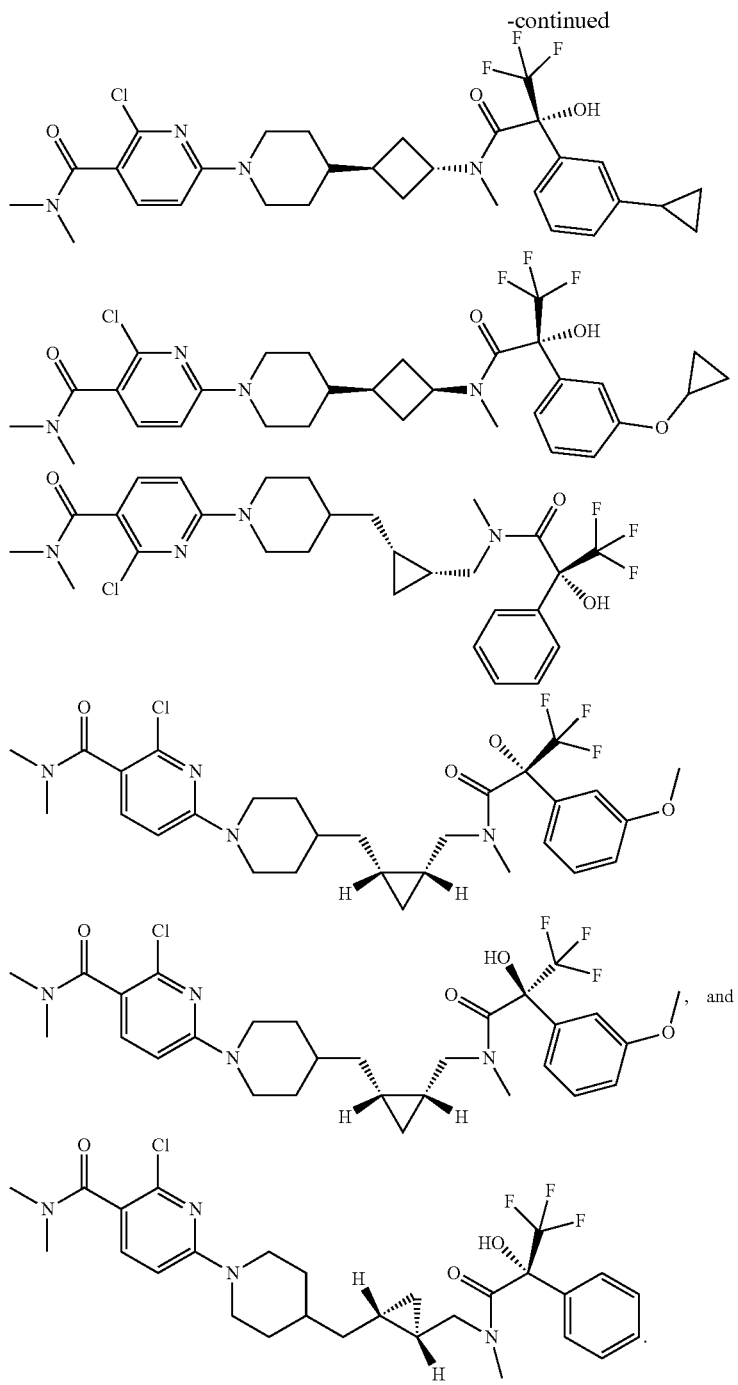
19. A pharmaceutical composition comprising the compound of claim 1, or a pharmaceutically acceptable salt thereof, and a pharmaceutically acceptable carrier or diluent.
* * * * *